US008486374B2

(12) United States Patent
Tamarkin et al.

(10) Patent No.: US 8,486,374 B2
(45) Date of Patent: Jul. 16, 2013

(54) HYDROPHILIC, NON-AQUEOUS PHARMACEUTICAL CARRIERS AND COMPOSITIONS AND USES

(75) Inventors: Dov Tamarkin, Maccabim (IL); Meir Eini, Ness Ziona (IL); Doron Friedman, Karmei Yosef (IL); Alex Besonov, Rehovot (IL); David Schuz, Moshav Gimzu (IL); Tal Berman, Rishon LeZiyyon (IL); Jorge Danziger, Rishom Lezion (IL); Rita Keynan, Rehovot (IL); Ella Zlatkis, Rehovot (IL)

(73) Assignee: Foamix Ltd., Rehovot (IL)

( * ) Notice: Subject to any disclaimer, the term of this patent is extended or adjusted under 35 U.S.C. 154(b) by 1180 days.

(21) Appl. No.: 12/014,088

(22) Filed: Jan. 14, 2008

(65) Prior Publication Data

US 2008/0299220 A1    Dec. 4, 2008

Related U.S. Application Data

(63) Continuation-in-part of application No. 11/430,599, filed on May 9, 2006, now Pat. No. 7,704,518, which is a continuation-in-part of application No. 10/835,505, filed on Apr. 28, 2004, now Pat. No. 7,820,145, application No. 12/014,088, which is a continuation-in-part of application No. 11/653,205, filed on Jan. 12, 2007.

(60) Provisional application No. 60/919,303, filed on Mar. 21, 2007.

(51) Int. Cl.
| A61K 33/00 | (2006.01) |
| A61K 47/34 | (2006.01) |
| A61K 31/375 | (2006.01) |
| A61K 31/355 | (2006.01) |
| A61K 31/351 | (2006.01) |
| A61K 31/4412 | (2006.01) |
| A61K 31/47 | (2006.01) |
| A61K 31/57 | (2006.01) |
| A61K 9/12 | (2006.01) |
| A61K 31/522 | (2006.01) |
| A61K 31/135 | (2006.01) |
| A61K 31/00 | (2006.01) |

(52) U.S. Cl.
USPC ........ 424/45; 424/600; 514/178; 514/263.38; 514/345; 514/458; 514/460; 514/474; 514/649; 514/772.7

(58) Field of Classification Search
USPC .................... 514/178, 263.38, 345, 458, 474, 514/649, 772.7
See application file for complete search history.

(56) References Cited

U.S. PATENT DOCUMENTS

| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |

(Continued)

FOREIGN PATENT DOCUMENTS

| AU | 198780257 | 9/1986 |
| CA | 2422244 | 9/2003 |

(Continued)

OTHER PUBLICATIONS

Alcohol SDA 40B.http://www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, http://www.arisankimya.com/kozmetik.htm Accessed Dec. 10, 2008, 8 pages.
Barry, B.W. et al, Comparative bio-availability and activity of proprietary topical corticosteroid preparations: vasoconstrictor assays on thirty-one ointments, British Journal of Dermatology, 93, 563-571, 1975.

(Continued)

*Primary Examiner* — Ernst Arnold
(74) *Attorney, Agent, or Firm* — Fish & Richardson P.C.

(57) ABSTRACT

A waterless composition suitable for delivery of an active agent to a body surface or cavity includes a vehicle having about 70% to about 99% by weight of a hydrophilic polar solvent, said hydrophilic solvent selected from the group consisting of (i) a mixture of two or more different polyethylene glycols (PEGs), wherein at least one PEG is a high molecular weight PEG having a melting point greater than 25° C.; and (ii) propylene glycol (PG); about 0% to about 10% of at least one surface active agent; about 0% to about 5% of a polymeric agent; about 0% to about 30% of a secondary hydrophilic solvent; and about 0% to about 5% of a silicone oil; and about 3% to about 25% hydrophobic propellant. The composition is otherwise substantially free of a hydrophobic solvent and includes at least one of a surface active agent and a polymeric agent. The vehicle and the propellant are sufficiently miscible that the components may be homogeneously distributed with mild shaking.

22 Claims, 4 Drawing Sheets

U.S. PATENT DOCUMENTS

| | | |
|---|---|---|
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,083,974 A | 4/1978 | Turi |
| 4,100,426 A | 7/1978 | Baranowski et al. |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |

| | | | | | | |
|---|---|---|---|---|---|---|
| 4,985,459 | A | 1/1991 | Sunshine et al. | 5,512,555 | A | 4/1996 | Waldstreicher |
| 4,992,478 | A | 2/1991 | Geria | 5,514,367 | A | 5/1996 | Lentini et al. |
| 4,993,496 | A | 2/1991 | Riedle et al. | 5,514,369 | A | 5/1996 | Salka et al. |
| 5,002,540 | A | 3/1991 | Brodman et al. | 5,520,918 | A | 5/1996 | Smith |
| 5,002,680 | A | 3/1991 | Schmidt et al. | 5,523,078 | A | 6/1996 | Baylin |
| 5,007,556 | A | 4/1991 | Lover | 5,527,534 | A | 6/1996 | Myhling |
| 5,013,297 | A | 5/1991 | Cattanach | 5,527,822 | A | 6/1996 | Scheiner |
| 5,015,471 | A | 5/1991 | Birtwistle et al. | 5,529,770 | A | 6/1996 | McKinzie et al. |
| 5,019,375 | A | 5/1991 | Tanner et al. | 5,531,703 | A | 7/1996 | Skwarek et al. |
| 5,034,220 | A | 7/1991 | Helioff et al. | 5,534,261 | A | 7/1996 | Rodgers et al. |
| 5,035,895 | A | 7/1991 | Shibusawa et al. | 5,536,743 | A | 7/1996 | Borgman |
| 5,053,228 | A | 10/1991 | Mori et al. | 5,540,853 | A | 7/1996 | Trinh et al. |
| 5,071,648 | A | 12/1991 | Rosenblatt | 5,545,401 | A | 8/1996 | Shanbrom |
| 5,071,881 | A | 12/1991 | Parfondry et al. | 5,567,420 | A | 10/1996 | McEleney et al. |
| 5,073,371 | A | 12/1991 | Turner et al. | 5,576,016 | A | 11/1996 | Amselem et al. |
| 5,082,651 | A | 1/1992 | Healey et al. | 5,578,315 | A | 11/1996 | Chien et al. |
| 5,087,618 | A | 2/1992 | Bodor | 5,585,104 | A | 12/1996 | Ha et al. |
| 5,089,252 | A | 2/1992 | Grollier et al. | 5,589,157 | A | 12/1996 | Hatfield |
| 5,091,111 | A | 2/1992 | Neumiller | 5,589,515 | A | 12/1996 | Suzuki et al. |
| 5,094,853 | A | 3/1992 | Hagarty | 5,597,560 | A | 1/1997 | Bergamini et al. |
| 5,100,917 | A | 3/1992 | Flynn et al. | 5,603,940 | A | 2/1997 | Candau et al. |
| 5,104,645 | A | 4/1992 | Cardin et al. | 5,605,679 | A | 2/1997 | Hansenne et al. |
| 5,112,359 | A | 5/1992 | Murphy et al. | 5,608,119 | A | 3/1997 | Amano et al. |
| 5,114,718 | A | 5/1992 | Damani | 5,611,463 | A | 3/1997 | Favre |
| 5,122,519 | A | 6/1992 | Ritter | 5,612,056 | A | 3/1997 | Jenner et al. |
| 5,130,121 | A | 7/1992 | Kopolow et al. | 5,613,583 | A | 3/1997 | Kono et al. |
| 5,133,972 | A | 7/1992 | Ferrini et al. | 5,613,623 | A | 3/1997 | Hildebrandt |
| 5,135,915 | A | 8/1992 | Czarniecki et al. | 5,614,171 | A | 3/1997 | Clavenna et al. |
| 5,137,714 | A | 8/1992 | Scott | 5,614,178 | A | 3/1997 | Bloom et al. |
| 5,143,717 | A | 9/1992 | Davis | 5,635,469 | A | 6/1997 | Fowler et al. |
| 5,156,765 | A | 10/1992 | Smrt | 5,641,480 | A | 6/1997 | Vermeer |
| 5,164,357 | A | 11/1992 | Bartman et al. | 5,643,600 | A | 7/1997 | Mathur |
| 5,164,367 | A | 11/1992 | Pickart | 5,645,842 | A | 7/1997 | Gruning et al. |
| 5,167,950 | A | 12/1992 | Lins | 5,650,554 | A | 7/1997 | Moloney |
| 5,171,577 | A | 12/1992 | Griat et al. | 5,658,575 | A | 8/1997 | Ribier et al. |
| 5,196,405 | A | 3/1993 | Packman | 5,658,749 | A | 8/1997 | Thornton |
| 5,204,093 | A | 4/1993 | Victor | 5,658,956 | A | 8/1997 | Martin et al. |
| 5,208,031 | A | 5/1993 | Kelly | 5,663,208 | A | 9/1997 | Martin |
| 5,217,707 | A | 6/1993 | Szabo et al. | 5,672,634 | A | 9/1997 | Tseng et al. |
| 5,219,877 | A | 6/1993 | Shah et al. | 5,679,324 | A | 10/1997 | Lisboa et al. |
| 5,221,696 | A | 6/1993 | Ke et al. | 5,683,710 | A | 11/1997 | Akemi et al. |
| 5,230,897 | A | 7/1993 | Griffin et al. | 5,686,088 | A | 11/1997 | Mitra et al. |
| 5,236,707 | A | 8/1993 | Stewart, II | 5,693,258 | A | 12/1997 | Tonomura et al. |
| 5,252,246 | A | 10/1993 | Ding et al. | 5,695,551 | A | 12/1997 | Buckingham et al. |
| 5,254,334 | A | 10/1993 | Ramirez et al. | 5,700,396 | A | 12/1997 | Suzuki et al. |
| 5,262,407 | A | 11/1993 | Leveque et al. | 5,716,611 | A | 2/1998 | Oshlack et al. |
| 5,266,592 | A | 11/1993 | Grub et al. | 5,716,621 | A | 2/1998 | Bello |
| 5,279,819 | A | 1/1994 | Hayes | 5,719,122 | A | 2/1998 | Chiodini et al. |
| 5,286,475 | A | 2/1994 | Louvet et al. | 5,719,197 | A | 2/1998 | Kanios et al. |
| 5,300,286 | A | 4/1994 | Gee | 5,725,872 | A | 3/1998 | Stamm et al. |
| 5,301,841 | A | 4/1994 | Fuchs et al. | 5,725,874 | A | 3/1998 | Oda et al. |
| 5,308,643 | A | 5/1994 | Osipow et al. | 5,730,964 | A | 3/1998 | Waldstreicher |
| 5,314,904 | A | 5/1994 | Egidio et al. | 5,733,558 | A | 3/1998 | Breton et al. |
| 5,322,683 | A | 6/1994 | Mackles et al. | 5,733,572 | A | 3/1998 | Unger et al. |
| 5,326,557 | A | 7/1994 | Glover et al. | 5,747,049 | A | 5/1998 | Tominaga |
| 5,344,051 | A | 9/1994 | Brown | 5,753,241 | A | 5/1998 | Ribier et al. |
| 5,346,135 | A | 9/1994 | Vincent | 5,753,245 | A | 5/1998 | Fowler et al. |
| 5,352,437 | A | 10/1994 | Nakagawa et al. | 5,759,520 | A | 6/1998 | Sachetto |
| 5,369,131 | A | 11/1994 | Poli et al. | 5,759,579 | A | 6/1998 | Singh et al. |
| 5,378,451 | A | 1/1995 | Gorman et al. | 5,767,104 | A | 6/1998 | Bar-Shalom et al. |
| 5,378,730 | A | 1/1995 | Lee et al. | 5,773,410 | A | 6/1998 | Yamamoto |
| 5,380,761 | A | 1/1995 | Szabo et al. | 5,783,202 | A | 7/1998 | Tomlinson et al. |
| 5,384,308 | A | 1/1995 | Henkin | 5,788,664 | A | 8/1998 | Scalise |
| 5,385,943 | A | 1/1995 | Nazzaro-Porro | 5,792,448 | A | 8/1998 | Dubief et al. |
| 5,389,676 | A | 2/1995 | Michaels | 5,792,922 | A | 8/1998 | Moloney et al. |
| 5,397,312 | A | 3/1995 | Rademaker et al. | 5,797,955 | A | 8/1998 | Walters |
| 5,398,846 | A | 3/1995 | Corba et al. | 5,804,546 | A | 9/1998 | Hall et al. |
| 5,399,205 | A | 3/1995 | Shinohara et al. | 5,817,322 | A | 10/1998 | Xu et al. |
| 5,411,992 | A | 5/1995 | Eini et al. | 5,824,650 | A | 10/1998 | De Lacharriere et al. |
| 5,422,361 | A | 6/1995 | Munayyer et al. | 5,833,960 | A | 11/1998 | Gers-Barlag et al. |
| 5,429,815 | A | 7/1995 | Faryniarz et al. | 5,833,961 | A | 11/1998 | Siegfried et al. |
| 5,435,996 | A | 7/1995 | Glover et al. | 5,837,270 | A | 11/1998 | Burgess |
| 5,447,725 | A | 9/1995 | Damani et al. | 5,840,744 | A | 11/1998 | Borgman |
| 5,449,520 | A | 9/1995 | Frigerio et al. | 5,840,771 | A | 11/1998 | Oldham et al. |
| 5,451,404 | A | 9/1995 | Furman | 5,843,411 | A | 12/1998 | Hernandez et al. |
| 5,482,965 | A | 1/1996 | Rajadhyaksha | 5,846,983 | A | 12/1998 | Sandborn et al. |
| 5,491,245 | A | 2/1996 | Gruning et al. | 5,849,042 | A | 12/1998 | Lim et al. |
| 5,500,211 | A | 3/1996 | George et al. | 5,856,452 | A | 1/1999 | Moloney et al. |
| 5,508,033 | A | 4/1996 | Briand | 5,858,371 | A | 1/1999 | Singh et al. |

| | | | | | | |
|---|---|---|---|---|---|---|
| 5,865,347 | A | 2/1999 | Welschoff | 6,231,837 | B1 | 5/2001 | Stroud et al. |
| 5,866,040 | A | 2/1999 | Nakama et al. | 6,232,315 | B1 | 5/2001 | Shafer et al. |
| 5,869,529 | A | 2/1999 | Sintov et al. | 6,251,369 | B1 | 6/2001 | Stoltz |
| 5,871,720 | A | 2/1999 | Gutierrez et al. | 6,258,374 | B1 | 7/2001 | Friess et al. |
| 5,877,216 | A | 3/1999 | Place et al. | 6,271,295 | B1 | 8/2001 | Powell et al. |
| 5,879,469 | A | 3/1999 | Avram et al. | 6,274,150 | B1 | 8/2001 | Simonnet et al. |
| 5,881,493 | A | 3/1999 | Restive | 6,287,546 | B1 | 9/2001 | Reich et al. |
| 5,885,581 | A | 3/1999 | Massand | 6,294,550 | B1 | 9/2001 | Place et al. |
| 5,889,028 | A | 3/1999 | Sandborn et al. | 6,299,023 | B1 | 10/2001 | Arnone |
| 5,889,054 | A | 3/1999 | Yu et al. | 6,299,032 | B1 | 10/2001 | Hamilton |
| 5,891,458 | A | 4/1999 | Britton et al. | 6,299,900 | B1 | 10/2001 | Reed et al. |
| 5,902,574 | A | 5/1999 | Stoner et al. | 6,305,578 | B1 | 10/2001 | Hildebrandt et al. |
| 5,902,789 | A | 5/1999 | Stoltz | 6,306,841 | B1 | 10/2001 | Place et al. |
| 5,905,092 | A | 5/1999 | Osborne et al. | 6,308,863 | B1 | 10/2001 | Harman |
| 5,910,382 | A | 6/1999 | Goodenough et al. | 6,319,913 | B1 | 11/2001 | Mak et al. |
| 5,911,981 | A | 6/1999 | Dahms et al. | 6,328,950 | B1 | 12/2001 | Franzke et al. |
| 5,912,007 | A | 6/1999 | Pan et al. | 6,328,982 | B1 | 12/2001 | Shiroyama et al. |
| 5,914,122 | A | 6/1999 | Otterbeck et al. | 6,333,362 | B1 | 12/2001 | Lorant |
| 5,914,310 | A | 6/1999 | Li et al. | 6,335,022 | B1 | 1/2002 | Simonnet et al. |
| 5,922,331 | A | 7/1999 | Mausner | 6,341,717 | B2 | 1/2002 | Auer |
| 5,925,669 | A | 7/1999 | Katz et al. | 6,344,218 | B1 | 2/2002 | Dodd et al. |
| 5,948,682 | A | 9/1999 | Moloney | 6,348,229 | B1 | 2/2002 | Eini et al. |
| 5,951,544 | A | 9/1999 | Konwitz | 6,358,541 | B1 | 3/2002 | Goodman |
| 5,951,989 | A | 9/1999 | Heymann | 6,364,854 | B1 | 4/2002 | Ferrer et al. |
| 5,951,993 | A | 9/1999 | Scholz et al. | 6,372,234 | B1 | 4/2002 | Deckers et al. |
| 5,952,373 | A | 9/1999 | Lanzendorfer et al. | 6,375,960 | B1 | 4/2002 | Simonnet et al. |
| 5,952,392 | A | 9/1999 | Katz et al. | 6,383,471 | B1 | 5/2002 | Chen et al. |
| 5,955,414 | A | 9/1999 | Brown et al. | 6,395,258 | B1 | 5/2002 | Steer |
| 5,959,161 | A | 9/1999 | Kenmochi et al. | 6,395,300 | B1 | 5/2002 | Straub et al. |
| 5,961,957 | A | 10/1999 | McAnalley | 6,403,061 | B1 | 6/2002 | Candau et al. |
| 5,961,998 | A | 10/1999 | Arnaud et al. | 6,403,069 | B1 | 6/2002 | Chopra et al. |
| 5,972,310 | A | 10/1999 | Sachetto | 6,410,036 | B1 | 6/2002 | De Rosa et al. |
| 5,976,555 | A | 11/1999 | Liu et al. | 6,423,323 | B2 | 7/2002 | Neubourg |
| 5,980,904 | A | 11/1999 | Leverett et al. | 6,428,772 | B1 | 8/2002 | Singh et al. |
| 5,990,100 | A | 11/1999 | Rosenberg et al. | 6,433,003 | B1 | 8/2002 | Bobrove et al. |
| 5,993,846 | A | 11/1999 | Friedman et al. | 6,433,024 | B1 | 8/2002 | Popp et al. |
| 6,001,341 | A | 12/1999 | Genova et al. | 6,433,033 | B1 | 8/2002 | Isobe et al. |
| 6,006,948 | A | 12/1999 | Auer | 6,437,006 | B1 | 8/2002 | Yoon et al. |
| 6,019,967 | A | 2/2000 | Breton et al. | 6,440,429 | B1 | 8/2002 | Torizuka et al. |
| 6,024,942 | A | 2/2000 | Tanner et al. | 6,447,801 | B1 | 9/2002 | Salafsky et al. |
| 6,030,630 | A | 2/2000 | Fleury et al. | 6,455,076 | B1 | 9/2002 | Hahn et al. |
| 6,033,647 | A | 3/2000 | Touzan et al. | 6,468,989 | B1 | 10/2002 | Chang et al. |
| 6,039,936 | A | 3/2000 | Restle et al. | 6,479,058 | B1 | 11/2002 | McCadden |
| 6,042,848 | A | 3/2000 | Lawyer et al. | 6,486,168 | B1 | 11/2002 | Skwierczynski et al. |
| 6,045,779 | A | 4/2000 | Mueller et al. | 6,488,947 | B1 | 12/2002 | Bekele |
| 6,071,536 | A | 6/2000 | Suzuki et al. | 6,511,655 | B1 | 1/2003 | Muller et al. |
| 6,075,056 | A | 6/2000 | Quigley, Jr. et al. | 6,514,487 | B1 | 2/2003 | Barr |
| 6,080,394 | A | 6/2000 | Lin et al. | 6,524,594 | B1 | 2/2003 | Santora et al. |
| 6,087,317 | A | 7/2000 | Gee | 6,531,118 | B1 | 3/2003 | Gonzalez et al. |
| 6,090,772 | A | 7/2000 | Kaiser et al. | 6,534,455 | B1 | 3/2003 | Maurin et al. |
| 6,093,408 | A | 7/2000 | Hasenoehrl et al. | 6,536,629 | B2 | 3/2003 | van der Heijden |
| 6,096,756 | A | 8/2000 | Crain et al. | 6,544,530 | B1 | 4/2003 | Friedman |
| 6,110,477 | A | 8/2000 | Hernandez et al. | 6,544,562 | B1 | 4/2003 | Singh et al. |
| 6,110,966 | A | 8/2000 | Pollock | 6,547,063 | B1 | 4/2003 | Zaveri et al. |
| 6,113,888 | A | 9/2000 | Castro et al. | 6,548,074 | B1 | 4/2003 | Mohammadi |
| 6,116,466 | A | 9/2000 | Gueret et al. | 6,562,355 | B1 | 5/2003 | Renault |
| 6,121,210 | A | 9/2000 | Taylor | 6,566,350 | B2 | 5/2003 | Ono et al. |
| 6,126,920 | A | 10/2000 | Jones et al. | 6,582,679 | B2 | 6/2003 | Stein et al. |
| 6,140,355 | A | 10/2000 | Egidio et al. | 6,582,710 | B2 | 6/2003 | Deckers et al. |
| 6,146,645 | A | 11/2000 | Deckers et al. | 6,589,509 | B2 | 7/2003 | Keller et al. |
| 6,146,664 | A | 11/2000 | Siddiqui | 6,596,287 | B2 | 7/2003 | Deckers et al. |
| 6,162,834 | A | 12/2000 | Sebillotte-Arnaud et al. | 6,599,513 | B2 | 7/2003 | Deckers et al. |
| 6,165,455 | A | 12/2000 | Torgerson et al. | 6,620,773 | B1 | 9/2003 | Stork et al. |
| 6,168,576 | B1 | 1/2001 | Reynolds | 6,638,981 | B2 | 10/2003 | Williams et al. |
| 6,171,347 | B1 | 1/2001 | Kunz et al. | 6,649,571 | B1 | 11/2003 | Morgan |
| 6,180,669 | B1 | 1/2001 | Tamarkin | 6,649,574 | B2 | 11/2003 | Cardis et al. |
| 6,183,762 | B1 | 2/2001 | Deckers et al. | 6,672,483 | B2 | 1/2004 | Roy et al. |
| 6,186,367 | B1 | 2/2001 | Harrold | 6,682,726 | B2 | 1/2004 | Marchesi et al. |
| 6,187,290 | B1 | 2/2001 | Gilchrist et al. | 6,691,898 | B2 | 2/2004 | Hurray et al. |
| 6,189,810 | B1 | 2/2001 | Nerushai et al. | 6,709,663 | B2 | 3/2004 | Espinoza |
| 6,190,365 | B1 | 2/2001 | Abbott et al. | 6,723,309 | B1 | 4/2004 | Deane |
| 6,204,285 | B1 | 3/2001 | Fabiano et al. | 6,730,288 | B1 | 5/2004 | Abram |
| 6,210,656 | B1 | 4/2001 | Touzan et al. | 6,753,000 | B2 | 6/2004 | Breton et al. |
| 6,210,742 | B1 | 4/2001 | Deckers et al. | 6,753,167 | B2 | 6/2004 | Moloney et al. |
| 6,214,318 | B1 | 4/2001 | Osipow et al. | 6,762,158 | B2 | 7/2004 | Lukenbach et al. |
| 6,214,788 | B1 | 4/2001 | Velazco et al. | 6,765,001 | B2 | 7/2004 | Gans et al. |
| 6,221,381 | B1 | 4/2001 | Shelford et al. | 6,774,114 | B2 | 8/2004 | Castiel et al. |
| 6,221,823 | B1 | 4/2001 | Crisanti et al. | 6,777,591 | B1 | 8/2004 | Chaudhary et al. |
| 6,224,888 | B1 | 5/2001 | Vatter et al. | 6,790,435 | B1 | 9/2004 | Ma et al. |

| | | | | | |
|---|---|---|---|---|---|
| 6,796,973 B1 | 9/2004 | Contente et al. | 2003/0078172 A1 | 4/2003 | Guiramand et al. |
| RE38,623 E | 10/2004 | Hernandez et al. | 2003/0114520 A1 | 6/2003 | Pereira et al. |
| 6,811,767 B1 | 11/2004 | Bosch et al. | 2003/0118515 A1 | 6/2003 | Jew et al. |
| 6,834,778 B2 | 12/2004 | Jinbo et al. | 2003/0130247 A1 | 7/2003 | Gans et al. |
| 6,843,390 B1 | 1/2005 | Bristor | 2003/0175232 A1 | 9/2003 | Elliott et al. |
| 6,875,438 B2 | 4/2005 | Kraemer et al. | 2003/0175315 A1 | 9/2003 | Yoo et al. |
| 6,881,271 B2 | 4/2005 | Ochiai | 2003/0180347 A1 | 9/2003 | Young et al. |
| 6,890,567 B2 | 5/2005 | Nakatsu et al. | 2003/0185839 A1 | 10/2003 | Podolsky |
| 6,902,737 B2 | 6/2005 | Quemin et al. | 2003/0194379 A1 | 10/2003 | Brugger et al. |
| 6,911,211 B2 | 6/2005 | Eini et al. | 2003/0195128 A1 | 10/2003 | Deckman et al. |
| 6,946,120 B2 | 9/2005 | Wai-Chiu So et al. | 2003/0206955 A1 | 11/2003 | Sonneville-Aubrun et al. |
| 6,946,139 B2 | 9/2005 | Henning | 2003/0215472 A1 | 11/2003 | Bonda et al. |
| 6,951,654 B2 | 10/2005 | Malcolm et al. | 2004/0018228 A1 | 1/2004 | Fischell et al. |
| 6,955,816 B2 | 10/2005 | Klysz | 2004/0028752 A1 | 2/2004 | Kamm et al. |
| 6,956,062 B2 | 10/2005 | Beilfuss et al. | 2004/0038912 A1 | 2/2004 | Michelet et al. |
| 6,958,154 B2 | 10/2005 | Andolino Brandt et al. | 2004/0053797 A1 | 3/2004 | Chen et al. |
| 6,967,023 B1 | 11/2005 | Eini et al. | 2004/0058878 A1 | 3/2004 | Walker |
| 6,968,982 B1 | 11/2005 | Burns | 2004/0063787 A1 | 4/2004 | Villanueva |
| 6,969,521 B1 | 11/2005 | Gonzalez et al. | 2004/0067970 A1 | 4/2004 | Foster et al. |
| RE38,964 E | 1/2006 | Shillington | 2004/0072638 A1 | 4/2004 | Enos et al. |
| 6,994,863 B2 | 2/2006 | Eini et al. | 2004/0076651 A1 | 4/2004 | Brocks et al. |
| 7,002,486 B2 | 2/2006 | Lawrence | 2004/0078896 A1 | 4/2004 | Hellyer et al. |
| 7,014,844 B2 | 3/2006 | Mahalingam et al. | 2004/0079361 A1 | 4/2004 | Clayton et al. |
| 7,021,499 B2 | 4/2006 | Hansen et al. | 2004/0105825 A1 | 6/2004 | Henning |
| 7,029,659 B2 | 4/2006 | Abram et al. | 2004/0120917 A1 | 6/2004 | Perrier et al. |
| 7,060,253 B1 | 6/2006 | Mundschenk | 2004/0127554 A1 | 7/2004 | Ghisalberti |
| 7,078,058 B2 | 7/2006 | Jones et al. | 2004/0138179 A1 | 7/2004 | Goldstein et al. |
| 7,083,799 B1 | 8/2006 | Giacomoni | 2004/0151671 A1 | 8/2004 | Abram et al. |
| 7,137,536 B2 | 11/2006 | Walters et al. | 2004/0151756 A1 | 8/2004 | Richards et al. |
| 7,195,135 B1 | 3/2007 | Garcia et al. | 2004/0161447 A1 | 8/2004 | Paul |
| 7,222,802 B2 | 5/2007 | Sweeton | 2004/0184992 A1 | 9/2004 | Abram |
| 7,225,518 B2 | 6/2007 | Eidenschink et al. | 2004/0185123 A1 | 9/2004 | Mazzio et al. |
| 7,226,230 B2 | 6/2007 | Liberatore | 2004/0191196 A1 | 9/2004 | Tamarkin |
| 7,235,251 B2 | 6/2007 | Hamer et al. | 2004/0192754 A1 | 9/2004 | Shapira et al. |
| 7,270,828 B2 | 9/2007 | Masuda et al. | 2004/0195276 A1 | 10/2004 | Fuchs |
| 7,455,195 B2 | 11/2008 | Mekata | 2004/0197276 A1 | 10/2004 | Takase et al. |
| 7,497,354 B2 | 3/2009 | Decottignies et al. | 2004/0197295 A1 | 10/2004 | Riedel et al. |
| 7,575,739 B2 | 8/2009 | Tamarkin et al. | 2004/0219122 A1 | 11/2004 | Masuda et al. |
| 7,645,803 B2 | 1/2010 | Tamarkin et al. | 2004/0219176 A1 | 11/2004 | Dominguez |
| 7,654,415 B2 | 2/2010 | van der Heijden | 2004/0220187 A1 | 11/2004 | Stephenson et al. |
| 7,682,623 B2 | 3/2010 | Eini et al. | 2004/0229813 A1 | 11/2004 | DiPiano et al. |
| 7,700,076 B2 | 4/2010 | Tamarkin et al. | 2004/0234475 A1 | 11/2004 | Lannibois-Drean et al. |
| 7,704,518 B2 | 4/2010 | Tamarkin et al. | 2004/0241099 A1 | 12/2004 | Popp et al. |
| 7,820,145 B2 | 10/2010 | Tamarkin et al. | 2004/0247531 A1 | 12/2004 | Riedel et al. |
| 7,960,416 B2 | 6/2011 | Sato et al. | 2004/0253275 A1 | 12/2004 | Eini et al. |
| 2001/0006654 A1 | 7/2001 | Cannell et al. | 2004/0258627 A1 | 12/2004 | Riedel et al. |
| 2001/0027218 A1 | 10/2001 | Stern et al. | 2004/0265240 A1 | 12/2004 | Tamarkin et al. |
| 2001/0027981 A1 | 10/2001 | Yquel | 2005/0002976 A1 | 1/2005 | Wu |
| 2001/0036450 A1 | 11/2001 | Verite et al. | 2005/0013853 A1 | 1/2005 | Gil-Ad et al. |
| 2002/0002151 A1 | 1/2002 | Ono et al. | 2005/0031547 A1 | 2/2005 | Tamarkin et al. |
| 2002/0004063 A1 | 1/2002 | Zhang | 2005/0042182 A1 | 2/2005 | Arkin |
| 2002/0013481 A1 | 1/2002 | Schonrock et al. | 2005/0054991 A1 | 3/2005 | Tobyn et al. |
| 2002/0015721 A1 | 2/2002 | Simonnet et al. | 2005/0069566 A1 | 3/2005 | Tamarkin et al. |
| 2002/0032171 A1 | 3/2002 | Chen et al. | 2005/0074414 A1 | 4/2005 | Tamarkin et al. |
| 2002/0035046 A1 | 3/2002 | Lukenbach et al. | 2005/0075407 A1 | 4/2005 | Tamarkin et al. |
| 2002/0035070 A1 | 3/2002 | Gardlik et al. | 2005/0079139 A1 | 4/2005 | Jacques et al. |
| 2002/0035087 A1 | 3/2002 | Barclay | 2005/0084551 A1 | 4/2005 | Jensen et al. |
| 2002/0035182 A1 | 3/2002 | L'Alloret et al. | 2005/0085843 A1 | 4/2005 | Opolski et al. |
| 2002/0039591 A1 | 4/2002 | Dahle | 2005/0101936 A1 | 5/2005 | Gonzales et al. |
| 2002/0045659 A1 | 4/2002 | Michelet et al. | 2005/0106197 A1 | 5/2005 | Blin et al. |
| 2002/0048798 A1 | 4/2002 | Avery et al. | 2005/0123494 A1 | 6/2005 | Swaile et al. |
| 2002/0058010 A1 | 5/2002 | Picard-Lesboueyries et al. | 2005/0123496 A1 | 6/2005 | Shah et al. |
| 2002/0072544 A1 | 6/2002 | Miller et al. | 2005/0186142 A1 | 8/2005 | Tamarkin et al. |
| 2002/0090386 A1 | 7/2002 | Haslwanter et al. | 2005/0186147 A1 | 8/2005 | Tamarkin et al. |
| 2002/0098215 A1 | 7/2002 | Douin et al. | 2005/0189377 A1 | 9/2005 | Lanzendorfer et al. |
| 2002/0111281 A1 | 8/2002 | Vishnupad | 2005/0196414 A1 | 9/2005 | Dake et al. |
| 2002/0117516 A1 | 8/2002 | Lasserre et al. | 2005/0205086 A1 | 9/2005 | Tamarkin et al. |
| 2002/0134376 A1 | 9/2002 | Castro et al. | 2005/0207837 A1 | 9/2005 | Kosh et al. |
| 2002/0136755 A1 | 9/2002 | Tyrrell et al. | 2005/0222090 A1 | 10/2005 | Cheng et al. |
| 2002/0143188 A1 | 10/2002 | Garvey et al. | 2005/0232869 A1 | 10/2005 | Tamarkin et al. |
| 2002/0153390 A1 | 10/2002 | Vlodek | 2005/0244342 A1 | 11/2005 | Friedman et al. |
| 2002/0165170 A1 | 11/2002 | Wilson et al. | 2005/0244354 A1 | 11/2005 | Speron |
| 2002/0182162 A1 | 12/2002 | Shahinpoor et al. | 2005/0245902 A1 | 11/2005 | Cornish et al. |
| 2002/0187181 A1 | 12/2002 | Godbey et al. | 2005/0252995 A1 | 11/2005 | Westphal et al. |
| 2002/0198136 A1 | 12/2002 | Mak et al. | 2005/0255048 A1 | 11/2005 | Hirsh et al. |
| 2003/0006193 A1 | 1/2003 | Ikeda et al. | 2005/0258189 A1 | 11/2005 | Peterson et al. |
| 2003/0031693 A1 | 2/2003 | Breton et al. | 2005/0266035 A1 | 12/2005 | Healy et al. |
| 2003/0053961 A1 | 3/2003 | Eccard | 2005/0268416 A1 | 12/2005 | Sommers |
| 2003/0077297 A1 | 4/2003 | Chen et al. | 2005/0271596 A1 | 12/2005 | Friedman et al. |

| | | | | | | |
|---|---|---|---|---|---|---|
| 2005/0271598 | A1 | 12/2005 | Friedman et al. | 2008/0153789 A1 | 6/2008 | Dmowski et al. |
| 2005/0276836 | A1 | 12/2005 | Wilson et al. | 2008/0166303 A1 | 7/2008 | Tamarkin et al. |
| 2005/0281755 | A1 | 12/2005 | Zarif et al. | 2008/0167376 A1 | 7/2008 | Bar-Or et al. |
| 2005/0281766 | A1 | 12/2005 | Martin et al. | 2008/0181854 A1 | 7/2008 | Eini et al. |
| 2005/0285912 | A1 | 12/2005 | Delametter et al. | 2008/0188445 A1 | 8/2008 | Muldoon et al. |
| 2005/0287081 | A1 | 12/2005 | Aust et al. | 2008/0188446 A1 | 8/2008 | Muldoon et al. |
| 2006/0008432 | A1 | 1/2006 | Scarampi et al. | 2008/0193762 A1 | 8/2008 | Dubertret et al. |
| 2006/0018937 | A1 | 1/2006 | Friedman et al. | 2008/0206155 A1 | 8/2008 | Tamarkin et al. |
| 2006/0018938 | A1 | 1/2006 | Neubourg | 2008/0206159 A1 | 8/2008 | Tamarkin et al. |
| 2006/0029565 | A1 | 2/2006 | Xu et al. | 2008/0206161 A1 | 8/2008 | Tamarkin et al. |
| 2006/0051301 | A1 | 3/2006 | Galopin et al. | 2008/0241079 A1 | 10/2008 | Neubourg |
| 2006/0054634 | A1 | 3/2006 | Mekata | 2008/0253973 A1 | 10/2008 | Tamarkin et al. |
| 2006/0057168 | A1 | 3/2006 | Larm | 2008/0255498 A1 | 10/2008 | Houle |
| 2006/0088561 | A1 | 4/2006 | Eini et al. | 2008/0260655 A1 | 10/2008 | Tamarkin et al. |
| 2006/0099151 | A1 | 5/2006 | Neubourg | 2008/0292560 A1 | 11/2008 | Tamarkin et al. |
| 2006/0108377 | A1 | 5/2006 | Glynn et al. | 2008/0299220 A1 | 12/2008 | Tamarkin et al. |
| 2006/0110418 | A1 | 5/2006 | Johnson | 2008/0311167 A1 | 12/2008 | Oronsky et al. |
| 2006/0114745 | A1 | 6/2006 | Ollmann et al. | 2008/0317679 A1 | 12/2008 | Tamarkin et al. |
| 2006/0121073 | A1 | 6/2006 | Goyal et al. | 2009/0041680 A1 | 2/2009 | Tamarkin et al. |
| 2006/0140984 | A1 | 6/2006 | Tamarkin et al. | 2009/0068118 A1 | 3/2009 | Eini et al. |
| 2006/0140990 | A1 | 6/2006 | Bortz et al. | 2009/0093514 A1 | 4/2009 | Statham et al. |
| 2006/0160713 | A1 | 7/2006 | Sekine et al. | 2009/0130029 A1 | 5/2009 | Tamarkin et al. |
| 2006/0165616 | A1 | 7/2006 | Brock et al. | 2009/0131488 A1 | 5/2009 | Harel et al. |
| 2006/0177392 | A1 | 8/2006 | Walden | 2009/0175799 A1 | 7/2009 | Tamarkin et al. |
| 2006/0193789 | A1 | 8/2006 | Tamarkin et al. | 2009/0180970 A1 | 7/2009 | Tamarkin et al. |
| 2006/0193813 | A1 | 8/2006 | Simonnet | 2009/0291917 A1 | 11/2009 | Akama et al. |
| 2006/0204446 | A1 | 9/2006 | Lulla et al. | 2009/0317338 A1 | 12/2009 | Tamarkin et al. |
| 2006/0222675 | A1 | 10/2006 | Sabnis et al. | 2010/0111879 A1 | 5/2010 | Tamarkin et al. |
| 2006/0233721 | A1 | 10/2006 | Tamarkin et al. | 2010/0221194 A1 | 9/2010 | Loupenok |
| 2006/0239937 | A2 | 10/2006 | Neubourg | 2011/0002857 A1 | 1/2011 | Tamarkin et al. |
| 2006/0251684 | A1 | 11/2006 | Annis et al. | 2011/0002969 A1 | 1/2011 | Serraima et al. |
| 2006/0254597 | A1 | 11/2006 | Thompson | 2011/0212033 A1 | 9/2011 | Tamarkin et al. |
| 2006/0263323 | A1 | 11/2006 | Hoang et al. | 2011/0268665 A1 | 11/2011 | Tamarkin et al. |
| 2006/0269485 | A1 | 11/2006 | Friedman et al. | | | |
| 2006/0272199 | A1 | 12/2006 | Licciardello | | | |

FOREIGN PATENT DOCUMENTS

| | | |
|---|---|---|
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0156507 A1 | 10/1985 |
| EP | 0 186 453 | 7/1986 |
| EP | 0186453 | 7/1986 |
| EP | 211550 | 2/1987 |
| EP | 0214865 A2 | 3/1987 |
| EP | 0 216 856 | 4/1987 |
| EP | 0270316 | 6/1988 |
| EP | 297436 | 1/1989 |
| EP | 0 326 196 | 8/1989 |
| EP | 0 336 812 | 10/1989 |
| EP | 0 391 124 | 10/1990 |
| EP | 0404376 | 12/1990 |
| EP | 414920 | 3/1991 |
| EP | 0 485 299 | 5/1992 |
| EP | 0484530 A1 | 5/1992 |
| EP | 0488089 A1 | 6/1992 |
| EP | 0 504 301 | 9/1992 |
| EP | 0 528 190 | 2/1993 |
| EP | 0535327 | 4/1993 |
| EP | 0 552 612 | 7/1993 |
| EP | 0569773 A2 | 11/1993 |
| EP | 0598412 | 11/1993 |
| EP | 0 662 431 | 7/1995 |
| EP | 0676198 | 10/1995 |
| EP | 0738516 | 10/1996 |
| EP | 0 757 959 | 2/1997 |
| EP | 0824911 | 2/1998 |
| EP | 0 829 259 | 3/1998 |
| EP | 0 928 608 | 7/1999 |
| EP | 0979654 A1 | 2/2000 |
| EP | 0993827 A1 | 4/2000 |
| EP | 1 025 836 | 8/2000 |
| EP | 1055425 A2 | 11/2000 |
| EP | 0 506 197 | 7/2001 |
| EP | 1215258 | 6/2002 |
| EP | 1287813 | 3/2003 |

(continued listings for 2006/0275218 through 2008/0152596 with Tamarkin et al., Eini et al., Abram et al., Jones, Lin et al., Tamarkin, Koivisto et al., Baker, Popp et al., Eini et al., Illel et al., Neubourg, Irwin et al., Puglia et al., Stahl et al., Dingley et al., Amiji et al., Trumbore et al., Riccardi et al., Abram et al., Tamarkin et al., Yosha et al., Frank et al., Tamarkin et al., Fox et al., Tamarkin et al., Friedman et al., Tamarkin et al., Kisilev, Bolotin et al., Abram et al., Tamarkin et al., Aubrun-Sonneville et al., Dahl, Tamarkin et al., LeMay et al., Cashman et al., Tamarkin et al., Keller et al., Tamarkin et al., Tamarkin et al., Friedman et al.)

| | | | | | | |
|---|---|---|---|---|---|---|
| EP | 1 308 169 | 5/2003 | | JP | 6100414 | 4/1994 |
| EP | 1 375 386 | 1/2004 | | JP | 06-263630 | 6/1994 |
| EP | 1428521 | 6/2004 | | JP | 6329532 | 11/1994 |
| EP | 1438946 | 7/2004 | | JP | 2007/155667 | 6/1995 |
| EP | 1189579 | 9/2004 | | JP | 7215835 | 8/1995 |
| EP | 1475381 | 11/2004 | | JP | 8501529 | 2/1996 |
| EP | 1 483 001 | 12/2004 | | JP | 2008040899 | 2/1996 |
| EP | 1500385 | 1/2005 | | JP | 8119831 | 5/1996 |
| EP | 1 537 916 | 6/2005 | | JP | 8165218 | 6/1996 |
| EP | 1 600 185 | 11/2005 | | JP | 8277209 | 10/1996 |
| EP | 1 670 698 | 6/2006 | | JP | 09 084855 | 3/1997 |
| EP | 1 734 927 | 12/2006 | | JP | 9099553 | 4/1997 |
| EP | 1 758 547 | 3/2007 | | JP | 9110636 | 4/1997 |
| EP | 1584324 | 11/2007 | | JP | 10114619 | 5/1998 |
| EP | 1 889 609 | 2/2008 | | JP | 3050289 | 9/1998 |
| FR | 2 591 331 | 6/1987 | | JP | 2010/332456 | 12/1998 |
| FR | 2 640 942 | 6/1990 | | JP | 11501045 | 1/1999 |
| FR | 2 736 824 | 1/1997 | | JP | 11250543 | 9/1999 |
| FR | 2774595 A | 8/1999 | | JP | 2000/017174 | 1/2000 |
| FR | 2 789 371 | 8/2000 | | JP | 2000080017 | 3/2000 |
| FR | 2 793 479 | 11/2000 | | JP | 2000128734 | 5/2000 |
| FR | 2 814 959 | 4/2002 | | JP | 2000191429 | 7/2000 |
| FR | 2 833 246 | 6/2003 | | JP | 2000/239140 | 9/2000 |
| FR | 2 840 903 | 12/2003 | | JP | 2000/354623 | 12/2000 |
| FR | 2 843 373 | 2/2004 | | JP | 2000351726 | 12/2000 |
| FR | 2 845 672 | 4/2004 | | JP | 2001/002526 | 1/2001 |
| FR | 2 848 998 | 6/2004 | | JP | 2001019606 | 1/2001 |
| FR | 2 860 976 | 4/2005 | | JP | 2001072963 | 3/2001 |
| FR | 2915891 | 11/2008 | | JP | 2002012513 | 1/2002 |
| GB | 808104 | 1/1959 | | JP | 2002/047136 | 2/2002 |
| GB | 808105 | 1/1959 | | JP | 2002047136 | 2/2002 |
| GB | 922930 | 4/1963 | | JP | 2002/524490 | 8/2002 |
| GB | 933486 | 8/1963 | | JP | 2002/302419 | 10/2002 |
| GB | 998 490 | 7/1965 | | JP | 2003/012511 | 1/2003 |
| GB | 1026831 | 4/1966 | | JP | 2003055146 | 2/2003 |
| GB | 1 033 299 | 6/1966 | | JP | 2004/250435 | 9/2004 |
| GB | 1 081 949 | 9/1967 | | JP | 2004/348277 | 12/2004 |
| GB | 1121358 | 7/1968 | | JP | 2005/314323 | 11/2005 |
| GB | 1 162 684 | 8/1969 | | JP | 2005350378 | 12/2005 |
| GB | 1 170 152 | 11/1969 | | JP | 2006008574 | 1/2006 |
| GB | 1 201 918 | 8/1970 | | JP | 2006/036317 | 2/2006 |
| GB | 1 347 950 | 2/1974 | | JP | 2006/103799 | 4/2006 |
| GB | 1 351 761 | 5/1974 | | JP | 2006525145 | 11/2006 |
| GB | 1 351 762 | 5/1974 | | JP | 2007131539 | 5/2007 |
| GB | 1 353 381 | 5/1974 | | JP | 4892282 | 3/2012 |
| GB | 1 376 649 | 12/1974 | | KR | 143232 | 7/1998 |
| GB | 1397285 | 6/1975 | | KR | 2001/003063 | 1/2001 |
| GB | 1 408 036 | 10/1975 | | RU | 2277501 | 6/2006 |
| GB | 1 457 671 | 12/1976 | | UA | 66796 | 6/2004 |
| GB | 1 489 672 | 10/1977 | | WO | 82/01821 | 6/1982 |
| GB | 2 004 746 | 4/1979 | | WO | WO-86/05389 | 9/1986 |
| GB | 1 561 423 | 2/1980 | | WO | 88/01502 | 3/1988 |
| GB | 2114580 | 8/1983 | | WO | WO-88/01863 | 3/1988 |
| GB | 2 153 686 | 8/1985 | | WO | 88/08316 | 11/1988 |
| GB | 2 172 298 | 9/1986 | | WO | WO-89/06537 | 7/1989 |
| GB | 2 206 099 | 12/1988 | | WO | WO-90/05774 | 5/1990 |
| GB | 2166651 | 5/1996 | | WO | WO 91/11991 | * 8/1991 |
| GB | 2337461 | 11/1999 | | WO | WO-92/00077 | 1/1992 |
| GB | 2 367 809 | 4/2002 | | WO | 92/05142 | 4/1992 |
| GB | 2 406 330 | 3/2005 | | WO | 92/05763 | 4/1992 |
| GB | 2 406 791 | 4/2005 | | WO | WO-92/11839 | 7/1992 |
| IL | 49491 | 9/1979 | | WO | 93/25189 | 12/1993 |
| IL | 0152486 | 5/2003 | | WO | 94/06440 | 3/1994 |
| JP | 60001113 | 4/1978 | | WO | WO-96/03115 | 2/1996 |
| JP | 55069682 | 5/1980 | | WO | WO-96/19921 | 7/1996 |
| JP | 57044429 | 3/1982 | | WO | 96/24325 | 8/1996 |
| JP | 56039815 | 4/1984 | | WO | 96/26711 | 9/1996 |
| JP | 61275395 | 12/1986 | | WO | WO-96/27376 | 9/1996 |
| JP | 62241701 | 10/1987 | | WO | WO-96/39119 | 12/1996 |
| JP | 6357511 | 3/1988 | | WO | 97/03638 | 2/1997 |
| JP | 63119420 | 5/1988 | | WO | WO-97/39745 | 10/1997 |
| JP | 01100111 | 4/1989 | | WO | 98/017282 | 4/1998 |
| JP | 01156906 | 6/1989 | | WO | WO-98/18472 | 5/1998 |
| JP | 2184614 | 7/1990 | | WO | WO-98/19654 | 5/1998 |
| JP | 2255890 | 10/1990 | | WO | WO-98/21955 | 5/1998 |
| JP | 04282311 | 10/1992 | | WO | WO-98/23291 | 6/1998 |
| JP | 4312521 | 11/1992 | | WO | WO-98/36733 | 8/1998 |
| JP | 5070340 | 3/1993 | | WO | 98/52536 | 11/1998 |
| JP | 5213734 | 8/1993 | | WO | WO-99/08649 | 2/1999 |

| | | |
|---|---|---|
| WO | WO-99/20250 | 4/1999 |
| WO | WO-99/37282 | 7/1999 |
| WO | 99/53923 | 10/1999 |
| WO | WO-00/09082 | 2/2000 |
| WO | WO-00/15193 | 3/2000 |
| WO | 00/23051 | 4/2000 |
| WO | 00/33825 | 6/2000 |
| WO | 00/38731 | 7/2000 |
| WO | WO-00/61076 | 10/2000 |
| WO | WO-00/76461 | 12/2000 |
| WO | 01/05366 | 1/2001 |
| WO | 01/10961 | 2/2001 |
| WO | WO-01/08681 | 2/2001 |
| WO | 01/53198 | 7/2001 |
| WO | 01/54212 | 7/2001 |
| WO | 01/62209 | 8/2001 |
| WO | WO-01/54679 | 8/2001 |
| WO | WO-01/70242 A2 | 9/2001 |
| WO | 01/82890 | 11/2001 |
| WO | 01/85102 | 11/2001 |
| WO | 01/85128 | 11/2001 |
| WO | WO-01/82880 | 11/2001 |
| WO | 01/95728 | 12/2001 |
| WO | WO-02/00820 | 1/2002 |
| WO | 02/15860 | 2/2002 |
| WO | 02/15873 | 2/2002 |
| WO | WO-02/28435 | 4/2002 |
| WO | WO-02/41847 A1 | 5/2002 |
| WO | WO-02/43490 | 6/2002 |
| WO | WO-02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | WO-03/051294 | 6/2003 |
| WO | 03/055454 | 7/2003 |
| WO | WO-03/053292 | 7/2003 |
| WO | WO-03/055445 | 7/2003 |
| WO | 03/070301 | 8/2003 |
| WO | 03/071995 | 9/2003 |
| WO | WO-03/075851 | 9/2003 |
| WO | 03/097002 | 11/2003 |
| WO | WO-03/092641 | 11/2003 |
| WO | 2004/017962 | 3/2004 |
| WO | 2004/037197 | 5/2004 |
| WO | WO-2004/037225 | 5/2004 |
| WO | 2004/003284 | 8/2004 |
| WO | 2004/064769 | 8/2004 |
| WO | WO-2004/064833 | 8/2004 |
| WO | WO-2004/071479 A1 | 8/2004 |
| WO | 2004/078158 | 9/2004 |
| WO | WO-2004/078896 | 9/2004 |
| WO | 2004/093895 | 11/2004 |
| WO | WO-2004/112780 | 12/2004 |
| WO | WO-2005/011567 A2 | 2/2005 |
| WO | WO-2005/018530 | 3/2005 |
| WO | WO-2005/018530 A2 | 3/2005 |
| WO | WO-2005/032522 | 4/2005 |
| WO | WO-2005/044219 | 5/2005 |
| WO | 2005/063224 | 7/2005 |
| WO | WO-2005/065652 | 7/2005 |
| WO | WO-2005/076697 | 8/2005 |
| WO | WO-2005/097068 | 10/2005 |
| WO | 2005/102282 | 11/2005 |
| WO | WO-2005/102539 A | 11/2005 |
| WO | WO-2005/117813 | 12/2005 |
| WO | WO-2006/003481 A2 | 1/2006 |
| WO | 2006/011046 | 2/2006 |
| WO | 2006/020682 | 2/2006 |
| WO | WO-2006/010589 | 2/2006 |
| WO | 2006/028339 | 3/2006 |
| WO | WO-2006/031271 | 3/2006 |
| WO | 2006/045170 | 5/2006 |
| WO | 2006/079632 | 8/2006 |
| WO | 2006/081327 | 8/2006 |
| WO | WO-2006/091229 | 8/2006 |
| WO | WO-2006/100485 | 9/2006 |
| WO | 2006/121610 | 11/2006 |
| WO | 2006/122158 | 11/2006 |
| WO | WO-2006/120682 | 11/2006 |
| WO | WO-2006/129161 | 12/2006 |
| WO | WO-2006/131784 | 12/2006 |
| WO | WO-2007/007208 | 1/2007 |
| WO | WO-2007/012977 | 2/2007 |
| WO | WO-2007/023396 | 3/2007 |
| WO | WO-2007/031621 A2 | 3/2007 |
| WO | WO-2007/039825 | 4/2007 |
| WO | WO-2007/050543 | 5/2007 |
| WO | WO-2007/054818 | 5/2007 |
| WO | WO-2007/072216 | 6/2007 |
| WO | WO-2007/085899 | 8/2007 |
| WO | WO-2007/085902 | 8/2007 |
| WO | WO-2007/099396 | 9/2007 |
| WO | 2007/111962 | 10/2007 |
| WO | 2008/010963 | 1/2008 |
| WO | WO-2008/008397 | 1/2008 |
| WO | 2008/041045 | 4/2008 |
| WO | WO-2008/038147 | 4/2008 |
| WO | WO-2008/075207 | 6/2008 |
| WO | WO-2008/087148 | 7/2008 |
| WO | WO-2008/110872 A2 | 9/2008 |
| WO | 2008/152444 | 12/2008 |
| WO | WO-2009/007785 A2 | 1/2009 |
| WO | WO-2009/069006 A2 | 6/2009 |
| WO | WO-2009/072007 A2 | 6/2009 |
| WO | WO-2009/087578 A2 | 7/2009 |
| WO | WO-2009/090495 A2 | 7/2009 |
| WO | WO-2009/090558 A2 | 7/2009 |
| WO | WO 2009090558 | 7/2009 |
| WO | WO-2009/098595 A2 | 8/2009 |
| WO | 2011/039637 | 4/2011 |
| WO | 2011/039638 | 4/2011 |

OTHER PUBLICATIONS

Benet, et al., Application of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance Technique," Journal of Investigative Dermatology, vol. 91, No. 1, Jul. 1988, pp. 29-33.
Carbowax 1000MSDS; http://www.sciencelab.com/xMSDS-Polyethylene_glycol_1000-9926622. Accessed Dec. 13, 2008, 6 pages.
Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Denatonium Benzoate http://www.newdruginfo.com/pharmaceopeia/usp28/v28230/usp28nf23s0_m22790.htm Accessed Dec. 9, 2008, 2 pages.
disorder. (2007). In the American Heritage Dictionary of the English Language. Retrieved from http://www.credoreference.com/entry/hmdictenglang/disorder.
Edirisinghe, et al., "Effect of fatty acids on endothelium-dependent relaxation in the rabbit aorta", Clin Sci (Lond). Aug. 2006; 111(2): 145-51.
Emulsifiers with HLB values. http://www.theherbarie.com/files/resources-center/formulating/Emulsifiers_HLB_Values.pdf accessed Aug. 5, 2009 (3 pps).
Encyclopedia of Pharmaceutical Technology, Second Edition, vol. 3, Copyright 2002.
Ethanol, Accessed http://www.sigmaaldrich.com/catalog/ProductDetail.do?N4=E7023SIAL&N5=SEARCH_CONCAT_PNOBRAND_KEY&F=SPEC Dec. 9, 2008, 2 pages.
European Patent Application No. 06831721, Official Action, Feb. 3, 2009, 9 pages.
Flick, Cosmetic and Toiletry Formulations, vol. 5, 2nd Edition, Copyright 1996.

Fontana, Anthony, J., "Water Activity: Why It Is Important for Food Safety," International Conference on Food Safety, Nov. 16-18, 1998, 9 pages.

Galligan, John et al., "Adhesive Polyurethane Liners for Anterior Restorations," J. Dent. Res., Jul.-Aug. 1968, pp. 629-632.

Gill, A.M, et al., "Adverse Drug Reactions in a Paediatric Intensitve Care Unit," Acta Paediatr 84:438-441, 1995.

Glaser, et al., Hyperhidrosis: A Comprehensive and Practical Approach to Patient Management, Expert Rev. Dermatol. 1(6), 773-775 (2006).

Gschnait, F., et al., "Topical Indomethacin Protects from UVB and UVA Irradiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, No. 2, pp. 155-161.

Hall, Karla, "Diaper Area Hemanglomas: A Unique Set of Concerns," http://members.tripod.com/~Michelle_G/diaper.html, Dec. 1, 2008, 8 pages.

Hashim, et al. "Tinea versicolor and visceral leishmaniasis," Int J Dermatol., Apr. 1994; 33(4), pp. 258-259 (abstract only).

Heart Failure, The Merck Manual, 2008 <<http://www.merck.com/mmhe/sec03/ch025a.html>>.

Hepburn, NC., "Cutaneous leishmaniasis," Clin Exp Dermatol, Jul. 2000; 25(5), pp. 363-70 (abstract only).

Hill, Randall M. (Ed.) Silicone Surfactants, Table of Contents and Chapter 7, "Silicone Surfactants: Applicants in the Personal Care Industry," by David T. Floyd, 1999 (30 pages).

http://ibabydoc.com/online/diseaseeczema.asp., Atopic Dermatitis, Copyright 2000.

http://web.archive.org/web/20000106225413/http://pharmacy.wilkes.edu/kibbeweb/lab7.html, Characteristics of Surfactants and Emulsions, Jan. 29, 2010, 5 pages.

http://www.agworkshop.com/p3.asp, AG&Co. Essential oil workshop.

International Search Report and Written Opinion, International Application No. PCT/IB2006/003628, Foamix Ltd., Dec. 7, 2007, 15 pages.

International Search Report and Written Opinion, International Application No. PCT/US2007/004459, Foamix Ltd., Dec. 9, 2008, 2 pages.

International Search Report for International Application No. PCT/IB2006/003974, Feb. 25, 2008 (7 pages).

International Search Report, International Patent Application No. PCT/IB2007/003463, Foamix, Ltd., Jul. 18, 2008, 6 pages.

International Search Report, International Patent Application No. PCT/IB2007/003759, Foamix Ltd., Jul. 8, 2008 (7 pages).

Kalkan, et al., The Measurement of Sweat Intensity Using a New Technique, Tr. J. of Medical Sciences 28, 515-517 (1998).

Kanamoto, et al., "Pharmacokinetics of two rectal dosage forms of ketoprofen in patients after anal surgery," J Pharmacobiodyn., Mar. 1988; 11(3):141-5.

Karasu, T.B. et al., "Treatment of Patients with Major Depressive Disorder, Second Edition," pp. 1-78, 2000.

Kathon ™CG (product information sheet by Rohm and Haas, Jun. 2006).

Kinnunen, Contact Dermatitis Sep. 1989; 21(3): 154-8, 2 pages.

Kleber, M.D., H.D. et al., "Treatment of Patients with Substance Use Disorders, Second Edition," pp. 1-276, 2006.

Koerber, S., "Humectants and Water Activity," Water Activity News, 2000, ISSN No. 1083-3943, 8 pages.

Kumar, J. et ak., "Application of Broad Spectrum Antiseptic Povidone Iodine as Powerful Action: A Review," Journal of Pharmaceutical Science and Technology vol. 1(2), 2009, 48-58.

Leung, et al., "Bioadhesive Drug Delivery in Water-Soluble Polymers," American Chemical Society, Chapter 23, 1991, pp. 350-366.

Licking Vaginal Dryness without a Prescription. Accessed http://www.estronaut.com/a/vag_dryness.htm on Dec. 14, 2008.

Machine Translation of JP-08165218 (1996).

Martindale, The extra pharmacopoeia [28th] edition, Eds.: Reynolds, J.E.F. and Prasad, A.B., The Pharmaceutical Press, London, pp. 862-864, 1982.

Material Safety Data Sheet, Progesterone, Apr. 26, 2006, 5 pages.

Material Safety Data Sheet, Science Lab.com, Polyethylene Glycol 1000, MSDS, Nov. 6, 2008, 6 pages.

Merriam-Webster Online Dictionaary, 2008, "Mousse," Merriam-Webster Online, Dec. 8, 2008 http://www.merriam-webster.com/dictionary/mousse, 2 pages.

Metronidazole. www.usp.org/pdf/EN/veterinary/metronidazole.pdf. accessed Sep. 10, 2009, 4 pages.

Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.

OM Cinnamate. http://www.makingcosmetics.com/sunscreens/OM-Cinnamate-p102.html accessed Sep. 26, 2009, 1 page.

Pendergrass, "The shape and dimensions of the human vagina as seen in three-dimensional vinyl polysiloxane casts," Gynecol Obstet. Invest. 1996:42(3):178-82 (abstract).

prevent. (2007). In the American Heritage Dictionary of the English Language. Retrieved from http://www.credoreference.com/entry/hmdictenglang/prevent.

Progesterone MSDS. http://www.usp.org.pdf.EN/referenceStandards/msds/1568007.pdf on Dec. 14, 2002, 5 pages.

Psoriasis. http://www.quickcare.org/skin/causes-of-psoriasis.html. Accessed Sep. 9, 2010.

Raymond, Iodine as an Aerial Disinfectant, Journal of Hygiene, vol. 44, No. 5 (May, 1946), pp. 359-361.

Rosacea. http://clinuvel.com/skin-conditions/common-skin-conditions/rosacea#h0-6- prevention. Accessed Sep. 9, 2010.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-4 (abstract).

Schutze, M.D., Harry "Iodine and Sodium Hypochlorite as Wound Disinfectants," The British Medical Journal, pp. 921-922, 1915.

Scott as Published in Pharmaceutical Dosage Forms; Disperse Systems, vol. 3, Copyright 1998.

Seborrheic Dermatitis. http://www.cumc.columbia.edu/student/health/pdf/R-S/Seborrhea%20Dermatitis.pdf. Access Sep. 9, 2010.

Shear, et al., "Pharmacoeconomic analysis of topical treatments for tinea infections," Pharmacoeconomics. Mar. 1995; 7(3); pp. 251-267 (abstract only).

Sigma Aldrich, "HLB-Numbers In Lithography Nanopatterning," http://www.sigmaaldrich.com/materials-science/micro-and-nanoelectronics/lithography-nanopatterning/hlb-numbers.html, accessed: Feb. 2, 2009, pp. 1-3.

Skin Biology, CP Serum—Copper-Peptide Serum for Skin Regeneration and Reducing Wrinkles, Skin Biology, http;//web.archive.org/web/20030810230608/http://www.skinbio.com/cpserum.html, Dec. 1, 2008, 21 pages.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Tan et al., "Effect of Carbopol and Polyvinylpyrrolidone on the Mechanical, Rheological, and Release Properties of Bioadhesive Polyethylene Glycol Gels," AAPS PharmSciTech, 2000; 1 (3) article 24 (2000), 10 pages.

Tarumoto, et al., Studies on toxicity of hydrocortisone 17-butyrate 21-propionate-1. Accute toxicity of hydrocortisone 17-butyrate 21-propionate and its analogues in mice, rats and dogs (authors trans), J Toxicol Sci., Jul. 1981; 6 Suppl: 1-16.

Torres-Rodriguez, JM., "New topical antifungal drugs," Arch Med Res. 1993 Winter; 24(4), pp. 371-375 (abstract).

Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008.

Wormser et al., Early and topical treatment with povidone-iodine ointment reduces, and sometimes prevents, skin damage following heat stimulus, Letters to the Editor, Burns, 1998, 24, 383.

Wormser et al., Protective effect of povidone-iodine ointment against skin lesions induced by sulphur and nitrogen mustards and by non-mustard vesicants, Arch. Toxicol., 1997, 71, 165-170.

U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.
"Minocycline" accessed on Ocotober 21, 2011 at en.wikipedia.org/wiki/Minocycline, 7 pages.
"Reaction Rate" Accessed at en.wikipedia.org/wiki/Reactionrate on Dec. 18, 2011, 6 pages.
'Niram Chemicals' [online] Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Anton, N. et al. "Water-in-Oil Nano-Emulsion Formation by the phase inversion Temperature Method: A Novel and General Concept, a New Template for Nanoencapsulation," *Proceedings of The 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology*, 1978, 1:33-36.
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blute, "Phase behavior of alkyl glycerol ether surfacants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)—Abstrace, 1 page.
Bronopol. Revtrieved online on Jun. 4, 2011. <URL:http://chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).
Burton, et al., "Hypertrichosis Due to Minoxidil", British Journal of Dermatology, 101:593-595 (1979).
Campos, et al., "Ascorbic Acid and Its Derivatives in Cosmetic Formulations", Cosmetics and Toiletries, 115(6):59-62 (2000)—Abstract, 1 page.
Carelli, et al., "Effect of Vehicles on Yohimbine Permeation Across Excised Hairless Mouse Skin", Pharm Acta Helv, 73(3):127-134 (1998)—Abstract, 1 page.
Chebil, et al., "Soulbility of Flavonoids in Organic Solvents", J. Chem. Eng. Data, 52(5):1552-1556 (2007)—Abstract, 1 page.
Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.
Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (Nov.), p. S475 (1997), 2 pages.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.
Croda. Aracel 165 Product Summary. 2011 (no month given). 1 page.
Dawber, et al., "Hypertrichosis in Females Applying Minoxidil Topical Solution and in Normal Controls", JEADV, 17:271-275 (2003).
Dentinger, et al., "Stability of Nifedipine in an Extemporaneously Compounded Oral Solution", American Journal of Health-System Pharmacy, 60(10):1019-1022 (2003)—Abstract, 1 page.
Draelos, Z. D. "Antiperspirants and the Hyperhidrosis Patients." Dermatologic Therapy. 2001. vol. 14. pp. 220-224.
Edens, et al., "Storage Stability and Safey of Active Vitamin C in a New Dual-Chamber Dispenser", Journal of Applied Cosmetology, 17(4):136-143 (1999)—Abstract, 1 page.
Edwards, "Imiquimod in Clinical Practice", J. Am Acad Dermatol., 43(1, Pt 2):512-517 (2000)—Abstract, 1 page.
Esposito, E. et al. "Nanosystems for Skin Hydration: A Comparative Study." International Journal of Cosmetic Science. 29. 2007. pp. 39-47.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., Dec. 16, 2008, 24 pages.
Gallarate, et al., "On the Stability of Ascorbic Acid in Emulsified Systems for Topical and Cosmetic Use", International Journal of Pharmaceutics, 188:233-241 (1999).
Gelbard et al. "Primary Pediatric Hyperhidrosis: A Review of Current Treatment Options." Pediatric Dermatology. 2008. 25 (6). pp. 591-598.
Gladkikh, "Ascorbic Acid and Methods of Increasing its Stability in Drugs", Translated from Khimiko-Farmatsevticheskii Zhurnal, 4(12):37-42 (1970)—1 page.
Graves, S. et al. "Structure of Concentrated Nanoemulsions." the Journal of Chemical Physics. 122 America Institute of Physics. Published Apr. 1, 2005. 6 pages.
Groveman, et al., "Lack of Efficacy of Polysorbate 60 in the Treatment of Male Pattern Baldness", Arch Intern Med, 145:1454-1458 (1985).
Hallstar. Retrieved online on Jun. 4, 2011. <URL:http://www.hallstar.com/pis.php?product=1H022>. 1 page.
Hargreaves, "Chemical Formulation, An Overview of Surfactant-Based Preparations Used in Everyday Life", *The Royal Society of Chemistry*, pp. 114-115 (2003).
Harrison, et al., "Effects of cytokines and R-837, a cytokine inducer, on UV-irradiation augmented recurrent genital herpes in guinea pigs", Antivial Res., 15(4):315-323 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of Hsv-Specific T-Cell Memory by Imiquimod in Guinea Pigs", Antimicrobial Agents and Chemotherapy, 38(9):2059-2064 (1994).

Hormones. Http://www.greenwillowtree.com/Page.bok?file=libido.html. Jan 2001.

Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.

Hydroxyethylcellulose. Http://terpconnect.umd.edu/-choi/MSDS/Sigma-Aldrich/HYDROXYETHYL%20CELLULOSE, 5 pages, Jan. 14, 2004.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03.net/com/oxymatrine/down/1249534834.pdf>. Aug. 15, 2009. 3 pages.

Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

Izquierdo, P. et al. "Formation and Stability of Nano-Emulsions Prepared Using the Phase Inversion Temperature Method." University of Barcelona. Sep. 17, 2001. 1 page.

Jan. "Troubled Times: Detergent Foam." http://zetatalk.com/health/theall7c.htm. Accessed Feb. 9, 2012. 2 pages.

Joseph, "Understanding foams & foaming," University of Minnesota (1997), at http://www.aem.umn.edu/people/faculty/joseph/archive/docs/understandingfoams.pdf, pp. 1-8.

Kang,et al., "Enhancement of the Stability and Skin Penetration of Vitamin C by Polyphenol", Immune Netw., 4(4):250-254 (2004)—Abstract, 1 page.

Kim, "Stability of Minoxidil in Aqueous Solution", Yakhak Hoechi, 30(5):228-231 (1986)—Abstract, 1 page.

Kreuter, J. "Nanoparticles and microparticles for drug and vaccine delivery," J. Anat. (1996) 189, pp. 503-505.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." *J Am. Acad. Dermatol.* 45:487-498. Oct. 2001.

Lebwohl et al., "A randomized, double-blind, placebo-controlled study of clobestasol propionate 0.05% foam in the treatment of nonscalp psoriasis," *International Journal of Dermatology*, 2002, 41(5): 269-274.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Li, et al., "Solubility Behavior of Imiquimod in Alkanoic Acids", Abstract 3029, Pharmaceutical Research, vol. 14, No. 11 Supplemental (Nov.), p. S475 (1997), 2 pages.

Lippacher, A. et al. "Liquid and Semisolid SLN Dispersions for Topical Application" Rheological Characterization. European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Martindale. 33 ed. London, Bath Press, 2002. pp. 1073 and 1473.

Merck index, 10th edition, Merck & Co., Inc.: Rahway, NJ, 1983, pp. 39 (entry 242 for allantoin).

Merck index, 14th edition, O'Neill, ed., 2006, entry for p-amino benzoic acid.

Merck index, 14th edition, O'Neill, ed., 2006, entry for zinc oxide.

Merck Index, An Encyclopedia of Chemicals, Drugs, and Biologicals. 13th Edition. O'Neil et al eds. Entries 1058, 2350, 6143, and 8803. 2001. 7 pages.

Merck Manual Home Edition. "Excessive Sweating: Sweating Disorders." Accessed Apr. 14, 2011 at www.merckmanuals.com/home/print/sec18/ch206/ch206c.html. 2 pages.

Merriam Webster Online Dictionary [online] retrieved from http://www.merriam-webster.com/cgi-bin/dictionary?book=dictionary&va=derivative on Jul. 5, 2008; 1 page.

Messenger, et al., "Minoxidil: Mechanisms of Action on Hair Growth", British Journal of Dermatology, 150:186-194 (2004).

Metz, et al., "A Phase I Study of Topical Tempol for the Prevention of Alopecia Induced by Whole Brain Radiotherapy", Clinical Cancer Research, 10:6411-6417 (2004).

Meucci, et al., "Ascorbic Acid Stability in Aqueous Solutions", Acta Vitaminol Enzymol, 7(3- 4):147-153 (1985)—Abstract, 1 page.

Molan, Peter Clark, "World Wide Wounds," Dec. 2001, 13 pages.

Neutrogena. Http://www.cosmetoscope.com/2010/04/neutrogea-clinic al-with-johnson-johnsons-cytomimic-techology/. Published Apr. 28, 2010. Accessed Sep. 11, 2010, 5 pages.

Nietz, "Molecular orientation at surfaces of solids," *J. Phys. Chem.*, 1928, 32(2): 255-269.

No Author Listed. "Opitmization of Nano-Emulsions Production by Microfluidization." European Food Research and Technology. Volume 225, No. 5-6. Sep. 2007. Abstract. 1 page.

Office Action for U.S. Appl. No. 11/430,437, Tamarkin et al., May 9, 2008, 27 pages.

Office Action received from the U.S. Patent Office, U.S. Appl. No. 11/430,599, Jul. 28, 2008 (59 pages).

Oil. Dictionary of Chemistry. Editor: DWA Sharp. Copyright 1990.

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

Padhi et al., "Phospho-olicines as positive-electrode materials for rechargeable lithium batteries," *J. Electrochemical Soc.*, 1997, 144(4): 1188-1194.

Pakpayat, et al., "Formulation of Ascorbic Acid Microemulstions with Alkyl Polyglycosides", European Journal of Pharmaceutics and Biopharmaceutics, 72:444-452 (2009).

Paula. http://ww.cosmeticscop.com/cosmetic-ingredient-dictionary/definition/259/c12-15-alkyl-benzoate.aspx. Printed Oct. 24, 2010. 1 page.

Prescription Information for Aldara, Mar. 2007 (29 pages).

Purcell, Hal C. "Natural Jojoba Oil Versus Dryness and Free Radicals." Cosmetics and Toiletries Manufacture Worldwide. 1988. 4 pages.

Raschke, et al., "Topical Activity of Ascorbic Acid: From In Vitro Optimization to In Vivo Efficacy", Skin Pharmacology and Physiology, 17(4):200-206 (2004)—Abstract, 1 page.

Ravet et al., "Electroactivity of natural 503-507 and synthetic triphylite," *J. of Power Sources*, 2001, 97-98: 503-507.

Receptacle. Merriam Webster. Http://www.merriam-webster.com/dictionary/receptacle. Accessed Jul. 12, 2011. 1 page.

Richwald, "Imiquimod", Drugs Today, 35(7):497 (1999)—Abstract, 1 page.

Rieger and Rhein. "Emulsifier Selection/HLB." Surfactants in Cosmetics. 1997 (no month given). 1 page.

Scientific Discussion for the approval of Aldara, EMEA 2005 (10 pages).

Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.

Shim, et al., "Transdermal Delivery of Mixnoxidil with Block Copolymer Nanoparticles", J. Control Release, 97(3):477-484 (2004)—Abstract, 1 page.

Shrestha et al., Forming properties of monoglycerol fatty acid esters in nonpolar oil systems, *Langmuir*, 2006, 22: 8337-8345.

Silicone. Definition. Retrieved Apr. 19, 2011 from http://www.oxforddictionaries.com/definition/silicone?view=uk. 1 page.

Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.

Sonneville-Aubrun, O. et al. "Nanoemulsions: A New Vehicle for Skincare Products." Advances in Colloid and Interface Science. 108-109.. 2004. pp. 145-149.

Sreenivasa, et al., "Preparation and Evaluation of Minoxidil Gels for Topical Application in Alopecia", Indian Journal of Pharmaceutical Sciences, 68(4):432-436 (2006), 11 pages.

Stehle et al., Uptake of minoxidil from a new foam formulation devoid of propylene glycol to hamster ear hair follicles, *J. Invest. Dermatol.*, 2005, 124(4), A101.

Sugisaka, et al., "The Physiochemical Properties of Imiquimod, the First Imidazoquinoline Immune Response Modifier", Abstract 3030, Pharmaceutical Research, vol. 14, No. 11 Supplemental (Nov.), p. S475 (1997), 2 pages.

Surfactant. Chemistry Glossary. Http://chemistry.about.com/od/chemistryglossary/g/surfactant.htm, 2012, 1 page.

Sweetman, Sean C. Martindale: The Complete Drug Reference. 33rd Edition. London. Pharmaceutical Press. Jun. 21, 2002. pags. 1073 and 1473. 5 pages.

Tadros, Tharwat F. "Surfactants in Nano-Emulsions." Applied Surfactants: Principles and Applications. Wiley-VCH Verlag GmbH & Co. Weinheim. Isbn: 3-527-30629-3. 2005. pp. 285-308.

Tanhehco, "Potassium Channel Modulators as Anti-Inflammatory Agents", Expert Opinion on Therapeutic Patents, 11(7):1137-1145 (2001)—Abstract, 3 pages.

Tata, et al., "Penetration of Minoxidil from Ethanol Propylene Glycol Solutions: Effect of Application vol. on Occlusion", Journal of Pharmaceutical Sciences, 84(6):688-691 (1995).

Tata, et al., "Relative Influence of Ethanol and Propylene Glycol Cosolvents on Deposition of Minoxidil into the Skin", Journal of Pharmaceutical Sciences, 83(10):1508-1510 (1994).

Third Party Submission for U.S. Appl. No. 12/014,088, Feb 4, 2009, 4 pages, cited by other.

Trofatter, "imiquimod in clinical Practice", European Journal of Dermatology, 8(7 Supp.):17- 19 (1998)—Abstract, 1 page.

Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.

Tsai, et al., "Effect of Minoxidil Concentration on the Deposition of Drug and Vehicle into the Skin", International Journal of Pharmaceutics, 96(1-3):111-117 (1993)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Tzen, Jason T.C. et al. "Surface Structure and Properties of Plant Seed Oil Bodies." Department of Botany and Plant Sciences, University of California, Riverside, California 92521. Apr. 15, 1992. 9 pages.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Wermuth, C.G. "Similarity in drugs: reflections on analogue design," Drug Discovery Today, vol. 11, Nos. 7/8, Apr. 2006, pp. 348-354.

Williams, "Scale up of an olive/water cream containing 40% diethylene glycol momoethyl ether", Dev. Ind. Pharm., 26(1):71-77 (2000).

Yamada and Chung, "Crystal Chemistry Possible 4 V Cathode Materials for Lithium 967 of the Olivine-Type Li(Mn$_y$Fe$_{1-y}$)PO$_4$ and (Mn$_y$Fe$_{1-y}$)PO$_4$ as Batteries," J. Electrochemical Soc., 2001, 148(8): A960-967.

"Coal tars and coal-tar pitches," *Report on Carcinogens, Twelfth Edition*, 2011, 3 pages.

Adisen et al. "Topical tetracycline in the treatment of acne vulgaris," *J Drugs Dermatol.*, 2008, 7:953-5.

Baskaran et al., "Poloxamer-188 improves capillary blood flow and tissue viability in a cutaneous burn wound," *J. Surg. Res.*, 2001, 101(1):56-61.

Bell-Syer et al. "A systematic review of oral treatments for fungal infections of the skin of the feet," *J. Dermatolog. Treat.*, 2001, 12:69-74.

Boehm et al. 1994, "Synthesis of high specific activity [.sup.3 H]-9-cis-retinoic acid and its application for identifying retinoids with unusual binding properties," *J. Med. Chem.*, 37:408-414.

Carapeti et al., "Topical diltiazem and bethanechol decrease anal sphincter pressure and heal anal fissures without side effects," *Dis Colon Rectum*, 2000, 43(10):1359-62.

Cook and Mortensen, "Nifedipine for 43(3):430-1 treatment of anal fissures," *Dis Colon Rectum*, 2000, 43(3):430-1.

Dumortier et al., "A review of poloxamer 407 pharmaceutical and pharmacological characteristics," *Pharmaceutical Res.*, 2006, 23(12):2709-2728.

Ebadi et al., "Healing effect of topical nifedipine on skin wounds of diabetic rats," *DARU*, 2003, 11(1):19-22.

Effendy and Maibach. "Surfactants and Experimental Irritant Contact Dermatitis." *Contact Dermatol.*, 1995, 33:217-225.

Elias and Ghadially, "The aged epidermal permeability barrier," *Clinical Geriatric Medicine*, Feb. 2002, pp. 103-120.

Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery*, 1999, 39:400-405.

Fluhr et al., "Glycerol accelerates recovery of barrier function in vivo," *Acta Derm. Venereol,.* 1999, 79:418-21.

Garti et al. "Sucrose Esters microemulsions," *J. Molec. Liquids*, 1999, 80:253-296.

Hammer et al. "Anti-Microbial Activity of Essential Oils and other Plant extracts," *J. Applied Microbiology*, 1999, 86:985-990.

Hwang et al. "Isolation and identification of mosquito repellents in *Artemisia vulgaris*," *J. Chem. Ecol.*, 11: 1297-1306, 1985.

Knight et al., "Topical diltiazem ointment in the treatment of chronic anal fissure," *Br. J. Surg.*, 2001, 88(4):553-6.

Kucharekova et al., "Effect of a lipid-rich emollient containing ceramide 3 in experimentally induced skin barrier dysfunction," *Contact Dermatitis*, Jun. 2002, pp. 331-338.

Leive et al, "Tetracyclines of various hydrophobicities as a probe for permeability of *Escherichia coli* outer membrane," *Antimicrobial Agents and Chemotherapy*, 1984, 25:539-544.

Luepke and Kemper, "The HET-CAM Test: An Alternative to the Draize Eye Test," *FD Chem. Toxic.*, 1986, 24:495-196.

Osborne and Henke, "Skin Penetration Enhancers Cited in the Technical Literature," *Pharm. Technology*, Nov. 1997, pp. 58-86.

Padi. "Minocycline prevents the development of neuropathic pain, but not acute pain: possible anti-inflammatory and antioxidant mechanisms," *Eur J. Pharmacol*, 2008, 601:79-87.

Palamaras and Kyriakis, "Calcium antagonists in dermatology: a review of the evidence and research-based studies," *Derm. Online Journal*, 2005, 11(2):8.

Passi et al., Lipophilic antioxidants in human sebum and aging, *Free Radical Research*, 2002, pp. 471-477.

Perrotti et al., "Topical Nifedipine With Lidocaine Ointment vs. Active Control for Treatment of Chronic Anal Fissure," *Dis Colon Rectum*, 2002, 45(11):1468-1475.

Repa et al. "All-trans-retinol is a ligand for the retinoic acid receptors," *Proc. Natl. Acad Sci, USA*, 90: 7293-7297, 1993.

Ruledge, "Some corrections to the record on insect repellents and attractants," *J. Am. Mosquito Control Assoc*, 1988, 4(4): 414-425.

Sakai et al., "Characterization of the physical properties of the stratum corneum by a new tactile sensor," *Skin Research and Technology*, Aug. 2000, pp. 128-134.

Schaefer, "Silicone Surfactants," *Tenside, Surfactants, Deterg.*, 1990, 27(3): 154-158.

Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.

Smith, "Hydroxy acids and skin again," *Soap Cosmetics Chemical Specialties*, 1993, pp. 54-59.

Solans et al. "Overview of basic aspects of microemulsions," Industrial Applications of Microemulsions, Solans et al Eds, New York, 1997, 66:1-17.

Squillante et al., "Codiffusion of propylene glycol and dimethyl isosorbide in hairless mouse skin," *European J. Pharm. Biopharm.*, 1998, 46(3):265-71.

Todd et al. "Volatile Silicone Fluids for Cosmetics," *91 Cosmetics and Toiletries*, 1976, 27-32.

Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.

USP23/NF 18 The United States Pharmacopeia: The National Formulary, US Pharmacopoeia, 1995, p. 10-14.

Van Slyke, "On the measurement of buffer values and on the relationship of the buffer value to the dissociation constant of the buffer and the concentration and reaction of the buffer solution," *J. Biol. Chem.*, 1922, 52:525.

Van Cutsem et al., "The antiinflammatory efects of ketoconazole," *J. AM. ACAD. Dermatol.*,1991, (2 pt 1): 257-61.

Wang and Chen, "Preparation and surface active properties of biodegrabable dextrin derivative surfactants," *Colloids and Surfaces A: Physicochemical and Engineering Aspects*, 2006, 281(1-3):190-193.

Weindl et al., "Hyaluronic acid in the treatment and prevention of skin diseases: molecular biological, pharmaceutical and clinical aspects," *Skin Pharmacology and Physiology*, 2004, pp. 207-213.

Xynos et al., "Effect of nffedipine on rectoanal motility," *Dis Colon Rectum*, 1996, 39(2):212-6.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No. 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. " Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

\* cited by examiner

Candida albicans
Composition A effective
Compositions B and C ineffective
Trichophyton rubrum
Compositions A, B and C effective
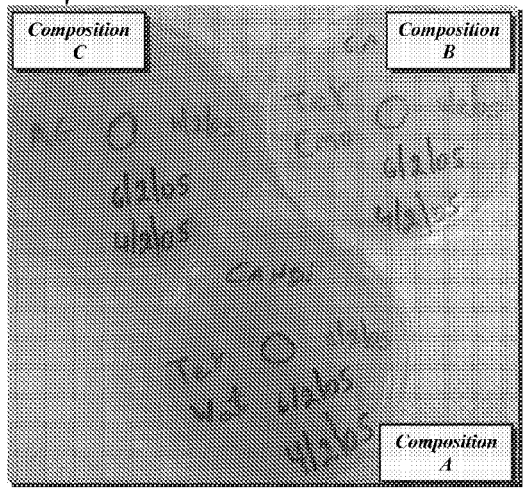
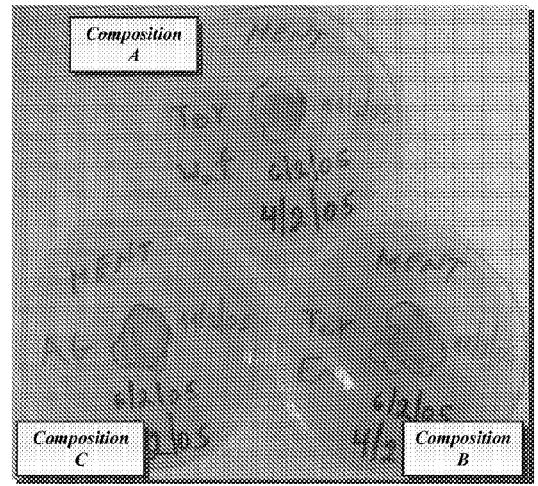
FIGURE 1A
FIGURE 1B

Trichophyton mentagrophytes
Compositions A and B effective
Composition C ineffective
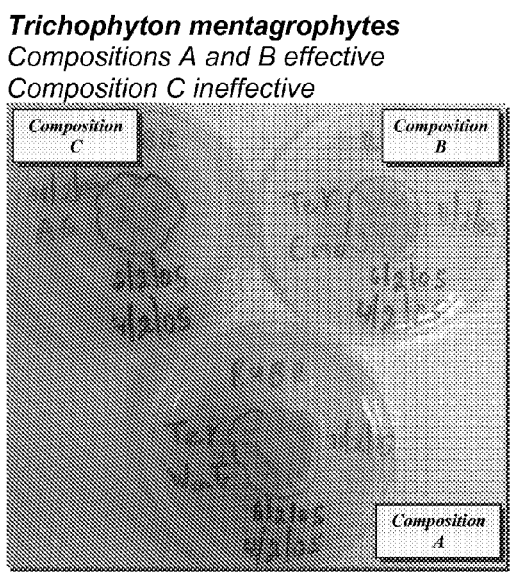
Microsporum canis
Composition A and B effective
Composition C ineffective
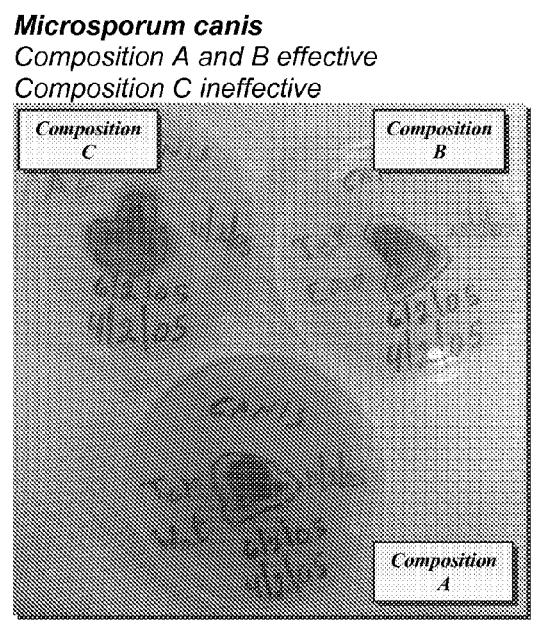
FIGURE 1C
FIGURE 1D

HYDROPHILIC, NON-AQUEOUS PHARMACEUTICAL CARRIERS AND COMPOSITIONS AND USES

CROSS REFERENCE TO RELATED APPLICATIONS

This application claims the benefit of priority under 35 U.S.C. §199(e) to co-pending U.S. Provisional Application No. 60/880,434 filed Jan. 12, 2007, and entitled "Hydrophilic or Waterless Vehicle and Foamable Pharmaceutical Compositions," which is incorporated in its entirety by reference.

This application claims the benefit of priority under 35 U.S.C. §199(e) to co-pending U.S. Provisional Application No. 60/919,303 filed Mar. 21, 2008, and entitled "Hydrophilic and Non-Aqueous Pharmaceutical Carriers and Compositions and Uses," which is incorporated in its entirety by reference.

This application is a continuation-in-part application of co-pending U.S. patent application Ser. No. 11/430,599, filed on May 9, 2006, entitled "Foamable Vehicle and Pharmaceutical Compositions Thereof," which is a continuation-in-part application of co-pending U.S. patent application Ser. No. 10/835,505, filed on Apr. 28, 2004, entitled "Oleaginous Pharmaceutical and Cosmetic Foam, which claims the benefit of priority under 35 U.S.C. §119(e) to U.S. Patent Application Ser. No. 60/530,015, filed on Dec. 16, 2003, entitled "Oleaginous Pharmaceutical Foam", and U.S. Patent Application Ser. No. 60/492,385, filed on Aug. 4, 2003, entitled "Cosmetic and Pharmaceutical Foam;" and which claims the benefit under 35 U.S.C. §119(e) of U.S. Provisional Patent Application No. 60/679,020, filed on May 9, 2005, entitled "Hygroscopic Anti-Infective Compositions;" and of U.S. Provisional Patent Application No. 60/784,793, filed on Mar. 21, 2006, entitled "Polyol Foamable Vehicle and Pharmaceutical Compositions Thereof, which are herein incorporated by reference in their entirety.

This application is a continuation-in-part application of co-pending application U.S. patent application Ser. No. 11/653,205, filed on Jan. 12, 2007, which is a continuation-in-part application of co-pending U.S. patent application Ser. No. 10/835,505, filed on Apr. 28, 2004, both entitled "Oleaginous Pharmaceutical And Cosmetic Foam," which claims the benefit of priority under 35 U.S.C. §119(e) to U.S. Patent Application Ser. Nos. 60/530,015, filed on Dec. 16, 2003, entitled "Oleaginous Pharmaceutical Foam", and 60/492, 385, filed on Aug. 4, 2003, entitled "Cosmetic and Pharmaceutical Foam", which are herein incorporated by reference in their entirety.

This application is a continuation-in-part application of co-pending U.S. patent application Ser. No. 11/947,751, filed on Nov. 29, 2007, entitled "Compositions With Modulating Agents", which claims the benefit under 35 U.S.C. §119(e) of U.S. Provisional Patent Application No. 60/861,620, filed on Nov. 29, 2006, entitled "Foamable Compositions With Modulating Agents," which is herein incorporated by reference in its entirety.

BACKGROUND

This invention relates to hygroscopic carriers and compositions, foamable carriers, and foamable pharmaceutical and cosmetic compositions, and the use of them.

External topical administration is an important route for the administration of drugs in disease treatment. Many groups of drugs, including, for example, antibiotic, anti-fungal, anti-inflammatory, anesthetic, analgesic, anti-allergic, corticosteroid, retinoid and anti-proliferative medications are preferably administered in hydrophobic media, namely ointment. However, ointments often form an impermeable barrier, so that metabolic products and excreta from the wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based products relates to the greasy feeling left following their topical application onto the skin, mucosal membranes and wounds.

Foams and, in particular, foams that are substantially based on non-aqueous solvents are complicated systems which do not form under all circumstances.

There remains an unmet need for improved, easy to use, stable and non-irritating foam formulations, intended for treatment of dermal and mucosal tissues. Particularly, there remains an unmet need for improved, easy to use, stable and non-irritating foam formulations, with unique therapeutic properties. There is more particularly a need to develop hygroscopic carriers and compositions, foamable carriers and foamable compositions and foams with active agents, which are stable, are non irritating, that facilitate penetration at a target, that are presentable in an easily applicable stable form, that can be handled with ease thereby facilitating compliance and that are adaptable where there is a need to minimize the amount of free water and in consequence, the potential breakdown of ingredients/agents by oxidation/hydrolysis.

Some active agents are known to be generally unstable or susceptible to isomerization or to breakdown, resulting in loss of activity and the use of stabilizers, anti oxidants antimicrobials and buffers and the like in aqueous compositions to protect active or cosmetic agents is known. The problems of protecting active pharmaceutical and cosmetic agents in waterless environments, such as polar compositions are multifold and can vary according to the type of waterless environment and the nature of the agent being used. It has been surprisingly found that factors like small levels of acid residues in the raw materials can be significant in influencing agent stability. Similarly, the presence of low levels of metal ions can act to catalyze reactions or breakdown. There is therefore a need for simple and elegant solutions to stabilize active ingredients in a waterless or substantially waterless environment. On one level it is far from simple or obvious to produce waterless foamable compositions that, when released, produce foams of quality suitable for pharmaceutical or cosmetic application. On a further level having realized a carrier that will produce a waterless foam of quality there is an additional difficulty to be overcome, namely how to adapt the formula and achieve a formulation, which can accept a range of various active pharmaceutical and cosmetic agents such that the composition and active agent are stable and the foam produced remains of quality. Specifically, one of the challenges in preparing such waterless or substantially waterless foamable compositions is ensuring that the active pharmaceutical or therapeutic agent does not react, isomerizes or otherwise break down to any significant extent during its storage and use. Particularly, there remains an unmet need for improved, easy to use, stable and non-irritating foam formulations, with unique therapeutic or beneficial properties containing a stable or stabilized active pharmaceutical or cosmetic agent.

Polyethylene glycol or derivatives or mixtures thereof and propylene glycol or derivatives are believed, in addition to their function as a solvent, to support, facilitate, improve or optimize the function and effect of active agents and may themselves have a therapeutic effect. There is thus, also an unmet need for compositions especially foamable compositions comprising combinations of polyethylene glycols or derivatives or mixtures thereof and polyethylene glycol or derivatives with an active agent, especially synergistic compositions.

SUMMARY

This invention relates to hygroscopic carriers and compositions, foamable carriers, and foamable pharmaceutical and cosmetic compositions, wherein the solvent includes a polyethylene glycol or derivative or mixtures thereof or includes a propylene glycol derivative or combinations of polyethylene glycols with or without propylene glycol.

This invention relates more particularly to hygroscopic glycol composition comprising a polyethylene glycol or derivatives and mixtures thereof or comprising a propylene glycol or derivatives at a sufficient concentration alone as a component in the composition or with one or more other hygroscopic substances to provide (a) at least one hygroscopic substance at a sufficient concentration to provide an Aw value of the hygroscopic therapeutic containing composition of less than 0.9; and
(b) a therapeutic agent thereof or combinations thereof.

In one aspect, the invention provides a hygroscopic composition comprising polyethylene glycol or derivatives and mixtures thereof or comprising propylene glycol or derivatives being or having at least one hygroscopic substance at a sufficient concentration alone or with one or more other hygroscopic substances to provide an Aw value of the hygroscopic pharmaceutical composition (1) of about less than 0.9 or (2) the Aw value is in the range of about 0.8 and about 0.9; (3) about 0.7 and about 0.8; and (4) less than about 0.7 and a n or a derivative thereof or a combinations thereof.

In one or more embodiments, the hygroscopic pharmaceutical composition further includes at least one component, selected from the group consisting of about 0.01% to about 5% by weight of at least one polymeric agent selected from a bioadhesive agent, a gelling agent, a film forming agent and a phase change agent; and a surface-active agent.

In one or more embodiments, the one or more hygroscopic substance is selected from the group consisting of polyethylene glycols (Pegs), surfactants comprising PEG, polyols, monosaccharides, disaccharides, oligosaccharides and sugar alcohols in an amount to provide hygroscopic properties, and honey.

In another aspect, the invention provides a foamable carrier including about 25% to about 98% by weight of a solvent selected from the group consisting of (1) a propylene glycol or derivative and (2) a polyethylene glycol (PEG) or derivative or mixtures thereof, 0% to about 48% by weight of a secondary solvent; a surface-active agent; about 0.01% to about 5% by weight of at least one polymeric agent; and a liquefied or compressed gas propellant at a concentration of about 3% to about 25% by weight of the total composition.

In another aspect, the invention provides a foamable carrier including about 50% to about 98% by weight of a solvent selected from the group consisting of (1) a propylene glycol or derivative and (2) a polyethylene glycol (PEG) or derivative or mixtures thereof, 0% to about 48% by weight of a secondary solvent; about 0.01% to about 10% by weight of a surface-active agent; about 0.01% to about 5% by weight of at least one polymeric agent; and a liquefied or compressed gas propellant at a concentration of about 3% to about 25% by weight of the total composition.

It was discovered that in certain embodiments it is possible to create a hydrophilic foam with silicone.

In one or embodiments there is provided a foamable hydrophilic carrier or therapeutic composition, comprising:

a waterless solvent comprising about 25% to about 95% of at least a polar solvent selected from the group consisting of (1) a propylene glycol or derivative and (2) a polyethylene glycol (PEG) or derivative or mixtures thereof; and a surface-active agent and or at least one polymeric agent at a concentration of about 0.1% to about 5% by weight of the total composition, wherein the at least one polymeric agent is selected from a bioadhesive agent, a gelling agent, a film forming agent and a phase change agent which is selected such that it has some surfactant properties if it is used in the absence of surface active agent.

In one or embodiments there is provided a foamable hydrophilic therapeutic composition, comprising:

a waterless solvent comprising about 25% to about 95% of at least a polar solvent selected from the group consisting of (1) a propylene glycol or derivative and (2) a polyethylene glycol (PEG) or derivative or mixtures thereof;

0% to about 48% of a secondary waterless solvent
a surface-active agent at a concentration of about 0.1% to less than about 10% by weight of the total composition; and or
at least one polymeric agent at a concentration of about 0.1% to about 5% by weight of the total composition, wherein the at least one polymeric agent is selected from a bioadhesive agent, a gelling agent, a film forming agent and a phase change agent which is selected such that it has some surfactant properties if it is used in the absence of surface active agent.

(a) optionally a silicone and
(b) a liquefied or compressed gas propellant at a concentration of about 3% to about 25% by weight of the total composition; and
a therapeutically effective amount of an active agent; and wherein the composition is stored in an aerosol container and upon release expands to form a breakable foam.

In one or more embodiments, the compositions further comprise co-surfactants.

In one or more embodiments, the compositions further comprise up to 10% of water.

In one or more embodiments, the composition is substantially non-aqueous and/or substantially alcohol-free.

In one or more embodiments, the composition is non-aqueous.

In one or more embodiments, the composition ingredients are pretreated to reduce, remove or eliminate any residual or associated or absorbed water.

In one or more embodiments, the composition is substantially non-aqueous and/or substantially alcohol-free.

In one or more embodiments, the composition further comprises an therapeutically effective concentration of one or more active, therapeutic, pharmaceutical or cosmetic agents.

In one or more embodiments, the composition further comprises one or more modulating agents.

In one or more embodiments, the secondary solvent is a polyol selected from the group consisting of a diol, a triol and a saccharide, and the triol may be selected from the group consisting of glycerin, butane-1,2,3-triol, butane-1,2,4-triol and hexane-1,2,6-triol, or the diol is selected from the group consisting of propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol.

In one or more embodiments, the polyol consists of at least one diol and at least one triol, and wherein the ratio between the diol and triol is between 9:1 and 1:1.

In one or more embodiments, the composition includes a mixture of PEGs, and the PEG may be selected from the group consisting of PEG 200, PEG 300, PEG 400, PEG 600, PEG 1000, PEG 1500, PEG 4000, PEG 6000 and PEG 8000.

In one or more embodiments, the composition contains one or more PEGs in a concentration to provide viscosity of less than 52,000 CPs.

In one or more embodiments, the composition includes a mixture of at least one polyol and at least one PEG, and the PEG may be selected from the group consisting of PEG 200, PEG 300, PEG 400, PEG 600, PEG 1000, PEG 1500, PEG 4000, PEG 6000 and PEG 8000.

In one or more embodiments, the composition includes a secondary solvent selected from the group consisting of dimethyl isosorbide, tetrahydrofurfuryl alcohol polyethyleneglycol, ether, DMSO, a pyrrolidone, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid.

In one or more embodiments, the secondary solvent is dimethyl isosorbide.

In one or more embodiments, the composition includes (1) at least one solvent selected from a propylene glycol and a PEG, and (2) at least one secondary solvent, and for example, the solvent comprises a mixture of at least one polyol and at least one PEG, and for example, the polyol comprises a mixture of at least two polyols.

In one or more embodiments, the ratio between the propylene glycol and/or PEG and the secondary solvent is between 9:1 and 1:1.

In another aspect there is provided a foamable therapeutic composition including about 25% to about 98% by weight of a solvent selected from the group consisting of (1) a propylene glycol or derivative and (2) a polyethylene glycol (PEG) or derivative or mixtures thereof; 0% to about 48% by weight of a secondary solvent; about 0.01% to about 10% by weight of a surface-active agent; about 0.01% to about 5% by weight of at least one polymeric agent; a therapeutic agent at a therapeutically effective concentration; and a liquefied or compressed gas propellant at a concentration of about 3% to about 25% by weight of the total composition.

In another aspect there is provided a foamable therapeutic composition including about 50% to about 98% by weight of a solvent selected from the group consisting of (1) a propylene glycol or derivative and (2) a polyethylene glycol (PEG) or derivative or mixtures thereof; 0% to about 48% by weight of a secondary solvent; about 0.01% to about 10% by weight of a surface-active agent; about 0.01% to about 5% by weight of at least one polymeric agent; a therapeutic agent at a therapeutically effective concentration; and a liquefied or compressed gas propellant at a concentration of about 3% to about 25% by weight of the total composition.

In another aspect there is provided a foamable therapeutic composition including about 50% to about 98% by weight of a solvent selected from the group consisting of (1) a propylene glycol or derivative and (2) a polyethylene glycol (PEG) or derivative or mixtures thereof; 0% to about 48% by weight of a secondary solvent; about 0.01% to about 10% by weight of a surface-active agent; about 0.01% to about 5% by weight of at least one polymeric agent; a therapeutic agent at a therapeutically effective concentration; a modulating agent; and a liquefied or compressed gas propellant at a concentration of about 3% to about 25% by weight of the total composition.

In yet an additional embodiment, the foamable therapeutic composition further contains an additional therapeutic agent.

In another aspect, a method of treating, ameliorating or preventing a disorder of mammalian subject includes administering a foamable therapeutic composition to a target area, the composition comprising a therapeutically effective concentration of an active agent, about 50% to about 98% of a solvent selected from the group consisting of (1) a propylene glycol or derivative and (2) a polyethylene glycol (PEG) or derivative or mixtures thereof; 0% to about 48% of a secondary solvent; about 0.01% to about 5% by weight of at least one polymeric agent; about 0.01% to about 10% by weight of a surface-active agent; a modulating agent; and a liquefied or compressed gas propellant at a concentration of about 3% to about 25% by weight of the total composition.

In one or more embodiments, the target site is selected from the group consisting of the skin, a body cavity, a mucosal surface, the nose, the mouth, the eye, the ear canal, the respiratory system, the vagina and the rectum.

In one or more embodiments the surface active agent can be increased from about 10% up to about 15% or up to about 20% by weight of composition depending on the surfactant selected.

In one aspect, a waterless composition suitable for delivery of an active agent to a body surface or cavity includes a vehicle comprising:
 about 70% to about 99% by weight of a hydrophilic polar solvent, said hydrophilic solvent selected from the group consisting of:
  i) a mixture of two or more different polyethylene glycols (PEGs), wherein at least one PEG is a high molecular weight PEG having a melting point greater than 25° C.; and
  ii) propylene glycol (PG);
 about 0% to about 10% of at least one surface active agent;
 about 0% to about 5% of a polymeric agent;
 about 0% to about 30% of a secondary hydrophilic solvent; and
 about 0% to about 5% of a silicone oil; and
 about 3% to about 25% hydrophobic propellant;
 wherein the composition is otherwise substantially free of a hydrophobic solvent;
 wherein the composition includes at least one of a surface active agent and a polymeric agent; and
 wherein the vehicle and the propellant are sufficiently miscible that the components may be homogeneously distributed with mild shaking.

In one or more embodiments, the hydrophilic solvent is PEG and the high molecular weight PEG is selected from the group consisting of PEG 1000, PEG 1500, PEG 4000, PEG 6000 and PEG 8000, and the balance of the PEG is selected from the group consisting of PEG 200, PEG 300, PEG 400, and PEG 600.

In one or more embodiments, the high molecular weight PEG comprises about 1% to about 15% of the composition.

In one or more embodiments, the mixture of two or more different PEGs are selected to provide viscosity of the vehicle of less than 52,000 CPs, as measured at room temperature at 10 rmp spindle speed, or are less than 12,000 CPs or are less than 10,000 CPs.

In one or more embodiments, the hydrophilic polar solvent is PG and the components of the composition are sufficiently miscible that the vehicle and the propellant do not phase separate upon centrifugation at 1000 rpm.

In one embodiment, the hydrophilic solvent is PG, the composition includes a steareth surface active agent and a hydroxypropylcellulose polymeric agent, and is substantially free of silicone and a secondary hydrophilic solvent.

In one or more embodiments, one or both of the surface active agent and the polymeric agent are selected to increase the solubility of the propellant in the vehicle.

In one or more embodiments, the a polymeric agent is present in the composition and is selected from the group consisting of locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, an amine-bearing polymer, chitosan, alginic acid, hyaluronic acid, a chemically modified starch, a carboxyvinyl polymer, polyvinylpyrrolidone, polyvinyl alcohol, a polyacrylic acid polymer, a polymethacrylic acid polymer, polyvinyl acetate, a polyvinyl chloride polymer, a polyvinylidene chloride polymer, methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, a cationic cellulose PEG 1000, PEG 4000, PEG 6000 and PEG 8000, polycarbophil, carbomer, ASOS, klucel and permulen.

In one or more embodiments, a surface active agent is present in the composition and is selected from the group consisting of a polysorbate, including polysorbate 80 and Twin 80, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, including polyoxyethylene cetyl ether, polyoxyethylene palmityl ether, polyethylene oxide hexadecyl ether, polyethylene glycol cetyl ether, Brij 10, Brij, 21, Brij 38, Brij 52, Brij 56, Brij 72, Brij 721 and Brij W1, a sucrose ester, including Span 20, Span 60 and Span 80, a partial ester of sorbitol, including sorbitan monolaurate, sorbitan monolaurate, and Surphope 1811, a monoglyceride, a diglyceride, isoceteth-20, a mono, di or tri fatty acid sucrose ester, laureth-4, glyceryl stearate, polyoxyl-100 stearate, glyceryl monostearate, PEG-100 stearate, PEG-40 stearate, ceteareth-6, ceteareth-16, ceteareth-20, stearyl alcohol, myrj 52, steareth-2, steareth-20, isosteareth-20, polyglyceryl 10 laurate, POE (2) cetyl ether, cetearyl glucoside, cetyryl alcohol, methyl glucose sesquistearate, span 60, sucrose stearic acid esters, sorbitan stearate, sucrose cocoate, sucrose stearate, Peg 40 stearate, isosteareth 20, methyl glucose sesquistearate, polyoxyl 100 stearate, macrogel cetostearyl ether, a polymeric emulsifier, including Permulen (TR1 or TR2); and liquid crystal systems, including Arlatone (2121), Stepan (Mild RM1), Nikomulese (41) and Montanov (68); and a combination of surfactants selected from the group consisting of a Brij surfactant and a Twin surfactant, wherein the Brij surfactant is the major component of the combination, combinations of polyoxyethylene alkyl ethers, including Brij 59/Brij 10; Brij 52/Brij 10; Steareth 2/Steareth 20; Steareth 2/Steareth 21 (Brij 72/BRIJ 721); Myrj 52/Myrj 59, Steareth 2/Laureth 4; combinations of sucrose esters, including Surphope 1816/Surphope 1807; combinations of sorbitan esters, including Span 20/Span 80; Span 20/Span 60; combinations of sucrose esters and sorbitan esters, including Surphope 1811 and Span 60; and combinations of liquid polysorbate detergents and PEG compounds, particularly Twin 80/PEG-40 stearate/methyl glucose sequistearate, glyceryl stearate/ PEG-100 stearate; ceteareth-6/stearyl alcohol; cetearyl glucoside/cetyryl alcohol; sorbitan stearate/sucrose cocoate; and polysorbate 80/PEG-40 stearate.

In one or more embodiments, silicone oil is present in the composition and is selected from the group consisting of dimethicone, cyclomethicone and mixtures thereof.

In one or more embodiments, the second hydrophilic solvent is present in the composition and is a polyol selected from the group consisting of a diol, a triol and a saccharide, wherein the triol is selected from the group consisting of glycerin, butane-1,2,3-triol, butane-1,2,4-triol and hexane-1, 2,6-triol, and wherein the diol is selected from the group consisting of propylene glycol, butanediol, butenediol, butynediol, pentanediol, hexanediol, octanediol, neopentyl glycol, 2-methyl-1,3-propanediol, diethylene glycol, triethylene glycol, tetraethylene glycol, dipropylene glycol and dibutylene glycol.

In one or more embodiments, the ratio between the polyethylene glycol and the secondary hydrophilic solvent is between about 9:1 and about 1:1.

In one or more embodiments, the composition further comprises one or more modulating agents, and are for example, selected from the group of triethanol amine, sodium citrate and citric acid.

In one or more embodiments, the composition includes an active agent and the active agent is selected from the group consisting of antiinfectives, antifungals, antivirals, anesthetic analgesic, corticosteroids, non steroid anti inflammatory, retinoids, lubricating agents anti warts, antiproliferative, vasoactive, keratolytic, insecticide and repellants, dicarboxylic acids and esters; calcium channel blockers, cholinergic, N-oxide doners, photodynamic, anti acne, anti wrinkle, antioxidants, self tanning active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamins A, B, C, D, E, K and derivatives, wound healing agents and wart removers.

In one or more embodiments, the active agent is selected from the group consisting of: Acyclovir, Azelaic acid, Benzoyl peroxide, Betamethasone 17 valerate micronized, Caffeine, Calcipotriol hydrate, Ciclopiroxolamine, Diclofenac sodium, Ketoconazole, Miconazole nitrate, Minoxidil, Mupirocin, Nifedipine regular, Permethrin BPC (cis:trans 25:75), Piroxicam, Salicylic acid, Terbinafine HCl, estradiol hemihydrate and progesterone or combinations thereof.

In one or more embodiments, the active agent includes progesterone, estrogen, a derivative thereof or mixtures thereof, or the active agent includes a vitamin, such as Vitamin D, retinol, retinoic acid, tocopherol, Vitamin K, Vitamin C or Vitamin B or a derivatives thereof, or a steroid, or a mixture of a steroid and a vitamin.

In one or more embodiments, the composition comprises a polymeric agent and the polymeric agent is selected from the group of bioadhesive polymers, and for example, the polymeric agent is selected from the group consisting of hydroxypropylcellulose and carbomer. The composition has a bioadhesive force in the range of about −3 g to about −25 g.

In another aspect, a waterless composition suitable for delivery of an active agent to a body surface or cavity includes a vehicle, comprising:
  about 70% to about 99% by weight of a hydrophilic polar solvent comprising butylene glycol (BG)
  about 0% to about 10% of at least one surface active agent;
  about 0% to about 5% of a polymeric agent;
  about 0% to about 30% of a secondary hydrophilic solvent; and
  about 0% to about 5% of an unmodified silicone; and
  about 3% to about 25% hydrophobic propellant;
  wherein the composition is otherwise substantially free of a hydrophobic solvent;
  wherein the composition includes at least one of a surface active agent and a polymeric agent; and
  wherein the components of the composition are sufficiently miscible that the vehicle and the propellant do not phase separate upon centrifugation at about 1000 rpm for about 10 mins, or at about 3000 rpm for about 10 mins.

In one or more embodiments, the hydrophilic solvent further comprises a polyol selected from the group consisting of propylene glycol and hexylene glycol, and the ratio of butylene glycol to hexylene glycol is in the range of 1:0.5 to about 1:3.

In another aspect, a waterless composition suitable for delivery of an active agent to a body surface or cavity includes a vehicle, comprising:
  about 70% to about 99% by weight of a hydrophilic polar solvent, said hydrophilic solvent selected from the group consisting of polyethylene glycols (PEGs) and propylene glycol (PG);
  about 0.1% to about 10% of at least one surface active agent, a surface active agent is present in the composition and is a mixture of a Brij surfactant and a Twin surfactant, wherein the Brij surfactant is the major surface active agent component;
  about 0% to about 5% of a polymeric agent;
  about 0% to about 30% of a secondary hydrophilic solvent; and
  about 0% to about 5% of an unmodified silicone; and
  about 3% to about 25% hydrophobic propellant;
  wherein the composition is otherwise substantially free of a hydrophobic solvent; and
  wherein the components of the composition are sufficiently miscible that the propellant and vehicle may be homogeneously distributed with mild shaking.

In another aspect, a waterless composition suitable for delivery of an active agent to a body surface or cavity includes:
  about 70% to about 99% by weight of a mixture of two or more different polyethylene glycols (PEGs), wherein at least one PEG is a high molecular weight PEG having a melting point greater than 25° C., and wherein the mixture of two or more different PEGs is selected to provide an gel, ointment or cream; and
  about 0% to about 10% of at least one surface active agent;
  about 0% to about 5% of a polymeric agent; and
  about 0% to about 30% of a secondary hydrophilic solvent;
  wherein the composition includes at least one of a surface active agent and a polymeric agent.

In one or more embodiments, the high molecular weight PEG is present in an amount greater than about 10% by weight of the composition.

In one or more embodiments, the PEG is a combination of a high and low molecular weight PEG selected from the group consisting PEG6000/PEG200; PEG400/PEG1500, PEG4000/PEG200; PEG4000/PEG400, PEG 4000/PEG 600, PEG4000/PEG400/PEG200; and the like.

In another aspect, a waterless composition suitable for delivery of an active agent to a body surface or cavity includes a vehicle comprising:
  about 70% to about 99% by weight of a hydrophilic polar solvent, said hydrophilic solvent comprising a mixture of PEG 200 and PEG 400;
  about 0% to about 10% of at least one surface active agent;
  about 0% to about 5% of a polymeric agent;
  about 0% to about 30% of a secondary hydrophilic solvent; and
  about 0% to about 5% of a silicone oil; and
  about 3% to about 25% hydrophobic propellant;
  wherein the composition is otherwise substantially free of a hydrophobic solvent;
  wherein the composition includes at least one of a surface active agent and a polymeric agent; and
  wherein the vehicle and the propellant are sufficiently miscible that the components may be homogeneously distributed with mild shaking.

Compositions including a polyethylene glycol solvent or derivative or mixtures thereof or includes a propylene glycol derivative or combinations of polyethylene glycols with or without propylene glycol containing an effective amount of one or more active, therapeutic, pharmaceutical or cosmetic agents can be applied to the skin, a body cavity, a mucosal surface, the nose, the mouth, the eye, the ear canal, the respiratory system, the vagina and the rectum. Such carriers and compositions are adaptable to deliver active, therapeutic, pharmaceutical or cosmetic agents with water as a minor constituent or with little or no water. This can be convenient where agents are susceptible to oxidation and breakdown in solution. Vitamins may for example breakdown in the presence of water and may not be stable in compositions for sufficiently long periods of time to facilitate satisfactorily cosmetic and pharmaceutical uses.

The compositions as described hereinabove can be used for treating disorders of the skin, mucosa, and body cavities as described in greater detail herein.

BRIEF DESCRIPTION OF THE DRAWING

FIG. 1: The in vitro anti-infective effect of pharmaceutical foamable compositions as prepared as described in Example 22.

DETAILED DESCRIPTION

Figure 2:
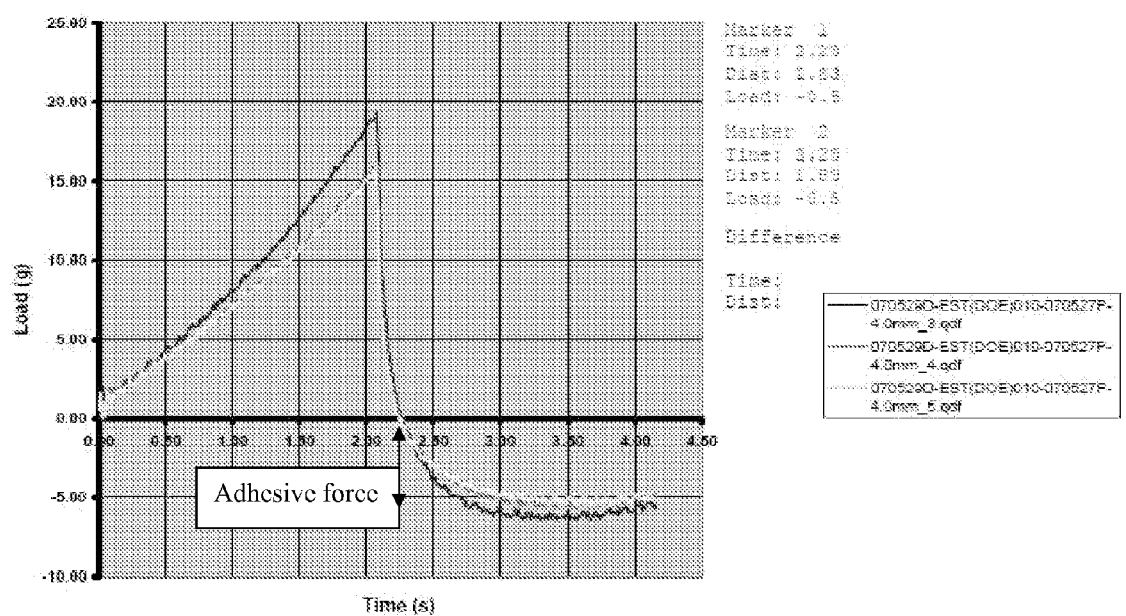
FIG. 2 is a plot of load vs time for the foamable composition as prepared in Example 50, sample EST-010.

Waterless foamable carriers are disclosed for use as foamable vehicles and carriers for the delivery of an active agent. In various embodiments, hydrophilic solvents, such as polyethylene glycol or propylene glycol, are used as solvents in a waterless system. These hydrophilic solvents, while not as polar a water, nonetheless provide a degree of polarity that is useful in solubilizing polar or hydrophilic active agents. In addition, the use of a hydrophilic solvent provides advantages over water-based formulations, in those frequent instances when an active agent is water-unstable. Active pharmaceutical and cosmetic agents are more generally referred to as a therapeutic agent.

The use of hydrophilic solvents nonetheless presents some challenges. In a foamable system, it is common to store the foamable carrier in a pressurized carrier and to charge the container with a hydrophobic propellant such as a hydrocarbon or hydrofluorocarbon. The hydrophilic carrier on its own is usually not miscible in the propellant and the hydrophobic components, including the propellant, tend to phase separate quite quickly from the hydrophilic component, including PEGs and PG.

PG and PEG are not as polar as water, so the propellant solubility in PG or PEG should be greater than in water. However, PEG and PG do not dissolve in propellant alone and if shaken together will quickly separate. Upon shaking together, the combination is only lightly opaque suggesting that some kind of quickly reversible micelles are formed. While surfactants and other surface active agents can help to stabilize the two phases, this is a challenge without the presence of an aqueous phase (for which many surfactants have been developed and for which the formation of water emulsions is well understood).

According to one or more embodiments, stable foamable compositions including a PEG or PG or mixtures provide a composition that is resistant to phase separation, or that is easily mixed by mild agitation, e.g., by a few simple shakes of a pressurized container. "Mild agitation" or "lightly shaking" refers to the force applied to a canister containing a shakable foamable formulation with propellant, which is raised to about the level of head height and mildly brought to about waist height and back again a few times by an average adult without excessive or vigorous force. Formulations of PEG and/or PG with surface active agents and/or a polymeric agents that stabilize the foamable carrier when stored under pressure with a hydrophobic propellant and which, when released from the pressurized container provide an excellent quality foam, are disclosed. The surface active agents and polymeric agents promote the formation of a waterless emulsion between the hydrophilic glycol and the hydrophobic propellant.

In one or more embodiments, the foamable carriers are substantially free of additional hydrophobic solvents, as additional hydrophobic is likely to make the task of formulating even harder as the formulation would need more stabilization One of the advantages of these hydrophilic waterless formulations, which are stored in sealed canisters, is that they can provide a safe medium for active agents that tend to break down upon exposure to one or more of water, light or air. They can also be formulated to exhibit bioadhesive properties and can be used for body cavity applications with minimal or no leakage. They are also of pleasant appearance and skin feeling.

According to one or more embodiments, the foamable carrier, comprises:
A waterless composition suitable for delivery of an active agent to a body surface or cavity comprising:
  a vehicle comprising:
    a) about 70% to about 99% by weight of a hydrophilic polar solvent, said hydrophilic solvent selected from the group consisting of:
      i) a mixture of two or more different polyethylene glycols (PEGs), wherein at least one PEG is a high molecular weight PEG having a melting point greater than 25° C.; and
      ii) propylene glycol (PG);
    b) about 0% to about 10% of at least one surface active agent;
    c) about 0% to about 5% of a polymeric agent;
    d) about 0% to about 30% of a secondary hydrophilic solvent; and
    e) about 0% to about 5% of a silicone oil; and
    about 3% to about 25% hydrophobic propellant;
    wherein the composition is otherwise substantially free of a hydrophobic solvent;
  wherein the composition includes at least one of a surface active agent and a polymeric agent; and
  wherein the vehicle and the propellant are sufficiently miscible that the components may be homogeneously distributed with mild shaking.

All % values are provided on a weight (w/w) basis.

In one or more embodiments the surface active agent ranges from about less than 0.01% up to about 5% up to about 10% up to about 15% or up to about 20% by weight of composition depending on the surfactant selected or preferably is about 0.2% to about 10% by weight of composition more preferably 0.5% to about 5% by weight of composition.

Water, up to 25% of the composition, and more preferably up to 10%, and optional ingredients can be added to complete the total mass to 100%. In certain cases, the composition contains two active agents that require different pH environments in order to remain stable. For example, corticosteroids are typically stable at acidic pH (they have a maximum stability at a pH of about 4-6) and vitamin D analogues are typically stable at basic pH (they have a maximum stability at pH values above about 8). In other cases, the active agent degrades in the presence of water, and therefore, in such cases the present of water in the composition is not desirable. Thus, in certain preferred embodiments, the composition is substantially non-aqueous. The term "substantially non-aqueous" or "substantially waterless" is intended to indicate that the composition has a water content below about 5%, preferably below about 2%, such as below about 1.5%. In certain other preferred embodiments the composition is non aqueous or waterless.

According to one or more embodiments, the foamable carrier, includes a waterless solvent, a stabilizing surfactant, a polymeric agent, a modulating agent and a propellant.

According to one or more embodiments, the foamable pharmaceutical or cosmetic foamable composition, includes a waterless solvent, a stabilizing surfactant, a polymeric agent, a modulating agent, a propellant and an active pharmaceutical or cosmetic agents.

According to one or more embodiments, the foamable carrier, includes:
  a. a waterless solvent comprising about 25% to about 98% of at least polar solvent selected from the group consisting of (1) a propylene glycol or derivative and (2) a polyethylene glycol (PEG) or derivative or mixtures thereof;
  b. a surface-active agent;
  c. about 0.01% to about 5% by weight of at least one polymeric agent; and
  d. a liquefied or compressed gas propellant at a concentration of about 3% to about 25% by weight of the total composition;

wherein the composition is shakable; and
wherein the composition is stored in an aerosol container and upon release expands to form a breakable foam.

According to one or more embodiments, the foamable carrier, includes:

A waterless composition suitable for delivery of an active agent to a body surface or cavity comprising:
  a vehicle, comprising:
   a) about 70% to about 99% by weight of a hydrophilic polar solvent comprising butylene glycol (BG)
   b) about 0% to about 10% of at least one surface active agent;
   c) about 0% to about 5% of a polymeric agent;
   d) about 0% to about 30% of a secondary hydrophilic solvent; and
   e) about 0% to about 5% of an unmodified silicone; and about 3% to about 25% hydrophobic propellant;
   wherein the composition is otherwise substantially free of a hydrophobic solvent;
   wherein the composition includes at least one of a surface active agent and a polymeric agent; and
   wherein the components of the composition are sufficiently miscible that the vehicle and the propellant do not phase separate upon centrifugation at about 1000 rpm for about 10 mins.

According to one or more embodiments, the foamable composition, includes:

A waterless composition suitable for delivery of an active agent to a body surface or cavity comprising:
  a vehicle, comprising:
   a) about 70% to about 99% by weight of a hydrophilic polar solvent, said hydrophilic solvent selected from the group consisting of polyethylene glycols (PEGs) and propylene glycol (PG);
   b) about 0.1% to about 10% of at least one surface active agent, a surface active agent is present in the composition and is a mixture of a Brij surfactant and a Twin surfactant, wherein the Brij surfactant is the major surface active agent component;
   c) about 0% to about 5% of a polymeric agent;
   d) about 0% to about 30% of a secondary hydrophilic solvent; and
   e) about 0% to about 5% of an unmodified silicone; and about 3% to about 25% hydrophobic propellant;
   wherein the composition is otherwise substantially free of a hydrophobic solvent; and
   wherein the components of the composition are sufficiently miscible that the propellant and vehicle may be homogeneously distributed with mild shaking.

'Shakability' means that the composition contains some or sufficient flow to allow the composition to be mixed or remixed on shaking. That is, it has fluid or semi fluid properties. A breakable foam is that is thermally stable, yet breaks under sheer force.

The breakable foam is not "quick breaking", i.e., it does not readily collapse upon exposure to body temperature environment. Sheer-force breakability of the foam is clearly advantageous over thermally induced breakability, since it allows comfortable application and well directed administration to the target area.

In one or more embodiments the ratio of polymeric agent to surfactant is about 1:10 to about 10:1; about 1:5 to about 5:1; about 3:7 to about 7:3; and about 2:1 to about 1:2.

The provision and selection of polymeric agent is however not straightforward. The polymers should be miscible or swell in the waterless solvent. It has been found that in the case of modified cellulose that lower molecular weight cellulose polymer derivatives are preferable.

In one embodiment the polymeric agent is hydroxypropyl cellulose.

In another embodiment the polymeric agent is or Carbomer such as Carbopol 934®.

According to one or more embodiments, the pre-foamable carrier; the pre-foamable pharmaceutical or cosmetic composition; the foamable carrier, or the foamable pharmaceutical or cosmetic composition further includes 0.1% to about 75% of a secondary solvent.

In one or more embodiments there is provided a foamable vehicle that is suitable for use as a base for delivery of not merely one type of active pharmaceutical ingredient ("API") but is adaptable for use with one or more API's from a wide range of different types of API's with appropriate and usually relatively minimal or minor adjustment to the vehicle. For example, by altering the amount of a component or by the addition of a stabilizer or an antioxidant as would be appreciated by a person skilled in the art.

In a further embodiment the surfactant and polymeric agent and their amounts are selected so that the composition is sufficiently so that foam extrusion and substantially uniform foam formation is not hampered. To this extent, the maximum effective amount of surfactant and polymeric agent that may be used for a foam may be limited by the need for shakability. For example as the level of waxy surfactants and or polymeric agents the composition will become thicker until it reaches a point where it will no longer be shakable or flowable. And whilst for an ointment or gel the levels may be further increased a solid non flowable composition is not suitable for foams.

In a further embodiment the propellant is preferably between about 5% to about 12% by weight of the composition.

In one or more embodiments of the pharmaceutical or cosmetic foamable product is non-flammable.

By waterless is meant that the composition contains no or substantially no, free or unassociated or absorbed water. It will be understood by a person of the art that the waterless solvents and substances miscible with them can be hydrophilic and can contain water in an associated or unfree or absorbed form and may absorb water from the atmosphere and the ability to do so is its hygroscopic water capacity. In some embodiments the composition ingredients are pre-treated to reduce, remove or eliminate any residual or associated or absorbed water.

Upon release from an aerosol container, the foamable carrier or composition forms an expanded foam suitable for the treatment of an infected surface and for topical administration to the skin, a body surface, a body cavity or a mucosal surface.

Polyol

In one or more embodiments, the solvent or secondary solvent is a polyol. A polyol is an organic substance that contains at least two hydroxy groups in its molecular structure.

In one or more embodiments, the foamable carrier contains at least one diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the foamable carrier contains at least one triol (a compound that contains three hydroxy groups in its molecular structure), such as glycerin, butane-1,2,3-triol, butane-1,2,4-triol and hexane-1,2,6-triol.

In one or more embodiments, the polyol is a mixture of polyols. In one or more embodiments, the mixture of polyols contains at least one diol and at least one triol. According to certain embodiments the ratio between the diol and triol is between 9:1 and 1:1.

In one or more embodiments, part of mixture of polyols is a saccharide. Exemplary saccharides include, but are not limited to monosaccharide, disaccharides, oligosaccharides and sugar alcohols.

A monosaccharide is a simple sugar that cannot be hydrolyzed to smaller units. Empirical formula is $(CH2O)n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol.) Mixtures of polyols, including (1) at least one polyol selected from a diol and a triol; and (2) a saccharide are contemplated within the scope.

Polyethylene Glycol

In an embodiment, the solvent consists of a polymerized ethylene glycol, namely polyethylene glycol, which is also termed "PEG". Exemplary PEGs are provided in the following table.

| Composition | Av. Molecular weight | Appearance | Melting point (° C.) |
|---|---|---|---|
| PEG 200 | 190~210 | Oily liquid | |
| PEG 300 | 285~315 | Oily liquid | |
| PEG 400 | 380~420 | Oily liquid | |
| PEG 600 | 570~630 | Oily liquid | 17~22 |
| PEG 1000 | 950~1050 | Solid | 35~40 |
| PEG 4000 | 3800~4400 | Solid | 53~58 |
| PEG 6000 | 5600~6400 | Solid | 55~60 |
| PEG 8000 | 7500~8500 | Solid | 58~65 |

Thus, in an embodiment, the PEG is selected from the group consisting of PEG 200, PEG 300, PEG 400, PEG 600, PEG 1000, PEG 4000, PEG 6000 and PEG 8000. Polyethylene glycol of average molecular weight 1500 (PEG 1500) is a solid and melts at about 45 degrees C. In an embodiment the High molecular weight PEG is 1500. In one or more embodiments it can be used in combination with one or more of PEG 200; PEG 400 and PEG 600. The foamable carrier according to the present invention can contain a single PEG or a mixture of two or more PEGs. PEGs having molecular weight of more that about 1000 possess gelling properties; i.e., they increase the viscosity of a composition. Therefore, by combining PEGs with different molecular weights/melting points, one can attain varying levels of flowability as desirable for the treatment of a given target site. The concentration of the PEG should be in a level that results in viscosity, prior to filling of the composition into aerosol canisters in the range of 100 to 5200 cps [typically measured at room temperature on a Brookfield Viscometer with a spindle speed of 10 RPM]. In some embodiments, the viscosity is less than 12,000 CPs, or less than 10,000 CPs.

Secondary Solvent

Optionally, a secondary solvent is added to the foamable composition. The secondary solvent is selected from a variety of organic solvents that are typically miscible on both water and oil. Examples of solvent that can be contained in the foamable carrier include dimethyl isosorbide, tetrahydrofurfuryl alcohol polyethyleneglycol ether (glycofurol), DMSO, pyrrolidones, (such as N-Methyl-2-pyrrolidone and 1-Methyl-2-pyrrolidinone), ethyl proxitol, dimethylacetamide (DMAc), PEG-type surfactants and alpha hydroxy acids, such as lactic acid and glycolic acid.

Appropriate use of a secondary solvent in a waterless foam composition can help improve delivery of active agents to a target area. Foam compositions, for which the solvent includes a secondary solvent, can increase the levels of the active agent in the waterless composition and thus, provide high delivery and improved therapy.

Solubilization and Penetration Enhancement

In many cases, polyols, PEGs and polar solvents possess a high solubilizing power and thus, they can enable increased concentrations of an active agent. Polyols, PEGs and polar solvents are also known for their skin penetration enhancement properties. These properties enable high drug bioavailability in the target area of treatment, resulting in an enhanced therapeutic effect. Occasionally, combinations of a polyol, PEGs and a secondary polar solvent, exhibit an increased permeability across the skin, as suggested, for example, in Eur J Pharm Biopharm. 1998 November; 46(3):265-71.

Thus, in one or more embodiments, the foamable carrier contains (1) at least one polar solvent, selected from a polyol (selected from a diol and a triol) and PEG; and (2) at least one secondary polar solvent.

In one or more embodiments, the foamable carrier contains (1) a mixture of at least two polyols; and (2) at least one secondary polar solvent. In additional embodiments, the foamable carrier contains a mixture of at least one polyol and at least one PEG; yet in other embodiments the foamable carrier contains (1) a mixture of at least one polyol and at least one PEG and (2) at least one secondary polar solvent.

According to certain embodiments the ratio between the polyol and/or PEG and the secondary polar solvent is between 9:1 and 1:1.

In certain embodiments, the polyol is selected from the group consisting of propylene glycol, butylene glycol. hexylene glycol and glycerin (and mixtures thereof); and the secondary polar solvent is selected from the group consisting of dimethyl isosorbide, diethylene glycol monoethyl ether, a liquid polyethylene glycol and glycofurol.

In certain embodiments, the foamable carrier contains (1) at least one polyol; and (2) dimethyl isosorbide.

Short chain alcohols, such as ethanol and propanol are known as polar solvents, however, according to one or more embodiments, the composition is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable polar solvents due to their skin-irritating effect.

Thus, in certain embodiments, the composition is substantially alcohol-free and includes less than about 5% final concentration of lower alcohols, preferably less than about 2%, more preferably less than about 1%. However, in other embodiments, a short chain alcohol can be included in the composition, as long as the ratio between the short chain alcohol and the polyol is less than 1:4 by weight.

Modulating Agent

The term modulating agent is used to describe an agent which can improve the stability of or stabilize a foamable carrier or composition and or an active agent by modulating the effect of a substance or residue present in the carrier or composition. The substance or residue may for example be acidic or basic and potentially alter an artificial pH in a waterless or substantially non aqueous environment or it may be one or more metal ions which may act as a potential catalyst in a waterless or substantially non aqueous environment.

In one or more embodiments, the modulating agent is used to describe an agent which can affect pH in an aqueous solution. The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments, the modulating agent is used to describe an agent, which is a chelating or sequestering or complexing agent that is sufficiently soluble or functional in the waterless solvent to enable it to "mop up" or "lock" metal ions.

In the embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of a waterless or substantially non aqueous carrier, composition, foamable carrier or foamable composition or resultant foam.

The substance or residue can be introduced into the formulation from any one or more of the ingredients, some of which themselves may have acidic or basic properties. For example the polymer or solvent may contain basic residues in which case it may be desirable or beneficial to add an acid. Alternatively the surfactant may contain some acid residues in which case the addition of a base may be desirable and beneficial. In some cases more than one ingredient may contain residues which may ameliorate or compound their significance. For example if one ingredient provided weak acid residues and another stronger acid residues the artificial pH in a waterless environment should be lower. In contrast if one residue was acid and the other basic the net effect in the formulation maybe significantly reduced. In an embodiment sufficient modulating agent is added to achieve an artificial pH in which the active agent is preferably stable.

The terms pH, pKa, and pKb, buffers and the like are used in classical measurements of an aqueous solution. Such measurements are artificial in a waterless environment. Nevertheless, reference to and description below of such terms are made for convenience and clarity, since such terms are well defined and understood with reference to aqueous solutions and further due to the lack of an appropriate uniform way of describing and identifying the artificial or virtual pH, pK etc in a waterless environment in relation to the present invention. Although predictions of artificial pH can be made using dilution techniques of measurements of waterless formulations diluted in water they are formulation sensitive and specific and have to be carefully calibrated with complex formulas.

Waterless medium can be polar and protic yet it does not conform to classical ionic behavior.

A buffer, as defined by Van Slyke [Van Slyke, *J. Biol. Chem.* 52, 525 (1922)], is "a substance which by its presence in solution increases the amount of acid or alkali that must be added to cause unit change in pH."

A buffer solution is a solution of a definite pH made up in such a way that this pH alters only gradually with the addition of alkali or acid. Such a solution consists of a solution of a salt of the week acid in the presence of the three acid itself. The pH of the solution is determined by the dissociation equilibrium of the free acid.

An acid can be a strong acid or a weak acid. A strong acid is an acid, which is a virtually 100% ionized in solution. In contrast, a week acid is one which does not ionize fully. When it is dissolved in water. The lower the value for pKa, the stronger is the acid and likewise, the higher the value for pKa the weaker is the acid.

A base can be a strong base or a weak base. A strong base is something, which is fully ionic with 100% hydroxide ions. In contrast, a weak base is one which does not convert fully into hydroxide ions in solution. The lower the value for pKb, the stronger is the base and likewise, the higher the value for pKb the weaker is the base.

In one or more preferred embodiments the chelating agent is selected from the group consisting of ethylenediaminetetraacetic acid ("EDTA") and salts thereof such as disodium EDTA, tetrasodium EDTA and calcium disodium EDTA; diethylenetriaminepentaacetic acid ("DTPA") and salts thereof, hydroxyethylethylenediaminetriacetic acid ("HEDTA") and salts thereof and nitrilotriacetic acid ("NTA"); more preferably EDTA, HEDTA and their salts; most preferably EDTA and its salts.

In one or more embodiments a preferred non limiting example of the chelating agent is EDTA. Typically, the chelating and sequestering agent is present in the composition at a level of up to about 5.0%, preferably 1.0 percent, by weight, of the composition.

In another aspect the active agents are ideally so far as is possible delivered onto the skin or within a body cavity at a pH of from about 3.5 to about 7.5, more preferably at a pH of about 4.5 to about 6.5. Thus in another aspect the modulating agents may help to create an artificial pH more suited to the skin or mucosal membrane requirements.

In one or more embodiments, the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. In one or more embodiments the modulating agent is a flavonoid. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

In one or more embodiments the formulations described herein may further contain a modulating agent.

Microsponges

The Microsponges are rigid, porous and spongelike round microscopic particles of cross-linked polymer beads (e.g., polystyrene or copolymers thereof), each defining a substantially noncollapsible pore network. The Microsponges can be loaded with an active ingredient and can provide a controlled time release of the active ingredient to skin or to a mucosal membrane upon application of the formulation. The slow release is intended to reduce irritation by the active. Microsponge® delivery technology was developed by Advanced Polymer Systems. In one or more embodiments the composition comprises one or more active agents loaded into Microponges with an aqueous carrier or with a waterless carrier described herein which may comprise a modulating agent.

Polymeric Agent

In one or more embodiments the composition contains a polymeric agent. It has been documented that the presence of a polymeric agent is necessary for the creation of foam, having fine bubble structure, which does not readily collapse upon release from the pressurized aerosol can. The polymeric agent serves to stabilize the foam composition and to control drug residence in the target organ. Preferably, the polymeric agent is soluble or readily dispersible in the polyol; or in the mixture of a polyol and an additional polar solvent.

Non-limiting examples of polymeric agents that are soluble or readily dispersible in propylene glycol are Hydroxypropylcellulose and carbomer (homopolymer of acrylic acid is crosslinked with an allyl ether pentaerythritol, an allyl ether of sucrose, or an allyl ether of propylene, such as Carbopol® 934, Carbopol® 940, Carbopo® 941, Carbopol® 980 and Carbopol® 981.

Other polymeric agents are suitable for use according to the present invention provided that they are soluble or readily dispersible in the polyol; or in the mixture of a polyol and an additional polar solvent, on a case by case basis.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses. Polyethylene glycol, having molecular weight of 1000 or more (e.g., PEG 1,000, PEG 1500 PEG 4,000, PEG 6,000 and PEG 10,000) also have gelling capacity and while they are considered herein as "secondary polar solvents", as detailed herein, they are also considered polymeric agents.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 52,000 CPS, less than 12,000 CPs, and more preferably, less than 10,000 CPs.

Surface-Active Agent

The composition can further contain a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. As will be appreciated by a person skilled in the art which surfactant or surfactant system is more appropriate is related to the vehicle and intended purpose. In general terms a combination of surfactants is usually preferable where the vehicle is an emulsion. In a waterless or substantially waterless environment it has been discovered that the presence of a surfactant or combination of surfactants can be significant in producing breakable forms of good quality. It has been further discovered that the generally thought considerations for oil in water emulsions of using a surfactant or sufactant combination with preferably a HLB value or average in or towards the lipophilic side of the scale are not binding for waterless or substantially waterless systems as described herein and that good quality foams can be produced with a surfactant or surfactant combination both where the HLB values are in or towards the lipophilic side of the scale and more surprisingly where the HLB values are in or towards the hydrophilic side of the scale.

According to one or more embodiments the composition contains a single surface active agent having an HLB value between about 2 and 9, or more than one surface active agent and the weighted average of their HLB values is between about 2 and about 9.

According to one or more embodiments the composition contains a single surface active agent having an HLB value between about 7 and 14, or more than one surface active agent and the weighted average of their HLB values is between about 7 and about 14.

According to one or more other embodiments the composition contains a single surface active agent having an HLB value between about 9 and about 19, or more than one surface active agent and the weighted average of their HLB values is between about 9 and about 19.

Preferably, the composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, brij 38, brij 52, brij 56 and brij W1, a sucrose ester, a partial ester of sorbitol and its anhydrides, sorbitan monolaurate, sorbitan monolaurate a monoglyceride, a diglyceride, isoceteth-20 and mono-, di- and tri-esters of sucrose with fatty acids.

Non-limiting examples of non-ionic surfactants that have HLB of about 7 to about 12 include steareth 2 (HLB~4.9); glyceryl monostearate/PEG 100 stearate (Av HLB~11.2); stearate Laureth 4 (HLB~9.7) and cetomacrogol ether (e.g., polyethylene glycol 1000 monocetyl ether). Exemplary stabilizing surfactants which may be suitable for use in the present invention are found below.

| PEG-Fatty Acid Monoester Surfactants | | |
|---|---|---|
| Chemical name | Product example name | HLB |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

| PEG-Fatty Acid Diester Surfactants | | |
|---|---|---|
| Chemical name | Product example name | HLB |
| PEG-4 dilaurate | Mapeg .RTM. 200 DL (PPG), Kessco .RTM. PEG 200 DL (Stepan), LIPOPEG 2-DL (Lipo Chem.) | 7 |
| PEG-4 distearate | Kessco .RTM. 200 DS (Stepan.sub) | 5 |
| PEG-32 dioleate | Kessco .RTM. PEG 1540 DO (Stepan) | 15 |
| PEG-400 dioleate ) | Cithrol 4DO series (Croda) | >10 |
| PEG-400 disterate | Cithrol 4DS series (Croda) | >10 |
| PEG-20 glyceryl oleate | Tagat .RTM. O (Goldschmidt) | >10 |

| Transesterification Products of Oils and Alcohols | | |
|---|---|---|
| Chemical name | Product example name | HLB |
| PEG-30 castor oil | Emalex C-30 (Nihon Emulsion) | 11 |
| PEG-40 hydrogenated castor oil) | Cremophor RH 40 (BASF), Croduret (Croda), Emulgin HRE 40 (Henkel) | 13 |

| Polyglycerized Fatty Acids | | |
|---|---|---|
| Chemical name | Product example name | LB |
| Polyglyceryl-6 dioleate | Caprol .RTM. 6G20 (ABITEC); PGO-62 (Calgene), PLUROL OLEIQUE CC 497 (Gattefosse)Hodag | 8.5 |

| PEG-Sorbitan Fatty Acid Esters | | |
|---|---|---|
| Chemical name | Product example name | HLB |
| PEG-20 sorbitan monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan | Tween-80 (Atlas/ICI), Crillet 4 (Croda) | 15 |
| PEG-20 sorbitan | Tween-80 (Atlas/ICI), Crillet 4 (Croda) | 15 |

| Polyethylene Glycol Alkyl Ethers | | |
|---|---|---|
| Chemical name | Product example name | HLB |
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

| Sugar Ester Surfactants | | |
|---|---|---|
| Chemical name | Product example name | HLB |
| Sucrose distearate | Sisterna SP50, Surfope 1811 | 11 |

| Sorbitan Fatty Acid Ester Surfactants | | |
|---|---|---|
| Chemical name | Product example name | HLB |
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable emulsion or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij 10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequestrate; polymeric emulsifiers, such as Permulen (TR1 or TR2); liquid crystal systems, such as Arlatone (2121), Stepan (Mild RM1), Nikomulese (41) and Montanov (68) and the like.

In certain embodiments the surfactant is preferably a combination of steareth-2 and steareth-21; in certain other embodiments the surfactant is a combination of polysorbate 80 and PEG-40 stearate. In certain other embodiments the surfactant is a combination of glyceryl monostearate/PEG 100 stearate In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect. Non limiting examples of surfactants with postulated tendency to form interfacial liquid crystals are: phospholipids, alkyl glucosides, sucrose esters, sorbitan esters. In certain embodiments surfactants which tend to form liquid crystals may improve the quality of foams produced from compositions.

In one or more embodiments the surfactant is a surfactant or surfactant combination is capable of or which tends to form liquid crystals.

In one or more embodiments the at least one surface active agent is solid, semi solid or waxy.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide formulations and foams of good or excellent quality in the waterless and substantially waterless carriers and compositions.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In further embodiments, surface active agent comprises a combination of a non-ionic surfactant and an ionic surfactant, at a ratio of between 1:1 and 20:1.

In selecting a suitable surfactant or combination thereof it should be borne in mind that the upper amount of surfactant that may be used may be limited by the shakability of the composition. In general terms, as the amount of non liquid surfactant is increased the shakability of the formulation reduces until a limitation point is reached where the formulation becomes non shakable and unsuitable. Thus in an embodiment any effective amount of surfactant may be used provided the formulation remains shakable. In the present invention where it is desirable to use a high molecular weight solvent and more particularly significant amounts it may be helpful to include a liquid surfactant in addition to or in place of a more waxy surfactant and or to increase the level of the surfactant.

In certain embodiments the amount of surfactant or combination of surfactants is between about 0.05% to about 20%; between about 0.05% to about 15%. or between about 0.05% to about 10%. In a preferred embodiment the concentration of surface active agent is between about 0.2% and about 5%. In a more preferred embodiment the concentration of surface active agent is between about 1% and about 4%

If the composition is formulated as a substantially non flowing composition for use as a gel, ointment or cream, then the above limitation of shakability does not apply. Suitable formulations include polyethylene glycol or derivatives or mixtures thereof or propylene glycol comprising higher levels of waxy or semi solid or solid surfactants and/or comprising higher molecular weight polymers or polymer combinations which are usually waxy or solid at room temperature such as PEG 4000 or Peg 4000/400 combination with significant amounts of say PEG 4000 of 5% of 10% of 15% of 20% of 25% of 30% of as a basis for gels, ointments or creams. Other similar combinations may be envisaged of say PEG6000/PEG200; PEG4000/PEG200; PEG4000/PEG400/PEG200; and the like.

In one or more embodiments there is provided a composition, comprising:
  about more than 3% of high molecular weight solid PEG;
  a waterless solvent comprising about 25% to about 95% of at least a polar solvent selected from the group consisting of (1) a propylene glycol or derivative and (2) a polyethylene glycol (PEG) or derivative or mixtures thereof;
  0% to about 48% of a secondary waterless solvent;
  a surface-active agent at a concentration of about 0.1% to less than about 10% by weight of the total composition; and or
  at least one polymeric agent at a concentration of about 0.1% to about 5% by weight of the total composition, wherein the at least one polymeric agent is selected from a bioadhesive agent, a gelling agent, a film forming agent and a phase change agent which is selected such that it has some surfactant properties if it is used in the absence of surface active agent; and
  a therapeutically effective amount of an active agent.

In one or more further embodiments there is provided a composition, comprising:
  a mixture of polyethylene glycol (PEG) or PEG derivatives, wherein the PEG mixtures is present at a concentration of about 70% to about 96.5% by weight of the total composition;
  0% to about 28% of a secondary solvent
  a surface-active agent at a concentration of about 0.1% to less than about 10% by weight of the total composition; and or
  at least one polymeric agent at a concentration of about 0.1% to about 5% by weight of the total composition, wherein the at least one polymeric agent is selected from a bioadhesive agent, a gelling agent, a film forming agent and a phase change agent which is selected such that it has some surfactant properties if it is used in the absence of surface active agent; and
  a therapeutically effective amount of an active agent
  wherein at least one PEG comprises about more than 5% of high molecular weight solid PEG.

As will be appreciated by someone skilled in the art as the levels of PEG are increased the composition will become more suitable for a gel or ointment pharmaceutical or cosmetic composition.

Silicon Oil

Optionally, the foamable carrier may contain silicon oil. In one or more embodiments, the silicone oils, is dimethicone, cyclomethicone, polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers.

Heumectant

A heumectant, is a substance that helps retain moisture and also prevents rapid evaporation. Non limiting examples of suitable heumectants are propylene glycol, propylene glycol derivatives, and glycerin. Further examples are provided elsewhere in the description. Other examples of humectants and moisturizers may be found in the *Handbook of Pharmaceutical Additives* published by Gower. Suitable ones for use with and soluble in the waterless and substantially waterless compositions may be selected as will be appreciated by a person skilled in the art.

In an embodiment, the additional component is a humectant. Suitable humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof.

Pharmaceutical compositions may in one or more embodiments usefully comprise in addition a heumectant or a moisturizer or combinations thereof.

Foam Adjuvant

Optionally, a foam adjuvant is included in the foamable carriers to increase the foaming capacity of surfactants and/or to stabilize the foam. In one or more embodiments, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

Additional Components

In an embodiment, a composition includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, and viscosity modifiers. As is known to one skilled in the art, in some instances a specific additional component may have more than one activity, function or effect.

In an embodiment, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment, the additional component is an emollient. Suitable emollients include but are not limited to mineral oil, lanolin oil, coconut oil, cocoa butter, olive oil, aloe vera extract, jojoba oil, castor oil, fatty acids, fatty alcohols, diisopropyl adipate, hydroxybenzoate esters, benzoic acid esters of C9 to C15 alcohols, isononyl iso-nonanoate, silicone oils, polyethers, C12 to C15 alkyl benzoates, oleic acid, stearic fatty acid, cetyl alcohols, hexadecyl alcohol, dimethyl polysiloxane, polyoxypropylene cetyl ether, polyoxypropylene butyl ether, and derivatives, esters, salts and mixtures thereof.

In an embodiment, the additional component is a preservative. Suitable preservatives include but are not limited to C12 to C15 alkyl benzoates, alkyl p-hydroxybenzoates, aloe vera extract, ascorbic acid, benzalkonium chloride, benzoic acid, benzoic acid esters of C9 to C15 alcohols, butylated hydroxytoluene, castor oil, cetyl alcohols, chlorocresol, citric acid, cocoa butter, coconut oil, diazolidinyl urea, diisopropyl adipate, dimethyl polysiloxane, DMDM hydantoin, ethanol, fatty acids, fatty alcohols, hexadecyl alcohol, hydroxybenzoate esters, iodopropynyl butylcarbamate, isononyl iso-nonanoate, jojoba oil, lanolin oil, methylparaben, mineral oil, oleic acid, olive oil, polyethers, polyoxypropylene butyl ether, polyoxypropylene cetyl ether, potassium sorbate, silicone oils, sodium propionate, sodium benzoate, sodium bisulfite, sorbic acid, stearic fatty acid, vitamin E, vitamin E acetate and derivatives, esters, salts and mixtures thereof.

In an embodiment, the additional component is a skin penetration enhancer. Suitable skin penetration enhancers include but are not limited to acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl)ether, diisopropyl adipate, diisopropyl sebacate, N,N-dimethyl acetamide, dimethyl azelate, N,N-dimethyl formamide, 1,5-dimethyl-2-pyrrolidone, dimethyl sebacate, dimethyl sulphoxide, dioctyl adipate, dioctyl azelate, dioctyl sebacate, 1,4 dioxane, 1-dodecylazacycloheptan-2-one, dodecyl dimethyl amine oxides, ethyl caprate, ethyl caproate, ethyl caprylate, 2-ethyl-hexyl pelargonate, ethyl-2-hydroxypropanoate, ethyl laurate, ethyl myristate, 1-ethyl-2-pyrrolidone, ethyl salicylate, hexyl laurate, 2-hydroxyoctanoic acid, 2-hydroxypropanoic acid, 2-hydroxypropionic acid, isethionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methyl propan-2-ol, 1-methyl-2-pyrrolidone, 5-methyl-2-pyrrolidone, methyl taurides, miranol, nonionic surface-active agents, octyl alcohol, octylphenoxy polyethoxyethanol, oleic ethanolamide, pleyl alcohol, pentan-2,4-diol, phenoxyethanol, phosphatidyl choline, phosphine oxides, polyalkoxylated ether glycollates, poly(diallylpiperidinium chloride), poly(dipropyldiallylammonium chloride), polyglycerol esters, polyoxyethylene lauryl ether, polyoxy:polyoxyethylene stearate, polyoxypropylene 15 stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternised poly (dimethylaminoethylmethacryl-ate), quaternised poly (vinyl alcohol), sapamin hydrochloride, sodium cocaminopropionate, sodium dioctyl sulphonsuccinate, sodium laurate, sodium lauryl ether sulphate, sodium lauryl sulphate, sugar esters, sulphosuccinate, tetrahydrofuran, tetrahydrofurfural alcohol, transcutol, triethanolamine dodecyl benzene sulphonate, triethanolamine oleate, urea, water and derivatives, esters, salts and mixtures thereof.

Lubricants may be introduced into any of the formulations to reduce friction during application. This may be useful for producing a good skin feeling or ease of body cavity use. Any pharmaceutically or cosmetically acceptable lubricant may be used. Non limiting examples of general categories of lubricants are; polymeric substances such as celluloses, natrosol; hyaluronic acid; glycerin; silicones (e.g. dimethicone); and oil based lubricants such as plant based oils (e.g. olive oil, sweet almond oil; avocado oil and the like); petrolatum; and fats. In some situations it may be appropriate to select a polymeric agent having a viscosity and also a lubricating effect such that it has some adherence to the site of application but displays a reduced fricion and is easier and more pleasant to use.

In one or more embodiments there are provided compositions comprising polymeric agents which have both a viscosity and anti friction effect.

Propellants

Examples of suitable propellants include volatile hydrocarbons such as butane, propane, isobutane and fluorocarbon gases, or mixtures thereof.

In an embodiment the propellant is 1681, which is a mixture of propane, isobutene and butane. In another embodiment it is AP 70, which is a mixture of propane, isobutene and butane with a higher pressure.

The propellant makes up about 5-25 wt % of the foamable composition. In some circumstances the propellant may be up to 35%. The propellants are used to generate and administer the foamable composition as a foam. The total composition including propellant, foamable compositions and optional ingredients is referred to as the foamable composition.

Alcohol and organic solvents render foams inflammable. It has been surprisingly discovered that fluorohydrocarbon propellants, other than chloro-fluoro carbons (CMCs), which are non-ozone-depleting propellants, are particularly useful in the production of a non-flammable foamable composition. Such propellants include, but are not limited to, hydrofluorocarbon (HFC) propellants.

In one or more embodiments, the non inflammable propellants are used in combination with the more traditional hydrocarbon propellants.

In one or more embodiments foamable compositions comprise a combination of a HFC such as dimethyl ether and a hydrocarbon propellant such as n-butane or mixtures of hydrocarbon propellants such as propane, isobutane and butane.

In certain embodiments, fluorohydrocarbon propellants, other than chloro-fluoro carbons (CMCs) which are non-ozone-depleting propellants, are particularly useful in the production of a non-flammable foamable composition.

Such propellants include, but are not limited to hydrofluorocarbon (HFC) propellants, that contain no chlorine atoms, and as such, falls completely outside concerns about stratospheric ozone destruction by chlorofluorocarbons or other chlorinated hydrocarbons. Exemplary non-flammable propellants according to this aspect include propellants made by DuPont under the registered trademark Dymel, such as 1,1, 1,2 tetrafluoroethane (Dymel 134), and 1,1,1,2,3,3,3 heptafluoropropane (Dymel 227), 1,1, difluoro ethane (Dymel 152) and 1,1,1,3,3,3 hexafluoropropane. HFCs possess Ozone Depletion Potential of 0.00 and thus, they are allowed for use as propellant in aerosol products.

The propellant makes up about 5-25 wt % of the foamable composition. Aerosol propellants are used to generate and administer the foamable composition as a foam. The total composition including propellant, foamable compositions and optional ingredients is referred to as the foamable composition.

Hygroscopic Property of the Composition

A hydroscopic substance is a substance that absorbs water readily from its surroundings. Microorganisms require water to grow and reproduce, and such water requirements are best defined in terms of water activity of the substrate. The water activity of a solution is expressed as Aw=P/Po, where P is the water vapor pressure of the solution and Po is the vapor pressure of pure water at the same temperature. Addition of a hygroscopic substance to an aqueous solution in which a microorganism is growing will have the effect of lowering the Aw, with a consequent effect upon cell growth. Every microorganism has a limiting Aw, below which it will not grow, e.g., for *streptococci, klebsiella* spp., *escherichia coli, clostridium perfringens*, and *pseudomonas* spp., the Aw value is 0.95. *Staphylococcus aureus* is most resistant and can proliferate with an Aw as low as 0.86.

The water activity of a product can be determined from the relative humidity of the air surrounding the sample when the air and the sample are at equilibrium. Measurement is performed by placing a sample in an enclosed space where this equilibrium can take place. Once this occurs, the water activity of the sample and the relative humidity of the air are equal. The measurement taken at equilibrium is called an equilibrium relative humidity or ERH. The relationship between the water activity and ERH is in accordance with the following formula:

$$Aw=ERH/100$$

Various types of water activity instruments are commercially available. One exemplary instrument uses chilled-mirror dewpoint technology while other instruments measure relative humidity with sensors that change electrical resistance or capacitance.

Polyols, PEG's propylene glycols and other polar solvents have a great affinity for water, and as such, they exhibit hygroscopic properties. The concentration of the polyol, the PEG and/or other polar solvents determines the Aw of the carrier. In one or more embodiments, the polyols, the PEG and/or the secondary polar solvent is contained in the composition at a sufficient concentration to provide an Aw value of the hygroscopic carrier of less than 0.9. In other embodiments, the concentration of the polyol, the PEG and/or secondary polar solvent in the composition is selected to provide a Aw value selected from the ranges of (1) about 0.8 and about 0.9; (2) about 0.7 and about 0.8; and (3) less than about 0.7.

As such, a composition containing a polyol, a PEG with or without a secondary polar solvent can be used as topical treatment of superficial infectious conditions.

The advantage of providing a hygroscopic composition in a pressurized packaging presentation is readily perceived. The usage of all other presentations, such as solutions, creams, lotions, ointments and the like involves repeated opening of the package closure, resulting in absorption of water from the surrounding environment and a subsequent elevation of the Aw (thus lowering the hygroscopicity of the product, and therefore decreasing its anti-infective potential. By contrast, a pressurized packaging does not allow for any humidity to be absorbed by the preparation, and therefore, the hygroscopic character of the composition cannot be damaged.

In one or more embodiments, the hygroscopic composition further contains an anti-infective agent, selected from the group of an antibiotic agent, an antibacterial agent, an antifungal agent, an agent that controls yeast, an antiviral agent and an antiparasitic agent. Combining the anti-infective effect of a hygroscopic composition, which acts through a dehydration mechanism, with an additional anti-infective agent that acts through alternate mechanisms results in a synergistic effect and consequently higher success rate of the treatment.

Composition and Foam Physical Characteristics and Advantages

A pharmaceutical or cosmetic composition manufactured using the foamable carrier is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition is stable, having an acceptable shelf-life of at least one year, or preferably, at least two years at ambient temperature, as revealed in accelerated stability tests. Organic carriers and propellants tend to impair the stability of emulsions and to interfere with the formation of stable foam upon release from a pressurized container. It has been observed, however, that the foamable compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

The foam has several advantages, when compared with hydroalcoholic foam compositions, such as described in WO 2004/071479.

Breakability. The foam is thermally stable. Unlike hydroalcoholic foam compositions of the prior art, the foam is not "quick breaking", i.e., it does not readily collapse upon exposure to body temperature environment. Sheer-force breakability of the foam is clearly advantageous over thermally induced breakability, since it allows comfortable application and well directed administration to the target area.

1. Skin drying and skin barrier function. Short chain alcohols are known to dry the skin and impair the integrity of the skin barrier. By contrast, including a film forming agent in the composition foes not cause unwanted skin barrier damage.
2. Irritability. Due to the lack of alcohol and improvement in skin barrier function, skin irritability is eliminated.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Pharmaceutical Composition

The foamable composition is an ideal vehicle for vitamins, active pharmaceutical ingredients and active cosmetic ingredients. In the context, active pharmaceutical ingredients and active cosmetic ingredients are collectively termed "active agent(s)" or "therapeutic agent(s)". A foamable composition, comprising an active agent has the following advantages:

1. The foamable composition provides a preferred solvent for active agents, particularly water-insoluble agents.
2. The inclusion of a propylene glycol and/or a PEG and a secondary polar solvent in the foamable composition facilitates a co-solvent effect, resulting increased concentrations of soluble active agent in the dosage form, thus facilitating enhanced skin penetration of the active agent. In many cases, increased penetration is positively correlated with improved clinical outcome. In certain case, attaining an increased drug penetration into the target site of action enables a decrease of treatment frequency, for example, from twice or three times daily to once daily.
3. Polyols and PEGs; and combinations of a polyol and/or PEG with a secondary polar solvent are known as skin penetration enhancers, thus, increasing drug residence in the target area and increasing clinical efficacy, as detailed above.
4. The fact that the composition contains no water, substantially no water or up to 10% water or up to 25% water and is hydrophilic minimizes the probability of degradation of water-sensitive active agents. Furthermore, as exemplified herein, a foam containing a polyol and/or PEG with no water at all can be formed in accordance with the composition and process. Such compositions ensure high stability of water sensitive active agents.
5. Combining the anti-infective effect of a hygroscopic composition, which acts through a dehydration mechanism, with an additional anti-infective agent, selected from the group of an antibiotic agent, an antibacterial agent, an antifungal agent, an agent that controls yeast, an antiviral agent and an antiparasitic agent, that acts through alternate mechanisms results in a synergistic effect and consequently higher success rate of the treatment.

6. The foamable polyol composition in contained in an impermeable pressurized packaging presentation is impermeable and thus, the active agent is not exposed to environmental degradation factors, such as light and oxidating agent during storage.

Thus, in a preferred embodiment, the composition includes at least one active agent being a therapeutically effective concentration of at least one active agent; and A waterless composition suitable for delivery of an active agent to a body surface or cavity comprising:
a vehicle comprising:
  a) about 70% to about 99% by weight of a hydrophilic polar solvent, said hydrophilic solvent selected from the group consisting of:
    i) a mixture of two or more different polyethylene glycols (PEGs), wherein at least one PEG is a high molecular weight PEG having a melting point greater than 25° C.; and
    ii) propylene glycol (PG);
  b) about 0% to about 10% of at least one surface active agent;
  c) about 0% to about 5% of a polymeric agent;
  d) about 0% to about 30% of a secondary hydrophilic solvent; and
  e) about 0% to about 5% of a silicone oil; and
  about 3% to about 25% hydrophobic propellant;
wherein the composition is otherwise substantially free of a hydrophobic solvent;
wherein the composition includes at least one of a surface active agent and a polymeric agent; and
wherein the vehicle and the propellant are sufficiently miscible that the components may be homogeneously distributed with mild shaking.

In another preferred embodiment, the composition includes at least one active agent being a therapeutically effective concentration of at least one active agent; and A waterless composition suitable for delivery of an active agent to a body surface or cavity comprising:
a vehicle, comprising:
  a) about 70% to about 99% by weight of a hydrophilic polar solvent comprising butylene glycol (BG)
  b) about 0% to about 10% of at least one surface active agent;
  c) about 0% to about 5% of a polymeric agent;
  d) about 0% to about 30% of a secondary hydrophilic solvent; and
  e) about 0% to about 5% of an unmodified silicone; and
  about 3% to about 25% hydrophobic propellant;
wherein the composition is otherwise substantially free of a hydrophobic solvent;
wherein the composition includes at least one of a surface active agent and a polymeric agent; and
wherein the components of the composition are sufficiently miscible that the vehicle and the propellant do not phase separate upon centrifugation at about 1000 rpm for about 10 mins.

In another preferred embodiment, the composition includes at least one active agent being a therapeutically effective concentration of at least one active agent; and A waterless composition suitable for delivery of an active agent to a body surface or cavity comprising:
a vehicle, comprising:
  a) about 70% to about 99% by weight of a hydrophilic polar solvent, said hydrophilic solvent selected from the group consisting of polyethylene glycols (PEGs) and propylene glycol (PG);
  b) about 0.1% to about 10% of at least one surface active agent, a surface active agent is present in the composition and is a mixture of a Brij surfactant and a Twin surfactant, wherein the Brij surfactant is the major surface active agent component;
  c) about 0% to about 5% of a polymeric agent;
  d) about 0% to about 30% of a secondary hydrophilic solvent; and
  e) about 0% to about 5% of an unmodified silicone; and
  about 3% to about 25% hydrophobic propellant;
wherein the composition is otherwise substantially free of a hydrophobic solvent; and
wherein the components of the composition are sufficiently miscible that the propellant and vehicle may be homogeneously distributed with mild shaking.

In another preferred embodiment, the composition includes at least one active agent being a therapeutically effective concentration of at least one active agent; and A waterless composition suitable for delivery of an active agent to a body surface or cavity comprising:
a vehicle comprising:
  a) about 70% to about 99% by weight of a hydrophilic polar solvent, said hydrophilic solvent comprising a mixture of PEG 200 and PEG 400;
  b) about 0% to about 10% of at least one surface active agent;
  c) about 0% to about 5% of a polymeric agent;
  d) about 0% to about 30% of a secondary hydrophilic solvent; and
  e) about 0% to about 5% of a silicone oil; and
  about 3% to about 25% hydrophobic propellant;
wherein the composition is otherwise substantially free of a hydrophobic solvent;
wherein the composition includes at least one of a surface active agent and a polymeric agent; and
wherein the vehicle and the propellant are sufficiently miscible that the components may be homogeneously distributed with mild shaking.

In the context of combining a hygroscopic carrier according to the present invention and an anti-infective active agent, a pharmaceutical composition is provided, including:
a. a hygroscopic substance at a sufficient concentration to provide an Aw value of the hygroscopic carrier of less than 0.9. The concentration of the hygroscopic substance in the composition can be designed to provide a Aw value selected from the ranges of (1) about 0.8 and about 0.9; (2) about 0.7 and about 0.8; and (3) less than about 0.7;
b. about 0.2% to about 5% by weight of a surface-active agent;
c. about 0.01% to about 5% by weight of at least one polymeric agent selected from a bioadhesive agent, a gelling agent, a film forming agent and a phase change agent;
d. a therapeutically effective concentration of an anti-infective agent; and
e. a liquefied or compressed gas propellant at a concentration of about 3% to about 25% by weight of the total composition.

An exemplary case for the inclusion of an anti-infective agent in a hygroscopic composition is provided herewith. It has been surprisingly discovered that combining an antifungal agent in a hygroscopic composition results in an anti-infective effect on strains that are not supposed to be affected by the said antifungal agent. For example, terbinafine is know to be highly effective against dermatophite pathogens, but not against candida. In-vitro studies have revealed, however that terbinafine, dissolved in a hygroscopic carrier, effectively inhibited the spreading of candida albicans, while a control preparation, comprising the same concentration of terbinafine in an emulsion base was not effective. Thus, combining an antifungal agent in a hygroscopic composition results in an expansion of the spectrum of infective strains that can benefit form the therapy, and furthermore, in can render an improved effect of such a composition on mixed infections or in infections that are not accurately diagnosed.

Consequently, in another aspect, a pharmaceutical composition, which possesses an improved antifungal activity or that possesses an antifungal activity on an expanded spectrum of pathogens, is provided, including:

a. a hygroscopic composition, comprising a hygroscopic substance at a sufficient concentration to provide an Aw value of the hygroscopic carrier of less than 0.9. The concentration of the hygroscopic substance in the composition can be designed to provide a Aw value selected from the ranges of (1) about 0.8 and about 0.9; (2) about 0.7 and about 0.8; and (3) less than about 0.7; and b. an anti-infective agent, selected from the group of an antibiotic agent, an antibacterial agent, an antifungal agent, an agent that controls yeast, an antiviral agent and an antiparasitic agent. Preferably, the anti-infective agent is an antifungal agent, and more preferably the anti-infective agent is terbinafine.

Active Agents

Active agents can be used on their own or in combination with other agents. Suitable therapeutic agents include but are not limited to active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin D derivatives, wound healing agents and wart removers. As is known to one skilled in the art, in some instances a specific active agent may have more than one activity, function or effect.

In an embodiment, the therapeutic agent is an active herbal extract. Suitable active herbal extracts include but are not limited to angelica, anise oil, astragali radix, azalea, benzyl acetate, birch tar oil, bornyl acetate, cacumen biotae, camphor, cantharidin, capsicum, cineole, cinnamon bark, cinnamon leaf, citronella, citroneliol, citronellyl acetate, citronellyl formate, eucalyptus, eugenyl acetate, flos carthami, fructus mori, garlic, geraniol, geranium, geranyl acetate, habanera, isobutyl angelicate, lavender, ledum latifolium, ledum palustre, lemongrass, limonene, linalool, linalyl acetate, methyl anthranilate, methyl cinnamate, mezereum, neem, nerol, neryl acetate, nettle root extract, oleum ricini, oregano, pinenes, .alpha.-pinene, .beta.-pinene, radix angelicae sinesis, radix paenoiae rubra, radix polygoni multiflori, radix rehmanniae, rhizoma pinelliae, rhizoma zingiberis recens, sabadilla, sage, sandalwood oil, saw palmetto extract, semen sesami nigrum, staphysagria, tea tree oil, terpene alcohols, terpene hydrocarbons, terpene esters, terpinene, terpineol, terpinyl acetate and derivatives, esters, salts and mixtures thereof. In an embodiment, the active agent is an acaricide. Suitable acaricides include but are not limited to amitraz, flumethrin, fluvalinate and derivatives, esters, salts and mixtures thereof.

In an embodiment, the therapeutic agent is an age spot and keratoses removing agent. Suitable age spot and keratoses removing agent include but are not limited to hydroxy acids, azelaic acid and other related dicarboxylic acids, retinoids, kojic acid, arbutin, nicotinic, ascorbic acid, hydroquinone and derivatives, esters, salts and mixtures thereof. Certain nonsteroidal anti-inflammatory agents, such as diclofenac are also useful for the treatment of keratoses.

In an embodiment, the therapeutic agent is an analgesic. Suitable analgesics include but are not limited to benzocaine, butamben picrate, dibucaine, dimethisoquin, dyclonine, lidocaine, pramoxine, tetracaine, salicylates and derivatives, esters, salts and mixtures thereof.

In an embodiment, the therapeutic agent is a local anesthetic. Suitable local anesthetics include but are not limited to benzocaine, benzyl alcohol, bupivacaine, butamben picrate, chlorprocaine, cocaine, dibucaine, dimethisoquin, dyclonine, etidocaine, hexylcaine, ketamine, lidocaine, mepivacaine, phenol, pramoxine, procaine, tetracaine, salicylates and derivatives, esters, salts and mixtures thereof.

In an embodiment, the therapeutic agent is an antiacne agent. Suitable antiacne agents include but are not limited to N-acetylcysteine, adapalene, azelaic acid, benzoyl peroxide, cholate, clindamycin, deoxycholate, erythromycin, flavinoids, glycolic acid, meclocycline, metronidazol, mupirocin, octopirox, phenoxy ethanol, phenoxy proponol, pyruvic acid, resorcinol, retinoic acid, salicylic acid, scymnol sulfate, sulfacetamide-sulfur, sulfur, tazarotene, tetracycline, tretinoin triclosan and derivatives, esters, salts and mixtures thereof.

In an embodiment, the therapeutic agent is an antiaging agent. Suitable antiaging agents include but are not limited to sulfur-containing D and L amino acids, alpha-hydroxy acids s, beta-hydroxy acids (e.g. salicylic acid), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate) skin barrier forming agents, melatonin and derivatives, esters, salts and mixtures thereof.

Dicarboxylic Acid and Esters Thereof

In an embodiment, the organic carrier comprises an ester of a dicarboxylic acid. In the context, a dicarboxylic acid is an organic material, having two carboxylic acid moieties on its carbon atom skeleton. They have the general molecular formula $HOOC-(CH_2)_n-COOH$.

In an embodiment, the dicarboxylic acid is a short-chain dicarboxylic acid. The simplest Short-chain dicarboxylic acid are oxalic acid (n=0), malonic acid (n=1), succinic acid (n=2) and glutaric acid (n=3).

Additional members of dicarboxylic acid group are derived from natural products or from synthesis, having "n" value from 4 up to 21. In one or more embodiments, the dicarboxylic acid is selected from the group consisting of adipic acid (hexanedioic acid; n=4), pimelic acid (heptanedioic acid; n=5), suberic acid (octanedioic acid; n=6), azelaic acid (nonanedioic acid; n=7), sebacic acid (decanedioic acid; n=8) and dodecanedioic acid (n=10).

In an additional embodiment, the dicarboxylic acid contains 10 to 32 carbon atoms in their carbon atom skeleton, such as brassylic acid (n=11), thapsic acid (n=14), 14-methylnonacosanedioic acid (C29) and 14,15-dimethyltriacontanedioic acid (C30).

The carbon atom skeleton of the dicarboxylic acid can be saturated or unsaturated, such as in the case of maleic acid and fumaric acid.

An ester of a dicarboxylic acid is a chemical compound produced by the reaction between a dicarboxylic acid and at least one alcohol, with the elimination of a molecule of water. The reaction of a dicarboxylic acid with one alcohol molecule results in a mono ester of said dicarboxylic acid, and the reaction of a dicarboxylic acid with two alcohol molecules results in a diester of the dicarboxylic acid.

The alcohol molecule, to be linked to the dicarboxylic acid, can be selected from the group of an alkyl an aryl alcohol. Exemplary alcohol, suitable according to the present invention include methyl alcohol, ethyl alcohol, propyl alcohol, isopropyl alcohol, butyl alcohol, isobutyl alcohol, t-butyl alcohol, pentyl alcohol, hexyl alcohol, octyl alcohol, decyl alcohol, capryl alcohol, phenol, benzyl alcohol and the like.

In one or more embodiments, the alcohol is a biologically active alcohol. In an embodiment, biologically active alcohol possesses keratolytic activities. Examples of keratolytically active alcohol suitable according to the present invention include ortho-, meta- and para-hydroxyalkylbenzoate, salicylic acid, ortho-, meta-, and para-dihydroxybenzene, ortho-, meta-, and para-hydroxytoluene, alpha-hydroxy acid, retinol, and derivatives thereof such as provided in U.S. Pat. No. 6,180,669. 22. In an embodiment, the biologically active alcohol is selected from the group consisting of steroidal hormones, steroidal anti-inflammatory agents, vitamin E and vitamin D, such as provided in U.S. Pat. Appl. 20040191196.

Antibiotics

In an embodiment, the therapeutic agent is an antibiotic. The terms "antibiotic" as used herein shall include, but is not limited to, any substance being destructive to or inhibiting the growth of bacteria or any substance having the capacity to inhibit the growth of or to destroy bacteria.

In one or more embodiments, the antibiotic agent is selected from the group consisting of a beta-lactam antibiotic, an aminoglycoside, an ansa-type antibiotic, an anthraquinone, an azole, an antibiotic glycopeptide, a macrolide, an antibiotic nucleoside, an antibiotic peptide, an antibiotic polyene, an antibiotic polyether, an antibiotic quinolone, an antibiotic steroid, a sulfonamide, an antibiotic metal, an oxidizing agent, a periodate, a hypochlorite, a permanganate, a substance that release free radicals and/or active oxygen, a cationic antimicrobial agent, a quaternary ammonium compound, a biguanide, a triguanide, a bisbiguanide, a polymeric biguanide, and analogs, derivatives, salts, ions and complexes thereof.

Suitable antibiotics include but are not limited to amanfadine hydrochloride, amanfadine sulfate, amikacin, arnikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocyldline, iodate, iodine, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, microcrystalline and nanocrystalline particles of silver, copper, zinc, mercury, tin, lead, bismuth, cadmium and chromium, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof.

In one or more embodiments, the antibiotic agent is selected from the classes consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds.

Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefmenoxime, cefmetazole, cefminox, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3',4'-dideoxykanamycin B, 1,2'-N-DL-isoserylkanamycin B, 1,2'-N—[(S)-4-amino-2-hydroxybutyryl]-3',4'-dideoxykanamycin B, 1,2'-N—[(S)-4-amino-2-hydroxybutyryl]-kanamycin B, 1-N-(2-Aminobutanesulfonyl) kanamycin A, 1-N-(2-aminoethanesulfonyl)3',4'-dideoxyribostamycin, 1-N-(2-Aminoethanesulfonyl)3'-deoxyribostamycin, 1-N-(2-aminoethanesulfonyl)3'4'-dideoxykanamycin B, 1-N-(2-aminoethanesulfonyl)kanamycin A, 1-N-(2-aminoethanesulfonyl)kanamycin B, 1-N-(2-aminoethanesulfonyl)ribostamycin, 1-N-(2-aminopropanesulfonyl)3'-deoxykanamycin B, 1-N-(2-aminopropanesulfonyl)3'4'-dideoxykanamycin B, 1-N-(2-aminopropanesulfonyl)kanamycin A, 1-N-(2-aminopropanesulfonyl)kanamycin B, 1-N-(L-4-amino-2-hydroxy-butyryl)2,'3'-dideoxy-2'-fluorokanamycin A, 1-N-(L-4-amino-2-hydroxy-propionyl)2,'3'-dideoxy-2'-fluorokanamycin A, 1-N-DL-3',4'-dideoxy-isoserylkanamycin B, 1-N-DL-isoserylkanamycin, 1-N-DL-isoserylkanamycin B, 1-N-[L-(−)-(alpha-hydroxy-gamma-aminobutyryl)]-XK-62-2,2',3'-dideoxy-2'-fluorokanamycin A,2-hydroxygentamycin A3,2-hydroxygentamycin B, 2-hydroxygentamycin B1,2-hydroxygentamycin JI-20A, 2-hydroxygentamycin JI-20B, 3"-N-methyl-4"-C-methyl-3',4'-dodeoxy kanamycin A, 3"-N-methyl-4"-C-methyl-3',4'-dodeoxy kanamycin B, 3"-N-methyl-4"-C-methyl-3',4'-dodeoxy-6'-methyl kanamycin B, 3',4'-Dideoxy-3'-enoribostamycin,3',4'-dideoxyneamine,3',4'-dideoxyribostamycin, 3'-deoxy-6'-N-methyl-kanamycin B,3'-deoxyneamine,3'-deoxyribostamycin, 3'-oxysaccharocin,3,3'-nepotrehalosadiamine, 3-demethoxy-2"-N-formimidoylistamycin B disulfate tetrahydrate, 3-demethoxyistamycin B,3-O-demethyl-2-N-formimidoylistamycin B, 3-O-demethylistamycin B,3-trehalosamine,4",6'-dideoxydibekacin, 4-N-glycyl-KA-6606VI, 5"'-Amino-3',4',5"-trideoxy-butirosin A, 6"-deoxydibekacin,6'-epifortimicin A, 6-deoxy-neomycin (structure 6-deoxy-neomycin B),6-deoxy-neomycin B, 6-deoxy-neomycin C, 6-deoxy-paromomycin, acmimycin, AHB-3',4'-dideoxyribostamycin,AHB-3'-deoxykanamycin B, AHB-3'-deoxyneamine,AHB-3'-deoxyribostamycin,AHB-4"-6"-dideoxydibekacin, AHB-6"-deoxydibekacin,AHB-dideoxyneamine,AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gamma1, coumamidine gamma2,D,L-1-N-(alpha-hydroxy-beta-aminopropionyl)-XK-62-2, dactimicin,de-O-methyl-4-N-glycyl-KA-6606VI, de-O-methyl-KA-6606I, de-O-methyl-KA-7038I,destomycin A, destomycin B, di-N6',O3-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KG1 (stereoisomer KG1/KG2), fortimicin KG2 (stereoisomer KG1/KG2), fortimicin KG3, framycetin, framycetin sulphate, gentamicin, gentamycin sulfate, globeomycin, hybrimycin A1, hybrimycin A2, hybrimycin B1, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethyl-7-O-demethyl-celesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Ansa-type antibiotics include, but are not limited to, 21-hydroxy-25-demethyl-25-methylthioprotostreptovaricin, 3-methylthiorifamycin, ansamitocin, atropisostreptovaricin, awamycin, halomicin, maytansine, naphthomycin, rifabutin, rifamide, rifampicin, rifamycin, rifapentine, rifaximin, rubradirin, streptovaricin, tolypomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazol, omidazole, oxiconazole, oxiconazole nitrate, propenidazole, secnidazol, sertaconazole, sertaconazole nitrate, sulconazole, sulconazole nitrate, tinidazole, tioconazole, voriconazole and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidyl fungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-O-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyldeltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, amfomycin, amythiamycin, antifungal from *Zalerion arboricola*, antrimycin, apid, apidaecin, aspartocin, auromomycin, bacileucin, bacillomycin, bacillopeptin, bacitracin, bagacidin, berninamycin, beta-alanyl-L-tyrosine, bottromycin, capreomycin, caspo fungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, janiemycin, janthinocin, jolipeptin, katanosin, killertoxin, lipopeptide antibiotic, lipopeptide from *Zalerion* sp., lysobactin, lysozyme, macromomycin, magainin, melittin, mersacidin, mikamycin, mureidomycin, mycoplanecin, mycosubtilin, neopeptifluorin, neoviridogrisein, netropsin, nisin, nocathiacin, nocathiacin 6-deoxyglycoside, nosiheptide, octapeptin, pacidamycin, pentadecapeptide, peptifluorin, permetin, phytoactin, phytostreptin, planothiocin, plusbacin, polcillin, polymyxin antibiotic complex, polymyxin B, polymyxin B1, polymyxin F, preneocarzinostatin, quinomycin, quinupristin-dalfopristin, safracin, salmycin, salmycin, salmycin, sandramycin, saramycetin, siomycin, sperabillin, sporamycin, a *streptomyces* compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In one or more embodiments, the antibiotic peptide is a naturally-occurring peptide that possesses an antibacterial and/or an antifungal activity. Such peptide can be obtained from a herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkyl-methylendioxy-4(1H)-oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascosteroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfacarbamide and analogs, salts and derivatives thereof.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Dicarboxylic acids, having between about 6 and about 14 carbon atoms in their carbon atom skeleton are particularly useful in the treatment of disorders of the skin and mucosal membranes that involve microbial. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred. It has antibacterial effects on both aerobic and anaerobic organisms, particularly *propionibacterium acnes* and *staphylococcus epidermidis*, normalizes keratinization, and has a cytotoxic effect on malignant or hyperactive melanocytes. In a preferred embodiment, the dicarboxylic acid is azelaic acid in a concentration greater than 10%. Preferably, the concentration of azelaic acid is between about 10% and about 25%. In such concentrates, azelaic acid is suitable for the treatment of a variety of skin disorders, such as acne, rosacea and hyperpigmentation.

In one or more embodiments, the antibiotic agent is an antibiotic metal. A number of metals ions been shown to possess antibiotic activity, including silver, copper, zinc, mercury, tin, lead, bismutin, cadmium, chromium and ions thereof. It has been theorized that these antibiotic metal ions exert their effects by disrupting respiration and electron transport systems upon absorption into bacterial or fungal cells. Anti-microbial metal ions of silver, copper, zinc, and gold, in particular, are considered safe for in vivo use. Anti-microbial silver and silver ions are particularly useful due to the fact that they are not substantially absorbed into the body.

Thus, in one or more embodiment, the antibiotic metal consists of an elemental metal, selected from the group consisting of silver, copper, zinc, mercury, tin, lead, bismutin, cadmium, chromium and gold, which is suspended in the composition as particles, microparticles, nanoparticles or colloidal particles. The antibiotic metal can further be intercalated in a chelating substrate.

In further embodiments, the antibiotic metal is ionic. The ionic antibiotic metal can be presented as an inorganic or organic salt (coupled with a counterion), an organometallic complex or an intercalate. Non binding examples of counter inorganic and organic ions are sulfadiazine, acetate, benzoate, carbonate, iodate, iodide, lactate, laurate, nitrate, oxide, palmitate, a negatively charged protein. In preferred embodiments, the antibiotic metal salt is a silver salt, such as silver acetate, silver benzoate, silver carbonate, silver iodate, silver iodide, silver lactate, silver laurate, silver nitrate, silver oxide, silver palmitate, silver protein, and silver sulfadiazine.

In one or more embodiments, the antibiotic metal or metal ion is embedded into a substrate, such as a polymer, a mineral (such as zeolite, clay and silica).

Oxidizing agents and substances that release free radicals and/or active oxygen. In one or more embodiments, the antibiotic agent comprises strong oxidants and free radical liberating compounds, such as oxygen, hydrogen peroxide, benzoyl peroxide, elemental halogen species, as well as oxygenated halogen species, bleaching agents (e.g., sodium, calcium or magnesium hypochloride and the like), perchlorite species, iodine, iodate, and benzoyl peroxide. Organic oxidizing agents are also included in the definition of "oxidizing agent" according to the present invention, such as quinones. Such agents possess a potent broad spectrum activity In one or more embodiments the antibiotic agent is a cationic antimicrobial agent. The outermost surface of bacterial cells universally carries a net negative charge, making them sensitive to cationic substances. Examples of cationic antibiotic agents include: quaternary ammonium compounds (QAC's)—QAC's are surfactants, generally containing one quaternary nitrogen associated with at least one major hydrophobic moiety; alkyltrimethyl ammonium bromides are mixtures of where the alkyl group is between 8 and 18 carbons long, such as cetrimide (tetradecyltrimethylammonium bromide); benzalkonium chloride, which is a mixture of n-alkyldimethylbenzyl ammonium chloride where the alkyl groups (the hydrophobic moiety) can be of variable length; dialkylmethyl ammonium halides; dialkylbenzyl ammonium halides; and QAC dimmers, which bear bi-polar positive charges in conjunction with interstitial hydrophobic regions.

In one or more embodiments, the antibiotic agent is selected from the group of biguanides, triguanides, bisbiguanides and analogs thereof.

Guanides, biguanides, biguanidines and triguanides are unsaturated nitrogen containing molecules that readily obtain one or more positive charges, which make them effective antimicrobial agents. The basic structures a guanide, a biguanide, a biguanidine and a triguanide are provided below.

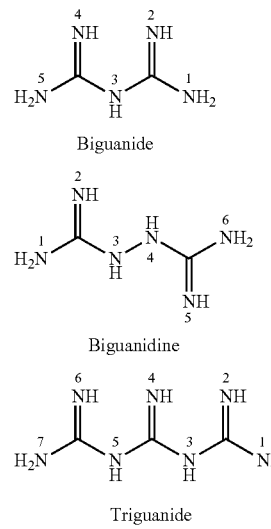

In one or more preferred embodiments, the guanide, biguanide, biguanidine or triguanide, provide bi-polar configurations of cationic and hydrophobic domains within a single molecule.

Examples of guanides, biguanides, biguanidines and triguanides that are currently been used as antibacterial agents include chlorhexidine and chlorohexidine salts, analogs and derivatives, such as chlorhexidine acetate, chlorhexidine gluconate and chlorhexidine hydrochloride, picloxydine, alexidine and polihexanide. Other examples of guanides, biguanides, biguanidines and triguanides that can conceivably be used according to the present invention are chlorproguanil hydrochloride, proguanil hydrochloride (currently used as antimalarial agents), metformin hydrochloride, phenformin and buformin hydrochloride (currently used as antidiabetic agents).

In one or more embodiments, the cationic antimicrobial agent is a polymer.

Cationic antimicrobial polymers include, for example, guanide polymers, biguanide polymers, or polymers having side chains containing biguanide moieties or other cationic functional groups, such as benzalkonium groups or quarternium groups (e.g., quaternary amine groups). It is understood that the term "polymer" as used herein includes any organic material comprising three or more repeating units, and includes oligomers, polymers, copolymers, block copolymers, terpolymers, etc. The polymer backbone may be, for example a polyethylene, polypropylene or polysilane polymer.

In one or more embodiments, the cationic antimicrobial polymer is a polymeric biguanide compound. When applied to a substrate, such a polymer is known to form a barrier film that can engage and disrupt a microorganism. An exemplary polymeric biguanide compound is polyhexamethylene biguanide (PHMB) salts. Other exemplary biguanide polymers include, but are not limited to poly(hexamethylenebiguanide), poly(hexamethylenebiguanide) hydrochloride, poly(hexamethylenebiguanide) gluconate, poly(hexamethylenebiguanide) stearate, or a derivative thereof. In one or more embodiments, the antimicrobial material is substantially water-insoluble.

Yet, in one or more embodiment, the antibiotic is a non-classified antibiotic agent, including, without limitation, aabomycin, acetomycin, acetoxycycloheximide, acetylnanaomycin, an *actinoplanes* sp. Compound, actinopyrone, aflastatin, albacarcin, albacarcin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis imune substance, anti-tuberculosis imune substance, antibiotic from *Escherichia coli*, antibiotics from *Streptomyces refuineus*, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cyclamidomycin, cycloheximide, dactylomycin, danomycin, danubomycin, delaminomycin, demethoxyrapamycin, demethylscytophycin, dermadin, desdamethine, dexylosyl-benanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, everninomicin, feldamycin, flambamycin, flavensomycin, florfenicol, fluvomycin, fosfomycin, fosfonochlorin, federicamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2',5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, prop-2-enylmonate, protomycin, pseudomonas antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *streptomyces arenae* antibiotic complex, streptonigrin, streptothricins, streptovitacin, streptozotocine, a strobilurin derivative, stubomycin, sulfamethoxazol-trimethoprim, sakamycin, tejeramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin and analogs, salts and derivatives thereof.

In one or more embodiments, the antibiotic agent is a naturally occurring antibiotic compound. As used herein, the term "naturally-occurring antibiotic agent" includes all antibiotic that are obtained, derived or extracted from plant or vertebrate sources. Non-limiting examples of families of naturally-occurring antibiotic agents include phenol, resorcinol, antibiotic aminoglycosides, anamycin, quinines, anthraquinones, antibiotic glycopeptides, azoles, macrolides, avilamycin, agropyrene, cnicin, aucubin antibioticsaponin fractions, berberine (isoquinoline alkaloid), arctiopicrin (sesquiterpene lactone), lupulone, humulone (bitter acids), allicin, hyperforin, echinacoside, coniosetin, tetramic acid, imanine and novoimanine.

Ciclopirox and ciclopiroxolamine possess fungicidal, fungistatic and sporicidal activity. They are active against a broad spectrum of dermatophytes, yeasts, moulds and other fungi, such as *trichophyton* species, microsporum species, *epidermophyton* species and yeasts (*candida albicans, candida glabrata*, other *candida* species and *cryptococcus neoformans*). Some *aspergillus* species are sensitive to ciclopirox as are some *penicillium*. Likewise, ciclopirox is effective against many gram-positive and gram-negative bacteria (e.g., *escherichia coli, proteus mirabilis, pseudomonas aeruginosa, staphylococcus* and *streptococcus* species), as well as *mycoplasma* species, *trichomonas vaginalis* and *actinomyces*.

Plant oils and extracts which contain antibiotic agents are also useful. Non limiting examples of plants that contain agents include thyme, *perilla*, lavender, tea tree, *terfezia clayeryi, Micromonospora, putterlickia verrucosa, putterlickia pyracantha, putterlickia retrospinosa, Maytenus ilicifolia, maytenus evonymoides, maytenus aquifolia, faenia interjecta, cordyceps sinensis*, couchgrass, holy thistle, plantain, burdock, hops, echinacea, buchu, chaparral, myrrh, red clover and yellow dock, garlic and St. John's wort.

Mixtures of these antibiotic agents may also be employed according to the present invention.

In an embodiment, the therapeutic agent is an antidandruff agent. Suitable antidandruff agents include but are not limited to aminexil, benzalkonium chloride, benzethonium chloride, 3-bromo-1-chloro-5,5-dimethyl-hydantoin, chloramine B, chloramine T, chlorhexidine, N-chlorosuccinimide,climbazole-, 1,3-dibromo-5,5-dimethylhydantoin, 1,3-dichloro-5,5-dimethyl-hydantoin, betulinic acid, betulonic acid, celastrol, crataegolic acid, cromakalin, cyproterone acetate, dutasteride, finesteride, ibuprofen, ketoconazole, oleanolic acid, phenyloin, picrotone olamine, salicylic acid, selenium sulphides, triclosan, triiodothyronine, ursolic acid, zinc gluconate, zinc omadine, zinc pyrithione and derivatives, esters, salts and mixtures thereof.

In an embodiment, the therapeutic agent is an antihistamine. Suitable antihistamines include but are not limited to chlorcyclizine, diphenhydramine, mepyramine, methapyrilene, tripelennamine and derivatives, esters, salts and mixtures thereof.

Antifungal

In an embodiment, the therapeutic agent is an antimycotic, also termed antifungal agent. The terms "antimycotic" and "antifungal" as used herein include, but is not limited to, any substance being destructive to or inhibiting the growth of fungi and yeast or any substance having the capacity to inhibit the growth of or to destroy fungi and/or yeast.

In one or more embodiments, the antifungal agent is an agent that is useful in the treatment of a superficial fungal infection of the skin, dermatophytosis, microsporum, *trichophyton* and *epidermophyton* infections, candidiasis, oral candidiasis (thrush), candidiasis of the skin and genital mucous membrane, candida paronychia, which inflicts the nail and nail bed and genital and vaginal candida, which inflict genitalia and the vagina. Thus, in one or more embodiments, the antifungal agent is selected from the group including but not limited to, azoles, diazoles, triazoles, miconazole, fluconazole, ketoconazole, clotrimazole, itraconazole, Climbazole, griseofulvin, ciclopirox, ciclopirox-olamine, amorolfine, terbinafine, Amphotericin B, potassium iodide and flucytosine (5FC) at a therapeutically effective concentration.

Azoles are pharmaceutically active compounds that are unsaturated five member ring heterocyclic compound, wherein one, two or three members of the ring are nitrogen atoms, as exemplified in a non-limiting way and illustrated in the following schemes:

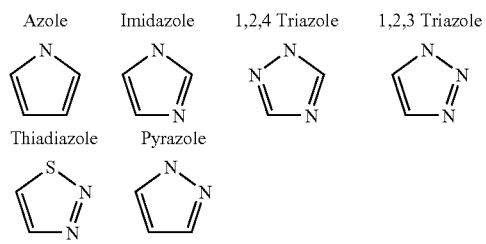

The azole is a compound including an unsaturated five member ring heterocyclic compound, wherein one, two or three members of the ring are nitrogen atoms.

Examples of therapeutic azoles include, but are not limited to, azanidazole, bifonazole, butoconazol, chlormidazole, climbazole, cloconazole, clotrimazole, dimetridazole, econazole, enilconazole, fenticonazole, fezatione, fluconazole, flutrimazole, isoconazole, itraconazole, ketoconazole, lanoconazole, metronidazole, metronidazole benzoate, miconazole, neticonazole, nimorazole, niridazole, omoconazol, ornidazole, oxiconazole, posaconazole, propenidazole, ravuconazole, secnidazol, sertaconazole, sulconazole, thiabendazole, tinidazole, tioconazole, voriconazol and salts and derivatives thereof. Such azoles are mainly used as antifungal agents, yet several of them also possess other therapeutic benefits, such as anti-inflammatory, antibacterial and antiviral effects.

Additional non-limiting exemplary classes of azoles include oxazoles, thiazoles, thiadiazoles and thiatriazoles, benzimidazoles, and salts and derivatives thereof.

In an embodiment, the azole is metronidazole.

In one or more embodiments, the antifungal agent is a peptide.

In certain embodiments, antifungal agent is a naturally-occurring peptide that possesses an antibacterial and/or an antifungal activity. Such peptide can be obtained from a herbal or a vertebrate source.

In an embodiment, the antifungal agent is a polyene. Polyene compounds are so named because of the alternating conjugated double bonds that constitute a part of their macrolide ring structure. Polyenes include, but are not limited to, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, oxypricin, partricin, pentamycin, perimycin, pimaricin, primycin, proticin, rimocidin, sistomycosin, sorangicin, trichomycin and analogs, salts and derivatives thereof.

In an embodiment, the antifungal agent is a pyrimidine, such as Flucytosine.

In an embodiment, the antifungal agent is an allylamine, such as terbinafine and naftifine.

In an embodiment, the antifungal agent is a morpholine derivative, such as amorolfine.

In an embodiment, the antifungal agent is selected from the group consisting of Ciclopirox, ciclopiroxolmine, griseofulvin.

In an embodiment, the antifungal agent is a Thiocarbamate, such as tolnaftate.

In an embodiment, the antifungal agent is a Sulfonamide, such as Mafenide and Dapsone.

In an embodiment, the antifungal agent consists of a plant oil or a plant extract possessing antifungal activity; or a plant oil or extract which contains antifungal agents. Non-limiting examples of plants containing agents include, but are not limited to, anise, basil, bergemont, burdock, buchu, chaparral, camphor, cardamom, carrot, canola, *cassia*, catnip, cedarwood, citronella, clove, couchgrass, cypress, echinacea, eucalyptus, faenia interjecta, garlic, ginger, grapefruit, holy thistle, hops, hyssop, jasmine, jojova, lavender, lavandin, lemon, lime, mandarin, marigold, marjoram, *maytenus ilicifolia, maytenus evonymoides, maytenus aquifolia*, micromonospora, myrrh, neroli, nutmeg, orange, *ordyceps sinensis*, peppermint, *perilla*, petitgrain, plantain, *putterlickia verrucosa, putterlickia pyracantha, putterlickia retrospinosa*, rosemary, sage, spearmint, star anise, St. John's wort, red clover, tangerine, tea tree, terfezia clayeryi, thyme vanilla, verbena, white clover and yellow dock.

In an embodiment, the antifungal agent is an anti-microbial metal. A number of metals ions been shown to possess antibiotic activity, including silver, copper, zinc, mercury, tin, lead, bismutin, cadmium, chromium and ions thereof. It has been theorized that these anti-microbial metal ions exert their effects by disrupting respiration and electron transport systems upon absorption into bacterial or fungal cells. Anti-microbial metal ions of silver, copper, zinc, and gold, in particular, are considered safe for in vivo use. Anti-microbial silver and silver ions are particularly useful due to the fact that they are not substantially absorbed into the body.

Thus, in one or more embodiment, the anti-microbial metal consists of an elemental metal, selected from the group consisting of silver, copper, zinc, mercury, tin, lead, bismutin, cadmium, chromium and gold, which is suspended in the composition as particles, microparticles, nanoparticles or colloidal particles. The anti-microbial metal can further be intercalated in a chelating substrate.

In further embodiments, the anti-microbial metal is ionic. The ionic antibiotic metal can be presented as an inorganic or organic salt (coupled with a counterion), an organometallic complex or an intercalate. Non binding examples of counter inorganic and organic ions are sulfadiazine, acetate, benzoate, carbonate, iodate, iodide, lactate, laurate, nitrate, oxide, palmitate, a negatively charged protein. In preferred embodiments, the antibiotic metal salt is a silver salt, such as silver acetate, silver benzoate, silver carbonate, silver iodate, silver iodide, silver lactate, silver laurate, silver nitrate, silver oxide, silver palmitate, silver protein, and silver sulfadiazine.

Yet, in another embodiment, the antifungal agent is an oxidizing agent or a substance that releases free radicals and/or active oxygen. Exemplary oxidizing agents are hydrogen peroxide, benzoyl peroxide, elemental halogen species (compounds), as well as oxygenated halogen species (compounds), bleaching agents (e.g., sodium, calcium or magnesium hypochloride and the like), perchlorite species (compounds), iodine and iodate compounds. Organic oxidizing agents are also included in the definition of "oxidizing agent" according to the present invention, such as quinones. Such agents possess a potent broad spectrum activity In further embodiments the antibiotic agent is a cationic antimicrobial agent. The outermost surface of bacterial and fungal cells universally carries a net negative charge, making them sensitive to cationic substances. Examples of cationic antibiotic agents include: quaternary ammonium compounds, such as alkyltrimethyl ammonium bromides, benzalkonium chloride, dialkylbenzyl ammonium halides, and dimmers thereof, which bear bi-polar positive charges in conjunction with interstitial hydrophobic regions.

In one or more embodiments, the antifungal agent is an agent that is useful in the treatment of a superficial fungal infection of the skin, dermatophytosis, microsporum, *trichophyton* and *epidermophyton* infections, candidiasis, oral candidiasis (thrush), candidiasis of the skin and genital mucous membrane, candida paronychia, which inflicts the nail and nail bed and genital and vaginal candida, which inflict genitalia and the vagina.

Suitable antimycotics include but are not limited to allylamines, amorolfine, amphotericin B, azole compounds, bifonazole, butoconazole, chloroxine, clotrimazole, ciclopirox olamine, clotrimazole, econazole, elubiol, fenticonazole, fluconazole, flucytosine (5FC), griseofulvin, itraconazole, ketoconazole, mafenide acetate, miconazole, naftifine, natamycin, tolnaftate, nystatin, polyenes, oxiconazole, sulbentine, sulconazole, terbinafine, terconazole, tioconazole, undecylenic acid and derivatives, esters, salts and mixtures thereof.

Vasoactive, Calcium Channel Blocker and Cholinergic Agent
Vasoactive

In the context, a vasoactive agent is a substance that changes the diameter of a blood vessel.

In one or more embodiments, the vasoactive agent is a vasodilator. A vasodilator is any of various agents that relax or widen blood vessels and thereby maintain or lower blood pressure.

Alteration in the release and action of endothelium-derived vasoactive factors is responsible for changes in vascular reactivity early in the course of vascular disease. These factors include nitric oxide, eicosanoids, endothelium-derived hyperpolarizing factor, endothelin, and angiotensin II.

Nitric oxide (NO) has been recognized as an important messenger molecule having a broad spectrum of functions in many biological systems ranging from physiological control to pathological cytotoxic effect1-3. Along with prostacyclin, NO is responsible for endothelium derived tonic relaxation of all types of blood vessels. NO is formed from L-arginine through the action of a family of isoenzymes, the nitric oxide synthases (NOS). Thus, in one or more embodiments, the vasoactive agent is selected from the group of therapeutic agents that modulate the production of nitric oxide or otherwise modulate or activate the effect of nitric oxide. In one or more embodiments, the vasoactive agent is selected from the group of therapeutic agents that modulate the activity of the enzyme nitric oxide synthase. In one or more embodiments, the vasoactive agent is selected from the group of therapeutic agents that enhance the effect of NO by inhibiting enzymes from the phosphodiesterase group, such as phosphodiesterase type 5 (PDE5).

In one or more embodiments, the vasoactive agent is selected from the group including nitrites, nitrates and their analogs, esters and salts. In one or more embodiments the vasoactive agent possesses a moiety selected from the group consisting of ONO, and ONO2.

Exemplary vasodilators include, but are not limited to, amyl nitrite, amyl nitrate, ethyl nitrite, butyl nitrite, isobutyl nitrite, glyceryl trinitrate, also known as nitroglycerin, octyl nitrite, sodium nitrite, sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, trolnitrate phosphate (triethanolamine trinitrate diphosphate), propatylnitrate, nitrite esters of sugars, nitrite esters of polyols, nitrate esters of sugars, nitrate esters of polyols, nicorandil, apresoline, diazoxide, hydralazine, hydrochlorothiazide, minoxidil, pentaerythritol, tolazoline, scoparone (6,7-dimethoxycoumarin) and salts, isomers, analogs and derivatives thereof.

In one or more embodiments, the vasoactive agent belongs to a class of drugs that are known of possess vasodilator properties. Non limiting examples of drug classes that possess vasodilator properties include, but are not limited to, beta-adrenergic blockers, alpha-adrenoceptor blockers, prostaglandin and prostaglandin-like compounds, inhibitors of type 5 phosphodiesterase (PDE-5), angiotensin converting enzyme inhibitors, calcium antagonists, angiotensin II receptor antagonists, direct acting smooth muscle vasodilators, adrenergic inhibitors, endothelin antagonists, mineralocorticoid receptor antagonists, vasopeptidase inhibitors and renin inhibitors. Active agents belonging to such drug classes, as well as active agents belonging to other classes, which cause a vasodilator effect are also included in the scope of vasoactive agents according to the present invention.

Non-nitrate vasodilators from different classes include, but are not limited to sildenafil, dipyridamole, catecholamine, isoproternol, furosemide, prostaglandin, prostacyclin, enalaprilat (ACE-inhibitor), morphine (opiate), acepromazine (α-blocker), prazosin (α-blocker), enalapril (ACE-inhibitor), captopril (ACE-inhibitor), amlodipine (Ca channel blocker), minoxidil, tadalafil, vardenafil, phenylephrine, etilefein, caffeine, capsaicin and salts, isomers, analogs and derivatives thereof.

In one or more embodiments, the vasoactive agent is selected from the group of vasodilator peptides and proteins. Non-limiting examples of vasodilator paprides include, but are not limited to bradykinin, bradykinin-like peptide I, bradykinin-like peptide III Phyllokinin (bradykinyl-isoleucyl-tyrosine O-sulfate), megascoliakinin ([Thr6]bradykinin-Lys-Ala), lysyl-bradykinin-like waspkinin, lysyl-bradykinin, maximakinin (Bombinakinin M), bombinakinin-GAP, kininogen-1 associated peptides, kininogen-2 associated peptides, T-kinin, thiostatin, prolixin-S, vespulakinin 2, vespakinin X, relaxin, adrenomedullin, ghrelin, maxadilan, substance P, calcitonin gene-related peptide (CGRP), Natriuretic peptides (NPs), e.g., atrial natriuretic peptide (ANP), C-type natriuretic peptide (CNP), and adrenomedullin (ADM), adrenomedullin, ovine corticotropin-releasing factor, sauvagine, urotensin and salts, isomers, analogs and derivatives thereof.

In one or more embodiments, the vasoactive agent is selected from the group of therapeutic agents that induce the production of a vasodilator peptide or otherwise enhance or activate the effect of a vasodilator peptide.

In one or more embodiments, the vasoactive agent is a substance derived or extracted from herbs having a vasodilator effect. Non limiting examples of herbs that contain vasoactive agents include *achillea millefolium* (Yarrow), *allium sativum* (garlic), *amoracia rusticana* (horseradish), *berberis vulgaris* (barberry), *cimicifuga racemosa* (black cohosh), *coleus forskholii* (coleus), *coptis* (Goldenthread), *crataegus* (hawthorn), *eleutherococcus senticosus* (siberian ginseng), *ginkgo biloba* (ginkgo), *melissa offiicnalis* (lemon balm), *olea europaea* (olive leaf), *panax ginseng* (Chinese ginseng), *petroselinum crispum* (parsley), *scutellaria baicalensis* (baical skullcap), *tilia europaea* (linden flower), *trigonella foenum-graecum* (fenugreek), *urtica dioica* (nettles), *valeriana officinalis* (valerian), *viburnum* (cramp, bark, black haw), *veratrum viride* (American hellebore), *verbena officinalis* (vervain), *xanthoxylum americanum* (prickly ash), *zingiber officinale* (ginger), *rauwolfia serpentina* (Indian snakeroot), *viscum album*, wild yam, sasparilla, licorice, damiana, yucca, saw palmetto, gotu kola (*centella asiatica*), yohimbine and salts, hazel nut, brazil nut, walnut and analogs and derivatives thereof.

According to one or more embodiments, the foamable composition includes a vasodilator and a vasoactive agent such that the vasodilator can have a synergistic effect by readily facilitating facile penetration of the vasoactive agent.

In one or more embodiments, the vasoactive agent is a vasoconstrictor. A vasoconstrictor is any of various agents that narrow blood vessels and thereby maintain or increase blood pressure, and/or decrease blood flow. There are many disorders that can benefit from treatment using a vasoconstrictor. For example, redness of the skin (e.g., erythema or cuperose), which typically involves dilated blood vessels, benefit from treatment with a vasoconstrictor, which shrinks the capillaries thereby decreasing the untoward redness.

Other descriptive names of the vasoconstrictor group include vasoactive agonists, vasopressor agents and vasoconstrictor drugs. Certain vasoconstrictors act on specific receptors, such as vasopressin receptors or adrenoreceptors.

In one or more embodiments, the vasoconstrictor is a calcium channel agonist. Calcium channel agonists are agents that increase calcium influx into calcium channels of excitable tissues, thereby causing vasoconstriction.

Non limiting examples of vasoconstrictors include ephedrine, epinephrine, phenylephrine, angiotensin, vasopressin, and analogs and derivatives thereof.

In one or more embodiments, the vasoactive agent is a substance derived or extracted from herbs, having a vasoconstrictor effect.

Thus, in one or more embodiments, the vasoactive agent is a substance derived or extracted from a herbal source, selected from the group including *ephedra sinica* (ma huang), *polygonum bistorta* (bistort root), *hamamelis virginiana* (witch hazel), *hydrastis canadensis* (goldenseal), *lycopus virginicus* (bugleweed), *aspidosperma quebracho* (quebracho blanco), *cytisus scoparius* (scotch broom), cypress and salts, isomers, analogs and derivatives thereof.

Yet, in additional embodiments, the vasoactive agent is a metal oxide or a mineral, such as zinc oxide and bismuth subgallate.

The McKenzie vasoconstrictor assay, as described, for example, in the *British Journal of Dermatology* 1975; 93:563-71 and versions thereof, has been the primary method used for classifying the strength of a vasoconstrictor clinical efficacy. Thus, in one or more embodiments, the vasoactive agent is an agent that positively affects the vasoconstrictor assay.

Mixtures of these vasoactive agents may also be employed according to the present invention.

Solubility of the vasoactive agent is an important factor in the development of a stable foamable composition according to the present invention.

Calcium Channel Blockers

Calcium channel blockers are a chemically and pharmacologically heterogeneous group of drugs, but physiologically they all share the ability to selectively antagonize the calcium ion movements that are responsible for the excitation-contraction coupling in the cardiovascular system. Beyond their cardiovascular effects, calcium channel blockers are known to possess other effects, such as inhibition of the growth and proliferation of vascular smooth muscle cells and fibroblasts, inhibition of the synthesis of extracellular matrix proteins, immunomodulation, inhibition of mast cell degranulation and platelet aggregation and suppression of neutrophil adhesion and superoxide anion (O-2) production. Some calcium channel blockers also have analgesic effects.

Current therapeutic uses of calcium channel blockers include (but are not limited to) hypertension, angina, arrhythmia and subarachnoid hemorrhage. Calcium channel blockers may further relieve or prevent reactive vasodilation of migraine sufferers by inhibiting the vasoconstriction during the prodromal phase.

There are two main classes of calcium channel blockers: dihydropyridines (e.g., nifedipine, nicardipine, amlodipine, felodipine and nimodipine) and nondihydropyridines which include diltiazem (a benzothiazepine) and verapamil (a phenylalkylamine). Flunarizine is an antihistamine with calcium channel blocking activity.

In an embodiment, the calcium channel blocker can be selected from the group consisting of an amlodipine, anipamil, bamidipine, benidipine, bepridil, darodipine, diltiazem, efonidipine, felodipine, isradipine, lacidipine, lercanidipine, lidoflazine, manidipine, mepirodipine, nicardipine, nifedipine, niludipine, nilvadipine, nimodipine, nisoldipine, nitrendipine, perhexyline, tiapamil, verapamil, pharmaceutically acceptable salts, isomers, analogs and derivatives thereof.

Cholinergic Drugs

Cholinergic drugs produce the same effects as acetylcholine. Acetylcholine is the most common neurohormone of the parasympathetic nervous system, the part of the peripheral nervous system responsible for the every day work of the body. A cholinergic agent, also known as a parasympathomimetic agent, is a chemical which functions to enhance the effects mediated by acetylcholine in the central nervous system, the peripheral nervous system, or both. These include acetylcholine receptor agonists muscarine and nicotine, as well as anticholinesterases.

Suitable cholinergic drugs in accordance with the present invention are selected from a cholinergic agonist of acetylcholine, bethanechol, carbachol, methacholine, and pilocarpine, or an anticholinesterase of ambenonium, neostigmine, physostigmine, pyridostigmine, dyflos, and ecothinopate, and pharmaceutically acceptable salts, isomers, analogs and derivatives thereof.

Nitric Oxide Donors

Nitric oxide is an inorganic free radical, which has the chemical formula of N=O and abbreviated to NO, and is a remarkably versatile biological messenger. The chemical properties of NO are crucial in defining its biological roles, both as a transcellular signal in the cardiovascular and nervous systems and as a cytotoxic antipathogenic agent released during an inflammatory response. Endogenous NO is synthesized from the amino acid L-arginine by three isoforms of the enzyme NO synthase (NOS). The endothelial (eNOS) and neuronal (nNOS) isoforms that synthesize NO for transcellular signaling are constitutively expressed tightly regulated by a number of cofactors. These NOS isoforms typically synthesize small amounts of NO and require activation by $Ca^{2+}$-calmodulin, making them sensitive to agents and processes that increase intracellular calcium levels. The NO generated diffuses to neighboring target cells where it acts primarily through activation of soluble guanylate cyclase (sGC) to generate cGMP from GTP, and bring about the cellular response through a reduction in intracellular calcium levels.

In an embodiment, the nitric oxide donors can be selected from several classes, including, but not limited to inorganic nitrites and nitrates (e.g., sodium nitrite), organic nitrites and nitrates, sodium nitroprusside, molsidomine and its metabolites, diazeniumdiolates, S-nitrosothiols, mesoionic oxatriazole and derivatives thereof, iron-sulphur nitrosyls, Sinitrodil, FK-409 (4-Ethyl-2-[(Z)-hydroxyiminol]-5-nitro-3 (E)-hexeneamide) and derivatives thereof and hybrid NO donor drugs.

In an embodiment, the organic nitric oxide donor includes at least one organic nitrate, which includes esters of nitric acid and may be an acyclic or cyclic compound. For instance, the organic nitrate may be ethylene glycol dinitrate; isopropyl nitrate; amyl nitrite, amyl nitrate, ethyl nitrite, butyl nitrite, isobutyl nitrite, octyl nitrite, glyceryl-1-mononitrate, glyceryl-1,2-dinitrate, glyceryl-1,3-dinitrate, nitroglycerin, butane-1,2,4-triol-trinitrate; erythrityl tetranitrate; pentaerythrityl tetranitrate; sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, trolnitrate phosphate (triethanolamine trinitrate diphosphate), propatylnitrate, nitrite esters of sugars, nitrate esters of sugars, nitrite esters of polyols, nitrate esters of polyols, nicorandil, apresoline, diazoxide, hydralazine, hydrochlorothiazide, minoxidil, pentaerythritol, tolazoline, scoparone (6,7-dimethoxycoumarin) and pharmaceutically acceptable salts, isomers, analogs and derivatives thereof.

In one embodiment, vasoactive drugs that act via eNOS activity enhancement, such as sildenafil, vardenafil and tadalafil are also regarded "nitric oxide donors."

In an embodiment, the active agent is an antipruritic. Suitable antipruritics include but are not limited to menthol, methdilazine, trimeprazine, urea and derivatives, esters, salts and mixtures thereof.

In an embodiment, the therapeutic agent is an additional antipsoriatic agent. Suitable additional antipsoriatic agents include but are not limited to 6-aminonicotinamide, 6-aminonicotinic acid, 2-aminopyrazinamide, anthralin, 6-carbamoylnicotinamide, 6-chloronicotinamide, 2-carbamoylpyrazinamide, corticosteroids, 6-dimethylaminonicotinamide, dithranol, 6-formylaminonicotinamide, 6-hydroxy nicotinic acid, 6-substituted nicotinamides, 6-substituted nicotinic acid, 2-substituted pyrazinamide, tazarotene, thionicotinamide, trichothecene mycotoxins and derivatives, esters, salts and mixtures thereof.

In an embodiment, the active agent is an antirosacea agent. Suitable antirosacea agents include but are not limited to azelaic acid, metronidazole, sulfacetamide and derivatives, esters, salts and mixtures thereof. Certain nonsteroidal antiinflammatory agents, such as salicylic acid, salicylates, piroxicam and diclofenac are also useful for the treatment of Rosacea.

In an embodiment, the therapeutic agent is an antiseborrheic agent. Suitable antiseborrheic agents include but are not limited to glycolic acid, salicylic acid, selenium sulfide, zinc pyrithione, a dicarboxylic acid, such as azelaic acid and derivatives, esters, salts and mixtures thereof.

In an embodiment, the therapeutic agent is an antiviral agent. Suitable antiviral agents include but are not limited to acyclovir, gancyclovir, ribavirin, amantadine, rimantadine nucleoside-analog reverse transcriptase inhibitors, such as zidovudine, didanosine, zalcitabine, tavudine, lamivudine and vidarabine, non-nucleoside reverse transcriptase inhibitors, such as nevirapine and delavirdine, protease inhibitors, such as saquinavir, ritonavir, indinavir and nelfinavir, and interferons and derivatives, esters, salts and mixtures thereof.

In an embodiment, the therapeutic agent is a chemotherapeutic agent. Suitable chemotherapeutic agents include but are not limited to daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, XR9576 and derivatives, esters, salts and mixtures thereof.

Steroids

In an embodiment, the therapeutic agent is a corticosteroid. Suitable corticosteroids include but are not limited to alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, difluorosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters, salts and mixtures thereof.

The steroid according to the present invention is selected from the group consisting of:
(i) a steroid compound containing a cyclopenta[a]phenanthrene skeleton;
(ii) a steroid compound containing a cyclopenta[a]phenanthrene skeleton carrying one or more functional groups selected from halogens, alkyl groups, aryl groups, benzyl groups, carboxy groups and alkoxy groups;
(iii) a steroid compound selected from the families of (a) cardanolides, (b) bufanolides, (c) spirostans, (d) furostans, (e) steroid alkaloids, (f) steroid lactones, (g) oxosteroids, (h) steroid-alcohols and (i) steroid-amines;
(iv) a steroid compound, where one or more of the cyclopenta[a]phenanthrene rings is contracted by loss of an unsubstituted methylene group;

(v) a steroid compound, where one or more of the cyclopenta[a]phenanthrene rings is expanded by inclusion of a methylene group;
(vi) a steroid compound containing a cyclopenta[a]phenanthrene skeleton and a carbocyclic or heterocyclic ring component fused to it;
(vii) a compound, wherein two or more steroid molecules are linked together covalently;
(viii) a compound selected from the group consisting of 5α-pregnane, 5β-pregnane, 5α-cholane (allocholane), 5β-cholane, 5α-cholestane, 5β-cholestane, 5α-ergostane, 5β-ergostane, 5α-campestane, 5β-campestane, 5α-poriferastane, 5β-poriferastane, 5α-stigmastane, 5β-stigmastane, 5α-gorgostaneacrihellin, actodigin, alfacalcidol, aldosterone, androsterone, betamethasone, brassinolide, calcidiol, calciol, calcitriol, canrenone, clomegestone, cholesterol, cholic acid, corticosterone, cortisol, cortisol acetate, cortisone, cortisone acetate, cyproterone, deoxycorticosterone, dexamethasone, disogluside, ecdysone, ercalciol, ergosterol, estradiol, estriol, estrone, ethinylestradiol, fluazacort, fluocortin, fusidic acid, gestrinone, gonane, halometasone, hydrocortisone, lanosterol, lithocholic acid, mebolazine, medroxyprogesterone, meproscillarin, mespirenone, mestranol, naflocort, norenthisterone, norgesterone, norgestrel, oxandrolone, oxymetholone, pancuronium bromide, prednisolone, prednisone, progesterone, proscillardin, pseudotigogenin, roxibolone, sarsasapogenin, smilagenin, spironolactone, timobesone, testosterone, tigogenin triamcinolone, ursodeoxycholic acid;
(ix) an anti-inflammatory steroid;
(x) a steroid possessing immunomodulating and/or anti-inflammatory properties;
(xi) a steroid, selected from the group of low-potency anti-inflammatory steroids, medium potency anti-inflammatory steroids and high potency anti-inflammatory steroids;
(xii) an anti-inflammatory steroid, selected from the group consisting of hydrocortisone, hydrocortisone acetate, desonide, betamethasone valerate, clobetasone-17-butyrate, flucinonide, fluocinolone acetonide, alcometasone dipropionate, mometasone furoate, prednicarbate, triamcinolone acetonide, betamethasone-17-benzoate, methylprednisolone aceponate, betamethasone dipropionate, halcinonide, triamcinolone acetonide, halobetasol, clobetasol-17-propionate;
(xiii) a steroid that positively affects the McKenzie vasoconstrictor assay;
(xiv) a steroid hormone;
(xv) a steroid hormone, selected from the group consisting of an androgen, an estrogen and a progestogen;
(xvi) an androgen, selected from the group consisting of testosterone, testosterone cipionate, testosterone decanoate, testosterone enantate, testosterone isocaproate, testosterone phenylpropionate, testosterone propionate, testosterone undecylate, 5α-dihydrotestosterone, dehydroepiandrosterone (also termed prasterone and DHEA), androstenedione, androstanediol, androsterone, androstenolone, prasterone enantate, prasterone sodium sulfate, ormeloxifene, mesterolone, fluoxymesterone, methyltestosterone, gestrinone, delmadinone, delmadinone acetate, chlormadinone, chlormadinone acetate, danazol and testolactone;
(xvii) an estrogen selected from the group consisting of estradiol, estradiol benzoate, estradiol cipionate, estradiol dipropionate, estradiol enantate, estradiol hexahydrobenzoate, estradiol phenylpropionate, estradiol valerate, polyestradiol phosphate, estriol, estriol sodium succinate, estriol succinate, polyestriol phosphate, quinestradol, ethinylestradiol, estrapronicate, mestranol, estrapronicate and equilin;
(xviii) a progestogen, selected from the group consisting of progesterone, norethisterone, norethisterone acetate, norethisterone enantate, medroxyprogesterone acetate, delmadinone acetate, flugestone acetate, dydrogesterone, desogestrel, norgestrel, levonorgestrel, dydrogesterone, gestodene, chlormadinone acetate, dienogest, drospirenone, lynestrenol, tybolone, cyproterone acetate, megestrol acetate, nomegestrol acetate;
(xix) an inhibitor of a steroid hormone;
(xx) an inhibitor of a steroid hormone selected from the group consisting of finasteride, dutasteride and spironolactone;
(xxi) a vitamin D;
(xxii) a steroid that exhibits qualitatively the biological activity of calciol;
(xxiii) a vitamin D selected from the group consisting of cholecalciferol, 25-hydroxycholecalciferol, 1α,25-dihydroxycholecalciferol, ergocalciferol, 1α,25-dihydroxyergocalciferol, 22,23-dihydroergocalciferol, 1,24,25-trihydroxycholecalciferol, previtamin $D_3$, tachysterol$_3$ (also termed tacalciol);
(xxiv) a vitamin D3 analogue;
(xxv) isovitamin $D_3$, dihydrotachysterol$_3$, (1S)-hydroxycalciol, (24R)-hydroxycalcidiol, 25-fluorocalciol, ercalcidiol, ertacalciol, (5E)-isocalciol, 22,23-dihydroercalciol, (24S)-methylcalciol, (5E)-(10S)-10,19-dihydroercalciol, (24S)-ethylcalciol and (22E)-(24R)-ethyl-22,23-didehydrocalciol;
(xxvi) a vitamin $D_3$ analogue selected from calcipotriol, tacalcitol, maxacalcitol, and calcitriol;
(xxvii) a phytosteroid or a phytosterol;
(xxviii) a steroid derived or extracted from one of the families of phytosteroids, phytosterols, phytostanols, ecdysones, withanolids, sterines, steroid saponins and soflavonoids;
(xxix) a steroid selected from the group consisting of alpha-sitosterol, beta-sitosterol, stigmastanol, campesterol, alpha-sitostanol, beta-sitostanol, stigmastanol, campestanol, avenosterol, brassicasterol, desmosterol, chalinosterol, beta-ecdysone, whithaferin A, beta-sitosterine, stigmasterine, campesterine, ergosterine, diosgenin, daidzein, glycitein, genistein, muristerone, poriferasterol, clionasterol, campestanol, and cycloartenol;
(xxx) a plant oil or a plant extract, which contains a steroid;
(xxxi) a plant oil or a plant extract, selected from the group consisting of nuts seeds, sprouted seeds and grains (such as alfalfa), St. Mary's thistle, *ginkgo biloba*, saw palmetto, *panax*, siberian ginseng, *foeniculum vulgare, cimicifuga racemosa*, licorice root, red clover, sage, sarsaparilla, sassafras, *angelica sinensis achillea millefolium, anemone pratensis, angelica sinensis, glycyrrhiza glabra, hypericum perforatum, larrea, panax, piscidia erythrina, plantago psyllium, serenoa repens, symphytum, taraxacum officinale, trifolium pratense, turnera spp., tussilago farfara, valeriana officinalis, viburnum prunifolium, calendula officinalis*;
(xxxii) any one of the compounds exemplified in the present specification; and salts thereof.

In the context, steroids are compounds possessing the skeleton of cyclopenta[a]phenanthrene or a skeleton derived therefrom by one or more bond scissions or ring expansions or contractions. Methyl groups are normally present at C-10 and C-13. An alkyl side chain may also be present at C-17. Sterols are steroids carrying a hydroxyl group at C-3 and most of the skeleton of cholestane. Additional carbon atoms may be present in the side chain.

Steroids are numbered and rings are lettered as in formula 1. If one of the two methyl groups attached to C-25 is substituted it is assigned the lower number (26); if both are substituted, that carrying the substituent cited first in the alphabetical order is assigned the lower number.

(1)

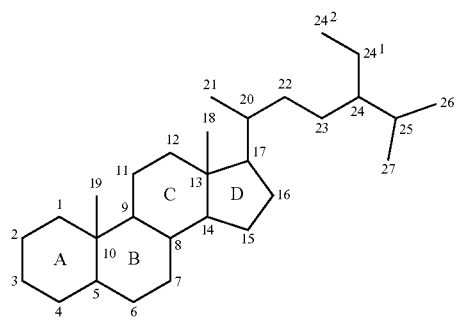

The steroids can have substituents on the steroid side chain as exemplified in formula 4-7:

(4)

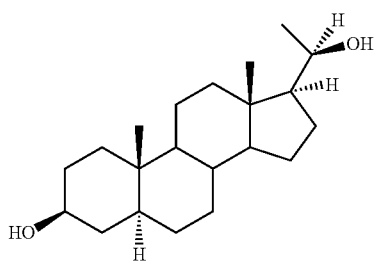

(20R)-5α-Pregnane-3β,20-diol (5)

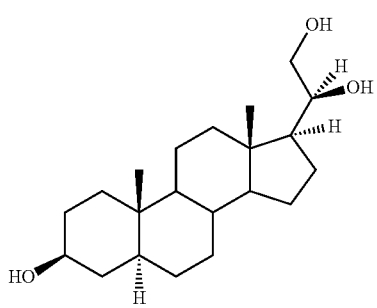

(20S)-5α-Pregnane-3β,20,21-triol

-continued (6)

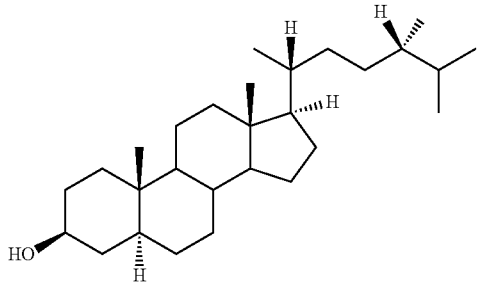

(24S)-24-Methyl-5α-cholestane-3β-ol
or 5α-ergostan-3β-ol (7)

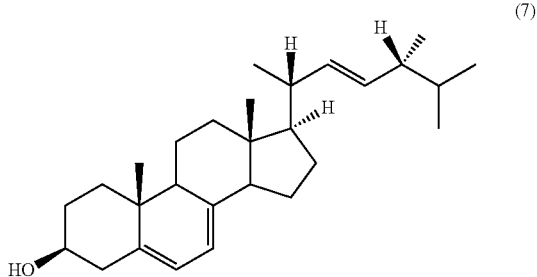

(22E)-(24R)-24-Methylcholesta-5,7,22-trien-3β-ol
or (22E)-ergosta-5,7,22-trien-3β-ol
trivial name ergosterol The steroids can have the formalae as exemplified in formula 9-18. In one or more embodiments, the steroid or sterol has no substitution at C-17, as exemplified by gonane, e.g., formulae 9 and 10, estrange (also termed oestrane), e.g. formulae 11 and 12, and androstane, e.g., formulae 13 and 14. In one or more embodiments, the steroid or sterol has methyl groups at both C-10 and C-13 and a side chain R at C-17 (formulae 15 and 16), as exemplified in Table 1.

(9)

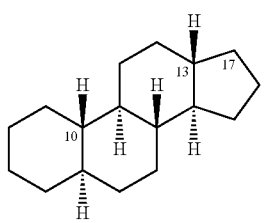

5α-Gonane (10)

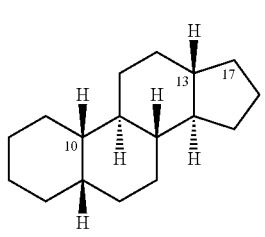

5β-Gonane

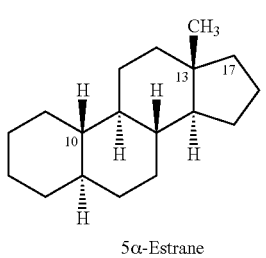

5α-Estrane

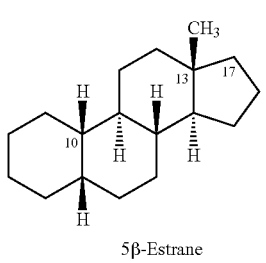

5β-Estrane

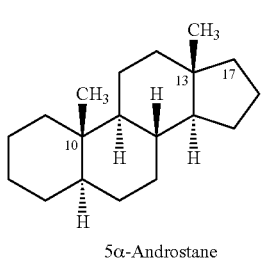

5α-Androstane

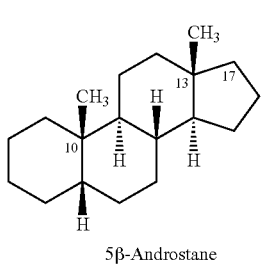

5β-Androstane

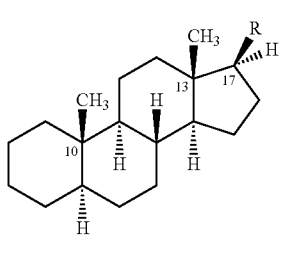

(15)

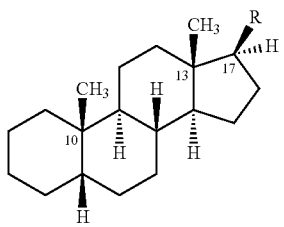

(16)

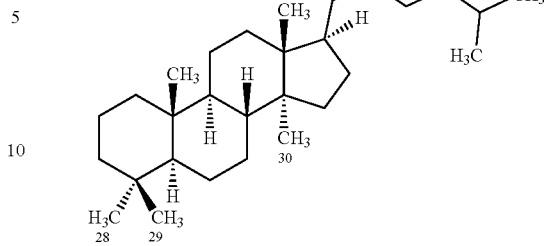

4,4,14-Trimethyl-5α-cholestane or lanostane

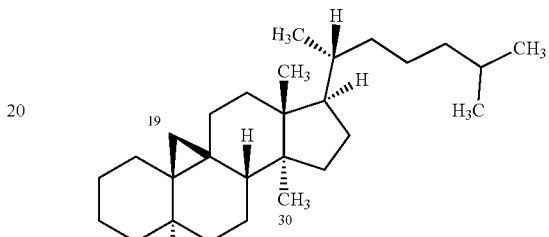

4,4,14-Trimethyl-9,19-cyclo-5α,9β-cholestane or cycloartane

TABLE 1

| Hydrocarbons with side chain at C-17 | | |
|---|---|---|
| Side chain | 5α-Series (15) | 5β-Series (16) |
| (21 H₃C—20—17) | 5α-pregnane (allopregnane) | 5β-pregnane |
| (21 H₃C—20 with CH₃, 17) | 5α-cholane (allocholane) | 5β-cholane |
| (21 H₃C—20—CH₃/CH₃ at 17) | 5α-cholestane | 5β-cholestane (coprostane) |
| (21 H₃C—20—24—CH₃/CH₃ at 17) | 5α-ergostane | 5β-ergostane |
| (21 H₃C—20—24—CH₃/CH₃ at 17) | 5α-campestane | 5β-campestane |

TABLE 1-continued

| Hydrocarbons with side chain at C-17 | | |
|---|---|---|
| Side chain | 5α-Series (15) | 5β-Series (16) |
| 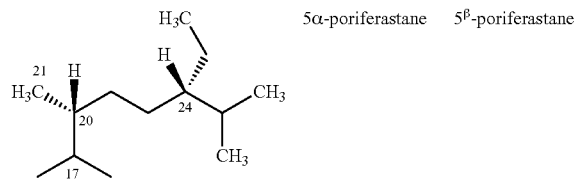 | 5α-poriferastane | 5β-poriferastane |
| 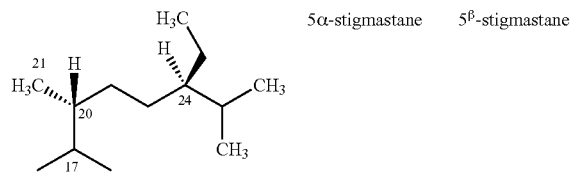 | 5α-stigmastane | 5β-stigmastane |
| 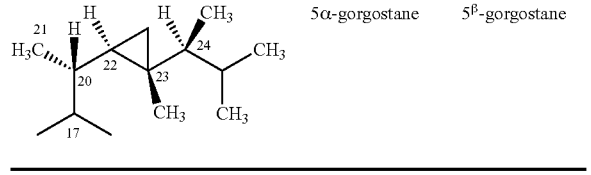 | 5α-gorgostane | 5β-gorgostane |

Examples of unsaturated steroids and sterols are provided in formulae 19-22:

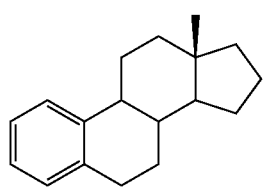

Estra-1,3,5(10)triene  (19)

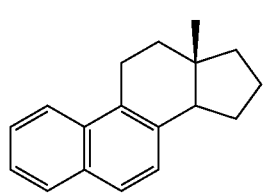

Estra-1,3,7,9-pentaene  (20)

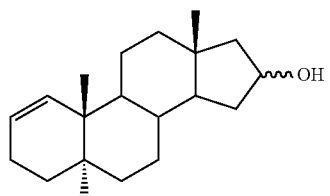

5α-Androst-1-en-16ξ-ol  (21)

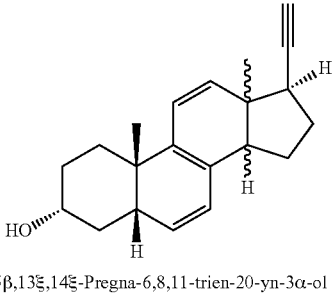

5β,13ξ,14ξ-Pregna-6,8,11-trien-20-yn-3α-ol  (22)

The stereochemistry of double bonds in the side chain is indicated using the E,Z convention. The same applies to the seco compounds of the vitamin D series (example in formula 23). In certain cases, the steroid has two carbon chains attached at position 17, e.g. 17-methyl-5α-pregnane 24, 17-methyl-5α,17β-pregnane 25, and 17-ethyl-5-cholestane and 17(2-bromoethyl)-5α,17α-cholestane 26. Other examples of a steroid that has two carbon chains attached at position 17, are 17,17-dimethyl-5a-androstane 27 and 17(3-methyl-17α-propyl-5α-androstane 28. In certain embodiments, the carbon skeleton of a steroid a carbon atom is replaced by a hetero atom, as exemplified by 17β-hydroxy-4-oxaandrost-5-en-3-one 29. Yet, in additional embodiments, an additional ring is formed by means of a direct link between any two carbon atoms of the steroid ring system or the attached side chain, as exemplified by formulae 30, 31 and 32.

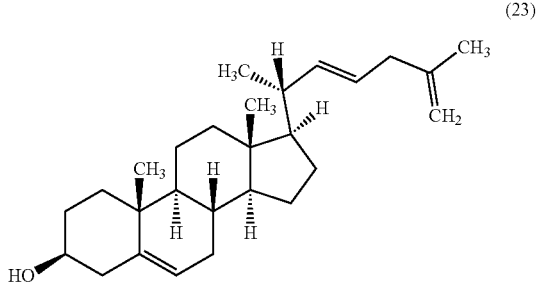

(22E)-Cholesta-5,22,25-trien-3β-ol cf. also formula 7  (23)

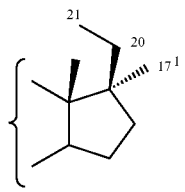

17-Methyl-5α-pregnane  (24)

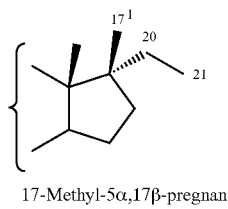

17-Methyl-5α,17β-pregnane  (25)

-continued (26)

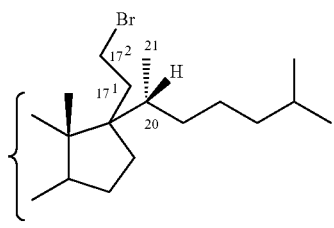

17-(2-Bromoethyl)-5α,17α-cholestane

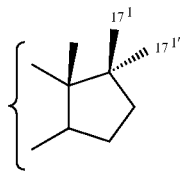

17,17-Dimethyl-5α-androstane (28)

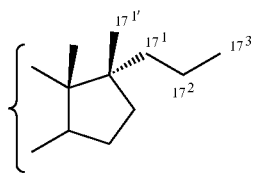

17β-Methyl-17α-propyl-5α-androstane (29)

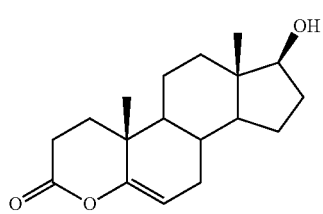

17β-Hydroxy-4-oxaandrost-5-en-3-one (30)

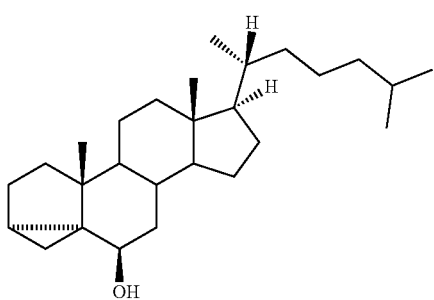

3α,5-Cyclo-5α-cholestan-6β-ol (31)

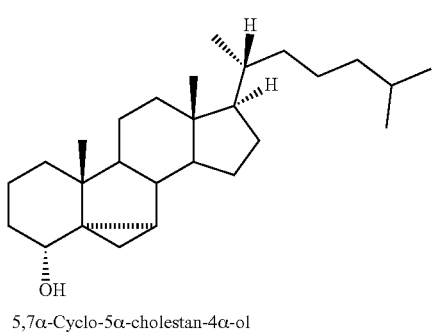

5,7α-Cyclo-5α-cholestan-4α-ol

-continued (32)

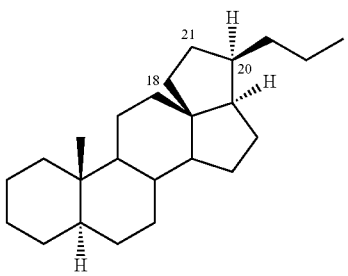

(20K)-18,21-Cyclo-5α-cholane

Many important naturally occurring steroids contain one or more additional heterocyclic ring(s), fused or attached to ring D, formed by modifications of the side chain. These steroids can be grouped into the following families: (a) cardanolides, e.g., 5β-cardanolide 33, 3β,14-dihydroxy-5β-card-20(22)-enolide (digitoxigenin) 34 and 3β,5,14-trihydroxy-19-oxo-5β-card-20(22)-enolide (strophanthidin) 35, as well as epoxycardanolides, containing a 14,21- or a 16,21-oxygen bridge, as shown in 36, (b) bufanolides, e.g., structures 37-39, (c) spirostans, e.g., structures 40-43, (d) furostans, e.g., structures 44-45, and (e) steroid alkaloids.

(33)

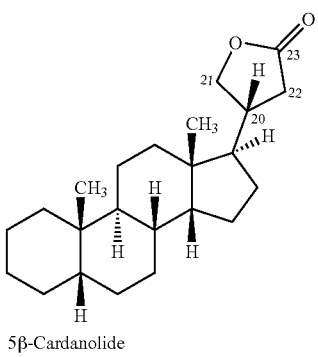

5β-Cardanolide (34)

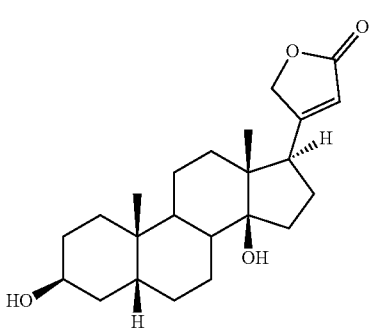

3β,14-Dihydroxy-5β-card-20(22)-enolide trivial name: digitoxigenin

(35)
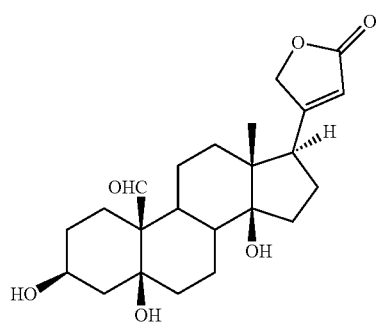
3β,5,14-Trihydroxy-19-oxo-5β-card-20(22)-enolide trivial name: strophanthidin
(36)
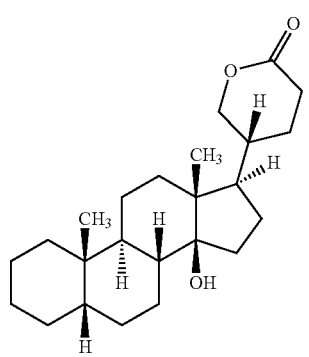
A 16β,21ξ-epoxy-20ξ-cardanolide
(37)
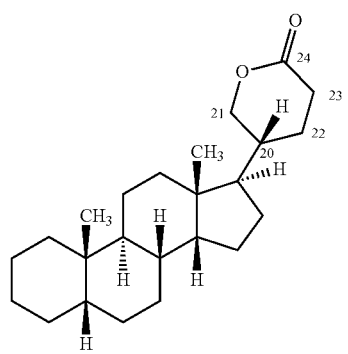
5β-Bufanolide
(38)
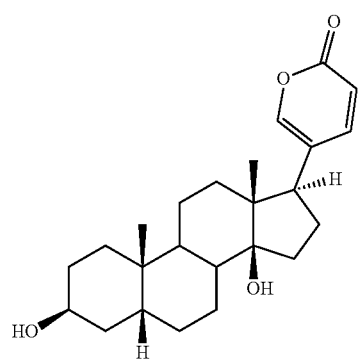
3β,14-Dihydroxy-5β-bufa-20,22-dienolide trivial name: bufalin
(39)
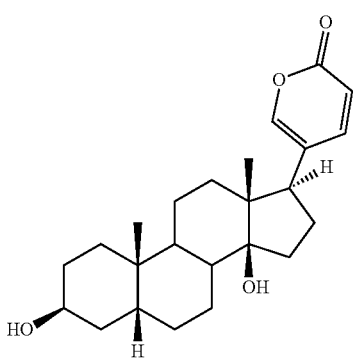
3β,14-Dihydroxy-5β-bufa-4,20,22-trienolide trivial name: scillarenin
(40)
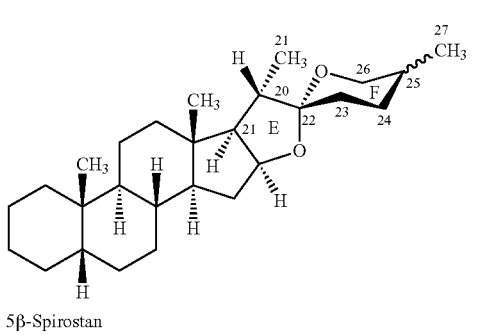
5β-Spirostan
(41)
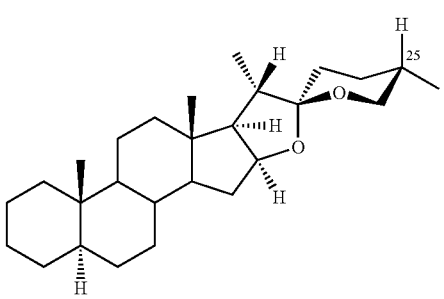
(22S,25R)-5α-Spirostan
(42)
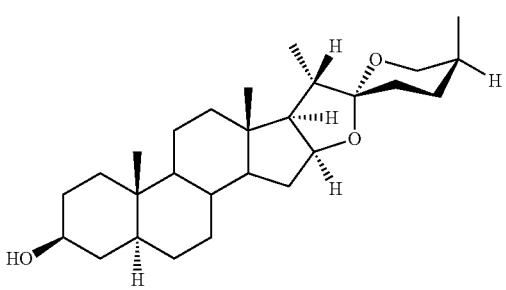
(25S)-5β-Spirostan-3β-ol
trivial name: sarsasapogenin

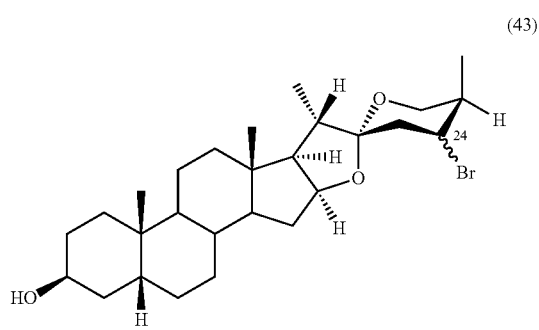

(25R)-24ξ-Bromo-5β-spirostan-3β-ol

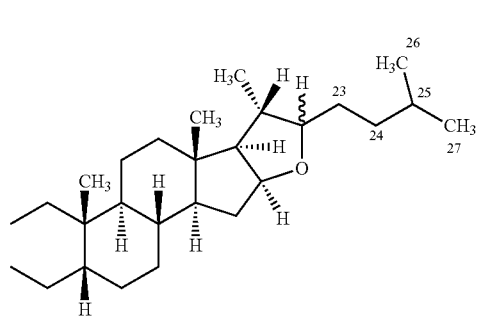

5β-Furostan

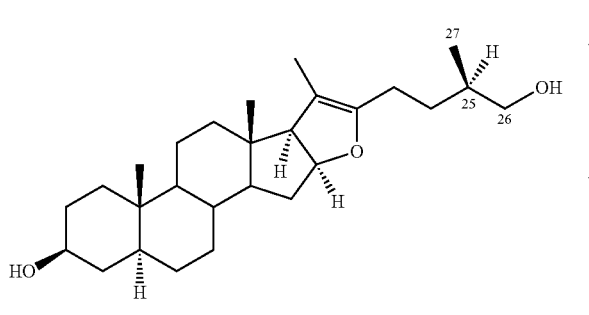

(25R)-5α-Furost-20(22)-ene-3β,26-diol
trivial name: pseudotigogenin

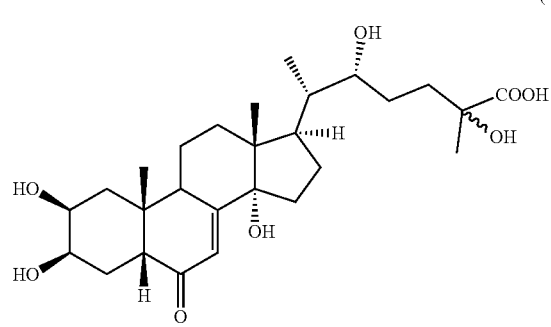

(22R)-2β,3β,14,22,25ξ-Pentahydroxy-6-oxo-5α-cholest-7-en-26-oic acid trivial name: ecdysonic acid

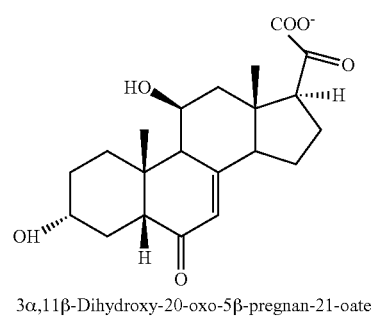

3α,11β-Dihydroxy-20-oxo-5β-pregnan-21-oate

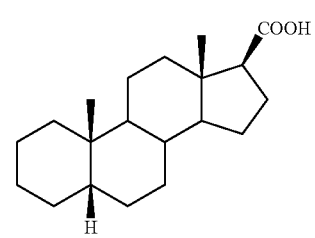

5β-Androstane-17β-carboxylic acid

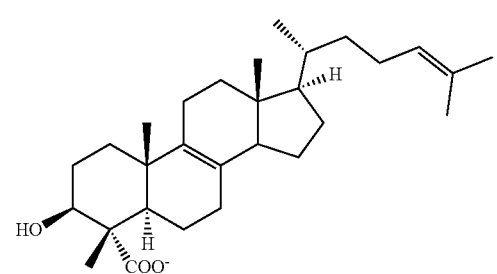

3β-Hydroxy-4β-methyl-5α-cholesta-8,24-diene-4α-carboxylate
or 3β-hydroxy-30-norlanosta-8,24-dien-28-oate

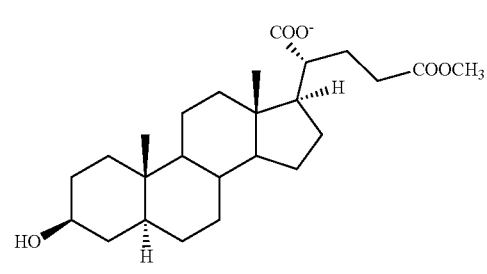

24-Methyl 3β-hydroxy-5α-cholane-21,24-dioate

Several biologically important steroids are derivatives of the parent hydrocarbons carrying various functional groups. Some of the common functional groups include but are not limited to halogens, alkyl groups, aryl groups, benzyl groups, carboxy groups and alkoxy groups.

In one or more embodiments, the steroid is selected from the group consisting of an acid, a salt of an acid, as exemplified in formulae 46-49, and esters, as exemplified in formulae 50 and 51. In one or more embodiments, the steroid is a lactone, as exemplified in formulae 52-54.

(51)

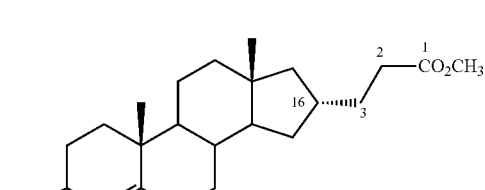

Methyl 3-(3β-hydroxyandrost-4-en-16α-yl)propanoate (52)

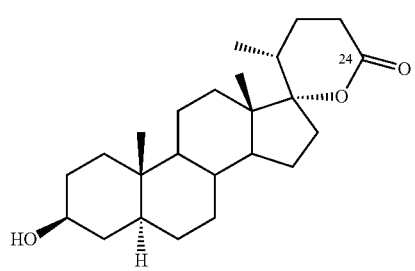

3β-Hydroxy-5α-cholane-24,17-lactone (53)

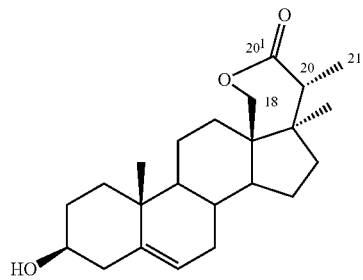

(20R)-3β-Hydroxypregn-5-ene-20,18-carbolactone (54)

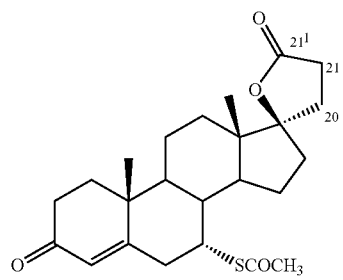

7β-Acetylthio-3-oxo-17α-pregn-4-ene-21,17-carbolactone
international non-proprietary name: spironolactone (55)

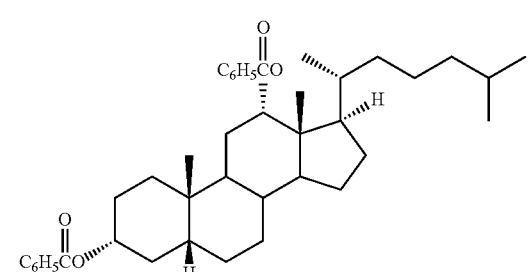

5β-Cholestane-3α,12α-diyl 12-acetate 3-benzoate (56)

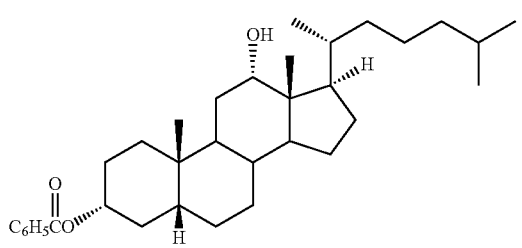

12α-Hydroxy-5β-cholestane-3α-yl benzoate (57)

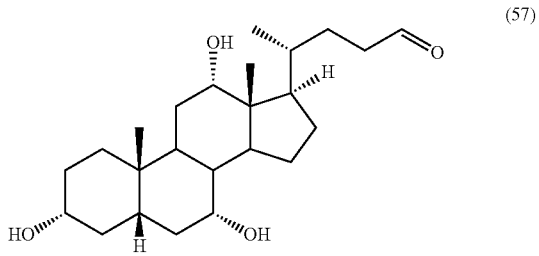

3α,7α,12α-Trihydroxy-5β-cholestan-24-al
or choladehyde (from cholic acid)

(58)

5α-Androstane-17β-carbaldehyde (59)

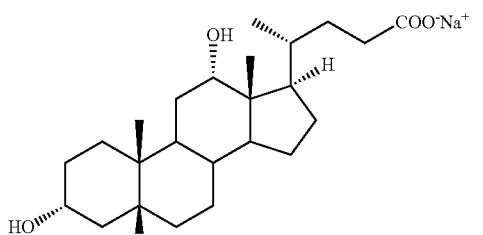

Sodium 3α,12α-dihydroxy-5β-cholan-24-oate
common name: sodium 7-deoxycholate

In one or more embodiments, the steroid is an ester of a steroid alcohol, as exemplified by 5-cholestan-3-yl acetate, 5-cholestane-3,12-diyl diacetate, 3-oxoandrost-4-en-17-yl acetate (trivial name testosterone acetate), 17-hydroxy-20-oxopregn-5-en-3-yl sulfate, 3-acetoxy-5-cardanolide, 3-benzoyl oxy-11-hydroxy-20-oxo-5-pregnan-21-oate (monobenzoate of 47), 3-acetoxy-5-cholano-24,17-lactone (acetate of 52), 3-O-acetylcholic acid, 17-O-benzoylestradiol-17, 3-O-linolenoylcholesterol, as well as in formulae 55 and 56.

In one or more embodiments, the steroid is an oxo compound. The oxo compound can be an aldehyde, as exemplified by 5-androstan-19-al, 5-cholan-24-al, 3-formyl-5-cholan-24-oic acid and by formulae 57 and 58, or a ketone, as exemplified by 5-androstan-3-one, pregn-5-ene-3,20-dione and 11-oxo-5-cholan-24-oic acid.

In one or more embodiment, the steroid is an alcohol as exemplified by 5-cholestane-3,11-diol, 3-hydroxy-5-androstan-17-one (trivial name: androsterone) and by formulae 59.

In additional embodiments, the steroid is an amine as exemplified by androst-5-en-3-amine and formula 60, an ether as exemplified by 17-methoxyandrost-4-en-3-one, (20S)-3,17,20-trimethoxy-5-pregnane, (20S)-3,17-dimethoxy-5-pregnan-20-ol, 21-O-methylcortisol and formula 61, an acetal or a ketal of an oxo steroid (also named as dialkoxy steroids) as exemplified by 3,3-dimethoxycholest-4-ene, 2,3-(methylenedioxy)pregn-5-ene and formula 62.

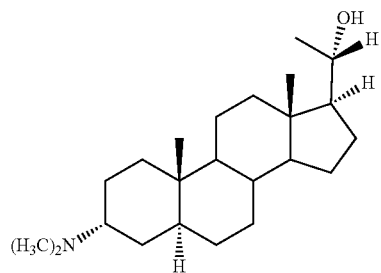

(60)

(20S)-3β-(Dimethylamino)-5α-pregnan-20-ol

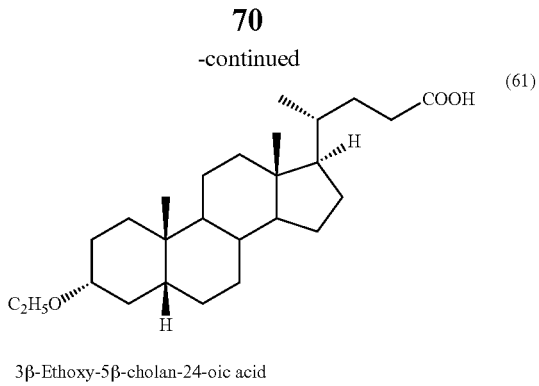

(61)

3β-Ethoxy-5β-cholan-24-oic acid

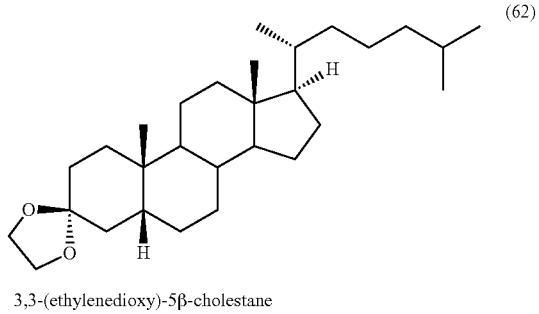

(62)

3,3-(ethylenedioxy)-5β-cholestane

Examples of trivial names retained for important steroid derivatives, these being mostly natural compounds of significant biological activity, are given in Table 2.

TABLE 2

Trivial names of some important steroid derivatives

| Trivial name | Systematic steroid name |
|---|---|
| Aldosterone | 18,11-hemiacetal of 11β,21-dihydroxy-3,20-dioxopregn-4-en-18-al or 11β,18-epoxy-18ξ,21-dihydroxypregn-4-ene-3,20-dione |
| Androsterone | 3α-hydroxy-5α-androstan-17-one |
| Brassinolide | (22R,23R)-2α,3α,22,23-tetrahydroxy-6,7-seco-5α-cmpestano-6,7-lactone |
| Calcidiol (93) | (5Z,7E)-(3S)-9,10-secocholesta-5,7,10(19)-triene-3,25-diol |
| Calciol = cholecalciferol (92) | (5Z,7E)-(3S)-9,10-secocholesta-5,7,10(19)-trien-3-ol |
| Calcitriol (94) | (5Z,7E)-(1S,3R)-9,10-secocholesta-5,7,10(19)-triene-1,3,25-triol |
| Cholesterol | cholest-5-en-3β-ol |
| Cholic acid | 3α,7α,12α-trihydroxy-5β-cholan-24-oic acid |
| Corticosterone | 11β,21-dihydroxypregn-4-ene-3,20-dione |
| Cortisol | 11β,17,21-trihydroxypregn-4-ene-3,20-dione |
| Cortisol acetate | 21-O-acetylcortisol |
| Cortisone | 17,21-dihydroxypregn-4-ene-3,11,20-trione |
| Cortisone acetate | 21-O-acetylcortisone |
| Deoxycorticosterone | 21-hydroxypregn-4-ene-3,20-dione (i.e. the 11-deoxy derivative of corticosterone) |
| Ecdysone | (22R)-2β,3β,14α,22,25-pentahydroxy-5β-cholest-7-en-6-one |
| Ercalciol = ergocalciferol | (5Z,7E,22E)-(3S)-9,10-secoergosta-5,7,10(19),22-tetren-3-ol |
| Ergosterol (7) | (22E)-ergosta-5,7,22-trien-3β-ol |
| Estradiol-17α | estra-1,3,5(10)-triene-3,17α-diol |
| Estradiol-17β | estra-1,3,5(10)-triene-3,17β-diol |
| Estriol | estra-1,3,5(10)-triene-3,16α,17β-triol |
| Estrone | 3-hydroxyestra-1,3,5(10)-trien-17-one |
| Lanosterol | lanosta-8,24-dien-3β-ol |
| Lithocholic acid | 3α-hydroxy-5β-cholan-24-oic acid |
| Progesterone | pregn-4-ene-3,20-dione |
| Pseudotigogenin | (25R)-5α-furost-20(22)-ene-3β,26-diol |
| Sarsasapogenin | (25S)-5β-spirostan-3β-ol |
| Smilagenin | (25R)-5β-spirostan-3β-ol |
| Testosterone (63) | 17β-hydroxyandrost-4-en-3-one |
| Tigogenin | (25R)-5α-spirostan-3β-ol |

Additional non-limiting examples of steroids that are applicable according to the present invention are provided in formulae 63-79.

(63)
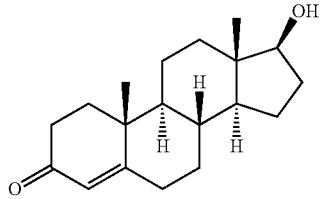
17β-Hydroxyandrost-4-en-3-one (testosterone)

(64)
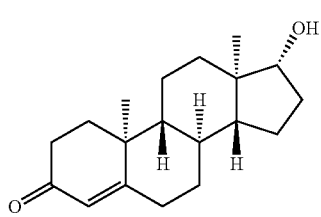
ent-17β-Hydroxyandrost-4-en-3-one (ent-testosterone)

(65)
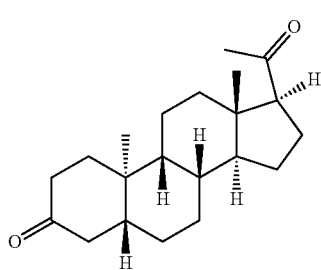
5β,9β,10α-Pregnane-3,20-dione

(66)
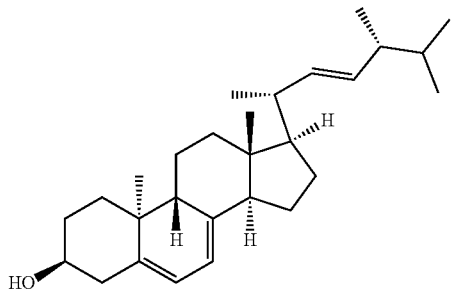
(22E)-9β,10α-Ergosta-5,7,22-trien-3β-ol
trivial name: lumisterol

(67)
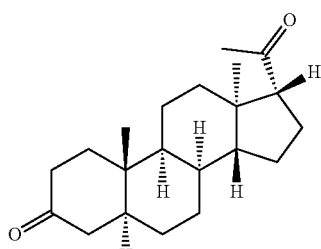
ent-5β,9β,10α-Pregnane-3,20-dione
(not 5α,8α,13α,14β,17α-pregnane-3,2-dione)

(68)
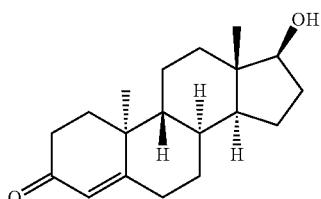
ent-17α-Hydroxy-13α,14β-androst-4-en-3-one
(not 17β-hydroxy-8α,9β,10α-androst-4-en-3-one)

(69)
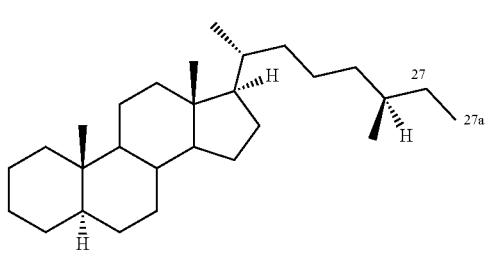
(25R)-27a-Homo-5α-cholestane

(70)
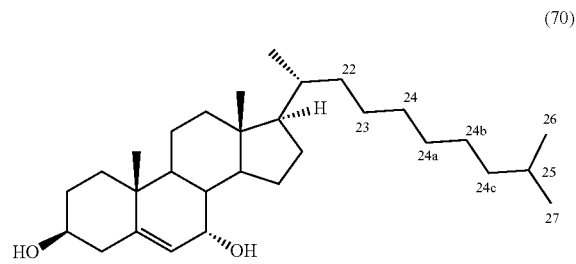
24a,24b,24c-Trihomocholest-5-ene-3β,7α-diol

(71)
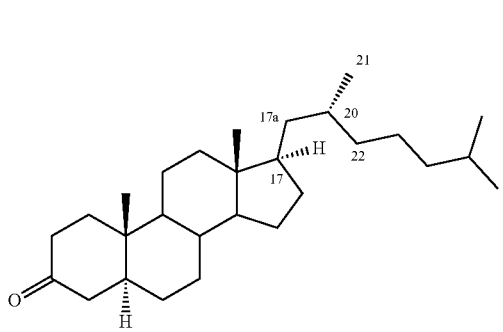
17(20)a-Homo-5α-cholestan-3-one

(72)
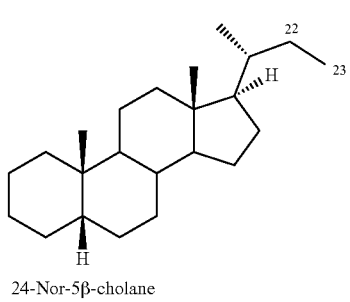
24-Nor-5β-cholane

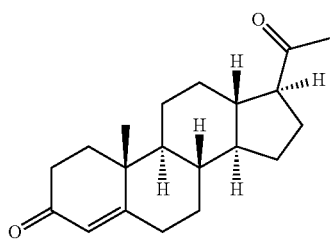

18-Norpregn-4-ene-3,20-dione

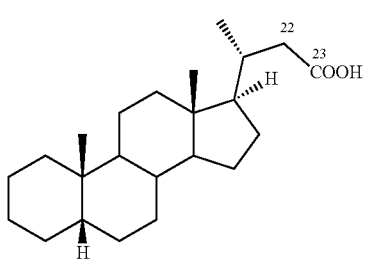

24-Nor-5β-choloan-23-oic acid

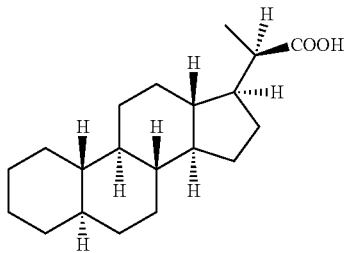

(20R)-18,19-Dinor-5α-pregnane-20-carboxylic acid
(not 18,19,23,24-tetranor-5α-cholan-21-oic acid

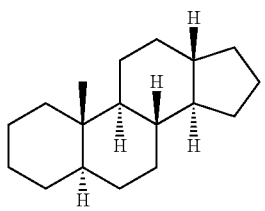

18-Nor-5α-androstane (not 10-methyl-5α-gonane)

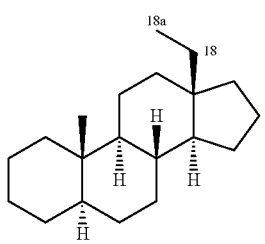

18a-Homo-5α-estane (not 13-ethyl-5α-gonane or
13-ethyl-18-nor-5α-estane)

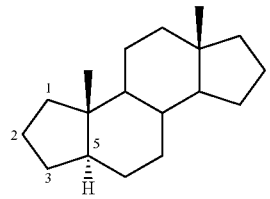

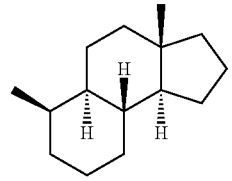

Des-A-androstane

In one or more embodiments according to the present invention, the steroid is a compound, in which one or more of the cyclopenta[a]phenanthrene rings is contracted by loss of an unsubstituted methylene group, as exemplified by 4-nor-5-androstane (78), where C-4 is missing. In other embodiments one or more of the cyclopenta[a]phenanthrene rings is expanded by inclusion of a methylene group, as exemplified by formulae 80-86.

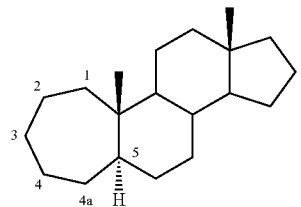

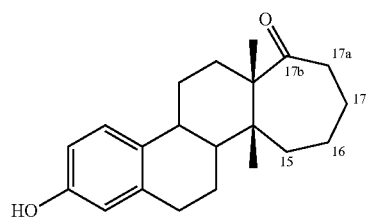

5-Hydroxy-17a,17b-dihomoestra-1,3,5(10)-trien-17b-one

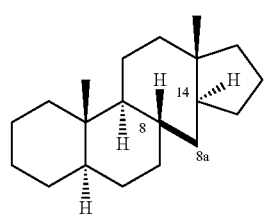

8(14)a-Homo-5α-androstane (83)

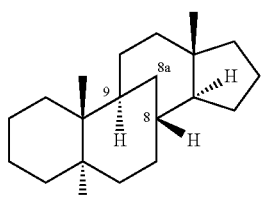

8(9)a-Homo-5α-androstane (84)

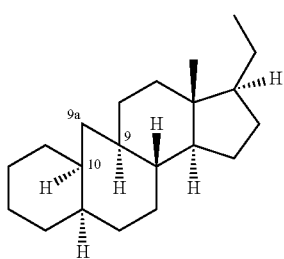

9(10)a-Homo-19-nor-5α,10α(H)-pregnane (85)

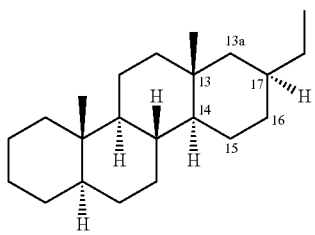

13(17)a-Homo-5α-pregnane (86)

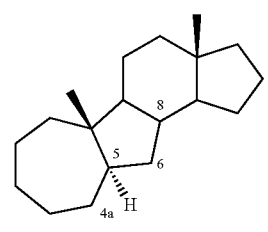

4a-Homo-7-nor-5α-androstane

In one or more embodiments, the steroid contains additional rings that are formed within, or on, a steroid nucleus. In additional embodiments, the steroids contains a bivalent bridge such as —O—O—, —[CH$_2$]$_n$—, linking non-adjacent ring positions as exemplified by formulae 99-102.

In one or more embodiments, the steroid contains a cyclopenta[a]phenanthrene skeleton and a carbocyclic or heterocyclic ring component fused to it, as exemplified by formulae 103-111, and in other embodiments, an additional ring is linked to the cyclopenta[a]phenanthrene skeleton through a spiro system, as exemplified by formula 112.

(99)

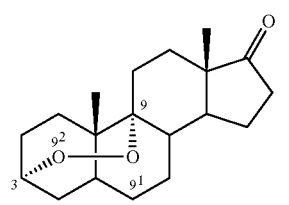

3α,9-Epidioxy-5α-androstan-17-one (100)

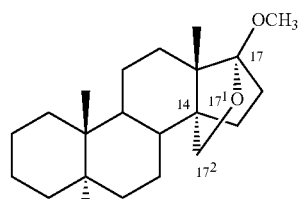

17β-Methoxy-17α,14-(epoxymethano)-5α-androstane (101)

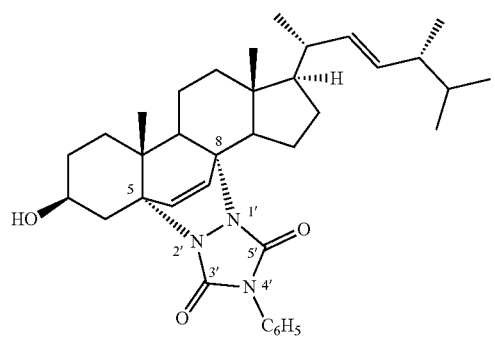

(22E)-3β-Hydroxy-4′-phenyl-5,8-[1,2]epi(1,2,4]triazole-5α,8α-ergosta-6,22-diene-3′,5′-dione (102)

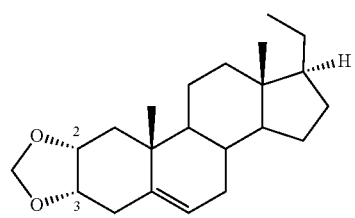

2α,3α-(Methylenedioxy)pregn-5-ene (103)

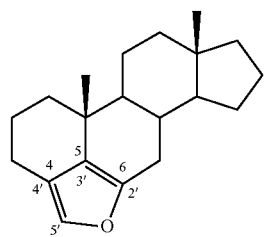

Furo[4′,3′,2′:4,5,6]androstane (104)
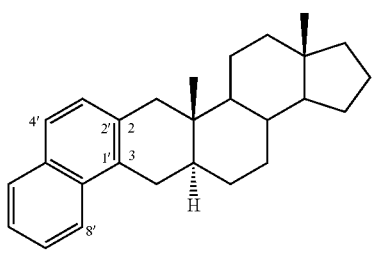
Naphtho[2',1',:2,3]-5α-androstane
(105)
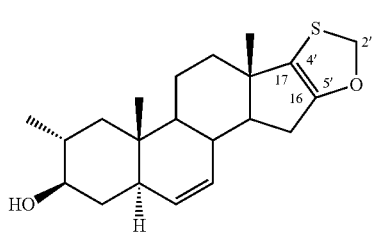
2α-Methyl[1,3]oxathiolo[5'4':16,17]-5α-androst-6-en-3β-ol
(106)
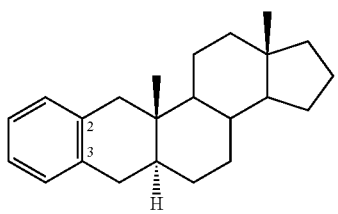
Benzo[2,3]-5α-androstane
(107)
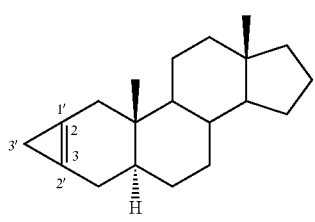
3'H-Cyclopropa[2,3]-5α-androstane
(108)
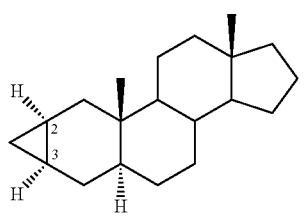
2α,3α-Dihydro-3'H-cyclopropa[2,3]-5α-androstane
(109)
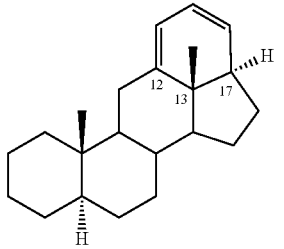
17αH-Benzo[12,13,17]-5α-androstane
(110)
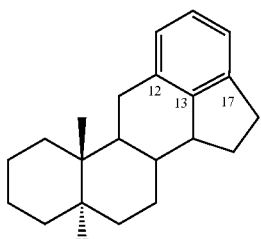
3'H-Cyclopropa[2,3]-5α-androstane
(111)
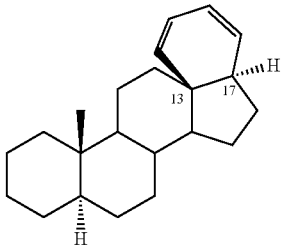
3'H-Cyclopropa[2,3]-5α-androstane
(112)
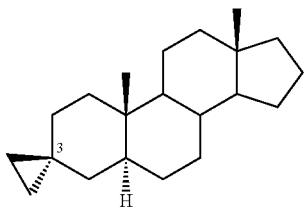
Spiro[5α-androstane-3,1'-cyclopropane]
(113)
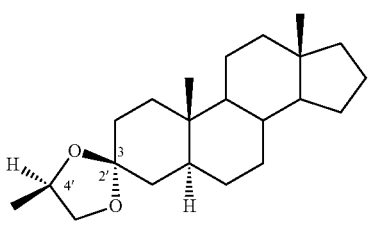
(4'R)-4'-Methyl-(3S)-spiro[5α-androstane-3,2'-[1,3]dioxolane]

TABLE 3

Exemplary steroids that are useful according to the present invention.

| Trivial name | Chemical name | Molecular formula |
|---|---|---|
| Acrihellin | 5,14-dihydroxy-3β-[(3-methylcrotonoyl)oxy]-19-oxo-5β-bufa-20,22-dienolide | $C_{29}H_{38}O_7$ |
| Actodigin | 3β-(β-D-glucopyranosyloxy)-14-hydroxy-24-nor-5β,14β-chol-20(2)-eno-21,23-lactone | $C_{29}H_{44}O_9$ |
| Alfacalcidol | (5Z,7E)-(1S,3R)-9,10-secocholesta-5,7,10(19)-triene-,3-diol | $C_{27}H_{44}O_2$ |
| Betamethasone | 9-fluoro-11β,17,21-trihydroxy-16β-methylpregna-1,4-diene-3,20-dione | $C_{22}H_{29}FO_5$ |
| Canrenone | 3-oxo-17α-pregna-4,6-diene-21,17-carbolactone | $C_{22}H_{28}O_3$ |
| Clomegestone | 6-chloro-17-hydroxy-16α-methylpregna-4,6-diene-3,20-dione | $C_{22}H_{29}ClO_3$ |
| Cyproterone | 6-chloro-1β,2β-dihydro-17-hydroxy-3'H-cyclopropa[1,2]pregna-4,6diene-3,20-dione | $C_{22}H_{27}ClO_3$ |
| Dexamethasone | 9-fluoro-11β,17,21-trihydroxy-16α-methylpregna-1,4-diene-3,20-dione | $C_{22}H_{29}FO_5$ |
| Disogluside | (25R)-3β-(β-D-glucopyranosyloxy)spirost-5-ene | $C_{33}H_{52}O_8$ |
| Ethinylestradiol | 19-nor-17α-pregna-1,3,5(10)-trien-20-yne-3,17-diol | $C_{20}H_{24}O_2$ |
| Fluazacort | 21-acetoxy-9-fluoro-11β-hydroxy-2'-methyl-16bH-oxazolo[5',4':16,17]pegna--1,4-diene-3,20-dione | $C_{25}H_{30}FNO_6$ |
| Fluocortin | 6α-fluoro-11β-hydroxy-16α-methyl-3,20-dioxopregna-1,4-dien-21-oic acid | $C_{22}H_{27}FO_5$ |
| Fusidic Acid | (17Z)-ent-16α-acetoxy-3β,11β-dihydroxy-4β,8,14-trimethyl-18-nor-5β,10α-cholesta--17(20),24-dien-21-oic acid | $C_{31}H_{48}O_6$ |
| Gestrinone | 17-hydroxy-18α-homo-19-nor-17α-pregna-4,9,11-trien-20-yn-3-one | $C_{21}H_{24}O_2$ |
| Halometasone | | |
| | 2-chloro-6α,9-difluoro-11β,17,21 -trihydroxy-16α-methylpregna-1,4-diene-3,20-dione | $C_{22}H_{27}ClF_2O_5$ |
| Hydrocortisone | 11β,17,21-trihydroxypregn-4-ene-3,20-dione | $C_{21}H_{30}O_5$ |
| Mebolazine | 17β-hydroxy-2α,17-dimethyl-5α-androstan-3-one azine | $C_{42}H_{68}N_2O_2$ |
| Medroxyprogesterone | 17-hydroxy-6α-methylpregn-4-ene-3,20-dione | $C_{22}H_{32}O_3$ |
| Meproscillarin | 3β-(6-deoxy-4-O-methyl-α-L-mannopyranosyloxy)-14-hydroxybufa-4,20,22-rienolide | $C_{31}H_{44}O_8$ |
| Mespirenone | 7α-acetylthio-15α,16α-dihydro-3-oxo-3'H-cyclopropa[15,1]-17α-pregna--1,4-diene-21,17-carbolactone | $C_{25}H_{30}O_4S$ |
| Mestranol | 3-methoxy-19-nor-17α-pregna-1,3,5(10)-trien-20-yn-17-ol | $C_{21}H_{26}O_2$ |
| Naflocort | 9-fluoro-1',4'-dihydro-11β,21-dihydroxy-16bH-naphtho[2',3':16,17]prena--1,4-diene-3,20-dione | $C_{29}H_{33}FO_4$ |
| Norenthisterone | 17-hydroxy-19-nor-17α-pregn-4-en-20-yn-3-one | $C_{20}H_{26}O_2$ |
| Norgesterone | 17-hydroxy-19-nor-17α-pregna-5(10),20-dien-3-one | $C_{20}H_{28}O_2$ |
| Norgestrel | rac-17-hydroxy-18α-homo-19-nor-17α-pregn-4-en-20-yn-3-one | $C_{21}H_{28}O_2$ |
| Oxandrolone | 17β-hydroxy-17α-methyl-2-oxa-5α-androstan-3-one | $C_{19}H_{30}O_3$ |
| Oxymetholone | 17β-hydroxy-2-(hydroxymethylene)-17α-methyl-5α-androstan-3-one | $C_{19}H_{28}O_3$ |
| Pancuronium bromide | 1,1'-(3α,17β-diacetoxy-5α-androstane-2β,16β-diyl)bis(-methylpiperidinium) dibromide | $C_{35}H_{60}Br_2N_2O_4$ |
| Prednisolone | 11β,17,21-trihydroxypregna-1,4-diene-3,20-dione | $C_{21}H_{28}O_5$ |
| Prednisone | 17,21-dihydroxypregna-1,4-diene-3,11,20-trione | $C_{21}H_{26}O_5$ |
| Proscillardin | 3β-(6-deoxy-α-L-mannopyranosyloxy)-14-hydroxybufa-4,20,22-trienolide | $C_{30}H_{42}O_8$ |
| Roxibolone | 11β,17β-dihydroxy-17α-methyl-3-oxoandrosta-1,4-diene-2-carboxylic acid | $C_{21}H_{28}O_5$ |
| Spironolactone | 7α-acetylthio-3-oxo-17α-pregn-4-ene-21,17-carbolactone | $C_{24}H_{32}O_4S$ |

TABLE 3-continued

Exemplary steroids that are useful according to the present invention.

| Trivial name | Chemical name | Molecular formula |
|---|---|---|
| Timobesone | S-methyl 9-fluoro-11β,17α-dihydroxy-16β-methyl-3-oxoandrosta- -1,4-diene-17β-carbothioate | $C_{22}H_{29}FO_4S$ |
| Triamcinolone | 9-fluoro-11β,16α,17,21-tetrahydroxypregna-1,4-diene-3,20-dione | $C_{21}H_{27}FO_6$ |
| Ursodeoxycholic acid | 3α,7β-dihydroxy-5β-cholan-24-oic acid | $C_{24}H_{40}O_4$ |

Mixtures of these steroids may also be employed according to the present invention.

The steroid is included in the composition in a concentration that provides a desirable ratio between the efficacy and safety. Typically, steroids are included in the composition in a concentration between about 0.005% and about 12%. However, in some embodiments, the concentration is between about 0.005% and about 0.5%, in other embodiment between about 0.5% and about 2%, and in additional embodiments between about 2% and about 5% or between about 5% and about 12%.

In one or more embodiments, the steroid possesses immunomodulating and/or anti-inflammatory properties. Without being bound to a specific theory, immunomodulating and/or anti-inflammatory steroids act, among other mechanisms, through inhibition of the activity of phospholipase $A_2$. They also may have anti-proliferative effects on keratinocytes and other cell types. They can suppress collagen synthesis by fibroblasts, but this may lead to adverse effects. Anti-inflammatory steroids are roughly grouped according to relative anti-inflammatory activity, but activity may vary considerably depending upon the vehicle, the site of application, disease, the individual patient and whether or not an occlusive dressing is used, as exemplified in the Table below.

TABLE

Exemplary anti-inflammatory steroids

| Relative Potency | Generic Name | Typical concentration in topical products |
|---|---|---|
| Low Potency | Hydrocortisone | 0.5%-1% |
|  | hydrocortisone acetate | 0.5-1.0% |
|  | Desonide | 0.02-0.2% |
| Medium Potency | Betamethasone valerate | 0.05%-0.1% |
|  | Prednicarbate | 0.02-0.2% |
|  | Clobetasone-17-butyrate | 0.05% |
|  | Flucinonide | 0.01%-0.05% |
|  | Fluocinolone acetonide | 0.01-0.01% |
|  | Alcometasone dipropionate | 0.01% |
|  | Mometasone furoate | 0.1% |
|  | Triamcinolone acetonide | 0.025%-0.1% |
| High Potency | Betamethasone-17-benzoate | 0.025% |
|  | Methylprednisolone aceponate | 0.1% |
|  | Betamethasone dipropionate | 0.025%, 0.05% |
|  | Halcinonide | 0.1% |
|  | Triamcinolone acetonide | 0.5% |
| Highest Potency | Halobetasol | 0.05% |
|  | Clobetasol-17-propionate | 0.05% |

In one or more embodiments, the steroid is selected from the group of low-potency anti-inflammatory steroids, medium potency anti-inflammatory steroids and high potency anti-inflammatory steroids.

In one or more embodiments, the anti-inflammatory steroid is included in the composition at a concentration between about 0.005% and about 1%.

The McKenzie vasoconstrictor assay, as described, for example, in the British Journal of Dermatology 1975; 93:563-71 and versions thereof, has been the primary method used for classifying the potency of a product, containing an anti-inflammatory steroids. Thus, in one or more embodiments, the anti-inflammatory steroid is a steroid that positively affects the vasoconstrictor assay.

In one or more embodiments, the steroid is a hormone. Hormones are known to affect a variety of biological processes in any organism, and thus, their inclusion in the composition, which is intended for local treatment of the skin, the vagina, the rectum as well as other body surfaces and cavities provided an advantageous treatment modality. Such compositions containing hormones can be further administered systemically, via the transdermal or transmucosal route, in order to alleviate a disorder that is affected by the specific hormone, or in order to tune the hormonal balance of the body in order to attain certain effects controlled by hormones, such as contraception and birth induction.

In one or more embodiments, the steroid hormone is a male hormone or an androgen. Non-limiting examples of male hormones/androgens include testosterone, testosterone cipionate, testosterone decanoate, testosterone enantate, testosterone isocaproate, testosterone phenylpropionate, testosterone propionate, testosterone undecylate, 5α-dihydrotestosterone, dehydroepiandrosterone (also termed prasterone and DHEA), androstenedione, androstanediol, androsterone, androstenolone, prasterone enantate, prasterone sodium sulfate, ormeloxifene, mesterolone, fluoxymesterone, methyltestosterone, gestrinone, delmadinone, delmadinone acetate, chlormadinone, chlormadinone acetate, danazol and testolactone.

In one or more embodiments, the steroid hormone is a female hormone or an estrogen. Non-limiting examples of female hormones/estrogens include estradiol, estradiol benzoate, estradiol cipionate, estradiol dipropionate, estradiol enantate, estradiol hexahydrobenzoate, estradiol phenylpropionate, estradiol valerate, polyestradiol phosphate, estriol, estriol sodium succinate, estriol succinate, polyestriol phosphate, quinestradol, ethinylestradiol, estrapronicate, mestranol, estrapronicate and equilin.

In one or more embodiments, the steroid hormone is a progestogen. Non-limiting examples of progestogens include progesterone, norethisterone, norethisterone acetate, norethisterone enantate, medroxyprogesterone acetate, delmadinone acetate, flugestone acetate, dydrogesterone, desogestrel, norgestrel, levonorgestrel, dydrogesterone, gestodene, chlormadinone acetate, dienogest, drospirenone, lynestrenol, tybolone, cyproterone acetate, megestrol acetate, nomegestrol acetate.

Yet, in additional embodiments, the steroid an inhibitor of a steroid hormone. Non-limiting examples of such inhibitors are finasteride, dutasteride and spironolactone.

In one or more embodiments, the steroid is a vitamin D. The term vitamin D is used to describe all steroids that exhibit qualitatively the biological activity of calciol (vitamin $D_3$). Non limiting examples of vitamin D compounds are provided in Table 5.

Yet, in additional embodiments, the steroid is a vitamin $D_3$ analogue. Exemplary vitamin $D_3$ analogs include calcipotriol, tacalcitol, maxacalcitol, and calcitriol, with calcipotriol being especially preferred. Vitamin $D_3$ analogues and derivatives are known to degrade at low pH levels. Therefore, in certain preferred embodiments, the steroid is a vitamin $D_3$ or an analogue or a derivative thereof, the pH is adjusted to the range between about 7 and about 10, or between about 7.5 and about 9. In one or more embodiments, the pH is adjusted using a buffering agent, suitable of maintaining a pH level between about 7 and about 10, or between about 7.5 and about 9.

TABLE 5

Examples of vitamin D compounds

| Vitamin D name | Systematic steroid name |
|---|---|
| Cholecalciferol (also termed calciol, cholecalciferol, vitamin $D_3$ and colecalciferol) | (5Z,7E)-(3S)-9,10-seco-5,7,10(19)-cholestatrien-3-ol |
| 25-Hydroxycholecalciferol (also termed calcidiol) | (5Z,7E)-(3S)-9,10-seco-5,7,10(19)-cholestatriene-3,25-diol |
| 1α,25-Dihydroxycholecalciferol (also termed calcitriol) | (5Z,7E)-(1S,3R)-9,10-seco-5,7,10(19)-cholestatriene-1,3,25-triol |
| Ergocalciferol (also termed ercalciol and ergocalciferol) | (5Z,7E,22E)-(3S)-9,10-seco-5,7,10(19),22-ergostatetraen-3-ol |
| 1α,25-Dihydroxyergocalciferol (also termed ercalcitriol) | (5Z,7E,22E)-(1S,3R)-9,10-seco-5,7,10(19),22-ergostatetraen-1,3,25-triol |
| 22,23-Dihydroergocalciferol (also termed (24S)-methylcalciol and 22,23-dihydroercalciol) | (5Z,7E)-(3S)-9,10-seco-5,7,10(19)-ergostatrien-3-ol |
| 1α,24R,25-Trihydroxycholecalciferol (also termed calcitetrol) | (5Z,7E)-(1S,3R,24R)-9,10-seco-5,7,10(19)-cholestatriene-1,3,24,25-tetrol |
| Previtamin $D_3$ (also termed precalciferol and (6Z)-tacalciol) | (6Z)-(3S)-9,10-seco-5(10),6,8-cholestatrien-3-ol |
| Tachysterol$_3$ (also termed tacalciol) | (6E)-(3S)-9,10-seco-5(10),6,8-cholestatrien-3-ol |
| Isovitamin $D_3$ (also termed (5E)-isocalciol) | (5E,7E)-(3S)-9,10-seco-1(10),5,7-cholestatrien-3-ol |
| Dihydrotachysterol$_3$ (also termed dihydroercalciol) | (5E,7E)-(3S,10S)-9,10-seco-5,7-cholestadien-3-ol |

Further examples of vitamin D compounds include, but are not limited to (1S)-Hydroxycalciol (also termed 1α-hydroxycholecalciferol and alfacaleidol), (24R)-Hydroxycalcidiol (also termed 24(R),25-dihydroxycholecalciferol), 25-Fluorocalciol (also termed 25-fluorocholecalciferol), Ercalcidiol (also termed 25-hydroxyergocalciferol), Ertacalciol (also termed tachysterol$_2$, (5E)-Isocalciol (also termed isovitamin $D_3$, 22,23-Dihydroercalciol), (24S)-methylcalciol (also termed vitamin $D_4$), (5E)-(10S)-10,19-Dihydroercalciol, (also termed dihydrotachysterol$_2$, hytakerol, and dihydrotachysterol), (24S)-Ethylcalciol (also termed vitamin $D_5$) and (22E)-(24R)-Ethyl-22,23-didehydrocalciol, (also termed vitamin $D_6$).

In one or more embodiments, the steroid is a phytosteroid or a phytosterol. As used herein, the term "phytosteroid" or "phytosterol" includes all steroids that are obtained, derived or extracted from plant sources. Non-limiting examples of families of phytosteroids and phytosterols include ecdysones, withanolids, sterines, steroid saponins and soflavonoids. Non-limiting examples of phytosteroid and phytosterol compounds include alpha-sitosterol, beta-sitosterol, stigmastanol, campesterol, alpha-sitostanol, beta-sitostanol, stigmastanol, campestanol, avenosterol, brassicasterol, desmosterol, chalinosterol, beta-ecdysone, whithaferin A, beta-sitosterine, stigmasterine, campesterine, ergosterine, diosgenin, daidzein, glycitein, genistein, muristerone, poriferasterol, clionasterol, campestanol, and cycloartenol, as well as all natural or synthesized forms and derivatives thereof, such as fatty acid esters, such as ferulic acid esters, oleoyl esters, and cinnamic acid esters, including isomers.

Plant oils and extracts which contain steroids are also useful. Non limiting examples of plants that contain steroids include nuts seeds, sprouted seeds and grains (such as alfalfa), St. Mary's thistle, *ginkgo biloba*, saw palmetto, *panax*, siberian ginseng, *foeniculum vulgare, cimicifuga racemosa*, licorice root, red clover, sage, sarsaparilla, sassafras, *angelica sinensis achillea millefolium, anemone pratensis, angelica sinensis, glycyrrhiza glabra, hypericum perforatum, larrea, panax, piscidia erythrina, plantago psyllium, serenoa repens, symphytum, taraxacum officinale, trifolium pratense, turnera spp., tussilago farfara, valeriana officinalis, viburnum prunifolium, calendula officinalis*

In one or more embodiments, the steroid is a compound that is positively identified using a laboratory method, suitable of detecting a steroid.

Steroids in Combination with Other Agents

Several disorders of the skin, a body cavity or mucosal surface (e.g., the mucosa of the nose, mouth, eye, ear, vagina or rectum) involve a combination of inflammation, cell proliferation and differentiation abnormalities, and other biological abnormalities that can be effected by a steroid; and other etiological factors that require an additional therapeutic modality. For example, psoriasis involves inflammation as well as excessive cell proliferation and inadequate cell differentiation. Atopic dermatitis involves inflammation, skin dryness and keratinocyte growth abnormality. Bacterial, fungal and viral infections involve pathogen colonization at the affected site and inflammation. Likewise, hair growth disorders and other pilosebaceous disorders involve an impaired hormonal balance (which can be affected by a steroid hormone or a steroid hormone antagonist), together with other etiological factors, that can be affected a non-steroidal active agent. Hence, in many cases, the inclusion of an additional therapeutic agent in the foamable pharmaceutical composition, contributes to the clinical activity of the steroid. Thus, in one or more embodiments, the foamable composition further includes at least one additional therapeutic agent, in a therapeutically effective concentration.

In one or more embodiments, the at least one additional non-steroidal therapeutic agent is selected from the group consisting of an anti-infective, an antibiotic, an antibacterial agent, an antifungal agent, an antiviral agent, an antiparasitic agent, a nonsteroidal anti-inflammatory drug, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

In certain cases, the disorder to be treated involves unaesthetic lesions that need to be masked. For example, rosacea involves papules and pustules, which can be treated with a steroid, as well as erythema, telangiectasia and redness, which do not respond to treatment with a steroid. Thus, in one or more embodiments, the additional active agent is a masking agent, i.e., a pigment. Non limiting examples of suitable pigments include brown, yellow or red iron oxide or hydroxides, chromium oxides or hydroxides, titanium oxides or hydroxides, zinc oxide, FD&C Blue No. 1 aluminum lake, FD&C Blue No. 2 aluminum lake and FD&C Yellow No. 6 aluminum lake.

In an embodiment, the active agent is a hair growth regulator. Suitable hair growth regulators include but are not limited to N-acetylgalactosamine, N-acetylglucosamine, N-acetylmannosamine, acitretin, aminexil, ascomycin, asiatic acid, azelaic acid, benzalkonium chloride, benzethonium chloride, benzydamine, benzyl nicotinate, benzoyl peroxide, benzyl peroxide, betulinic acid, betulonic acid, calcium pantothenate, celastrol, cepharanthine, chlorpheniramine maleate, clinacycin hydrochloride, crataegolic acid, cromakalin, cyproterone acetate, diazoxide, diphenhydramine hydrochloride, dutasteride, estradiol, ethyl-2-hydroxypropanoate, finasteride, D-fucono-1,5-lactone,furoate, L-galactono-1,4-lactone, D-galactosamine, D-glucaro-1,4-lactone, D-glucosamine-3-sulphate, hinokitiol, hydrocortisone, 2-hydroxypropionic acid, isotretinoin, itraconazole, ketoconazole, latanoprost, 2-methyl propan-2-ol, minocyclin, minoxidil, mipirocin, mometasone, oleanolic acid, panthenol, 1,10-phenanthroline, phenyloin, prednisolone, progesterone, propan-2-ol, pseudoterins, resorcinol, selenium sulfide, tazarotene, triclocarbon, triclosan, triiodothyronine, ursolic acid, zinc pyrithione and derivatives, esters, salts and mixtures thereof.

In an embodiment, the therapeutic agent is a hormone. Suitable hormones include but are not limited to methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5a-dihydrotestosterone, testolactone, 17a-methyl-19-nortestosterone, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5a-pregnan-3b,20a-diol sulfate, 5a-pregnan-3b,20b-diol sulfate, 5a-pregnan-3b-ol-20-one, 16,5a-pregnen-3b-ol-20-one, 4-pregnen-20b-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone, progestins and derivatives, esters, salts and mixtures thereof.

In addition to what is stated above in relation to steroid hormones there is now provided particular description of estrogens, progesterone and progestins and their uses. A main source of information is AHFS Drug Information 2007 published by the American Society of Health-System Pharmacists.

Estrogens

Estrogens are naturally occurring hormones or synthetic steroidal and nonsteroidal compounds with estrogenic activity.

Estrogens are used for the treatment of moderate to severe vasomotor symptoms and other symptoms, including vulvar and vaginal atrophy, associated with menopause and for the prevention and treatment of osteoporosis. When estrogens are used alone, such therapy is referred to as estrogen replacement therapy (ERT); when estrogens are used in combination with progestin's, such therapy usually is referred to as hormone replacement therapy (HRT) or postmenopausal hormone therapy.

Estrogen or estrogen/progestin therapy is effective for the management of certain menopausal symptoms and for the prevention and treatment of osteoporosis.

Estrogen or estrogen/progestin therapy is the most effective therapy for the relief of vasomotor symptoms such as hot flushes (flashes) and sleep disturbances. Estrogen or estrogen/progestin therapy also is effective in the treatment of genitourinary symptoms such as vaginal dryness; however, the use of topical vaginal preparations should be considered when only vulvar and vaginal symptoms are being treated.

For symptoms such as vaginal dryness, topical administration of estrogen alone usually is effective. Although only limited amounts of estrogen are systemically absorbed from vaginal tablets and rings, limited data are available regarding long-term safety of vaginally administered estrogen.

Estrogens also are used in the treatment of a variety of other conditions associated with a deficiency of estrogenic hormones, including female hypogonadism and castration and primary ovarian failure. In addition, estrogens also may be used in the treatment of abnormal uterine bleeding caused by hormonal imbalance not associated with organic pathology; however, progestin's are usually preferred.

Estrogen replacement therapy (ERT) is effective for the prevention of osteoporosis in women and has been shown to reduce bone resorption and retard or halt bone loss associated with estrogen deficiency in postmenopausal women. Oral estrogens (e.g., estradiol, estropipate, conjugated estrogens) and transdermal estrogens (e.g., estradiol) are used adjunctively with other therapeutic measures (e.g., diet, calcium, vitamin D, weight-bearing exercise, physical therapy) to retard further bone loss and the progression of osteoporosis in postmenopausal women.

Estrogen replacement therapy has been effective in the treatment of osteoporosis in postmenopausal women and has been recommended as first-line therapy for women with osteoporosis.

Estrogens have been used in a limited number of anorexic women with chronic amenorrhea to reduce calcium lost and, thereby, reduce the risks of osteoporosis.

Some data from observational studies indicate that prior use of hormone replacement therapy (HRT), but not current HRT unless such use exceeds 10 years, is associated with reduced risk of Alzheimer's disease Estrogens are used in the palliative treatment of advanced, inoperable, metastatic carcinoma of the breast in postmenopausal women and in men. Estrogens are one of several second-line agents that can be used in certain postmenopausal women with metastatic breast cancer.

In males, estrogens are used for the palliative treatment of advanced carcinoma of the prostate.

Estrogen is also used in the therapy of vaginal atrophy, hypoestrogenism (as a result of hypogonadism, castration, or primary ovarian failure), amenorrhea, dysmenorrhea, and oligomenorrhea. Estrogens can also be used to suppress lactation after child birth.

Hormone-receptor-positive breast cancers are treated with drugs which suppress production in the body of estrogen. This technique, in the context of treatment of breast cancer, is know variously as hormonal therapy, hormone therapy, or anti-estrogen therapy (not to be confused with hormone replacement therapy).

At one time, estrogen was used to induce growth attenuation in tall girls.

Estrogen has been used in experimental research as a way to treat patients suffering from bulimia nervosa.

Estrogens also are used in combination with progestins for ovulation control in the prevention of conception and for the treatment of moderate acne vulgaris; estrogen-progestin combinations also are used in short-course, high-dose regimens in women for the prevention of contraception after unprotected intercourse (postcoital contraception, "morning-after pills") as emergency contraceptives.

Estrogens may be administered orally, parenterally, intravaginally, or topically.

Dosage equivalencies for estrogens have not been clearly established, and reported comparative values vary greatly. The dosage range of estrogens is generally wide, and dosage should be individualized according to the condition being treated and the response and tolerance of the patient. To minimize the risk of adverse effects, the lowest possible effective dosage should be used.

Estrogen therapy is administered in a continuous daily regimen or, alternatively, estrogens are administered cyclically. When estrogens are administered cyclically, the drugs are usually given once daily for 3 weeks, followed by 1 week without the drugs, and then this regimen is repeated as necessary. While estrogen therapy alone may be appropriate in women who have undergone a hysterectomy, a progestin generally is added to estrogen therapy in women with an intact uterus. Addition of a progestin for 10 or more days of a cycle of estrogen administration or daily with estrogen in a continuous regimen reduces the incidence of endometrial hyperplasia and the attendant risk of endometrial carcinoma in women with an intact uterus.

The most frequent adverse dermatologic reaction associated with estrogen therapy is chloasma or melasma. Women who have had melasma during pregnancy appear to be most susceptible. Irregular brown macules may develop slowly on the face within 1 month to 2 years following initiation of estrogen therapy. The macules fade more slowly than in melasma gravidarum and may be permanent.

Other dermatologic reactions include erythema multiforme, erythema nodosum, and hemorrhagic eruption. Hirsutism and alopecia have also occurred. Porphyria cutanea has reportedly been adversely affected in some women receiving estrogen therapy.

Estrogens are readily absorbed through the skin and mucous membranes. Depending on the amount of estrogen applied, systemic as well as local effects may occur following topical application. Penetration may be assisted by penetration enhancers for example like propylene glycol or isopropyl myristate.

Estrogens are naturally occurring hormones or synthetic steroidal and nonsteroidal compounds with estrogenic activity. The estrogens can be divided into 2 groups based on their chemical structures: steroidal and nonsteroidal compounds. All naturally occurring estrogens are steroids that contain a cyclopentanoperhydrophenanthrene ring structure with an unsaturated A ring, a methyl group at the C 13 position, a phenolic hydroxyl group at the C 3 position, and a ketone or hydroxyl group at the C 17 position. Only a limited number of changes can be made in this basic steroid structure without losing estrogenic activity. These changes are limited to an interconversion of the hydroxyl and ketone groups or the addition of various side chains at the C 3 and C 17 positions.

The natural steroidal estrogens (estradiol, estrone, estriol, equilin, and equilenin) and their conjugates are usually obtained from pregnant mares' urine or prepared synthetically. The natural steroidal estrogens, both those obtained exclusively from natural sources and those prepared synthetically, are insoluble in water but when conjugated as the sulfates or glucuronides, these hormones become water soluble. Synthetic derivatives of the natural steroidal estrogens were previously available. The nonsteroidal estrogens include diethylstilbestrol (DES) and dienestrol.

Progesterone

The use of progesterone, a hormone secreted by the corpus luteum, is well established in medicine. Its relative inactivity following oral administration and the local reactions and pain sometimes produced upon injection have led to the synthesis of chemical derivatives that are effective orally, are more potent, more specific in action, or have a longer duration of action.

Progesterone administration topically for example intravaginally may be a useful alternative to injection and for example may be desirable if the vagina or uterus is a target for its effect. Progesterone absorbance for topical and body cavity applications may be assisted for example by a penetration enhancer such as cylodextrins, isopropyl myristate, mineral oil or propylene glycol Progesterone is used to control anovulatory bleeding. It is also used to prepare uterine lining in infertility therapy and to support early pregnancy. Patients with recurrent pregnancy loss due to inadequate progesterone production may receive progesterone.

Progesterone is being investigated as potentially beneficial in treating multiple sclerosis, since the characteristic deterioration of nerve myelin insulation halts during pregnancy, when progesterone levels are raised; deterioration commences again when the levels drop.

Progesterone is used in hormone therapy for transsexual women, and some Intersex women—especially when synthetic progestins have been ineffective or caused side-effects—since normal breast tissue cannot develop except in the presence of both progestogen and estrogen. Mammary glandular tissue is otherwise fibrotic, the breast shape conical and the areola immature. Progesterone can correct those even after years of inadequate hormonal treatment. Research usually cited against such value was conducted using Provera, a synthetic progestin. Progesterone also has a role in skin elasticity and bone strength, in respiration, in nerve tissue and in female sexuality, and the presence of progesterone receptors in certain muscle and fat tissue may hint at a role in sexually-dimorphic proportions of those.

Progesterone receptor antagonists, or selective progesterone receptor modulators (SPRM)s, such as RU-486 (Mifepristone), can be used to prevent conception or induce medical abortions.

Ethisterone was the first synthetic progestin developed; the drug is not currently available. 19-Nor,17-acetoxy, and 6-methyl derivatives, which exhibit interesting structural-pharmacologic relationships, have been synthesized. Some estrogenic or androgenic activity, anabolic effects, nitrogen retention, and weight gain are exhibited by the 19-nor derivatives. The 17-hydroxy or acetoxy compounds, on the other hand, elicit responses more nearly resembling those of progesterone. They have little or no estrogenic or androgenic activity and may produce catabolic and slight diuretic effects. The 19-nor derivatives are more effective in postponing the normal menstrual period.

Progestins elicit, to varying degrees, all the pharmacologic responses usually produced by progesterone: induction of secretory changes in the endometrium, increase in basal body temperature (thermogenic action), production of histologic changes in vaginal epithelium, relaxation of uterine smooth muscle, stimulation of mammary alveolar tissue growth, pituitary inhibition, and production of withdrawal bleeding in the presence of estrogen.

Progestin's are used in the treatment of functional uterine bleeding caused by hormonal imbalance and involving a hyperplastic nonsecretory endometrium and the absence of underlying organic pathology such as fibroids or uterine cancer, and for the treatment of primary and secondary amenorrhea in the presence of estrogen. Medroxyprogesterone and hydroxyprogesterone also are used in the adjunctive and palliative treatment of some cancers. Some progestin's are used alone or in combination with estrogens for the prevention of conception. Medroxyprogesterone prevents follicular maturation and ovulation following IM administration, and the drug has been used parenterally for contraception.

Progestin's (e.g., drospirenone, medroxyprogesterone, norethindrone acetate, norgestimate) are used to reduce the incidence of endometrial hyperplasia and the attendant risk of endometrial carcinoma in postmenopausal women receiving estrogen replacement therapy.

Progestin's have been used beginning in the first trimester of pregnancy to prevent habitual abortion or to treat threatened abortion.

Hydroxyacid

In an embodiment, the therapeutic agent is a hydroxyacid. Suitable hydroxy acids include but are not limited to agaricic acid, aleuritic acid, allaric acid, altraric acid, arabiraric acid, ascorbic acid, atrolactic acid, benzilic acid, citramalic acid, citric acid, dihydroxytartaric acid, erythraric acid, galactaric acid, galacturonic acid, glucaric acid, glucuronic acid, glyceric acid, glycolic acid, gularic acid, gulonic acid, hydroxypyruvic acid, idaric acid, isocitric acid, lactic acid, lyxaric acid, malic acid, mandelic acid, mannaric acid, methyllacetic acid, mucic acid, phenyllacetic acid, pyruvic acid, quinic acid, ribaric acid, ribonic acid, saccharic acid, talaric acid, tartaric acid, tartronic acid, threaric acid, tropic acid, uronic acids, xylaric acid and derivatives, esters, salts and mixtures thereof.

Keratolytic

In an embodiment, the active agent is a keratolytic agent. The term "keratolytic agent" is used herein to mean a compound which loosens and removes the stratum corneum of the skin, or alters the structure of the keratin layers of skin. Keratolytic agents are used in the treatment of many dermatological disorders, which involve dry skin, hyperkeratiinization (such as psoriasis), skin itching (such as xerosis), acne and rosacea. Suitable keratolytic agents include but are not limited to N-acetylcysteine, azelaic acid, cresols, dihydroxy benzene compounds, such as resorcinol and hydroquinone, alpha-hydroxy acids, such as lactic acid and glycolic acid, phenol, pyruvic acid, resorcinol, sulfur, salicylic acid, retinoic acid, isoretinoic acid, retinol, retinal, urea and derivatives, esters, salts and mixtures thereof.

The term "keratolytic agent" refers herein to a compound which loosens and removes the stratum corneum of the skin, or alters the structure of the keratin layers of skin.

Suitable keratolytic agents also include alpha-hydroxy acids. Alfa hydroxy acids are keratolytic, and they are also capable of trapping moisture in the skin and initiating the formation of collagen. Suitable hydroxy acids include but are not limited to agaricic acid, aleuritic acid, allaric acid, altraric acid, arabiraric acid, ascorbic acid, atrolactic acid, benzilic acid, citramalic acid, citric acid, dihydroxytartaric acid, erythraric acid, galactaric acid, galacturonic acid, glucaric acid, glucuronic acid, glyceric acid, glycolic acid, gularic acid, gulonic acid, hydroxypyruvic acid, idaric acid, isocitric acid, lactic acid, lyxaric acid, malic acid, mandelic acid, mannaric acid, methyllacetic acid, mucic acid, phenyllacetic acid, pyruvic acid, quinic acid, ribaric acid, ribonic acid, saccharic acid, talaric acid, tartaric acid, tartronic acid, threaric acid, tropic acid, uronic acids, xylaric acid and derivatives, esters, salts and mixtures thereof.

Yet, another preferred keratolytic agent is urea, as well as derivatives thereof. Urea possesses both keratolytic and skin-hydration properties which are beneficial to the damaged tissue of the skin.

Another preferred group of keratolytic agents, suitable for inclusion in the therapeutic composition according to the present invention is beta-hydroxy acids, such as salicylic acid (o-hydroxybenzoic acid). Beta hydroxyl acids are keratolytic, and they are also have anti-inflammatory and antibacterial properties.

Short chain carboxylic acids (carboxylic acids having up to 6 carbon atoms in their skeleton) are also suitable for inclusion in the therapeutic composition as keratolytic agents. Examples of short chain carboxylic acid include, but are not limited to formic acid, acetic acid, propionic acid, butyric acid (Butanoic acid), valeric acid (pentanoic acid) and caproic acid (hexanoic acid). In the context, di-carboxylic acids having up to 6 carbon atoms in their skeleton are also suitable under the definition of short chain carboxylic acids having up to 6 carbon atoms in their skeleton. Non-limiting examples of suitable dicarboxylic acids are malonic acid (propanedioic acid), succinic acid (butanedioic acid), glutaric acid (Pentanedioic acid) and adipic acid (Hexanedioic acid). Also suitable under the definition of short chain carboxylic acid are unsaturated short chain carboxylic acids, i.e., short chain carboxylic acids, having one or more double bonds in their carbon skeleton; and halogenated short chain carboxylic acids, such as fluoroethanoic acid (CH2FCO2H), chloroethanoic acid (CH2ClCO2H) and dichloroethanoic acid (CHCl2CO2H). Dicarboxylic acids, having between about 6 and about 14 carbon atoms in their carbon atom skeleton also possess keratolytic properties. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid.

Another group of keratolytic agents include phenol and substituted phenolic compounds. Such compounds are known to dissolve and loosen the intracellular matrix of the hyperkeratinized tissue. Dihydroxy benzene and derivatives thereof have been recognized as potent keratolytic agents. Resorcinol (m-dihydroxybenzene) and derivatives thereof are used in anti-acne preparations. Hydroquinone (p-dihydroxybenzene), besides its anti-pigmentation properties, is also keratolytic.

Vitamin A and its derivatives, such as retinol, retinal, retinoic acid, retinyl acetate, retinyl palmitate, retinyl ascorbate, isotretinoin, tazarotene, adapalene, 13-cis-retinoic acid, acitretin all-trans beta carotene, alpha carotene, lycopene, 9-cis-beta-carotene, lutein and zeaxanthin are another class of keratolytic agents, which alter the structure of the skin and promote peeling.

In certain embodiments, the keratolytic agent includes at least two keratolytic agents. At least two or more keratolytic agents in the therapeutic composition, a safe and effective peeling agent is attained, which breaks down the keratin layer of the skin, where the microorganisms reside. As a result of such breaking down of the keratin layer, the microorganisms cannot further survive in the infected area. The combination of at least two keratolytic agents enables a selective breaking down of keratin in infected skin areas, while non-infected skin areas are not affected. This phenomenon is explained by the fact that the keratin layer in infected skin areas is deformed and thus it is more vulnerable to keratolytic disintegration. Furthermore, combining at least two keratolytic agents facilitates use of each agent in a substantially minimally-irritating concentration, thus decreasing the overall irritation of the therapeutic composition.

In one or more embodiments, the keratolytic agent includes at least two keratolytic agents, from different families of chemicals. Thus, in preferred embodiments, the keratolytic agent includes at east two agents, from different chemical families, selected from the group consisting of: (1) an alpha-hydroxy acid; (2) a beta-hydroxy acid; (3) a short-chain carboxylic acid; (4) a hydroxylbenzene; (5) a vitamin A derivative; and (6) urea. As detailed above, each of these keratolytic agent families possess, in addition to their keratolytic property, additional therapeutically-beneficial feature, such as anti-inflammatory, skin hydration and antibacterial properties for readily contributing to the overall therapeutic benefit of the therapeutic composition.

In an embodiment, the active agent is a lactam. Suitable lactams include but are not limited to L-galactono-1,4-lactam, L-arabino-1,5-lactam, D-fucono-1,5-lactam, D-glucaro-1,4-lactam, D-glucurono-6,3-lactam, 2,5-tri-O-acetyl-D-glucurono-6,3-lactam, 2-acetamido-2-deoxyglucono-1,5-1-actam, 2-acetamido-2-deoxygalactono-1,5-lactam, D-glucaro-1,4:6,3-dilactam-, L-idaro-1,5-lactam, 2,3,5,tri-O-acetyl-D-glucaro-1,4-lactam, 2,5-di-O-acetyl-D-glucaro-1,4:6,3-dilactam, D-glucaro-1,5-lactam methyl ester, 2-propionoamide-2-deoxyglucaro-1,5-lactam and derivatives, esters, salts and mixtures thereof.

Nonsteroidal Anti-Inflammatory Agent

In an embodiment, the therapeutic agent is a non-steroidal anti-inflammatory agent.

Inflammation is defined as "redness, swelling, and fever in a local area of the body, often with pain and disturbed function, in reaction to an infection or to a physical or chemical injury" (Random House Webster's Dictionary). Typical symptoms of disorders of the skin, body surfaces, body cavities and mucosal surfaces (e.g., the mucosa of the nose, mouth, eye, ear, respiratory system, vagina or rectum) that involve inflammation, as at least one of their etiological factors, include redness (rash, erythema), tissue thickening and/or swelling (oedema), itch (pruritus), blistering and exudate. Inflammatory disorders can by short term or long term (chronic). Inflammation typically involves overproduction of pro-inflammatory cytokines, such as TNF-alpha, TNF-beta, interleukin-1, interleukin-4, interleukin-6, interleukin-10, interleukin-12, IFN-gamma from T cells, or increased release of cytokines and pro-inflammatory mediators from mast cells.

In the context, a nonsteroidal immunomodulating agent (also termed herein "nonsteroidal anti-inflammatory agent" and "NSAID") is a pharmaceutically active compound, other than a corticosteroid, which affects the immune system in a fashion that results in a reduction, inhibition, prevention, amelioration or prevention of an inflammatory process and/or the symptoms of inflammation and or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is proinflammatory. Thus, in one or more embodiments, the NSAID is selected from the group consisting of a COX-1 inhibitor, a COX-2 inhibitor or a non-selective NSAID, which simultaneously inhibits both COX-1 and COX-2.

The term "selective COX-2 inhibitor" relates o a compound able to inhibit cyclooxygenase-2 without significant inhibition of COXe-1. Typically, it includes compounds that have a COX-2 $IC_{50}$ of less than about 0.2 micro molar, and also have a selectivity ratio of COX-2 inhibition over COX-1 inhibition of at least 50, and more typically, of at least 100. Inhibitors of the cyclooxygenase pathway in the metabolism of arachidonic acid used in the present invention may inhibit enzyme activity through a variety of mechanisms. By the way of example, and without limitation, the inhibitors used in the methods described herein may block the enzyme activity directly by acting as a substrate for the enzyme.

Selective COX-2 Inhibitors include, in an exemplary manner diaryl-substituted furanones (e.g., Rofecoxib); diaryl-substituted pyrazoles (e.g., Celecoxib); indole acetic acids (e.g., Etodolac); and sulfonanilides (e.g., Nimesulide) and salts and derivatives thereof.

In one or more embodiments, the selective COX-2 inhibitor is selected from the group consisting of celecoxib, deracoxib, valdecoxib, rofecoxib, lumiracoxib, etoricoxib, meloxicam, parecoxib, 4-(4-cyclohexyl-2-methyloxazol-5-yl)-2-fluorobenzenesulfonamide, 2-(3,5-difluorophenyl)-3-(4-(methylsulfonyl)phenyl)-2-cyclopenten-1-one, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)-phenyl]-3(2H)-pyridazinone, 2-[(2,4-dichloro-6-methylphenyl)amino]-5-ethyl-benzeneacetic acid, (3Z)-3-[(4-chlorophenyl)[4-(methylsulfonyl)phenyl]met-hylene]dihydro-2(3H)-furanone, and (S)-6,8-dichloro-2-(trifluoromethyl)-2H-1-benzopyran-3-carboxylic acid.

In additional embodiments, the selective COX-2 inhibitor is selected from the group consisting of ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenec, alclofenac, ibufenac, isoxepac, furofenac, tiopinac, zidometacin, acetyl salicylic acid, indometacin, piroxicam, tenoxicam, nabumetone, ketorolac, azapropazone, mefenamic acid, tolfenamic acid, diflunisal, podophyllotoxin derivatives, acemetacin, droxicam, floctafenine, oxyphenbutazone, phenylbutazone, proglumetacin, acemetacin, fentiazac, clidanac, oxipinac, mefenamic acid, meclofenamic acid, flufenamic acid, niflumic acid, flufenisal, sudoxicam, etodolac, piprofen, salicylic acid, choline magnesium trisalicylate, salicylate, benorylate, fentiazac, clopinac, feprazone, isoxicam, and 2-fluoro-a-methyl[1,1'-biphenyl]-4-acetic acid, 4-(nitrooxy)butyl ester.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is para-aminophenol (e.g., acetaminophen) and salts and derivatives thereof.

In one or more embodiments, the NSAID is an indole or an indole-acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Certain imidazole drugs (e.g., ketoconazole) also possess anti-inflammatory properties, (See: *J Am Acad. Dermatol.* 1991 August; 25(2 Pt 1):257-61).

Another group of nonsteroidal immunomodulating agents includes agents, which inhibit pro-inflammatory cytokines, such as TNF-alpha, TNF-beta, interleukin-1, interleukin-4, interleukin-6, interleukin-10, interleukin-12 and IFN-gamma from T cells, which are especially important in the induction of inflammation or inhibit the release of cytokines and pro-inflammatory mediators from mast cells.

Agents that are used to affect the untoward influence of pro-inflammatory cytokines are chemically or biologically-originated materials that suppress the pro-inflammatory effect of a pro-inflammatory cytokine via various mechanisms, including, but not limited to (a) inhibiting the formation of a pro-inflammatory cytokine; (b) suppressing the interaction of a pro-inflammatory cytokine with its receptors; or (c) neutralization the proinflammatory cytokine by direct or indirect interaction.

Examples of chemical anti TNF-α agents are known pharmaceutical materials, such as pentoxifylline, propentofylline, torbafylline (and other related xanthines), amiloride, chloroquine, thalidomide and structural analogs thereof. Examples for biological anti-TNF-α agents are anti-TNF-α antibodies and soluble TNF-α receptors. Additional compounds are those that impair the signal transduction cascade from the receptor to other functional organs of the living cell. Such active agents, as well additional compounds, which are capable of inhibiting the production or otherwise suppressing the pro-inflammatory effects of TNF-α can be used in the composition.

Immunosuppressant agents, immunoregulating agents and immunomodulators constitute an additional class of nonsteroidal anti-inflammatory agents, which are used according to the present invention. Such agents are chemically or biologically-derived agents that modify the immune response or the functioning of the immune system (as by the stimulation of antibody formation or the inhibition of white blood cell activity). Immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imiquimod. In one or more embodiments, the non steroidal immunomodulating agent is a calcineurin Inhibitor.

In one or more embodiments, the NSAID is a nitric oxide inhibitor. Nitric oxide (NO) is a potent secondary messenger that is both highly reactive and highly diffusible. It is generated physiologically by a family of enzymes, referred to as NO synthases (NOS). Overproduction of NO plays a key role in the pathology of a wide range of disorders including disorders that involve inflammation, and NOS inhibitors have been suggested as anti-inflammatory agents. Agents that neutralize NO (also called "NO scavengers") are considered as potential anti-inflammatory agents as well.

Also useful are compounds that inhibit or slow down the migration of leucocytes (white blood cell), e.g., macrophages, neutrophils, and monocytes towards an afflicted skin surface or mucosal membrane, which is known to accelerate the inflammatory process.

Among other inhibitors of leucocyte chemoaxis, dicarboxylic acids, having between about 6 and about 14 carbon atoms in their carbon atom skeleton are particularly useful in the treatment of disorders of the skin and mucosal membranes that involve inflammation. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred.

Certain preferred dicarboxylic acid derivatives include a dicarboxylic acid wherein at least one ester moiety of the compound comprises a keratolytic agent, selected from the group consisting of alpha-hydroxy acids and derivatives thereof, beta-hydroxy acids and derivatives thereof, hydroxybenzoic acid and their ester, anhydride and amine derivatives, alkylhydroxybenzoate, dihydroxy benzene and their ester, anhydride and amide derivatives, cresols and their ester, anhydride and amide derivatives. Keratolytic agents also include alcohol derivatives of Vitamin A (retinoic acid), e.g., retinol and derivatives thereof, as provided in U.S. Pat. No. 6,180,669. Additional preferred dicarboxylic acid derivatives comprise at least one ester of a active alcohol moiety, selected from the groups of steroid hormones, corticosteroids, vitamin E and vitamin D, as provided in US Patent Application 20040191196.

In one or more embodiments, the NSAID is an ion channel modulator. Ion channels are protein macromolecules located in the cell membranes that enable the selective movement of sodium, potassium, and calcium from outside the cell to inside the cell and vice-versa.

In one or more embodiments, the NSAID is a potassium ion channel modulator. It has been shown that the potassium ion channel modulator play important roles in controlling T-cell activation and thus, they can be used to control inflammation.

In one or more embodiments, the potassium ion channel modulator is selected from the group consisting of dendrotoxin, dendrotoxin I, dendrotoxin K, alpha-dendrotoxin, beta-dendrotoxin, gamma-dendrotoxin, margatoxin, stichodactyla toxin, tityustoxin K, apamin, charylotoxin, clotrimazole, dequalinium chloride, iberiotoxin, kaliotoxin, neuropeptide Y, noxiustoxin, tolbutamide, chlorpropamide, glibenclamide, glipizide, nategliniide, repagliniide, glyburide, tolazamide, nicorandil, fampridine and penitrem A, or is a pharmaceutically acceptable salt or prodrug thereof.

In an embodiment, the potassium ion channel modulator is selected from the list of potassium ion channel modulators, provided in WO 2004/093895.

In one or more embodiments, the NSAID is a sodium ion channel modulator. In one or more embodiments, the sodium ion channel blocker is selected from the group consisting of disopyramide, procainimide, quinidine, tocamide, mexiletene, lidocane, phenyloin, fosphenyloin, flecamide, propafenone, morcizine, lubeluzole, carbamazepine, sipatrigine, riluzole, tetrodotoxin, spheroidine, maculotoxin, vinpocetine, anthopleurin-c, lamotrigine, crobenetine, lifarizine, lanodipine, lomerizine, encamide, and flunarizine or is an isomer, a pharmaceutically acceptable salt, ester, or prodrug thereof.

In an embodiment, the potassium ion channel modulator is selected from the list of potassium ion channel modulators, provided in U.S. Pat. Appl. 20040224940 and 20040220187.

In one or more embodiments, the NSAID is a modulator of serotonin (5-hydroxytryptamine, 5-HT) activity. 5-HT is known to affect inflammation through its modulation effect on cytokine production (Cloëz-Tayarani et al. Int. Immunol. 2003, 15 233). In certain embodiments, the serotonin activity modulator is a serotonin reuptake inhibitor. It has been shown that serotonin reduces inflammation and assists healing of experimental skin wounds, and thus, serotonin reuptake inhibitor can be used to control inflammation and associated disorders.

In one or more embodiments, the serotonin reuptake inhibitor is selected from the group consisting of citalopram, fluoxetine, fluvoxamine, paroxetine, escitalopram oxalate, sertraline, norfluoxetine and N-demethylsertraline.

In an embodiment, the serotonin reuptake inhibitor is selected from the list of potassium ion channel modulators, provided in US Pat Appl. 20040171664.

In one or more embodiments, the NSAID is an antioxidant. Reactive oxygen species play an important role in mediating skin inflammation, and antioxidants may provide protection.

Non-limiting examples of antioxidant agents include 21-[4-[2-amino-6-(diethylamino)-4-pyrimidinyl]-1-piperazinyl]-17α-hydroxypregna-4,9(11)-diene-3,20-dione, 17α-hydroxy-21-[4-[2,6-bis(dimethylamino)-4-pyrimidinyl]-1-piperazinyl]pregna-4,9(11)-diene-3,20-dione, 21-[4-[2-(diethylamino)-6-(1-pyrrolidinyl)-4-pyrimidinyl]-1-piperazinyl]-17α-hydroxypregna-4,9(11)-diene-3,20-dione, 17α-hydroxy-21-[4-[2-(diethylamino)-6-(4-methyl-1-piperazinyl(4-pyrimidinyl))]-1-piperazinyl]pregna-4,9(11)-diene-3,20-dione, 17α-hydroxy-21-[4-[2,6-bis(diethylamino)-4-pyrimidinyl]1-piperazinyl]pregna-4,9(11)-diene-3,20-dione, 1α-hydroxy-21-[4-[2-(diethylamino-)-6-(1-piperidinyl)-4-pyrimidinyl]-1-piperazinyl]pregna-4,9(11)-diene-3,20-dione, 21-[4-[2,6-bis(diethylamino)-b4-pyrimidinyl)-4-pyrimidinyl]-1-piperazinyl]-1-piperazinyl]-17α-hydroxy-16α-methylpregna-1,4,9(11)-triene-3,20-dione, 17α-hydroxy-21-[4-[2,6-bis(4-methyl-1-piperazinyl] pregna-4,9(11)-diene-3,20-dione, 17α-hydroxy-6α-methyl-21 [4-2,6-bis-(1-pyrrolidinyl-4-pyrimidinyl]-1-piperazinyl] pregna-1,4,9(11)-triene-3,20-dione, 21-[4-2,6-bis (diethylamino)-4-pyrimidinyl]-1-piperazinyl]-1-1α,17α-dihydroxypregn-4-ene-3,20-dione, 21-[4-[2,6-bis (diethylamino)-4-pyrimidinyl[-1piperazinyl]-17α-hydroxypregn-4-ene-3,20-dione, 21-[4-[2,6-bis (diethylamino)-4-pyrimidinyl]-1-piperazinyl]-17α-hydroxy-6α-methylpregna-1,4,9(11)-triene-3,20-dione, 17α-hydroxy-21-[4-[2,6-bis(1-pyrrolidinyl)-4-pyrimidinyl]-1-piperazinyl]pregna-4,9(11)-diene-3,20-dione, 21-[4-[2,6-bis(diethylamino)-4-pyrimidinyl]-1-piperazinyl]-11α-hydroxypregn-4-ene-3,20-dione, 21-[4-[2,6-bis (diethylamino)-4-pyrimidinyl]-1-piperazinyl]-11α,17α-dihydroxypregn-4-ene-3,20-dione, 17α-hydroxy-16α-methyl-21-[4-[2,6-bis-(1-pyrrolidinyl)-4-pyrimidinyl]-1-piperazinyl]pregna-1,4,9(-11)-triene-3,20-dione, 17α-hydroxy-21-[4-[2,6-bis(1-pyrrolidinyl)-4-pyrimidinyl]-1-piperazinyl]pregna-1,4,9(11)-triene-3,20-dione, 21-[4-[2,6-bis(diethylamino)-4-pyrimidinyl]-1-piperazinyl]-17α-hydroxypregna-1,4,9(11)-triene-3,20-dione, 21-[4-[4,6-bis (diethylamino)-2-pyrimidinyl]-11-piperazinyl]-17α-hydroxypregna-1,4,9(11)-triene-3,20-dione, 21-[4-[2,6-bis (diethylamino)-4-pyrimidinyl]-1-piperazinyl]-16α-methylpregna-1,4,9(11)-triene-3,20-dione, 21-[4-[2,6-bis (diethylamino)-4-pyrimidinyl]-1-piperazinyl]-11. alpha.-hydroxy-16α-methylpregna-1,4-diene-3,20-dione, 21-[4-[2,6-bis(diethylamino)-4-pyrimidinyl]-1-piperazinyl]-1-6α-methylpregna-1,4-diene,3,20-dione, 16α-methyl-21-[4-[2,6-bis(1-pyrrolidinyl)-4-pyrimidinyl]-1-piperazinyl]pregna-1,4,9(11)-triene-3,2-0-dione, 11α-hydroxy-16α21-[4-[2,6-bis(1-pyrrolidinyl)-4-pyrimidinyl]piperazinyl]pregna-1,4-diene-3,20-dione, 16α-methyl-21-[4-[2,6-bis(1-pyrrolidinyl)-4-pyrimidinyl]-1-piperazinyl]pregna-1,4-diene-3,20-dione, 16.alpha.-methyl-21-[4-[2,6-bis(4-morpholino)-4-pyrimidinyl]-1-piperazinyl]pregna-1,4,9 (11)-triene-3,20-dione, 11α-hydroxy-16α-methyl-21-[4-[2, 6-bis(4-morpholino)-4-pyrimidinyl]-1-piperazinyl]pregna-1,4-diene-3,20-dione, 16.alpha.-methyl-21-[4-[2-,6-bis(4-morpholino(4-pyrimidinyl]-1-piperazinyl]pregna-1,4-diene- 3,20-dione, 21-[4-[2,6-bis(allylamino)-4-pyrimidinyl]-1-piperazinyl[-16α-methylpregna-1,4,9(11)-triene-3,20-dione, 21-[4-[2,6-bis(allylamino)-4-pyrimidinyl]-1-piperazinyl]-11α-hydroxy-16α-methylpregna-1,4-ene-3,2-0-dione, 21-[4-[2,6-bis(allylamino)-4-pyrimidinyl]-1-piperazinyl]-16α-methylpregna-1,4-ene-3,20-dione, 21-[4-[2,6-bis(1-pyrrolidinyl)-4-pyrimidinyl]-1-piperazinyl]pregn-4-ene-3,11,20-trione, 21-[4-[2,6-bis(1-pyrrolidinyl)-4-pyrimidinyl]-1-piperazinyl]pregna-4,9(11)-diene-3,20-dione, 21-[4-[2,6-bis(1-pyrrolidinyl)-4-pyrimidinyl]-1-piperazinyl]pregna-1,4-diene-3,20-dione, 21-[4-(2,6-bis(1-pyrrolidinyl)-4-pyrimidinyl)-1-piperazinyl]pregna-4,9(11)-diene-3,20-dione, 21-[4-(2,6-bis(4-morpholino)-4-pyrimidinyl)-1-piperazinyl]-17α-hydroxypregna-4,9(11)-diene-3,20-dione, 21-[4-(2,6-bis(1-pyrrolidinyl)-4-pyrimidinyl]-1-piperazinyl]pregna-4-en-3-one, 21-[4-(2,6-bis(1-pyrrolidinyl)-4-pyrimidinyl]-1-piperazinyl]pregn-4-en-3-one, 16α-methyl-21-[4-[2,6-bis(1-pyrrolidinyl)-4-pyrimidinyl]-1-piperazinyl]pregna-1,4,9(11)-triene-3,20-dione, 21-[4-(2,6-bis(1-pyrrolidinyl)-4-pyrimidinyl)-1-piperazinyl]pregna-1,4,9(11)-triene-3,20-dione, 21-[4-(2,6-bis(1-pyrrolidinyl)-4-pyrimidinyl)-1-piperazinyl]-20-methylpregna-1,4-dien-3-one, 21-[4-(2,6-bis(1-pyrrolidinyl)-4-pyrimidinyl)-1-piperazinyl]pregna-1,4,9(11),16-tetraene-3,20-dione, 21-[4-[2,6-bis(4-morpholino)-4-pyrimidinyl]-1-piperazinyl]pregna-1,4-diene-3,20-dione, 21-[4-[2,6-bis(diethylamino)-4-pyrimidinyl]-1-piperazinyl]-6α-fluoro-17α-hydroxy-16β-methylpregna-4,9(11)-diene-3,20-dione, 6α-fluoro-17α-hydroxy-16β-methyl-21-[4-[2,6-bis(1-pyrrolidinyl)-4-pyrimidinyl]-1-piperazinyl]pregna-4,9(11)-diene-3,20-dione, 16α-methyl-21-[4-[2,6-bis(1-pyrrolidinyl)-4-pyrimidinyl]-1-piperazinyl]pregna-1,4-diene-3,20-dione, 21-[4-(2,6-bis(1-pyrrolidinyl)-4-pyrimidinyl)-1-piperazinyl]-16α,17α-dimethylpregna-1,4,9(11)-riene-3,2-0-dione, 3β-hydroxy-16α-methyl-21-[4-[2,6-bis(1-pyrrolidinyl)-4-1-pyrimidinyl]-1-piperazinyl]-pregn-5-en-20-one, 16α-methyl-21-[4-[2,-6-bis-(1-pyrrolidinyl)-4-pyrimidinyl]-1-piperazinyl]pregna-1,4,6,9(11)-tetraene-3,20-dione, 3β-hydroxy-16α-methyl-21-[4-[2,6-bis(1-pyrrolidinyl)-4-pyrimidinyl]-1-piperazinyl]pregn-5-en-20-one, 16α-methyl-17β-(1-oxo-4-[4-[2,6-bis(1-pyrrolidinyl)-4-pyrimidinyl]-1-piperazinyl]butyl)-androsta-4,9(11)-dien-3-one, tocopherol, vitamin C, beta-carotene, lycopene, coenzyme Q, idebenone, lipoic acid, and *ginkgo biloba*; or is an isomer, a pharmaceutically acceptable salt, ester, or prodrug thereof.

In one or more embodiments, the NSAID is a cannabinoid. Cannabnoids are known to affect inflammation through suppression of runaway inflammation and other untoward effects of immune system activation, as well as pain.

In certain embodiments, the cannabinoid agent is selected from the group consisting of: 2-arachidonylglycerol; N-arachidonyl-1-(2,3-dichlorobenzoyl)-2-methyl-3-(2-[1-morpholino]ethyl)-5-methoxyindole; 2-methyl-1-propyl-3-(1-naphthoyl)indole; 1-methoxy-N,N-dimethylmethanamide; 1-methoxy-endo-4-hydroxy-9-oxabicyclo(3.3.1) nonane; dronabinol; (2-methyl-1-propyl-1H-indol-3-yl)-1-naphthalenylmethanone; 3-(1,1-dimethylbutyl)-6a,7,10,10a-tetrahydro-6,6,9-6h-dibenzo[b,d]pyran; [2,3-dihydro-5-methyl-3(4-morpholinylmethyl)pyrrolo[1,2,3-de]methane; 5-(1,1-dimethylheptyl)-2-[(1R,2R,5R)-5-hydroxy-2-(3-hydroxypropyl)cyclohexyl]phenol; 5-(4-chlorophenyl)-1-(2,4-dichlorophenyl)-4-methyl-N-1-piperidinyl-1H-pyrazole-3-caroxamide; [6-methoxy-2-(4-methoxyphenyl)benzo[b]furan-3-yl](4-cyanophenyl)methanone; [6-iodo-2-methyl-1-[2-(4-morpholinyl)ethyl]-1H-indol-3-yl](4-methoxy phenyl)methanone; 5-(4-chloro-3-methylphenyl)-1-[(4-methylphenyl)methyl]-N-(1,3,3-trimethyl-bicyclo[2.2.1]hept-2-yl)-(1S-endo)-1H-pyrazole-3-carboxamide; 1-(2,4-dichlorophenyl)-5-(4-iodophenyl)-4-methyl-n-1-piperidinyl-1H-pyrazole-3-carboxamide; 1-(2,4-dichlorophenyl)-5-(4-iodophenyl)-4-methyl-N-4-morpholinyl-1H-pyrazole-3-carboxamide; 3-(6-azido-2-hexynyl)-6a,7,10,10a-tetrahydro-6,6,9-trimethyl-(6aR,10aR)-6-H-dibenzo[b,d]pyran-1-ol; 3-[(2Z)-6-azido-2-hexynyl]-6a,7,10,10a-tetrahydro-6,6,9-trimethyl-(6aR,10-aR)-6H-dibenzo[b,d]pyran-1-ol; (−)-6,7-dichloro-1,4-dihydro-5-[3-(methoxymethyl)-5-(3-pyridinyl)-4H-1,2,-4-triazol-4-yl]-2,3-quinoxalinedione; (2R,4S)-rel-5,7-dichloro-1,2,3,4-tetrahydro-4-[[(phenylamino)carbonyl]amino]-2-quinolinecarboxylic acid; (2R,6S)-1,2,3,4,5,6-hexahydro-3-[(2S)-2-methoxypropyl]-6,11,11-trimethyl-2,6-methano-3-benzazocin-9-ol; (3E)-2-amino-4-(phosphonomethyl)-3-heptenoic acid; (3R,4S)-rel-3,4-dihydro-3-[4-hydroxy-4-(phenylmethyl)-1-piperidinyl]-2H-1-1-benzopyran-4,7-diol; (3S,4aR,6S,8aR)-decahydro-6-(phosphonomethyl)-3-isoquinoline carboxylic acid; (R)-9-bromo-2,3,6,7-tetrahydro-2,3-dioxo-N-phenyl-1H,5H-pyrido[1,2,-3-de]quinoxaline-5-acetamide; (.alpha.R)-.alpha.-amino-5-chloro-1-(phosphonomethyl)-1H-benzimidazole-2-propanoic acid; [2-(8,9-dioxo-2,6-diazabicyclo[5.2.0]non-1 (7)-en-2-yl]ethyl]-phosphonic acid; [5-(aminomethyl)-2-[[[(5S)-9-chloro-2,3,6,7-tetrahydro-2,3-dioxo-1H,5H-pyrido[1,2,3-de]quinoxalin-5-yl]acetyl]amino]phenoxy]-acetic acid; 1,4-dihydro-6-methyl-5-[(methylamino)methyl]-7-nitro-2,3-quinoxaline-dione monohdyrochloride; 1-[2-(4-hydroxyphenoxy)ethyl]-4-[(4-methylphenyl)methyl]-4-piperidinol hydrochloride; 1-[4-(1H-imidazol-4-yl)-3-butynyl]-4-(phenylmethyl)-piperidine; 1-aminocyclopentane-carboxylic acid (ACPC); 2-[(2,3-dihydro-1H-inden-2-yl)amino]-acetamide monohydrochloride; 2-hydroxy-5-[[(pentafluorophenyl)methyl]amino]-benzoic acid (PBAS); 2-methyl-6-(phenylethynyl)-pyridine (MPEP); 3-(phosphonomethyl)-L-phenylalanine; 3-[(1E)-2-carboxy-2-phenylethenyl]-4,6-dichloro-1H-indole-2-carboxylic acid; 4,6-dichloro-3-[(E)-(2-oxo-1-phenyl-3-pyrrolidinylidene)methyl]-1H-indole-2-carboxylic acid; 6-chloro-2,3,4,9-tetrahydro-9-methyl-2,3-dioxo-1H-indeno[1,2-b]pyrazine-9-acetic acid; 7-chlorothiokynurenic acid; 8-chloro-2,3-dihydropyridazino[4,5-b]quinoline-1,4-dione 5-oxide salt with 2-hydroxy-N,N,N-trimethyl-ethaanaminium; aptiganel; besonprodil; budipine; conantokin G; delucemine; dexanabinol; felbamate; fluorofelbamate; gacyclidine; glycine; ipenoxazone; kaitocephalin; lanicemine; licostinel; midafotel; milnacipran; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfiny-1]phenyl]-guanidine; neramexane; orphenadrine; remacemide; topiramate; .alpha.-amino-2-(2-phosphonoethyl)-cyclohexanepropanoic acid; .alpha.-amino-4-(phosphonomethyl)-benzeneacetic acid; 8-[4-(1,1-dimethylheptyl)-2-hydroxyphenyl]decahydro-2-naphthalene methanol; 5,6,6a,7,8,9,10,10a-octahydro-6-methyl-3-[(1R)-1-methyl-4-pheny-1 butoxy]-1,9-phenanthridinediol; Desacetyl-L-nantradol; R-(+)-methanandamide; 11-hydroxy-9,15-dioxoprosta-8,12,13-dienoic acid; 2-[3-methyl-6-(1-methylethenyl)-2-cyclohexen-1-yl]-5-pentyl-(1R-trans)-1,-3-benzenediol (cannabidiol); 3-amyl-1-hydroxy-6,6,9-trimethyl-6H-dibenzo[b,d]pyran (cannabinol); 3-(1,1-dimethylheptyl)-6a,7,8,9,10,10a-hexahydro-1-hydroxy-6,6-dimethyl-(-6aR,9R,10aR)-6H-dibenzo[b,d]pyran-9-methanol; 7-(1,1-dimethylheptyl)-1,2,3,4,4a,9b-hexahydro-2,2-dimethyl-4-methylene-1-,3-methanodibenzofuran-9-ol; 7-(1,1- dimethylheptyl)-1,2,3,4,4a,9b-hexahydro-2,2-dimethyl-4-methylene-1-(s),3-methanodibenzofuran-9-ol; 2-[4-[(acetyloxy)methyl]-6,6-dimethylbicyclo[3.1.1]hept-3-en-2-yl]-5-(1,1-dimethylheptyl)-diacetate[1R-(1a,2a,5a)]-1,3-benzenediol; 2-[4-[(acetyloxy)methyl]-6,6-dimethylbicyclo[3.1.1]hept-3-en-2-yl]-5-(1,1-dimethylheptyl)-diacetate[1S-(1a,2a,5a)]-1,3-benzenediol; 5-(1,1-dimethylheptyl)-2-[4-(hydroxymethyl)-6,6-dimethylbicyclo[3.1.1]hept-3-en-2-yl]-[1S-(1a,2a,5a)]-1,3-benzenediol; and 5-(1,1-dimethylheptyl)-2-[4-(hydroxymethyl)-6,6-dimethylbicyclo[3.1.1]hept-3-en-2-yl]-[1R-(1a,2a,5a)]-1,3-benzenediol; or is an isomer, a pharmaceutically acceptable salt, ester, or prodrug thereof.

In one or more embodiments, the NSAID is an angiotensin II receptor antagonist. Angiotensin II receptor antagonists are known to affect inflammation and pain, as shown, for example in *J Pharmacol Exp Ther.* 2003 October; 307(1):17-23. Epub 2003 Aug. 27.

In certain embodiments, the angiotensin II receptor antagonist is selected from the group consisting of candesartan, eprosartan, irbesartan, losartan, olmesartan, tasosartan, telmisartan, valsartan, saralasin, and 1-[[4-(dimethylamino)-3-methylphenyl]methyl]-5-(diphenylac-etyl)-4,5,6,7-tetrahydro-1H-imidazo[4,5-c]pyridine-6-carboxylic acid ditrifluoroacetate, or an isomer, a pharmaceutically acceptable salt, ester, or prodrug thereof.

In one or more embodiments, the NSAID is an UDP-glucuronosyltransferase inhibitor (UGT inhibitor).

In certain embodiments, the UGT inhibitor is selected from the group consisting of epicatechin gallate, epigallocatechin gallate, octyl gallate, propyl gallate, quercetin, tannic acid, benzoin gum, capsaicin, dihydrocapsaicin, eugenol, gallocatechin gallate, geraniol, menthol, menthyl acetate, naringenin, allspice berry oil, N-vanillylnonanamide, clovebud oil, peppermint oil, silibinin and silymarin.

Mixtures of these non-steroidal immunomodulators may also be employed according to the present invention.

Suitable non-steroidal anti-inflammatory agent include but are not limited to azelaic acid, oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof.

Insecticide

In an embodiment, the therapeutic agent is insecticide. In the context of one or more embodiments "insecticide, is used herein to mean a compound which kills, inhibits the growth of, impeded the proliferation of or repels insects or to kill or prevent the growth of parasite arthropods, such as insects, arachnids and crustaceans, or a compound used to repel or prevent infestation by these parasite arthropods.

The term insecticides include, for example, agents that can kill lice, flees, ticks, mites, scabies and mousquitos, as well as agents that repel such insects. Suitable insecticides include but are not limited to DDT, lindane, malathion, permethrin, allethrin, biopermethrin, transpermethrin, phenothrin, diethyl-m-toluamide, dimethyl phthalate, piperonyl butoxide, pyrethroids and derivatives, esters, salts and mixtures thereof.

In one or more embodiments, the insecticide is an antibiotic insecticide. Examples of antibiotic insecticides include allosamidin, thuringiensin, spinosad, avermectin insecticides, such as abamectin, doramectin, emamectin, eprinomectin, ivermectin and selamectin, milbemycin insecticides, such as lepimectin, milbemectin, milbemycin oxime and moxidectin, and arsenical insecticides.

In one or more embodiments, the insecticide is a botanical insecticide, such as anabasine, azadirachtin, d-limonene, nicotine, pyrethrins, cinerins, jasmolin, quassia, rotenone, ryania and sabadilla.

In one or more embodiments, the insecticide is a carbamate insecticide. Examples of carbamate insecticides include bendiocarb, carbaryl, benzofuranyl methylcarbamate insecticides, such as benfuracarb, carbofuran, carbosulfan, decarbofuran and furathiocarb, dimethylcarbamate insecticides, such as dimetan, dimetilan, hyquincarb and pirimicarb, oxime carbamate insecticides, such as alanycarb, aldicarb, aldoxycarb, butocarboxim, butoxycarboxim, methomyl, nitrilacarb, oxamyl, tazimcarb, thiocarboxime, thiodicarb and thiofanox, and phenyl methylcarbamate insecticides, such as allyxycarb, aminocarb, bufencarb, butacarb, carbanolate, cloethocarb, dicresyl, dioxacarb, ethiofencarb, fenethacarb, fenobucarb, isoprocarb, methiocarb, metolcarb, mexacarbate, promacyl, promecarb, propoxur, trimethacarb and xylylcarb.

In one or more embodiments, the insecticide is a dinitrophenol insecticides. Examples of dinitrophenol insecticides include dinex, dinopropand dinosam.

In one or more embodiments, the insecticide is a fluorine insecticide, such as barium hexafluorosilicate, cryolite, sodium fluoride, sodium hexafluorosilicate and sulfluramid.

In one or more embodiments, the insecticide is a formamidine insecticide, such as amitraz, chlordimeform, formetanate and formparanate.

In one or more embodiments, the insecticide is an insect growth regulator. Examples of insect growth regulators include chitin synthesis inhibitors, such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron, juvenile hormone mimics, such as epofenonane, fenoxycarb, hydroprene, kinoprene, methoprene, pyriproxyfen and triprene, juvenile hormones, moulting hormone agonists, such as chromafenozide, halofenozide, methoxyfenozide and tebufenozide, moulting hormones, such as α-ecdysone and ecdysterone, moulting inhibitors, such as diofenolan, precocenes, and dicyclanil.

In one or more embodiments, the insecticide is a nereistoxin analogue insecticide, such as bensultap, cartap, thiocyclam and thiosultap.

In one or more embodiments, the insecticide is a nicotinoid insecticide. Examples of nicotinide insecticides include flonicamid, nitroguanidine insecticides, such as clothianidin, dinotefuran, imidacloprid and thiamethoxam, nitromethylene insecticides, such as nitenpyram and nithiazine, and pyridylmethylamine insecticides, such as acetamiprid, imidacloprid, nitenpyram and thiacloprid.

In one or more embodiments, the insecticide is an organochlorine insecticide. Examples of organochlorine insecticides include bromo-DDT, camphechlor, DDT, lindane, methoxychlor, pentachlorophenol, cyclodiene insecticides, such as aldrin, bromocyclen, chlorbicyclen, chlordane, chlordecone, dieldrin, dilor, endosulfan, endrin, heptachlor, isobenzan, isodrin, kelevan and mirex.

In one or more embodiments, the insecticide is an organophosphorus insecticide. Examples of organophosphorus insecticides include organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naftalofos, phosphamidon, propaphos and tetrachlorvinphos, organothiophosphate insecticides, such as dioxabenzofos, fosmethilan, phenthoate, acethion, amiton, cadusafos, chlorethoxyfos, chlormephos, demephion, demephion, demeton, disulfoton, ethion, ethoprophos, isothioate, malathion, methacrifos, oxydemeton-methyl, oxydeprofos, oxydisulfoton, phorate, sulfotep, terbufos and thiometon, aliphatic amide organothiophosphate insecticides, such as amidithion, cyanthoate, dimethoate, ethoate-methyl, formothion, mecarbam, omethoate, prothoate, sophamide and vamidothion, oxime organothiophosphate insecticides, such as chlorphoxim, phoxim and phoxim-methyl, heterocyclic organothiophosphate insecticides, such as azamethiphos, coumaphos, coumithoate, dioxathion, endothion, menazon, morphothion, phosalone, pyraclofos, pyridaphenthion and quinothion, benzothiopyran organothiophosphate insecticides, such as dithicrofos and thicrofos, benzotriazine organothiophosphate insecticides, such as azinphos-ethyl and azinphos-methyl, isoindole organothiophosphate insecticides, such as dialifos and phosmet, isoxazole organothiophosphate insecticides, such as isoxathion and zolaprofos, pyrazolopyrimidine organothiophosphate insecticides, such as chlorprazophos and pyrazophos; pyridine organothiophosphate insecticides, such as chlorpyrifos and chlorpyrifos-methyl, pyrimidine organothiophosphate insecticides, such as butathiofos, diazinon, etrimfos, lirimfos, pirimiphos-ethyl, pirimiphos-methyl, primidophos, pyrimitate and tebupirimfos, quinoxaline organothiophosphate insecticides, such as quinalphos and quinalphos-methyl, thiadiazole organothiophosphate insecticides, such as athidathion, lythidathion, methidathion and prothidathion, triazole organothiophosphate insecticides, such as isazofos and triazophos, phenyl organothiophosphate insecticides, such as azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos, phosphonate insecticides, such as butonate and trichlorfon, phosphonothioate insecticides such as mecarphon, phenyl ethylphosphonothioate insecticides, such as fonofos and trichloronat, phenyl phenylphosphonothioate insecticides, such as cyanofenphos, EPN and leptophos, phosphoramidate insecticides, such as crufomate, fenamiphos, fosthietan, mephosfolan, phosfolan and pirimetaphos, phosphoramidothioate insecticides, such as acephate, isocarbophos, isofenphos, methamidophos and propetamphos, and phosphorodiamide insecticides, such as dimefox, mazidox, mipafox and schradan.

In one or more embodiments, the insecticide is an oxadiazine insecticide, such as indoxacarb.

In one or more embodiments, the insecticide is a phthalimide insecticide, such as dialifos, phosmet and tetramethrin.

In one or more embodiments, the insecticide is a pyrazole insecticide, such as acetoprole, ethiprole, fipronil, pyrafluprole, pyriprole, tebufenpyrad, tolfenpyrad and vaniliprole.

In one or more embodiments, the insecticide is a pyrethroid insecticide. Examples of pyrethroid insecticides include pyrethroid ester insecticides, such as acrinathrin, allethrin, bioallethrin, barthrin, bifenthrin, bioethanomethrin, cyclethrin, cycloprothrin, cyfluthrin, beta-cyfluthrin, cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin, and pyrethroid ether insecticides, such as etofenprox, flufenprox, halfenprox, protrifenbute and silafluofen.

In one or more embodiments, the insecticide is a pyrimidinamine insecticide, such as flufenerim and pyrimidifen.

In one or more embodiments, the insecticide is a pyrrole insecticide, such as chlorfenapyr.

In one or more embodiments, the insecticide is a tetronic acid insecticide, such as spiromesifen and spirotetramat.

In one or more embodiments, the insecticide is a thiourea insecticide, such as diafenthiuron.

In one or more embodiments, the insecticide is a urea insecticide, such as flucofuron and sulcofuron.

Yet, in additional embodiments, the insecticide is an unclassified insecticide, such as closantel, crotamiton, fenazaflor, fenoxacrim, flubendiamide, hydramethylnon, isoprothiolane, malonoben, metaflumizone, metoxadiazone, nifluridide, pyridaben, pyridalyl, rafoxanide, triarathene and triazamate.

The above listed insecticides, as well as others not listed, are suitable for use in the composition. It is preferred to use insecticides that are approved by the FDA or other health authorities for the treatment of animals and humans.

Non-limiting examples of approved insecticides include hexachlorobenzene, carbamate, naturally occurring pyrethroids, permethrin, allethrin, bioalethrin, phenothrin, malathion and piperonyl butoxide. In a preferred embodiment the insecticide is selected from the group consisting of hexachlorobenzene, carbamate, naturally occurring pyrethroids, permethrin, allethrin, bioalethrin, phenothrin, malathion and piperonyl butoxide.

In one or more embodiments, the insecticide is a naturally occurring insecticide compound. As used herein, the term "naturally-occurring insecticide" includes all insecticides that are obtained, derived or extracted from plant or vertebrate sources.

In the context, an agent that kills or otherwise affects parasites, such as protozoa is also termed an insecticide (for the purpose of this application terminology only). Exemplary antiparasites are mebendazole, thiabendazole, metronidazole, and praziquantel.

Mixtures of these insecticides may also be employed according to the present invention.

The insecticide is included in the composition in a concentration that provides a desirable ratio between the efficacy and safety. Typically, insecticides are included in the composition in a concentration between about 0.05% and about 12% by weight, depending on their potency against the parasitic arthropod to be eradicated. In some embodiments, the concentration is between about 0.5% and about 2% by weight; in other embodiment the concentration is between about 2% and about 5% by weight; and in other embodiments the concentration is between about 5% and about 12% by weight.

In one or more embodiments, the insecticide and the silicone work together for example by killing eggs and the latter by discouraging them from sticking to a surface.

In one or more embodiments, the insecticide is encapsulated in particles, microparticles, nanoparticles, microcapsules, spheres, microspheres, nanocapsules, nanospheres, liposomes, niosomes, polymer matrix, nanocrystals or microsponges, and may be manufactured according to known methods.

Vasodilators

In an embodiment, the therapeutic agent is a vasodilator. Suitable vasodilators include but are not limited to agents that modulate the activity of the enzyme nitric oxide synthase, nicotinic acid, ethyl nicotinate, amyl nitrite, amyl nitrate, ethyl nitrite, butyl nitrite, isobutyl nitrite, glyceryl trinitrate, octyl nitrite, sodium nitrite, sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, trolnitrate phosphate (triethanolamine trinitrate diphosphate), propatylnitrate, nitrite esters of sugars, nitrite esters of polyols, nitrate esters of sugars, nitrate esters of polyols, nicorandil, apresoline, diazoxide, hydralazine, hydrochlorothiazide, minoxidil, pentaerythritol, tolazoline, scoparone, a beta-adrenergic blocker, an alpha-adrenoceptor blocker, a prostaglandin, sildenafil, dipyridamole, catecholamine, isoproternol, furosemide, prostaglandin, prostacyclin, enalaprilat, morphine, acepromazine, prazosin (α-blocker), enalapril, Captopril, amlodipine, minoxidil, tadalafil, vardenafil, phenylephrin, etilefein, caffeine, capsaicin, an extract *capsicum, achillea millefolium* (Yarrow), *allium sativum* (garlic), *amoracia rusticana* (horseradish), *berberis vulgaris* (barberry), *cimicifuga racemosa* (black cohosh), *coleus forskholii* (coleus), *coptis* (goldenthread), *crataegus* (hawthorn), *eleutherococcus senticosus* (siberian ginseng), *ginkgo biloba*(ginkgo), *melissa offiicnalis* (lemon balm), *olea europaea* (olive leaf), *panax ginseng* (Chinese ginseng), *petroselinum crispum* (parsley), *scutellaria baicalensis* (baical skullcap), *tilia europaea* (linden flower), *trigonella foenum-graecum* (fenugreek), *urtica dioica* (nettles), *valeriana officinalis* (valerian), *viburnum* (cramp, bark, black haw), *veratrum viride* (American hellebore), *verbena officinalis* (vervain), *xanthoxylum americanum* (prickly ash), *zingiber officinale* (ginger), *rauwolfia serpentina* (Indian snakeroot), *viscum album*, wild yam, sasparilla, licorice, damiana, yucca, saw palmetto, gotu kola (*centella asiatica*), yohimbine and salts, hazel nut, brazil nut and walnut, and derivatives, esters, salts and mixtures thereof.

In an embodiment, the therapeutic agent is a vasoconstrictor. Suitable vasodilators include but are not limited to ephedrine, epinephrine, phenylephrine, angiotensin, vasopressin; an extract *ephedra sinica* (ma huang), *polygonum bistorta* (bistort root), *hamamelis virginiana* (witch hazel), *hydrastis canadensis* (goldenseal), *lycopus virginicus* (bugleweed), *aspidosperma quebracho* (quebracho blanco), *cytisus scoparius* (scotch broom) and cypress and and derivatives, esters, salts and mixtures thereof.

Retinoid

In an embodiment, the active agent is a retinoid.

In the context, a retinoids is a compound a class of compounds consisting of four isoprenoid units joined in a head-to-tail manner, and derivatives, salts, structural analogs and functional analogs thereof, as reviewed herein in a non-limiting fashion. Typically, retinoids may be formally derived from a monocyclic parent compound containing five carbon-carbon double bonds and a functional group at the terminus of the acyclic portion.

Suitable, but non-limiting, retinoids for use in the present invention are listed below.

It is convenient to omit the explicit representation of C and H atoms in the parent skeletal structure of retinoids as follows:

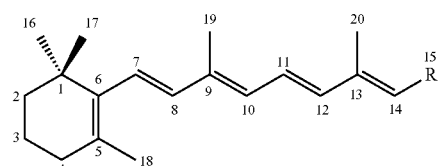

(1) R=CH$_2$OH (6) R=CH$_2$NH$_2$ (2) R=CHO (7) R=CH=NOH (3) R=CO$_2$H (8) R=CH=N[CH$_2$]$_4$—CHNH$_2$CO$_2$H (4) R=CH$_3$ (9) R=CO$_2$C$_2$H$_5$ (5) R=CH$_2$OCOCH$_3$

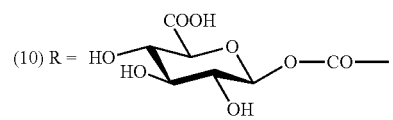

Compound (1) (2E,4E,6E,8E)-3,7-dimethyl-9-(2,6,6-trimethylcyclohex-1-en-1-yl)nona-2,4,6,8-tetraen-1-ol is also known as vitamin A, vitamin A alcohol, retinal, vitamin A$_1$, vitamin A$_1$ alcohol, axerophthol or axerol. Compound (2) also known as vitamin A aldehyde, vitamin A$_1$ aldehyde, retinene or retinene$_1$ and retinal or, if liable to be confused with the adjective retinal (pertaining to the retina), retinaldehyde. Compound (3) also known as tretinoin (see note), vitamin A acid or vitamin A$_1$ acid should be designated retinoic acid. Compound (4), is known as axerophthene. Functional substitution at the 15 position of the basic hydrocarbon is denoted by the use of the group names retinyl (R is CH$_2$—) or retinylidene (R is CH=), with retention of the original numbering of the basic hydrocarbon. For example (5) is retinyl acetate and (6) is retinylamine. Derivatives of retinal include for example Compound (7)—retinal oxime and Compound (8)—N$^6$-retinylidene-L-lysine. Other derivatives of retinoic acid, named as carboxylic acid derivatives Compound (9)—ethyl retinoate and Compound (10)—1-O-retinoyl-b-D-glucopyranuronic acid.

Retinoids that differ in hydrogenation level from the parent structure (displayed above) are named by use of the prefixes 'hydro' and 'dehydro' together with locants specifying the carbon atoms at which hydrogen atoms have been added or removed. Examples of such retinoid compounds are Compound (11)—3,4-Didehydroretinol (also known as dehydroretinol or vitamin A$_2$) and Compound (12)—4,5-Didehydro-5,6-dihydroretinol (also known as alpha-vitamin A).

Compound (11)
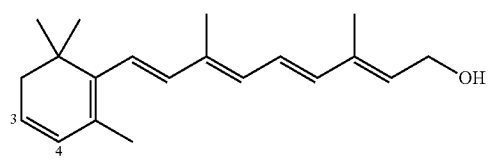
Compound (12)
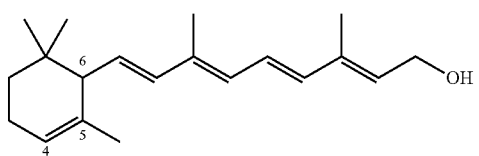
Compound (13)
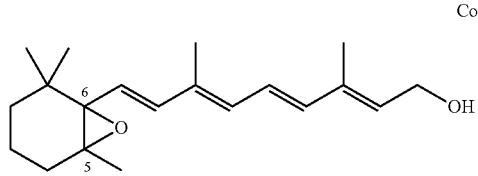
Compound (14)
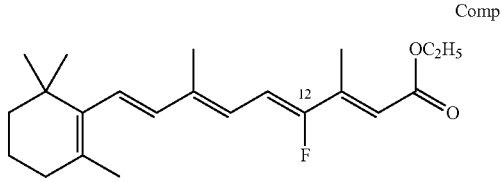
Compound (15)
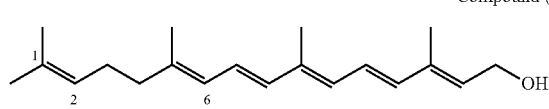
Compound (16)
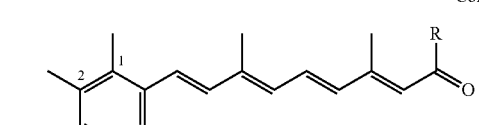
R = NHC$_2$H$_5$
Compound (17)
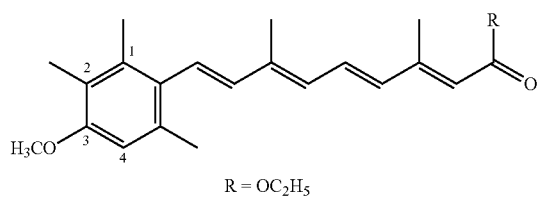
R = OC$_2$H$_5$
Compound (18)
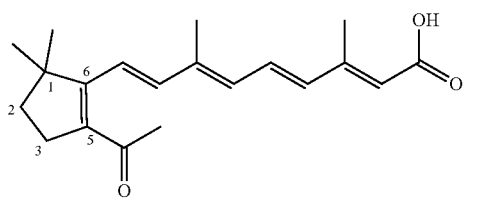
Compound (19)
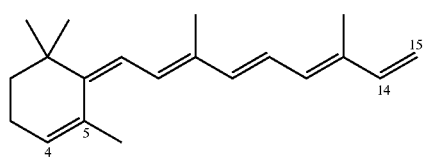
Compound (20)
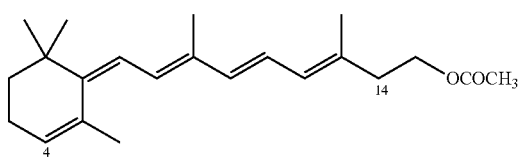
Compound (21)
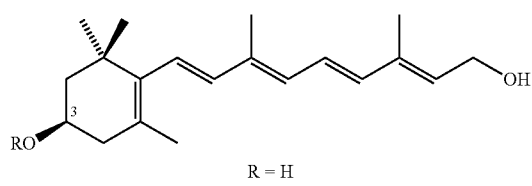
R = H
Compound (22)
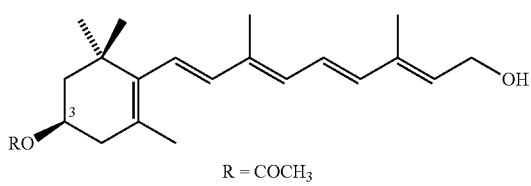
R = COCH$_3$
Compound (23)
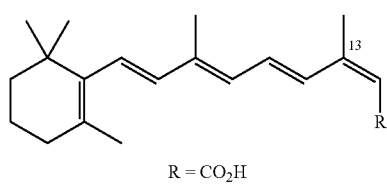
R = CO$_2$H
Compound (24)
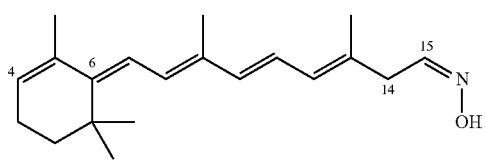

-continued

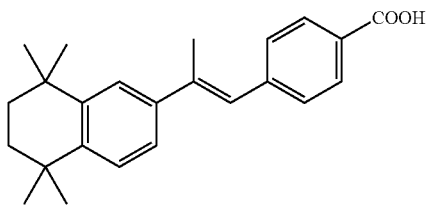
Compound (25)

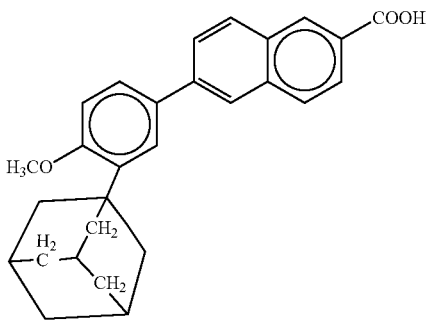
Compound (26)

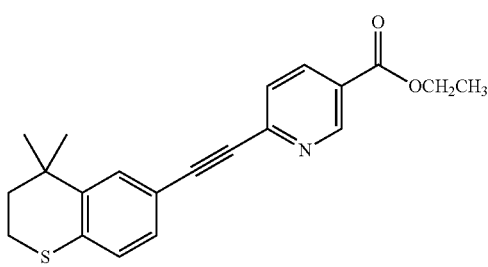
Compound (27)

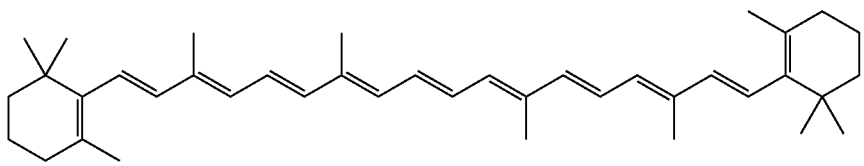
Compound (28)

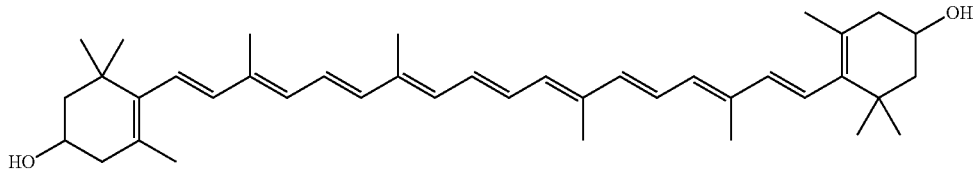
Compound (29)

Substituted derivatives of retinoids are exemplified by Compound (13)—5,6-Epoxy-5,6-dihydroretinol (also known as hepaxanthin) and Compound (14)—Ethyl 12-fluororetinoate. Seco Retinoids are exemplified by Compound (15)—1,6-Seco-1,2-didehydroretinol, also known as g-vitamin A, and Nor Retinoids, which result from the elimination of a $CH_3$, $CH_2$, CH or C group from a retinoid are exemplified by Compound (16)—N-Ethyl-3-methoxy-2-methyl-17-nor-1,2,3,4-tetradehydroretinamide (also known as motretinide), Compound (17)—Ethyl 3-methoxy-2-methyl-17-nor-1,2,3,4-tetradehydroretinoate (also known as etretinate), acitretin (Compound (17), wherein R=H) and Compound (18)—5-Acetyl-4,18-dinor-retinoic acid. Retro Retinoids are exemplified by Compound (19)—4,5-Didehydro-15,5-retro-deoxyretinol (also known as anhydro vitamin A and Compound (20)—4,14-retro-Retinyl acetate. Stereoisomers of retinoids are exemplified by Compound (21)—(3R)-3-Hydroxyretinol and Compound (22)—(3R)-3-Acetoxyretinol. Other stereochemical isomers can are exemplified by Compound (23)—13-cis-Retinoic acid or (7E,9E,11E,13Z)-retinoic acid (also known as isotretinoin) and Compound (24)—(6E,8E,10E,12E,15Z)-4,14-retro-Retinaloxime.

'Arotinoids or 'retinoidal benzoic acid derivatives' contain, aromatic rings replacing either the basic β-ionone type ring structure or unsaturated bonds of the tetraene side chain of the parent retinoid skeleton, as exemplified by Compound (25) and Compound (26)—6-[3-(1-adamantyl)-4-methoxyphenyl]-2-naphthoic acid, also known as adapalene. Several artinoids, possessing potent retinoid properties, including but not limited to short retinoids, short heterocyclic retinoids, isoxazole-containing retinoids, heterocyclic isoxazole-containing retinoids, isoxazoline-containing retinoids, stilbene retinoid analogs, are disclosed in Pure Appl. Chem., Vol. 73, No. 9, pp. 1437-1444, 2001.

Tazarotene (Ethyl 6-[2-(4,4-dimethylthiochroman-6-yl) ethynyl]nicotinate) is exemplary to a retinoid precursor—Compound (27), suitable as retinoid for use in the present invention.

Yet, other non-limiting exemplary retinoid precursors are carotenes, such as all-trans beta carotene—Compound (28), alpha carotene, lycopene and 9-cis-beta-carotene, as well as xanthophils (also termed "oxicarotenoids"), such as lutein and zeaxanthin—Compound (29).

Salts and derivatives of retinoid compounds are also suitable as "retinoid" for use in the present invention.

Retinoid compounds can be ascertained recognized and identified by methods known in the art. One method involves the use of competitive nuclear retinoic acid (RA and RX) receptor binding assays for identifying compounds which bind directly to the receptors. For instance, J. J. Repa et al., "All-trans-retinol is a ligand for the retinoic acid receptors", Proc. Natl. Acad. Sci. USA, Vol. 90, pp. 7293-7297, 1993, discloses a competitive RA receptor binding assay based on human neuroblastoma cell nuclear extracts. H. Torma et al. ((1994) "Biologic activities of retinoic acid and 3,4-dehydroretinoic acid in human keratinoacytes are similar and correlate with receptor affinities and transactivation properties," *J. Invest. Dermatology*, Vol. 102, pp. 49-54) discloses assays for measuring binding affinities for the nuclear retinoic acid receptors and for measuring transcriptional activation induction. M. F. Boehm et al. ((1994) "Synthesis of high specific activity [.sup.3H]-9-cis-retinoic acid and its application for identifying retinoids with unusual binding properties," *J. Med. Chem.*, Vol. 37, pp. 408-414) discloses a ligand-binding assay and a receptor/reporter cotransfection assay for monitor regulation of gene expression. EP 0 552 612 A2, published Jul. 28, 1993, describes ligand-binding trapping assays based on incubation of radiolabeled compounds with transfected COS-1 cells which express RA and RX receptors.

Mixtures of these retinoids may also be employed according to the present invention.

Suitable retinoids include but are not limited to retinol, retinal, retinoic acid, all-trans retinoic acid, isotretinoin, tazarotene, adapalene, 13-cis-retinoic acid, acitretin all-trans beta carotene, alpha carotene, lycopene, 9-cis-beta-carotene, lutein and zeaxanthin.

In an embodiment, the therapeutic agent is selected from the group consisting of an immunosuppressants and immunoregulating agents. Suitable immunosuppressants and immunoregulating agents include but are not limited to cyclic peptides, such as cyclosporine, tacrolimus, tresperimus, pimecrolimus, sirolimus (rapamycin), verolimus, laflunimus, laquinimod, imiquimod derivatives, esters, salts and mixtures thereof. In one or more embodiments, the immunomodulator is a calcineurin Inhibitor.

In an embodiment, the therapeutic agent is a wart remover. Suitable wart removers include but are not limited to imiquimod, podophyllotoxin and derivatives, esters, salts and mixtures thereof.

Vitamin

The term vitamin includes those vitamins and derivatives thereof (including salts) which are officially recognized as vitamins, and those vitamins which were once recognized or designated as vitamins but are now classified in another way (e.g. vitamin F) and pseudo vitamins including those substances which are a member of a group or complex but are not formally recognized (e.g. para-amino benzoic acid (PABA), which is claimed to prevent greying hair and to be useful as an anti aging supplement) and also vitamin mimetics, which have vitamin like properties or effects.

Suitable vitamins include vitamin A, vitamins of the B complex B1, B2, B3, B5, B6, B7, B9, B12, vitamin C, vitamins D1-D4, vitamin E, vitamin K and so called vitamin F and a derivative thereof and combinations thereof.

Vitamin A is a fat-soluble vitamin and describes compounds that exhibit the biological activity of retinol. The two main components in foods are retinol and the carotenoids. 'Retinoid' refers to the chemical entity retinol or other closely related naturally occurring derivatives. These include: retinal (retinaldehyde); retinoic acid; and retinyl esters (e.g. retinyl acetate, retinyl palmitate, retinyl propionate). Retinoids also include structurally related synthetic analogues which may or may not have retinol-like activity. Vitamin A (in the form of retinal) is essential for normal function of the retina and particularly for visual adaptation to darkness. Other forms (retinol, retinoic acid) are necessary for maintenance of the structural and functional integrity of epithelial tissue and the immune system, cellular differentiation and proliferation, bone growth, testicular and ovarian function and embryonic development. It may act also as a co-factor in biochemical reactions. Deficiency can amongst other things result in skin dryness and papular eruptions. Vitamin A and its derivatives have the ability to normalize keratinization. Note that vitamin C may ameliorate the toxic effects of vitamin A; that large doses increase the need for vitamin E; and that vitamin E protects against the oxidative destruction of vitamin A. Retinol is susceptible to breakdown from oxygen and light. Synthetic retinoids may be used for skin problems (e.g. acne).

According to certain embodiments the retinoid is selected from the group consisting of: (1) a compound consisting of four isoprenoid units joined in a head-to-tail manner, a compound having the formula:

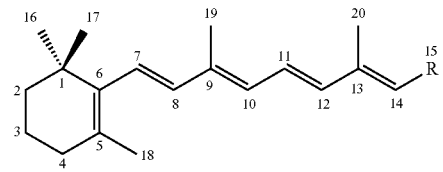

where R is selected from the group consisting of H, alkyl, aryl, alkenyl, benzyl, CH2OH, CH2NH2, CHO, CH=NOH, CO2H, CH=N[CH2]4CHNH2CO2H, CH3, CO2C2H5, CH2OCOCH3, a heteroatom, a saccharide and a polysaccharide; (2) a compound selected from the group consisting of a hydro retinoid, a dehydro retinoid, 3,4-Didehydroretinol, 4,5-Didehydro-5,6-dihydroretinol, a substituted derivative of a retinoid, 5,6-epoxy-5,6-dihydroretinol, ethyl 12-fluororetinoate, a seco retinoid, 1,6-Seco-1,2-didehydroretinol, a nor retinoid, (3) a compound which results from the elimination of a CH3, CH2, CH or C group from a retinoid, N-ethyl-3-methoxy-2-methyl-17-nor-1,2,3,4-tetradehydroretinamide, ethyl 3-methoxy-2-methyl-17-nor-1,2,3,4-tetradehydroretinoate, 5-acetyl-4,18-dinor-retinoic acid, a retro retinoid, 4,5-didehydro-15,5-retro-deoxyretinol, 4,14-retro-retinyl acetate, a stereoisomer of a retinoid, (3R)-3-hydroxyretinol, (3R)-3-Acetoxyretinol, (7E,9E,11E,13Z)-retinoic acid, (6E,8E,10E,12E,15Z)-4,14-retro-retinaloxime, an arotinoids, a retinoidal benzoic acid derivative, 6-[3-(1-adamantyl)-4-methoxyphenyl]-2-naphthoic acid, a short retinoid, a short heterocyclic retinoid, an isoxazole-containing retinoids, a heterocyclic isoxazole-containing retinoid, an isoxazoline-containing retinoid, a stilbene retinoid analog, a retinoid precursor, (ethyl 6-[2-(4,4-dimethylthiochroman-6-yl)ethynyl] nicotinate, a carotene, a xanthophil and an oxicarotenoid; (4) a compound selected from the group consisting of retinol, retinal, retinoic acid, all-trans retinoic acid, isotretinoin, tazarotene, adapalene, 13-cis-retinoic acid, acitretin, all-trans beta carotene, alpha carotene, lycopene, 9-cis-beta-carotene, lutein and zeaxanthin; (5) a compound that is positively identified using a laboratory method, suitable of detecting a retinoid, and salts and derivatives thereof.

Vitamin B is known as the vitamin B complex and comprises B1 (thiamine), B2 (riboflavin), B3 (niacin), B5 (pantothenic acid), B6 (pyridoxine), B7 (biotin), B9 (folic acid) and B12 (cyanocobalamin). Adequate amounts of all B vitamins are required for optimal functioning; deficiency or excess of one B may lead to abnormalities in the metabolism of another.

Thiamine is a water soluble vitamin and is also known as aneurine and functions as a co-enzyme in the oxidative decarboxylation of alpha ketoacids (involved in energy production) and in the transketolase reaction of the pentose phosphate pathway (involved in carbohydrate metabolism). Thiamine is also important in nerve transmission (independently of co-enzyme function). It may also act as an insect repellant.

Riboflavin is a water soluble vitamin and functions as a component of two flavin co-enzymes—flavin mononucleotide (FMN) and flavin adenine dinucleotide (FAD). It participates in oxidation-reduction reactions in numerous metabolic pathways and in energy production. Examples include: the oxidation of glucose, certain amino acids and fatty acids; reactions with several intermediaries of the Krebs cycle; conversion of pyridoxine to its active co-enzyme; and conversion of tryptophan to niacin. Riboflavin has a role as an antioxidant. It may be involved in maintaining the integrity of erythrocytes. Common forms are riboflavin, riboflavin butyrate and flavin adenine dinucleotide.

Niacin is a water-soluble vitamin and describes the compounds that exhibit the biological properties of nicotinamide. It occurs as nicotinamide and nicotinic acid. It is sometimes known as niacinamide. An example of a derivative is benzyl nicotinate. Niacin functions as a component of two co-enzymes, nicotinamide adenine dinucleotide (NAD) and nicotinamide adenine dinucleotide diphosphate (NADP). These co-enzymes participate in many metabolic processes including glycolysis, tissue respiration, lipid, amino acid and purine metabolism. It has been shown to have antiinflammatory properties that result in the improvement of acne. Topically it has showed benefit for various skin conditions including psoriasis and rosacea. It has also been said to have a photo protection role, perhaps through anti-oxidant activity and reduces or prevents UV damage to cells and UV induced disorders.

Pantothenic acid is also a water soluble vitamin and functions mainly as a component of co-enzyme A and acyl carrier protein. Co-enzyme A has a central role as a co-factor for enzymes involved in the metabolism of lipids, carbohydrates and proteins; it is also required for the synthesis of cholesterol, steroid hormones, acetylcholine and porphyrins. As a component of acyl carrier protein, pantothenic acid is involved in various transfer reactions and in the assembly of acetate units into longer-chain fatty acids. Pantothenic acid has been used for a wide range for disorders such as acne, alopecia, allergies, burning feet, asthma, grey hair, dandruff, and cholesterol lowering. Panthenol the alcoholic form functions as a humetic. Examples of pantothenic acid derivatives are calcium pantothenate, D-pantothenyl alcohol, pantothenyl ethyl ether, and acetylpentothenyl ethyl ether.

Vitamin B6 is water soluble vitamin. Vitamin B6 a generic term used to describe the compounds that exhibit the biological activity of pyridoxine. It occurs in food as pyridoxine, pyridoxal and pyridoxamine. Vitamin B6 is converted in erythrocytes to pyridoxal phosphate and, to a lesser extent, pyridoxamine phosphate. It acts as a co-factor for enzymes which are involved in more than 100 reactions that affect protein, lipid and carbohydrate metabolism. Pyridoxal phosphate is also involved in: the synthesis of several neurotransmitters; the metabolism of several vitamins (e.g. the conversion of tryptophan to niacin); haemoglobin and sphingosine formation. Lack of Vitamin B6 may affect vitamin C. Examples are pyridoxine hydrochloride and pyridoxine dioctanate.

Biotin is a water soluble vitamin which was formerly known as vitamin H or co-enzyme R. Biotin functions as an integral part of the enzymes that transport carboxyl units and fix carbon dioxide. Biotin enzymes are important in carbohydrate and lipid metabolism, and are involved in gluconeogenesis, fatty acid synthesis, propionate metabolism and the catabolism of amino acids. Biotin has been claimed to be of value in the treatment of brittle finger nails, acne, seborrhoeic dermatitis, hair fragility and alopecia.

Folic acid (pteroylglutamic acid) is a water soluble vitamin and is the parent compound for a large number of derivatives collectively known as folates. Folate is the generic term used to describe the compounds that exhibit the biological activity of folic acid; it is the preferred term for the vitamin present in foods which represents a mixture of related compounds (folates). Folates are involved in a number of single carbon transfer reactions, especially in the synthesis of purines and pyrimidines (and hence the synthesis of DNA), glycine and methionine. They are also involved in some amino acid conversions and the formation and utilization of formate. Deficiency leads to impaired cell division (effects most noticeable in rapidly regenerating tissues).

Vitamin B12 is a water-soluble vitamin and it is the generic term used to describe the compounds that exhibit the biological activity of cyanocobalamin. It includes a range of cobalt-containing compounds, known as cobalamins. Cyanocobalamin and hydroxocobalamin are the two principal forms in clinical use. Vitamin B12 is involved in the recycling of folate co-enzymes and the degradation of valine. It is also required for nerve myelination, cell replication, haematopoiesis and nucleoprotein synthesis.

Vitamin C is a water-soluble vitamin and describes the compounds that exhibit the biological activity of ascorbic acid. These include L-ascorbic acid (ascorbic acid) and L-dehydroascorbic acid (dehydroascorbic acid). The functions of vitamin C are based mainly on its properties as a reducing agent. It is required for: the formation of collagen and other organic constituents of the intercellular matrix in bone, teeth and capillaries; and the optimal activity of several enzymes—it activates certain liver-detoxifying enzyme systems (including drug-metabolizing enzymes) and is involved in the synthesis of carnitine and norepinephrine (noradrenaline) and in the metabolism of folic acid, histamine, phenylalanine, tryptophan and tyrosine. Vitamin C also acts: as an antioxidant (reacting directly with aqueous free radicals)-which is important in the protection of cellular function; and to enhance the absorption of non-haem iron. It can function as a whitening agent. Vitamin C may assist with wound healing. Vitamin C can spare vitamin E and vice versa and it may reduce toxic effects of vitamin A. Vitamin C is unstable in solution especially alkaline solution and readily undergoes oxidation on exposure to air. Oxidation is accelerated by light and heat. Cosmetic forms include calcium ascorbate, magnesium ascorbate, sodium ascorbate, sodium ascorbyl phosphate, ascorbyl palmitate, magnesium ascorbyl phosphate, L-ascorbic acid and magnesium-L-ascorbyl-2-phosphate., L-ascorbic acid palmitate, L-ascorbic acid 2-sulfate, L-ascorbic acid phosphate, and DL-.alpha.-tocopherol-L-ascorbic acid phosphate diester dipotassium. L-ascorbic acid is the most bioactive form and has been found to have many skin benefits but it is unstable in the presence of water and oxygen. Inclusion of ascorbic acid in the vitamin carrier, wherein the composition does not contain or is essentially free of water or wherein water is not freely available due to the hygroscopic properties of the composition r and or is not exposed to air during storage makes it possible to derive stable products with the most bioactive form of vitamin C.

Vitamin D is a fat-soluble vitamin and describes all sterols that exhibit the biological activity of cholecalciferol. These include: vitamin $D_1$ (calciferol), vitamin $D_2$ (ergocalciferol) vitamin $D_3$ (cholecalciferol), 1 (OH)$D_3$ (1 Hydroxycholecalciferol; alfacalcidol), 25(OH)$D_3$ (25 Hydroxycholecalciferol; calcifediol), 1,25(OH)$_2D_3$ (1,25, Dihydroxycholecalciferol; calcitriol), 24,25(OH)$_2D_3$ (24,25, Dihydroxycholecalciferol) and dihydrotachysterol, calcipotriene, 25-hydroxycholecalciferol, 1α,25-dihydroxycholecalciferol, 1α,25-dihydroxyergocalciferol, 22,23-dihydroergocalciferol, 1,24,25-trihydroxycholecalciferol, previtamin $D_3$, tachysterol$_3$ (also termed tacalciol), isovitamin $D_3$, dihydrotachysterol$_3$, (1S)-hydroxycalciol, (24R)-hydroxycalcidiol, 25-fluorocalciol, ercalcidiol, ertacalciol, (5E)-isocalciol, 22,23-dihydroercalciol, (24S)-methylcalciol, (5)-(10S)-10, 19-dihydroercalciol, (24S)-ethylcalciol and (22E)-(24R)-ethyl-22,23-didehydrocalciol. Vitamin D is essential for promoting the absorption and utilisation of calcium and phosphorus, and normal calcification of the skeleton. Along with parathyroid hormone and calcitonin, it regulates serum calcium concentration by altering serum calcium and phosphate blood levels, as needed, and mobilizing calcium from bone. It maintains neuromuscular function and various other cellular processes, including the immune system. Calcipotriene, as well as other vitamin C forms is useful in the treatment of psoriasis.

Vitamin E is a fat-soluble vitamin and describes all tocopherol and tocotrienol derivatives that exhibit the biological activity of alpha tocopherol. Those used commercially are d-alpha tocopherol (natural vitamin E), d-alpha tocopherol acetate, d-alpha tocopherol succinate, d,l-alpha tocopherol (synthetic vitamin E), d,l-alpha tocopherol acetate and d,l-alpha tocopherol succinate. Vitamin E is an antioxidant, protecting polyunsaturated fatty acids in membranes and other critical cellular structures from free radicals and products of oxidation. It works in conjunction with dietary selenium (a co-factor for glutathione peroxidase), and also with vitamin C and other enzymes, including superoxide dismutase and catalase. Vitamin E is not very stable. It may have an anti-inflammatory effect and some studies state that it improves immune function in the elderly. It is also said to reduce oxidative damage and to improve lung function. Vitamin E can spare vitamin C and vice versa. It is said to be photo protective and to have an anti aging effect on skin showing reduced wrinkles and tumors Vitamin K is a fat soluble vitamin and describes 2-methyl-1,4-naphthaquinone and all derivatives that exhibit qualitatively the biological activity of phytomenadione. The form of vitamin K present in foods is phytomenadione (vitamin $K_1$). The substances synthesized by bacteria are known as menaquinones (vitamin $K_2$). The parent compound of the vitamin K series is known as menadione (vitamin $K_3$); it is not natural substance and is not used in humans. Menadiol sodium phosphate is water-soluble derivative of menadione. Vitamin K is an essential co-factor for the hepatic synthesis of proteins involved in the regulation of blood clotting. These are: prothrombin (factor II), factors VII, IX, X and proteins C, S and Z. Vitamin K is responsible for the carboxylation of the bone protein, osteocalcin, to its active form. Osteocalcin regulates the function of calcium in bone turnover and mineralisation. Vitamin K is also required for the biosynthesis of some other proteins found in plasma and the kidney. It is reported to speed up resolution of bruising to decrease future bruising and correct aspects of photoaging.

Pseudo vitamins: Vitamin F was the designation originally given to essential fatty acids that the body cannot manufacture. They were "de-vitaminized" because they are fatty acids. Fatty acids are a major component of fats which, like water, are needed by the body in large quantities and thus do not fit the definition of vitamins which are needed only in trace amounts. Herbalists and naturopaths have named various therapedic chemicals "vitamins", even though they are not, including vitamin T, S-Methylmethionine (vitamin U) and vitamin X. Some authorities say that ubiquinone, also called coenzyme Q10, is a vitamin. Ubiquinone is manufactured in small amounts by the body, like vitamin D. Pangamic acid, vitamin B15; the related substance dimethylglycine is quite wrongly referred to as vitamin B15 but also labeled B16. The toxins laetrile and amygdaline are sometimes referred to as vitamin B17. Both pangamic acid and laetrile were first proposed as vitamins by Ernst T. Krebs; neither are recognized by the medical community. Flavonoids are sometimes called vitamin P. Animal, bird, and bacterial growth factors have been designated vitamins such as para-aminobenzoic acid (PABA) vitamin $B_{10}$, the folacin (see folic acid) pterylheptaglutamic acid vitamin $B_{11}$ or vitamin Bc-conjugate and orotic acid as vitamin $B_{13}$. A few substances were once thought to be B-complex vitamins and are referred to as B-vitamins in older literature, including $B_4$ (adenine) and $B_8$ (adenylic acid), but are no longer recognized as such. An antitumor pterin phosphate named Vitamin B-14 and later abandoned.

Vitamins as anti oxidants. The antioxidant vitamins can be divided into those that are water-soluble and exist in aqueous solution—primarily vitamin C—and those that are fat-soluble and exist in membranes or lipoproteins—vitamin E and betacarotene. Lipid membranes are particularly vulnerable to oxidative breakdown by free radicals. Vitamin E protects cell membranes from destruction by undergoing preferential oxidation and destruction. Some quinones, such as ubiquinone (co-enzyme Q) also appear to have antioxidant properties. All these substances can act as free radical scavengers and can react directly with free radicals. Riboflavin also has a role as an antioxident.

They are believed to protect against certain diseases by preventing the deleterious effects of free-radical-mediated processes in cell membranes and by reducing the susceptibility of tissues to oxidative stress. An article by MP Ludo entitled "Antioxidants and Vitamins in Cosmetics" *Clinics in Dermatology* (2001): 19:467-473 discusses the benefits of vitamins and derivatives in cosmetics. Note that carotenoids and flavonoids also act as antioxidants Synergism between vitamins is known, for example, synergism between vitamin A and vitamin E is described by Gallarate, Carlotti, Trotta, and Bovo in the International Journal of Pharmacuetics 188 (1999) 233-241 discussing a study on the stability of ascorbic acid. Any synergism known in the literature between vitamins to potentiate or facilitate their action can be used in the present invention. Details of the solubility of vitamins can be found for example in the Merck Index and other similar reference works and databases.

According to one or more embodiments a hygroscopic vitamin containing composition comprises:
   (a) at least one hygroscopic substance at a sufficient concentration to provide an Aw value of the hygroscopic vitamin containing composition of less than 0.9; and
   (b) a vitamin or a derivative thereof or a combinations thereof.

According to one or more embodiments a foamable vitamin composition comprises:
   a. a therapeutically effective concentration of a vitamin;
   b. about 50% to about 98% of a solvent selected from the group consisting of (1) a propylene glycol or derivative; and (2) a polyethylene glycol or derivatives and mixtures thereof;
   c. 0% to about 48% of a secondary solvent;
   d. a surface-active agent;
   e. about 0.01% to about 5% by weight of at least one polymeric agent; and f. a liquefied or compressed gas propellant at a concentration of about 3% to about 25% by weight of the total composition.

In one or more embodiments there is provided a method of treating a disorder or condition of mammalian subject, comprising: administering a foamable vitamin composition to a target site, the composition comprising one or more of the foamable compositions described here:

In one or more embodiment the surface active agent can range from about less than 0.1% up to about 15% or up to about 20% by weight of composition depending on the surfactant selected or preferably is about 0.2% to about 0.5% by weight of composition.

In one or more embodiments the vitamin is selected from the group consisting of vitamin A, B1, B2, B3, B5, B6, B7, B9, B12, PABA, C, D1-D4, E, K and F and a derivative thereof.

In another embodiment the vitamin or a derivative thereof is susceptible to oxidation.

In a further embodiment the vitamin or a derivative thereof is soluble in water.

In another embodiment the vitamin is selected from the group consisting of vitamin B1, B2, B3, B5, B6, B7, B9, B12, PABA and C and a derivative thereof.

In an embodiment the vitamin is vitamin B3 or a derivative thereof or combinations thereof.

In an embodiment the vitamin is vitamin C or a derivative thereof or combinations thereof.

In an embodiment the vitamin is the vitamin is vitamin K or a derivative thereof or combinations thereof.

In an embodiment the vitamin is vitamin A or a derivative thereof or combinations thereof.

In an embodiment the vitamin is vitamin E or a derivative thereof or combinations thereof.

In an embodiment the vitamin is the vitamin is vitamin F or a derivative thereof or combinations thereof.

In one or more embodiments the vitamin is a combination of two or more vitamins selected from the group comprising vitamin A, B3, C, K, E, and F and a derivative thereof.

In an embodiment the vitamin or a derivative thereof or combinations thereof comprises an antioxidant.

In another embodiment the vitamin or a derivative thereof or combinations thereof improves stimulates or promotes target site metabolism.

In a still further embodiment the vitamin or a derivative thereof or combinations thereof alleviates, ameliorates, treats, prevents, retards or otherwise has a beneficial effect on a skin or boy cavity condition.

In an embodiment the skin condition is selected from the group consisting of skin pigmentation, dry skin, a wound, acne, psoriasis and skin aging.

In one or more embodiments the vitamin is a combination of two or more vitamins selected from the group comprising vitamin B3, E and C and a derivative thereof.

In an embodiment, the therapeutic agent is a photodynamic therapy (PDT) agent. Suitable PDT agents include but are not limited to modified porphyrins, chlorins, bacteriochlorins, phthalocyanines, naphthalocyanines, pheophorbides, purpurins, m-THPC, mono-L-aspartyl chlorin e6, bacteriochlorins, phthalocyanines, benzoporphyrin derivatives, as well as photosensitiser precursors, such as aminolevulinic acid and derivatives, esters, salts and mixtures thereof.

In an embodiment, the therapeutic agent is an antioxidant or a radical scavenger. Suitable antioxidants and radical scavengers agents include but are not limited to ascorbic acid, ascorbyl esters of fatty acids, magnesium ascorbyl phosphate, sodium ascorbyl phosphate, ascorbyl sorbate, tocopherol, tocopheryl sorbate, tocopheryl acetate, butylated hydroxy benzoic acid, 6-hydroxy-2,5,7,8-tetramethylchroman-2-carboxylic acid, gallic acid, propyl gallate, uric acid, sorbic acid, lipoic acid, diethylhydroxylamine, amino-guanidine, glutathione, dihydroxy fumaric acid, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and polyunsaturated oils, containing omega-3 and omega-6 fatty acids (e.g., linoleic and linolenic acid, gamma-linoleic acid, eicosapentaenoic acid and docosahexaenoic acid and derivatives, esters, salts and mixtures thereof.

In an embodiment, the therapeutic agent is a self-tanning agent, such as dihydroxyacetone.

In an embodiment, the therapeutic agent is an agent, capable of treating hyperhidrosis. Suitable hyperhidrosis agents include but are not limited to anticholinergic drugs, boric acid, tannic acid, resorcinol, potassium permanganate, formaldehyde, glutaraldehyde, methenamine, a Lewis acid, aluminum chloride, aluminum chlorohydrates, zirconium chlorohydrates, aluminum-zirconium-Glycine (AZG) complex, aluminum hydroxybromide, a glycopyrrolate compound, a 5-alpha-reductase inhibitor, finasteride, episteride, flutamide, spironolactone, saw palmetto extract, cholestan-3-one, a mono- and dicarboxylic acid having 4 to 18 carbon atoms, botulinum toxin, a 5-HT2C receptor antagonist, a 5-HT2C receptor antagonist, ketanserin, ritanserin, mianserin, mesulergine, cyproheptadine, fluoxetine, mirtazapine, olanzapine and ziprasidone.

In an embodiment, the additional therapeutic agent is a sunscreen agent. Suitable sunscreen agents include but are not limited to titanium dioxide, zinc oxide, zirconium oxide, iron oxide, p-aminobenzoic acid and its derivatives (ethyl, isobutyl, glyceryl esters; p-dimethylaminobenzoic acid); anthranilic acid derivatives (i.e., o-amino-benzoates, methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid, o- and p-hydroxybiphenyldisulfonates, coumarin derivatives (7-hydroxy, 7-methyl, 3-phenyl), diazoles (2-acetyl-3-bromoindazole, phenyl benzoxazole, methyl naphthoxazole, quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane.

In an embodiment, the additional therapeutic agent is a figure-forming agent and an agent, capable of treating cellulite. Suitable such agents include but are not limited to balderwack extract, butcher's broom, cayenne, dandelion, red clover, *ginkgo biloba*, horse chestnut, witch hazel and borage oil, caffeic acid, nicotinic acid, theophiline and pentoxyphilline and salts and derivatives thereof.

Several disorders of the skin, body cavity or mucosal surface (e.g., the mucosa or the cavity of the nose, mouth, eye, ear, vagina or rectum) involve a combination of etiological factors. For example, fungal and bacterial infections and that are inflamed and have symptoms of redness and/or itching warrant therapy that combines an anti-infective agent and an anti-inflammatory agent. Thus, in several cases, combining at least two active agents that treat different etiological factors results in a synergistic effect and consequently higher success rate of the treatment.

In certain cases, the composition contains two active agents, where each of the active agents require a different pH environment in order to remain stable. For example, corticosteroids are typically stable at acidic pH values (they have a maximum stability at a pH of about 4-6) and of vitamin D analogues are typically stable at basic pH values (they have a maximum stability at pH values above about 8). In order to circumvent the problem of instability in such cases it is preferred that the composition is substantially non-aqueous. The term "substantially non-aqueous" is intended to indicate that the composition has a water content below about 5%, preferably below about 2%, such as below about 1.5%.

Fields of Applications

The foamable carrier is suitable for treating any infected surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

By selecting a suitable active agent, or a combination of at least two active agents, the foamable composition is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment, the composition is useful for the treatment of wound, ulcer and burn. This use is particularly important since the composition creates a thin, semi-occlusive layer, which coats the damaged tissue, while allowing exudates to be released from the tissue.

The composition is also suitable for administering a hormone to the skin or to a mucosal membrane or to a body cavity, in order to deliver the hormone into the tissue of the target organ, in any disorder that responds to treatment with a hormone.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

Substantially Alcohol-Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or solvents due to their skin-irritating effect. Thus, the composition is substantially alcohol-free and includes less than about 5% final concentration of lower alcohols, preferably less than about 2%, more preferably less than about 1%.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No.

06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. patent application Ser. No. 11/732,547, filed on Apr. 4, 2007, entitled ANTI-INFECTION AUGMENTATION OF FOAMABLE COMPOSITIONS AND KIT AND USES THEREOF; U.S. patent application Ser. No. 11/732,547, filed on Apr. 4, 2007, KERATOLYTIC ANTIFUNGAL FOAM; U.S. patent application Ser. No. 11/767,442, filed on Jun. 22, 2007, entitled FOAMABLE COMPOSITIONS AND KITS COMPRISING ONE OR MORE OF A CHANNEL AGENT, A CHOLINERGIC AGENT, A NITRIC OXIDE DONOR, AND RELATED AGENTS AND THEIR USES; U.S. patent application Ser. No. 11/825,406, filed on Jul. 5, 2007, entitled DICARBOXYLIC ACID FOAMABLE VEHICLE AND PHARMACEUTICAL COMPOSITIONS THEREOF; U.S. patent application Ser. No. 11/900,072, filed on Sep. 10, 2006, entitled FOAMABLE VEHICLE AND VITAMIN AND FLAVONOID PHARMACEUTICAL COMPOSITIONS THEREOF; and U.S. patent application Ser. No. 11/947,751, filed Nov. 29, 2007, entitled COMPOSITIONS WITH MODULATING AGENTS, all of which are incorporated herein by reference in their entirety. More particularly any of the active ingredients; the solvents; the surfactants; foam adjuvants; polymeric agents, penetration enhancers; preservatives, humectants; moisturizers; and other excipients as well as the propellants and methods listed therein can be applied herein and are incorporated by reference.

The invention is described with reference to the following examples. This invention is not limited to these examples and experiments. Many variations will suggest themselves and are within the full intended scope of the appended claims.

A "stable foam" is defined herein as a composition, which upon release from an aerosol can, creates a foam mass, which is sustained on a surface for at least one minute, more preferably at least two minutes, and yet more preferably for at least 5 minutes. A period of minutes is regarded as a short term, but nevertheless it allows a good and more than sufficient period of time for a subject to receive foam dispensed on a body surface and to spread it or to transfer it to another region and to spread it.

In terms of spreadability and absorption an acceptable foam is one, that does not readily collapse upon dispensing on the skin; spreads easily on a skin surface; at least partially absorbed following rubbing onto the skin, and more preferably, substantially absorbed following rubbing on the skin.

In terms of tactile properties an acceptable foam is one, that: creates a pleasant feeling after application; leaves minimal oily residue; and leaves minimal shiny residual look.

Shakability

'Shakability' means that the composition contains some or sufficient flow to allow the composition to be mixed or remixed on shaking. That is, it has fluid or semi fluid properties. In some very limited cases it may still be possible to have a foamable composition which is flowable but not apparently shakable.

Breakability

A breakable foam is thermally stable or substantially so, yet breaks under sheer force. The breakable foam of the present invention is not "quick breaking", i.e., it does not readily collapse upon exposure to body temperature environment. Sheer-force breakability of the foam is clearly advantageous over thermally induced breakability, (due to, for example, the presence of alcohol) since it allows comfortable application and well directed administration to the target area.

Foam Collapse

A further aspect of the foam is breakability. Thermally sensitive foams immediately collapse upon exposure to skin temperature and, therefore, cannot be applied on the hand and afterwards delivered to the afflicted area.

The foam of the present invention has several notable advantages, when compared with hydroalcoholic foam compositions, such as Breakability. The foam of the present invention is thermally stable and breakable under sheer force but is not "quick breaking which allows comfortable application and well directed administration to the target area.

Skin drying and skin barrier function. Short chain alcohols are known to dry the skin and impair the integrity of the skin barrier. By contrast, including a film forming agent in the composition of the present invention foes not cause unwanted skin barrier damage.

Irritability. Due to the lack of lower alcohols (C1-C5) and improvement in skin barrier function, skin irritability is eliminated.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

EXAMPLES

The invention is described with reference to the following examples. This invention is not limited to these examples and experiments. Many variations will suggest themselves and are within the full intended scope of the appended claims, For example although examples are provided below with specific active agents they may be replaced by other active agents in effective concentrations withor without appropriate changes as will be appreciated by someone in the art.

All % values are provided on a weight (w/w) basis.

In some cases the formulations are expressed in amounts up to 100% including the propellant. In other cases the formulations are expressed in amounts up to 100% not including the propellant, which is then added to the composition.

General Methodology

The formulas of the present invention may be made in the following general way with appropriate adjustments for each formulation as will be appreciated by someone skilled in the art. Polymers, if any, are mixed, swelled and solubilized in the waterless medium, when necessary, with appropriate heat until it forms a clear solution. Stabilizing surfactants added usually with heat, until a homogeneous mixture is obtained, the mixture is then allowed to cool. The remainder of the ingredients, are then added with mixing until they have dissolved in the medium. The active agent is usually added at the end once the modulating agent, if present, has been incorporated. For foam the canisters are then filled with the above waterless formula, sealed and crimped with a valve and pressurized with the propellant.

A general procedure for preparing foamable compositions is set out in WO 2004/037225, which is incorporated herein by reference.

In one or more various embodiments the compositions can be prepared according to the general methodology set out herein with appropriate changes as would be well appreciated by a man of the art.

Waterless Foam
1. Dissolve the polymers in the main solvent with heating or cooling as appropriate for specific polymer. Add the all other ingredients and heat to 75° C. to melt and dissolve the various ingredients.
2. Cool to below 40° C. and add sensitive ingredients with mild mixing.
3. Cool to room temperature.

Oily Waterless Foam
1. Mix all ingredients excluding polymers and heat to 75° C. to melt and dissolve and obtain homogeneous mixture.
2. Mix well and cool to below 40° C. and add the polymers and sensitive ingredients with moderate mixing.
3. Cool to room temperature.

Silicone in Glycol Emulsion
1 Mix main solvent emulsifiers and foam adjuvants and heat to 75° C. to melt and dissolve the various ingredients with vigorous mixing.
2 Homogenize the formulation with vigorous mixing.
4. Add the silicones at 60° C. with vigorous mixing.
5. Cool to below 40° C. and add sensitive ingredients with mild mixing.

Formulations with Silicones and HPMC

This methodology is suitable, for all formulations described comprising HPMC (Where the formulation is without polymer the production starts at section 2).
3 Dissolve the polymers in the main solvent with heating or cooling as appropriate for specific polymer and with vigorous mixing.
4 Add to main solvent emulsifiers and foam adjuvants and heat to 75° C. to melt and dissolve the various ingredients with vigorous mixing.
5 Homogenize the formulation with vigorous mixing.
6. Add the silicones at 60° C. with vigorous mixing.
7. Cool to below 40° C. and add sensitive ingredients with mild mixing.
8. Cool to room temperature.

Formulations with Silicones and ASOS

This methodology is suitable, for all formulation described above comprising ASOS
1. Add to main solvent emulsifiers and foam adjuvants and heat to 75° C. to melt and dissolve the various ingredients with vigorous mixing.
2. Homogenize the formulation with vigorous mixing
3. Add the silicones at 60° C. with vigorous mixing
4. Cool to below 40° C. and add sensitive ingredients with mild mixing.
5. Cool to room temperature.

Formulations with Silicones and Carbopol.

This methodology is suitable, for all formulation described comprising Carbopol.
1. Separate part fro the solvent and add the carbopol
2. Homogenize the carbopol at RT for few minutes until complete.
3. Add to the rest of main solvent emulsifiers and foam adjuvants and heat to 75° C. to melt and dissolve the various ingredients with vigorous mixing.
4. Homogenize the formulation with vigorous mixing
5. Add the silicones at 60° C. with vigorous mixing
6. Cool to below 40° C. and mix with carbopol mixture with vigorous mixing.
7. Cool to room temperature.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Canisters Filling and Crimping

Each aerosol canister is filled with PFF and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing

Propellant Filling

Pressurizing is carried out using a hydrocarbon gas or gas mixture. Canisters are filled and then warmed for 30 sec in a warm bath at 50° C. and well shaken immediately thereafter.

Closure Integrity Test

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Foam Tests

By way of non limiting example the objectives of hardness, collapse time and FTC stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can affect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 min.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

FTC (Freeze Thaw Cycles)

To check the foam appearance under extreme conditions of repeated cycles of cooling, heating, (first cycle) cooling, heating (second cycle) etc., commencing with −100° C. (24 hours) followed by +400° C. (24 hours) measuring the appearance and again repeating the cycle for up to three times.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at 5° C., at 25° C., at, 40° C. and at 50° C. At appropriate time intervals canisters are removed and the amount of active agent in the foam sample is measured.

Creaming by Centrifugation

Principle of Test

The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion.

Procedure

Following preparation of the experimental formulation/s, allow to stand at room temperature for ≧24 h. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.

Transfer each mixture to 1.5 mL microtubes. Tap each microtube on the table surface to remove entrapped air bubbles.

Place visually balanced microtubes in the centrifuge rotor and operate the centrifuge at one or more of 10,000 rpm for 10 min, 3,000 rpm for 10 min or at 1,000 rpm for 10 min.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

Foam Satisfaction Tests

Compositions of the present invention were separately applied to clean skin of a group of human subjects. After 5 minutes tested subjects were asked to provide a gauge of their satisfaction relating to the following parameters: Ease of application, skin absorption, stickiness, odor, oily residue, skin surface shiny appearance, composition stability; overall satisfaction; sensation change, such as cooling, relaxing, heating etc. The subjects gauged their response according to the following scoring system:

1—very bad feeling
2—Bad feeling
3—feels "OK"
4—Feels good
5—Feels excellent, want more The scores assigned by the subjects were added and an average result was recorded.

EXAMPLES

The invention is described with reference to the following examples. This invention is not limited to these examples and experiments. Many variations will suggest themselves and are within the full intended scope of the appended claims.

Section A

Example 1

Foamable Carriers Containing Polyols

| Ingredient | TECH PG-014 % W/W | TECH PG-015 % W/W | TECH PG-016 % W/W |
|---|---|---|---|
| Propylene glycol (PG) | 82.00 | 92.00 | 60.00 |
| Laureth-4 | 2.00 | 2.00 | 2.00 |
| Glyceryl stearate and PEG-100 stearate (Simulsol 165) | 4.00 | 4.00 | 3.00 |
| PEG 4000 | 10.00 | | |
| Glycerin anhydrous | | | 33.00 |
| Hydroxypropylcellulose (Klucel EF) | 2.00 | 2.00 | 2.00 |
| Total | 100.00 | 100.00 | 100.00 |

The following observation on the preparation and property of the foam samples were made:

The compositions are substantially non-aqueous

In order to create a foam, a propellant can be added at a concentration of about 3% to about 25%.

Composition TECH PG-015 contains the minimum number of components that constitute a foamable composition, which upon release from an aerosol pressurized container affords foam of Good or Excellent quality. It contains a diol (PG), a polymeric agent (Klucel EF), and a non-ionic surface active agent (PEG-100 stearate and Laureth 4)

Composition TECH PG-014 demonstrates that the addition of 10% PEG (secondary polar solvent) maintains Good foam quality.

Composition TECH PG-016 demonstrates that a mixture of two polyols (PG and glycerin maintains Good foam quality. This composition possesses high skin hydration effect.

Example 2

Foamable Carriers Containing Polyols

| Ingredient | TECH PG-021 % W/W | TECH PG-024 % W/W | TECH PG-025 % W/W |
|---|---|---|---|
| Propylene glycol (PG) | 91.00 | 58.00 | 43.00 |
| Stearyl alcohol | 2.00 | 1.00 | 1.00 |
| Laureth-4 | 2.00 | 2.00 | 2.00 |
| Glyceryl stearate and PEG-100 stearate (Simulsol 165) | 3.00 | 3.00 | 3.00 |
| Glycerin | | 33.00 | 33.00 |
| Hydroxypropylcellulose (Klucel EF) | 2.00 | 3.00 | 3.00 |
| Dimethyl isosorbide (DMI) | | | 15.00 |
| Total | 100.00 | 100.00 | 100.00 |

The following procedure was employed when the compositions of Example 2 were produced.

Step 1: Preparation of Phase A
 1. Heat Propylene glycol and stearyl alcohol to 80-85° C.
 2. Add Klucel while mixing.
 3. Cool to 70-75° C. Add all other ingredients while mixing. Agitation continues until solution uniformity is reached
 4. Cool solution to 30° C. with moderate mixing.

Step 2: Canisters Filling and Crimping
 1. Each aerosol canister 35×70 mm is filled with 30±5% g of the composition
 2. Each canister was closed with an aerosol valve, using a vacuum crimping machine.

Step 3: Pressurizing

Propellant (mix of propane, butane and isobutane) was added to each of the canisters The following observation on the preparation and properties of the foam were made:

Composition TECH PG-021, 24 and 25 demonstrates that the addition of 1-2% stearyl alcohol (foam adjuvant) facilitates the formation of foam with Excellent quality. Substituting Stearyl alcohol with stearic acid results in an excellent foam too.

Composition TECH PG-025 demonstrates that the addition of 15% DMI (foam adjuvant) facilitates the formation of foam with Excellent quality. This composition possesses high skin penetration enhancing properties.

In order to create a foam, a propellant can be added at a concentration of about 3% to about 25%.

Example 3

Foamable Carriers Containing Polyols

| Ingredient | TECH PG-026 % W/W | TECH PG-027 % W/W | TECH PG-028 % W/W |
|---|---|---|---|
| Stearyl alcohol | 2.00 | 1.00 | 1.00 |
| Propylene glycol (PG) | 76.00 | 46.00 | 78.00 |
| Laureth-4 | 2.00 | 2.00 | 2.00 |
| Glyceryl stearate (and) PEG-100 stearate (Simulsol 165) | | 1.50 | |
| Glycerin anhydrous | | 33.00 | |
| Hydroxypropylcellulose (Klucel EF) | 2.00 | 1.50 | 1.50 |
| Dimethyl isosorbide (DMI) | 15.00 | 15.00 | 15.00 |
| Glyceryl stearate | 1.00 | | 1.00 |
| Ceteareth-6 (and) stearyl alcohol (Macrogol cetostearyl ether) | 2.00 | | 1.50 |
| Total | 100.00 | 100.00 | 100.00 |
| Foam quality | Excellent | Excellent | Excellent |

The following observation on the preparation and properties of the foam were made:

Composition TECH PG-027 demonstrates that a mixture of two polyols (PG and glycerin, plus DMI (secondary polar solvent) maintains Exellent foam quality. This composition possesses high skin hydration effect. It further possesses high skin penetration enhancing properties.

In order to create a foam, a propellant can be added at a concentration of about 3% to about 25%.

Example 4

Additional Foamable Carriers Containing Polyols, Having Excellent Foam Structure

| Ingredient | TECH-PG 029 % w/w | TECH-PG 030 % w/w | TECH-PG 031 % w/w | TECH-PG 032 % w/w | TECH-PG 033 % w/w |
|---|---|---|---|---|---|
| Propylene Glycol | 91.0 | 58.0 | 43.0 | 46.0 | 78.0 |
| Stearyl Alcohol | 2.0 | 1.0 | 1.0 | 1.0 | 1.0 |
| Glycerin | — | 33.0 | 33.0 | 33.0 | — |
| Klucel EF | 2.0 | 3.0 | 3.0 | 1.5 | 1.5 |
| Laureth-4 | 2.0 | 2.0 | 2.0 | 2.0 | 2.0 |
| Simulsol 165 | 3.0 | 3.0 | 3.0 | 1.5 | — |
| Dimethyl Isosorbide | — | — | 15.0 | 15.0 | 15.0 |
| Macrogol Cetostearyl Ether | — | — | — | — | 1.5 |
| Glyceryl Stearate | — | — | — | — | 1.0 |

Example 5

Additional Foamable Carriers which can be Used for Vitamins with and without an Active Agent

| | Gel Phase 001 | Gel Phase 002 | Gel Phase 003 | Gel Phase 004 |
|---|---|---|---|---|
| Propylene glycol | 88.00 | 78.00 | 46.00 | 78.00 |
| Glycerin anhydrous | | | 33.00 | 10.00 |
| Stearyl Alcohol | 2.00 | 1.00 | 1.00 | 2.00 |
| Hydroxypropyl Cellulose | 2.00 | 1.50 | 1.50 | 2.00 |
| Laureth-4 | 2.00 | 2.00 | 2.00 | 2.00 |
| Glyceyl Monostearate/ PEG 100 Stearate | | | 1.50 | |
| GMS NE | 2.00 | 1.00 | | 2.00 |
| Macrogol Cetostearyl ether | 1.00 | 1.50 | | 1.00 |
| PPG-15 stearyl ether | 3.00 | | | 3.00 |
| Dimethyl isosorbide | | 15.00 | 15.00 | |
| Total: | 100.00 | 100.00 | 100.00 | 100.00 |

The polar solvents of the composition including propylene glycol, glycerin and dimethyl isosorbide act as penetration enhancers for the vitamins and optional additional therapeutic agents.

Example 6

Foamable Ascorbic Acid Compostions

Ascorbic acid was added to the carrier compositions of example 5, as follows.

| | WAS 001 | WAS 002 | WAS 003 | WAS 004 |
|---|---|---|---|---|
| Gel Phase Stock 001 | 95.00% | | | |
| Gel Phase Stock 002 | | 95.00% | | |
| Gel Phase Stock 003 | | | 95.00% | |

|  | WAS 001 | WAS 002 | WAS 003 | WAS 004 |
|---|---|---|---|---|
| Gel Phase Stock 004 |  |  |  | 95.00% |
| Ascorbic Acid | 5.00% | 5.00% | 5.00% | 5.00% |
| Total: | 100.00 | 100.00 | 100.00 | 100.00 |

The following observation on the preparation and properties of the foam were made:
   In order to create a foam, a propellant can be added at a concentration of about 3% to about 25%.
   Following addition of a propellant to the composition, foamable composition, which upon release from an aerosol pressurized container affords foam of Good or Excellent quality.
   Following application of each of the foams on facial skin is favorable. The foam is easily spread and immediately absorbed into the skin with no extensive rubbing.

Example 7

Foamable Ascorbic Acid and Nicinamide Compositions

Ascorbic acid and niacinamide were concurrently added to the carrier compositions of example 5, as follows.

|  | WAN 001 | WAN 002 | WAN 003 | WAN 004 |
|---|---|---|---|---|
| Gel Phase Stock 001 | 93.00% |  |  |  |
| Gel Phase Stock 002 |  | 93.00% |  |  |
| Gel Phase Stock 003 |  |  | 93.00% |  |
| Gel Phase Stock 004 |  |  |  | 93.00% |
| Ascorbic Acid | 5.00% | 5.00% | 5.00% | 5.00% |
| Niacinamide | 2.00% | 2.00% | 2.00% | 2.00% |
| Total: | 100.00 | 100.00 | 100.00 | 100.00 |

The following observation on the preparation and properties of the foam were made:
   In order to create a foam, a propellant can be added at a concentration of about 3% to about 25%.
   Following addition of a propellant to the composition, foamable composition, which upon release from an aerosol pressurized container affords foam of Good or Excellent quality.
   Following application of each of the foams on facial skin is favorable. The foam is easily spread and immediately absorbed into the skin with no extensive rubbing.

Example 8

Foamable Ascorbic Acid and Tocopheryl Acetate Compositions

Ascorbic acid and tocopheryl acetate were concurrently added to the carrier compositions of example 5, as follows.

|  | WAT 001 | WAT 002 | WAT 003 | WAT 004 |
|---|---|---|---|---|
| Gel Phase Stock 001 | 94.00% |  |  |  |
| Gel Phase Stock 002 |  | 94.00% |  |  |
| Gel Phase Stock 003 |  |  | 94.00% |  |
| Gel Phase Stock 004 |  |  |  | 94.00% |
| Ascorbic Acid | 5.00% | 5.00% | 5.00% | 5.00% |
| Tocopheryl Acetate | 1.00% | 1.00% | 1.00% | 1.00% |
| Total: | 100.00 | 100.00 | 100.00 | 100.00 |

The following observation on the preparation and properties of the foam were made:
   In order to create a foam, a propellant can be added at a concentration of about 3% to about 25%.
   Following addition of a propellant to the composition, foamable composition, which upon release from an aerosol pressurized container affords foam of Good or Excellent quality.

Example 9

Foamable Niacinamide Compositions

Niacinamide was added to the carrier compositions of example 5, as follows.

|  | WNI 001 | WNI 002 |
|---|---|---|
| Gel Phase Stock 001 | 96.00% |  |
| Gel Phase Stock 002 |  | 96.00% |
| Niacinamide | 4.00% | 4.00% |
| Control: | 100.00 | 100.00 |

The following observation on the preparation and properties of the foam were made:
   In order to create a foam, a propellant can be added at a concentration of about 3% to about 25%.
   Following addition of a propellant to the composition, foamable composition, which upon release from an aerosol pressurized container affords foam of Good or Excellent quality.

Example 10

Foamable Ascorbic Acid and Alpha Tocopherol Compositions

Ascorbic acid and alpha tocopherol were concurrently added to the carrier compositions of example 5, as follows.

|  | WAT 001 | WAT 002 | WAT 003 | WAT 004 |
|---|---|---|---|---|
| Gel Phase Stock 001 | 94.00% |  |  |  |
| Gel Phase Stock 002 |  | 94.00% |  |  |
| Gel Phase Stock 003 |  |  | 94.00% |  |
| Gel Phase Stock 004 |  |  |  | 94.00% |
| Ascorbic Acid | 5.00% | 5.00% | 5.00% | 5.00% |
| Alpha Tocopherol | 1.00% | 1.00% | 1.00% | 1.00% |
| Total: | 100.00 | 100.00 | 100.00 | 100.00 |

The following observation on the preparation and properties of the foam were made:

In order to create a foam, a propellant can be added at a concentration of about 3% to about 25%.

Following addition of a propellant to the composition, foamable composition, which upon release from an aerosol pressurized container affords foam of Good or Excellent quality.

Example 11 a) Foamable Polyols Compositions, Containing a Steroid Drug

The following steroids were included in formulations TECH-PG 30, 31 and 33 (see Example 4): betamethasone valerate 0.12%, clobetasol propionate 0.05%, betamethasone dipropionate 0.05%, fluocinolone acetonide 0.025%, hydrocortisone acetate 0.5% and hydrocortisone butyrate 0.1%. All samples were stored at 50° C. for 4 weeks, in order to assess their stability. The following table provides the results of this short-term stability study, which indicated high compatibility between the polyol composition and the steroid drugs, which are known to be temperature-sensitive.

|  | % Degradation after 4 weeks at 50° C. | |
| --- | --- | --- |
|  | TECH-PG 032 | TECH-PG 033 |
| Bethamethasone Valerate 0.12% | 1.8% | 1.7% |
| Clobetasol Propionate 0.05% | 4.2% | 5.0% |
| Bethamethasone Dipropionate 0.05% | 0 | 0 |
| Fluocinolone Acetonide 0.025% | 1.3% | 1.7% |
| Hydrocortison Acetate 0.5% | 1.6% | 2.1% |
| Hydrocortison Butyrate 0.1% | 2.6% | 2.8 | b) Foamable polyols compositions, containing a vitamin and a steroid drug

Additionally, one or more of the following vitamins can be included in formulations TECH-PG 30, 31 and 33 (see Example 4): vitamin C (ascorbic acid) between 0.1 and 5% say, 0.1% 1%, 2% 3%, 4%, or 5%, vitamin C (magnesium ascorbyl phosphate) 3%, retinol 1%, retinoic acid 0.1%, niacinamide 2% and tocopherol 1% and Vitamin K. between 0.1 and 2% say, 0.1% or 1% or 2%, and are made up as indicted in Example 18.

Example 12

Foamable Polyol Pharmaceutical Composition Comprising a Combination of Betamethasone Dipropionate and Calcipotriol

| Ingredient | FXCLB1 % W/W | FXCLB2 % W/W |
| --- | --- | --- |
| Propylene glycol | 90.945 | 77.945 |
| Stearyl alcohol | 2.00 | 1.00 |
| Klucel EF | 2.00 | 1.50 |
| Laureth-4 | 2.00 | 2.00 |
| Simulsol 165 | 3.00 |  |
| Macrogol Cetostearyl Ether |  | 1.50 |
| Glyceryl Stearate |  | 1.00 |
| Dimethyl isosorbide |  | 15.00 |
| Calcipotriol | 0.005 | 0.005 |
| Betamethasone Dipropionate | 0.05 | 0.05 |

The following observation on the preparation and properties of the foam were made:

Composition FXCLB 1 and FXCLB2 contain two active agents (a corticosteroid and a vitamin D derivative, which are known to exert a synergistic therapeutic effect in psoriasis. These compositions contribute to enhanced skin penetration of the active agents.

The liquefied or gas propellant can be added at a concentration of about 3% to about 25%.

Example 13

Foamable Compositions Containing Polyethylene Glycol

|  | % w/w | % w/w | % w/w | % w/w | % w/w | % w/w | % w/w |
| --- | --- | --- | --- | --- | --- | --- | --- |
| PEG400 | 87.50 | 91.50 | 87.50 | 89.50 | 87.50 | 87.50 | 87.50 |
| Klucel MX (hydroxypropyl cellulose) | 0.50 | 0 | 0.50 | 0 | 0.50 | 0 | 0.50 |
| Klucel LF (hydroxypropyl cellulose) | 0 | 0.50 | 0 | 0.50 | 0 | 0.50 | 0 |
| Lipocol C2 (POE (2) cetyl ether) | 2.00 | 2.00 | 0 | 0 | 0 | 0 | 0 |
| Myrj 52 | 0 | 0 | 2.00 | 2.00 | 0 | 0 | 0 |
| Steareth-2 | 0 | 0 | 0 | 0 | 2.00 | 2.00 | 0 |
| Dermofeel G10L (Polyglyceryl-10 Laurate) | 0 | 0 | 0 | 0 | 0 | 0 | 2.00 |
| Propellant | 10 | 6 | 10 | 8 | 10 | 10 | 10 |
| Density | 0.060 | 0.063 | 0.063 | 0.055 | 0.052 | 0.050 | 0.075 |

The following observation on the preparation and properties of the foam were made:

The liquefied or gas propellant can be added at a concentration of about 3% to about 25%.

The foams of this example have a non-ionic surface active agent at a concentration of 2%. Total amounts of surface active agent foam adjuvant and polymeric agent is in the range of 2.5%.

The compositions are useful as carriers of various active therapeutic active agents.

Example 14

Comparison Between Polyethylene-Based Foamable Compositions with and without Gelling Agent The compositions of the test articles are provided in the following table. All foams were dispensed on a warm surface (38° C.), and the time to full collapse of the foam was measured. As shown in the table, it has been strikingly demonstrated that foam compositions without a gelling agent exhibit a 100% breakdown within 30 seconds, while foams containing gelling agent remained, with and without surfactant, were stable for several minutes. This is relevant from the usability point of view, since a foam that is unstable at skin temperature cannot be applied to large areas effectively.

|  | Formulations without gelling agent | | | | Formulation with gelling agent | |
| --- | --- | --- | --- | --- | --- | --- |
|  | PG33 % w/w | PG34 % w/w | PG35 % w/w | PG36 % w/w | TEC49 % w/w | PG29 % w/w |
| PEG 400 | 87.25 | 93.00 | 91.00 | 92.00 | 90.50 | 93.50 |
| Klucel GF (gelling agent) | — | — | — | — | 0.50 | 0.50 |
| Ceteareth-16 | — | — | 2.00 | 1.00 | — | — |
| Emulsiying Wax NF | 1.80 | — | — | — | — | — |
| Steareth-10 | — | 0.40 | — | 0.50 | — | — |
| PEG-40 stearate | 1.35 | — | — | — | — | — |
| Steareth-2 | — | 0.60 | 1.00 | 0.50 | 1.00 | — |
| Span 60 | 2.70 | — | — | — | — | — |
| Polysorbate 60 | 0.90 | — | — | — | — | — |
| Propellant | 6.00 | 6.00 | 6.00 | 6.00 | 8.00 | 6.00 |
| Collapse time (Seconds; 38° C.) | <30 | <30 | <30 | <30 | 240 | >300 |

Example 15

Foamable Hygroscopic Composition Containing Polyethylene Glycol with no Surfactant

|  | % w/w |
| --- | --- |
| PEG 400 | 93.50 |
| Klucel GF | 0.50 |
| Propellant (Butane/propane) | 6.00 |
| Foam quality | E |
| Density | 0.09 |

Example 16

Foamable Vitamin Compositions with an Additional Therapeutic Agent

Foamable vitamin compositions are made up with an active agent at either say 1%, 2%, 3%, 4%, or 5%, by weight of composition and added to any of the compositions illustrated in Examples 5-10 wherein the percentage amount of one or both polar solvents is reduced by an approximately equivalent amount by weight in the composition.

More particularly exemplary concentrations of additional therapeutic agents in foamable compositions are set out in Table 1. Each active agent is added into, for example, any of the carriers listed in any of Examples 5-10 above in a therapeutically effective concentration and amount. The methodology of addition is well known to those of the art. The composition is adjusted in each case so that it is made up to 100% w/w as appropriate by polar solvent.

TABLE 1

Exemplary Concentrations of Examples of Active Agents

| Additional therapeutic agent | Exemplary Concentration | Exemplary Use |
| --- | --- | --- |
| Hydrocortisone acetate | 1% | Steroid responsive inflammation and psoriasis or atopic dermatitis |
| Betamethasone valerate | 0.1% |  |
| Clobetasol propionate | 0.05% |  |
| Acyclovir | 5% | Viral infection, herpes |
| Ciclopirox | 1% | Fungal infection, seborrhea, dandruff, |
| Clindamycin | 2% | Bacterial infection, acne, rosacea, |
| Azelaic acid | 15% | Acne, rosacea, pigmentation disorder and various dermatoses |
| Metronidazol | 0.25%-2% | Rosacea, bacterial infections and parasite infestations |
| Diclofenac | 1% | Osteoarthritis, joint pain |
| Tacrolimus | 0.2% | Atopic dermatitis, eczema and inflammation |
| Benzoyl peroxide | 1%-10% | Acne |
| Alpha-hydroxy acids | 1%-20% | Aging, wrinkles |
| Salicylic acid | 1%-10% | Acne |
| Hydroquinone | 1%-10% | Pigmentation disorders |
| Caffeine | 1%-10% | Cellulite |
| Coenzyme Q 10 | 0.1%-10% | Aging, pigmentation |

The above examples represent different drug classes and it is to be understood that other drugs belonging to each of the classes represented above may be included and used in the compositions in a safe and effective amount.

Example 17

Additional Foamable Carriers which can be Used for Vitamins with and without an Active Agent a) Foamable vitamin carriers are made up with PEG or hexylene glycol or butylene glycol instead of glycerin anhydrous by weight of composition and added to any of the compositions illustrated in Examples 5-10 b) Foamable vitamin carriers are made up with PEG or hexylene glycol or butylene glycol instead of propylene glycol by weight of composition and added to any of the compositions illustrated in Examples 5-10.

Example 18

More Foamable Vitamin Compositions with an Additional Active Agent

Foamable vitamin compositions are made up with an active agent at either say 1%, 2%, 3%, 4%, or 5%, by weight of composition and added to any of the compositions illustrated in Example 19 wherein the percentage amount of one or both polar solvents is reduced by an approximately equivalent amount by weight in the composition. More particularly examples of additional active agents are as described in Example 19 above.

Example 19

Foamable Polyol Pharmaceutical Composition Comprising Acyclovir

| Ingredient | % W/W |
|---|---|
| Acyclovir | 5.00 |
| Propylene Glycol | 43.70 |
| Stearyl Alcohol | 0.95 |
| Glycerin | 31.35 |
| Hydroxypropyl cellulose | 1.43 |
| Laureth-4 | 1.90 |
| Glyceryl Monostearate/PEG 100 Stearate | 1.43 |
| Dimethyl Isosorbide | 14.25 |

The following observation on the preparation and properties of the foam were made:
  The composition contains acyclovir, which is not fully soluble in the polyol and DMI mixture. However, due to the unique composition, the acyclovir does not readily precipitate and does not undergo caking. Furthermore, thanks to the low viscosity of the composition, upon shaking the active agent readily re-disperses in the composition, resulting in full formulation uniformity.
  The combination of polyols and dimethyl isosorbide contributes to enhanced skin bioavailability of the active agent.
  The liquefied or gas propellant can be added at a concentration of about 3% to about 25%.

Example 20

Foamable Hygroscopic Compositions Containing Mupirocin

The following table exemplifies the use of PEG as a hygroscopic substance, which also serves as an effective solvent for Mupirocin, which is practically insoluble in mineral oil and other commonly used ointment solvents. Note that Mupirocin is incompatible with most solvents and thus, a foam comprising PEG as the sole solvent is highly valuable.

|  | % w/w | % w/w | % w/w |
|---|---|---|---|
| Mupirocin | 2.00 | 2.00 | 2.00 |
| PEG400 | 89.50 | 89.50 | 89.50 |
| Hydroxypropyl cellulose | 0.50 | 0.50 | 0.50 |
| Steareth-2 | 2.00 | 1.00 | 0 |
| Polyglyceryl-10 Laurate |  |  | 2.00 |
| Propellant (Propane/butane)* | 6.0 | 6.0 | 6.0 |
| Density | 0.060 | 0.060 | 0.062 |

The following observation on the preparation and properties of the foam were made:
  The liquefied or gas propellant can be added at a concentration of about 3% to about 25%.
  The foams of this example have a non-ionic surface active agent at a concentration of 2%. Total amounts of surface active agent foam adjuvant and polymeric agent is in the range of 2.5% (w/w).

Example 21

Foamable Hygroscopic Compositions Containing Terbinafine

The following table exemplifies the use of PEG as a hygroscopic substance, which also serves as an effective solvent for terbinafine, which is hard to dissolve in common formulation excipients.

|  | % w/w | % w/w | % w/w |
|---|---|---|---|
| Terbinafine | 2.00 | 2.00 | 6.00 |
| PEG400 | 89.50 | 89.50 | 89.50 |
| Hydroxypropyl cellulose | 0.50 | 0.50 | 0.50 |
| Steareth-2 | 2.00 | 1.00 | 0 |
| Polyglyceryl-10 Laurate |  |  | 2.00 |
| Propellant (Propane/butane)* | 6.0 | 6.0 | 6.0 |
| Density | 0.060 | 0.060 | 0.062 |

Example 22

Comparative In-Vitro Activity of a Hygroscopic Composition Containing Terbinafine A comparative in-vitro study was set to evaluate the effect of Composition A, consisting of 2% terbinafine, 95.3% gr. polyethylene glycol, 0.5% hydroxypropyl cellulose and 2.2% steareth-2, in comparison with Composition B (an oil in water emulsion containing 2% terbinafine) and Composition C a commercial 1% bifonazole cream.

Three fungal strains (*microsporum canis, trichophyton mentagrophytes* and *trichophyton rubrum*) and one yeast (*candida albicans*) were seeded in the center of a Petri dish, and then, were surrounded by a film containing each of the compositions, using a swab, soaked with each of the compositions. The proliferation and spreading of the microorganisms was followed up for 14 day by visual and photographic observations.

As shown in FIG. 1, Composition A inhibited the proliferation and spreading of all the fungal and yeast strains effectively. By contrast, both Compositions B and C failed to inhibit the growth of candida. Composition C was also ineffective in the inhibition of *microsporum canis* and *Trichophyton rubrum*.

Example 23

Hygroscopic Antifungal Compositions

|  | Ointment Type | | | Lacquer Type | | |
|---|---|---|---|---|---|---|
|  | % w/w | % w/w | % w/w | % w/w | % w/w | % w/w |
| PEG 400 | 92.00 | 92.00 | 93.00 | — | 54.00 | 46.00 |
| PEG 4000 | 6.00 | — | — | — | — | — |
| PEG 6000 | — | 6.00 | 6.00 | — | 10.00 | 8.00 |
| Ethyl acetate/ Isopropanol | — | — | — | 30.00 | 30.00 | 30.00 |
| Urea | — | — | — | — | — | 10.00 |
| Terbinafine | 2.00 | 2.00 | — | 2.00 | 4.00 | — |
| Ciclopirox | — | — | 1.00 | — | — | 4.00 |

The lacquer type compositions are suitable for the treatment of infected cornified tissues, and particularly the nail. It will be appreciated that in the specific embodiment where the solvent is a polyethylene glycol or derivative or mixtures thereof where there is a significant level of high molecular weight PEG then the formulations can be used to produce an ointment a gel or a cream composition.

Example 24

A Waterless Vitamin D3 Derivative Foamable Composition where the Modulating Agent is Triethoanolamine The components of these waterless foamable compositions and the results of measurements of the properties of the resultant foams and of the stability of the active agent are set out below:

| :Ingredient name (INCI, CTFA) | Concentration (% w/w) |
|---|---|
| Calcipotriol | 0.005 |
| Polyethylene glycol 400 | 65 |
| Polyethylene glycol 200 | 32.925 |
| Hydroxypropyl cellulose | 0.5 |
| Steareth-2 | 1.5 |
| Triethanolamine | 0.07 |

Part A Where the waterless solvent is a combination of two polyethylene glycols.

| Results T-0 | |
|---|---|
| Quality | Good |
| Color | White |
| Odor | No odor |
| Density | 0.096 |

Part B Where the waterless solvent is a combination of two polyethylene glycols and propylene glycol:

| Ingredient name (INCI, CTFA) | Concentration (% w/w) |
|---|---|
| Calcipotriol | 0.005 |
| Polyethylene glycol 400 | 65 |
| Polyethylene glycol 200 | 27 |
| Propylene glycol | 4.895 |
| Hydroxypropyl cellulose | 1.5 |
| Steareth-2 | 1.5 |
| Triethanolamine | 0.1 |

| Results T-0 | |
|---|---|
| Quality | Good |
| Color | White |
| Odor | No odor |
| Density | 0.096 |

Part C Where the waterless solvent is propylene glycol:

| Ingredient name (INCI, CTFA) | Concentration (% w/w) |
|---|---|
| Calcipotriol | 0.005 |
| Propylene glycol | 87.895 |
| Stearyl alcohol | 2 |
| Hydroxypropyl cellulose | 2 |
| Laureth-4 | 2 |
| Glyceryl monostearate | 2 |
| Ceteareth-20 | 1 |
| PPG-15 Stearyl ether | 3 |
| Triethanolamine | 0.1 |

| Results T-0 | |
|---|---|
| Quality | Good |
| Color | White |
| Odor | No odor |
| Density | 0.064 |

Comment: The above three formulations demonstrate waterless breakable foams of good quality in which the active ingredient is sensitive to the presence of water and light and is stabilized by the absence of water coupled with the presence of a modulating agent triethanolamine. As will be appreciated from the results the physical characteristics are little varied following variations in the waterless solvent. Moreover, it can be seen that waterless foamable pharmaceutical and cosmetic compositions of good quality can be achieved with minimal ingredients comprising a waterless solvent, a surfactant, a polymeric agent, a propellant and an effective amount of an active ingredient.

Formulation Using Two Different Polyethylene Glycols

|  |  | Concentration (% w/w) | |
| --- | --- | --- | --- |
| Ingredient name | | CLX-043-061212 | CLX-044-061214 |
| Calcipotriol | | 0.005 | 0.005 |
| Polyethylene glycol 400 | | 65 | 65 |
| Polyethylene glycol 200 | | 27 | 32.925 |
| Propylene glycol | | 4.895 | — |
| Hydroxypropyl cellulose | | 1.5 | 0.5 |
| Steareth-2 | | 1.5 | 1.5 |
| Triethanolamine | | 0.1 | 0.07 |
| Results | | | |
| Calcipotriol concentration (% w/w) | T-0 | 0.0048 | 0.0049 |
|  | T-12, 25° C. | 0.0045 | 0.0046 |
| Foam Quality | T-0 | Good | Good |
|  | T-12, 25° C. | Good | Good |
| Density | T-0 | 0.070 | 0.085 |
|  | T-12, 25° C. | 0.060 | 0.070 |
| Hardness | T-0 | 50.0 | 42.7 |
|  | T-12, 25° C. | 46.9 | 42.8 |
| Collapse time | T-0 | >300 | >300 |
|  | T-12, 25° C. | >300 | >300 |
| Shakability | T-0 | Shakable | Shakable |
|  | T-12, 25° C. | Shakable | Shakable |

Comments: The combination was found to be stable physically and chemically for 12 months at 25 degrees C. The PEG 200 alters the formulation to provide a lower viscosity.

Example 25

A Tri-Ingredient Waterless Carrier

The components of this waterless foamable composition and the results of measurements of the properties of the resultant foam and of the stability of the active agent are set out below:

| Material chemical name | % W/W |
| --- | --- |
| Propylene glycol | 96.00 |
| Hydroxypropyl cellulose | 2.00 |
| Steareth 2 | 2.00 |
| Total | 100.00 |
| Results | |
| Quality | excellent |
| Color | white |
| Odor | no odor |

Comment: this carrier produces an excellent foam. Thus, it is predicted that addition of an active agent such as active steroids in low concentrations of the order of 0.01 to 0.5% for example BMV at 0.12% w/w. together with a modulating agent should have minimal effect on the physical characteristics of the resultant foam. Likewise, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated. Note propylene glycol can act as a penetration enhancer of estrogens and perhaps progesterone.

Example 26

Demonstration of Excellent Tri-Ingredient Foams Produced with Two Different Surfactants Steareth 2 and Montanov 68 (Cetearyl Alcohol and Cetearyl Glucoside)

The components of these waterless foamable compositions and the results of measurements of the properties of the resultant foams and of the stability of the active agent are set out below:

| Material chemical name | % W/W | % W/W | % W/W |
| --- | --- | --- | --- |
| Propylene glycol | 96.00 | 95.28 | 97.50 |
| Hydroxypropyl cellulose | 2.00 | 2.00 | 0.50 |
| Steareth 2 | 2.00 | 2.00 | |
| Citric acid | | 0.50 | |
| Sodium citrate | | 0.10 | |
| Cetearyl Glucoside and Cetearyl Alcohol | | | 2.00 |
| Betamethasone 17-Valerate | | 0.12 | |
| Results | | | |
| Total | 100.00 | 100.00 | 100.00 |
| quality | excellent | excellent | excellent |
| color | white | white | white |
| odor | no odor | no odor | no odor |
| shakability | shakable | shakable | shakable |

Comments: the above formulations demonstrate the preparation of excellent quality foams using two different non ionic surfactants and that the addition of buffer or active agent has no significant effect on foam quality.

Example 27

Examples of Foams Containing a Steroid Active Agent with Carbomer (Synthetic High Molecular Weight Crosslinked Polymers of Acrylic Acid) as the Polymeric Agent The components of these waterless foamable compositions and the results of measurements of the properties of the resultant foams and of the stability of the active agent are set out below:

| Material chemical name | % W/W | % W/W | % W/W | % W/W | % W/W | % W/W | % W/W | % W/W |
|---|---|---|---|---|---|---|---|---|
| Propylene glycol | 97.50 | 97.45 | 97.60 | 97.575 | 97.50 | 97.45 | 97.60 | 97.60 |
| Steareth 2 | 2.00 | 2.00 | 2.00 | 2.00 | | | | |
| Carbomer 934 | 0.50 | 0.50 | 0.20 | 0.20 | 0.50 | 0.50 | 0.20 | 0.20 |
| triethanolamine | | | 0.20 | 0.20 | | | 0.20 | 0.20 |
| Cetearyl Glucoside and Cetearyl Alcohol | | | | | 2.00 | 2.00 | | |
| Methyl glucose sesquistearate | | | | | | | 2.00 | |
| Span 60 | | | | | | | | 2.00 |
| Clobetasol propionate | | 0.05 | | | | 0.05 | | |
| Flucinolone acetonide | | | | 0.025 | | | | |
| Total | 100.00 | 100.00 | 100.00 | 100.00 | 100.00 | 100.00 | | |

Results

| | | | | | | | | |
|---|---|---|---|---|---|---|---|---|
| Quality E = excellent G = good | E | E | E | E | E | E | G | G |
| color | White | white | White | white | white | white | white | white |
| odor | no odor | no odor | no odor | no odor | no odor | no odor | no odor | no odor |
| shakability | yes. | yes | .yes | .yes | .yes | .yes | .yes | yes |

Comments: the above formulations demonstrate the preparation of excellent quality foam using Carbomer (synthetic high molecular weight crosslinked polymers of acrylic acid). Carbomer is acidic in nature and can stabilize an active agent alone or in combination with an organic base such as triethanolamine.

Example 29

Hydrophilic PEG Containing Compositions with Various Active Agents

Stock Solution

| Ingredient name | % w/w |
|---|---|
| PEG-400 | 97.50 |
| Hydroxypropyl cellulose | 0.50 |
| Steareth 2 | 2.00 |
| Total | 100.00 |

| | | | | | | | | |
|---|---|---|---|---|---|---|---|---|
| PEG 400 | 95.00 | 85.00 | 95.00 | 99.88 | 95.00 | 99.995 | 98.00 | 98.00 |
| Hydroxypropyl cellulose | | | | | | | | |
| Steareth 2 | | | | | | | | |
| Acyclovir | 5.00 | | | | | | | |
| Azelaic acid | | 15.00 | | | | | | |

-continued

| | | | | | | | | |
|---|---|---|---|---|---|---|---|---|
| Benzoyl peroxide | | 5.00 | | | | | | |
| Betamethasone 17 valerate micronized | | | 0.12 | | | | | |
| Caffeine | | | | | 5.00 | | | |
| Calcipotriol hydrate | | | | | | 0.005 | | |
| Ciclopiroxolamine | | | | | | | 2.00 | |
| Diclofenac sodium | | | | | | | | 1.00 |
| Total | 100 | 100 | 100 | 100 | 100 | 100 | 100 | 100 |

RESULTS/APPEARANCE

| | | | | | | | | |
|---|---|---|---|---|---|---|---|---|
| QUALITY | E | G | E | G | E | G | E | G+ |
| COLOR | W | W | W | W | W | W | W | W |
| ODOR | N.O | N.O | N.O | N.O | N.O | N.O | N.O | N.O |
| SHAKABILITY | Yes | Yes | Yes | Yes | Yes | Yes | Yes | Yes |

| | | | | | | | | |
|---|---|---|---|---|---|---|---|---|
| PEG 400 | 99.00 | 95.00 | 98.00 | 98.00 | 95.00 | 99.00 | 98.00 | 99.00 |
| Hydroxypropyl Steareth 2 | | | | | | | | |
| Ketoconazole | 1.00 | | | | | | | |
| Minoxidil | | 5.00 | | | | | | |
| Mupirocin | | | 2.00 | | | | | |
| Nifedipine regular | | | | 2.00 | | | | |
| Permethrin BPC (cis:trans 25:75) | | | | | 5.00 | | | |
| Piroxicam | | | | | | 1.00 | | |
| Salicylic acid | | | | | | | 2.00 | |
| Terbinafine HCl | | | | | | | | 1.00 |
| Total | 100 | 100 | 100 | 100 | 100 | 100 | 100 | 100 |

RESULTS

| | | | | | | | | |
|---|---|---|---|---|---|---|---|---|
| QUALITY | G | G | G | E | E | E | E | E |
| COLOR | W | W | W | Light | W | Light | W | W |
| ODOR | N.O | N.O | N.O | N.O | N.O | N.O | N.O | N.O |
| SHAKABILITY | Yes | Yes | Yes | Yes | Yes | Yes | Yes | Yes |

Comments: formulations based on PEG-400, polymeric agent and a surfactant, produced good (G) to excellent (E), white (W) to light yellow, No odor (N.O.) and shakable foams. The propellant can be added at a concentration of about 3% to about 25% or more.

Example 29

Hydrophilic Propylene Glycol Containing Compositions with Various Active Agents

Ex 30 Part A—Stock Solution

| | |
|---|---|
| Propylene glycol | 91.00 |
| Stearyl alcohol | 2.00 |
| Klucel EF | 2.00 |
| Laureth-4 | 2.00 |
| Glyceryl Monostearate/ PEG 100 Stearate | 3.00 |
| Total | 100.00 |

Part Bi—Formulations with Various Active Agents

| | | | | | | | | |
|---|---|---|---|---|---|---|---|---|
| Propylene glycol | 95.00 | 85.00 | 95.00 | 99.88 | 95.00 | 99.995 | 98.00 | 98.00 |
| Stearyl alcohol | | | | | | | | |
| Klucel EF | | | | | | | | |
| Laureth-4 | | | | | | | | |
| Glyceryl Monostearate/ PEG 100 Stearate | | | | | | | | |
| Acyclovir | 5.00 | | | | | | | |
| Azelaic acid | | 15.00 | | | | | | |
| Benzoyl peroxide | | | 5.00 | | | | | |
| Betametha-sone 17 valerate micronized | | | | 0.12 | | | | |
| Caffeine | | | | | 5.00 | | | |
| Calcipotriol hydrate | | | | | | 0.005 | | |
| Ciclopiroxolamine | | | | | | | 2.00 | |
| Diclofenac sodium | | | | | | | | 1.00 |
| Total | 100 | 100 | 100 | 100 | 100 | 100 | 100 | 100 |
| RESULTS/APPEARANCE | | | | | | | | |
| QUALITY | E | G | E | G | E | G | E | E |
| COLOR | O.W | W | W | W | W | W | W | W |
| ODOR | N.O | N.O | N.O | N.O | N.O | N.O | N.O | N.O |
| SHAKABILITY | Yes | Yes | Yes | Yes | Yes | Yes | Yes | Yes |

Part Bii—Formulations with Various Active Agents

| | | | | | | | | |
|---|---|---|---|---|---|---|---|---|
| Propylene glycol | 99.00 | 95.00 | 98.00 | 98.00 | 95.00 | 99.00 | 98.00 | 99.00 |
| Stearyl alcohol | | | | | | | | |
| Klucel EF | | | | | | | | |
| Laureth-4 | | | | | | | | |
| Glyceryl Monostearate/ PEG 100 Stearate | | | | | | | | |
| Ketoconazole | 1.00 | | | | | | | |
| Minoxidil | | 5.00 | | | | | | |
| Mupirocin | | | 2.00 | | | | | |
| Nifedipine regular | | | | 2.00 | | | | |
| Permethrin BPC (cis:trans 25:75) | | | | | 5.00 | | | |
| Piroxicam | | | | | | 1.00 | | |
| Salicylic acid | | | | | | | 2.00 | |
| Terbinafine HCl | | | | | | | | 1.00 |
| Total | 100 | 100 | 100 | 100 | 100 | 100 | 100 | 100 |
| RESULTS/APPEARANCE | | | | | | | | |
| QUALITY | E | G | G | G | E | E | E | E |
| COLOR | W | W | W | Light Yellow | O.W | O.W | O.W | W |
| ODOR | N.O | N.O Odor | N.O Odor | No Odor | No Odor | No Odor | No Odor | No Odor |
| SHAKABILITY | Yes | Yes | Yes | Yes | Yes | Yes | Yes | Yes |

Comments: formulations based on Propylene glycol, polymeric agent a surfactant and co-surfactant, produced good (G) to excellent (E), white (W) to light yellow, no odor (N.O.) and shakable foams.

The co emulsifiers are non essential and can be omitted although some adjustment may be needed to the surfactant combination as will be appreciated by someone skilled in the art. The propellant can be added at a concentration of about 3% to about 25% or m.

Example 30

Hydrophilic Propylene Glycol Containing Compositions with Another Solvent DMI and Various Active Agents Ex 31 Part A—Stock Solution

| | |
|---|---|
| Propylene glycol | 46.00 |
| Glycerin anhydrous | 33.00 |
| Stearyl alcohol | 1.00 |
| Hydroxypropyl cellulose | 1.50 |

| | | |
|---|---|---|
| Laureth-4 | 2.00 | |
| Glyceryl Monostearate/PEG 100 Stearate | 1.50 | |
| Dimethyl isosorbide | 15.00 | |
| Total | 100.00 | |

Part Bi—Formulations with Various Active Agents

| | | | | | | | | |
|---|---|---|---|---|---|---|---|---|
| Propylene glycol | 95.00 | 85.00 | 95.00 | 99.88 | 95.00 | 99.995 | 98.00 | 98.00 |
| Glycerin anhydrous | | | | | | | | |
| Stearyl alcohol | | | | | | | | |
| Hydroxypropyl cellulose | | | | | | | | |
| Laureth-4 | | | | | | | | |
| Glyceryl Monostearate/PEG 100 Stearate | | | | | | | | |
| Dimethyl isosorbide | | | | | | | | |
| Acyclovir | 5.00 | | | | | | | |
| Azelaic acid | | 15.00 | | | | | | |
| Benzoyl peroxide | | | 5.00 | | | | | |
| Betamethasone 7 valerate micronized | | | | 0.12 | | | | |
| Caffeine | | | | | 5.00 | | | |
| Calcipotriol hydrate | | | | | | 0.005 | | |
| Ciclopiroxol-amine | | | | | | | 2.00 | |
| Diclofenac sodium | | | | | | | | 1.00 |
| Total | 100 | 100 | 100 | 100 | 100 | 100 | 100 | 100 |
| RESULTS/APPEARANCE | | | | | | | | |
| QUALITY | G | G | E | G | E | G | G | G |
| COLOR | O.W | W | W | W | W | W | W | W |
| ODOR | N.O | N.O | N.O | N.O | N.O | N.O | N.O | N.O |
| SHAKABILITY | Yes | Yes | Yes | Yes | Yes | Yes | Yes | Yes |

Part Bii—Formulations with Various Active Agents

| | | | | | | | | |
|---|---|---|---|---|---|---|---|---|
| Propylene glycol | 99.00 | 95.00 | 98.00 | 98.00 | 95.00 | 99.00 | 98.00 | 99.00 |
| Glycerin anhydrous | | | | | | | | |
| Stearyl alcohol | | | | | | | | |
| Hydroxypropyl cellulose | | | | | | | | |
| Laureth-4 | | | | | | | | |
| Glyceryl Monostearate/PEG 100 Stearate | | | | | | | | |
| Dimethyl isosorbide | | | | | | | | |
| Ketoconazole | 1.00 | | | | | | | |
| Minoxidil | | 5.00 | | | | | | |
| Mupirocin | | | 2.00 | | | | | |
| Nifedipine regular | | | | 2.00 | | | | |
| Permethrin BPC (cis:trans 25:75) | | | | | 5.00 | | | |
| Piroxicam | | | | | | 1.00 | | |
| Salicylic acid | | | | | | | 2.00 | |

| | | | | | | | | |
|---|---|---|---|---|---|---|---|---|
| Terbinafine HCl | | | | | | | | 1.00 |
| Total | 100 | 100 | 100 | 100 | 100 | 100 | 100 | 100 |
| RESULTS/APPEARANCE | | | | | | | | |
| QUALITY | G | G | G | G | E | E | E | G |
| COLOR | W | W | W | Light Yello | O.W | O.W | O.W | W |
| ODOR | N.O | N.O | N.O | N.O | N.O | N.O | N.O | N.O |
| SHAKABILITY | Yes | Yes | Yes | Yes | Yes | Yes | Yes | Yes |

Comments: formulations based on Propylene glycol, polymeric agent, a solvent, a surfactant and co-surfactant, produced good (G) to excellent (E), white (W) to light yellow, n odor (N.O.) and shakable foams.

The co emulsifiers are non essential and can be omitted although some adjustment may be needed to the surfactant combination as will be appreciated by someone skilled in the art. The propellant can be added at a concentration of about 3% to about 25% or more.

Example 31

Hydrophilic PEG 200/400 Mixtures Containing Compositions with a Polymeric (Gelling) Agent: a Silicone Combination and Various Active Agents

| | | |
|---|---|---|
| PEG 400 | 40.38 | 38.50 |
| PEG 200 | 39.50 | 39.50 |
| DIMETHICONE | 3.00 | 3.00 |
| Cyclomethicone | 1.50 | 1.50 |
| ASOS | 3.00 | 3.00 |
| Stearic acid | 9.00 | 9.00 |
| Steareth-2 | 3.50 | 3.50 |
| Betamethasone 17 valerate micronized | 0.12 | |
| Mupirocin | | 2.00 |
| total | 100.00 | 100.00 |
| RESULTS/APPEARANCE | | |
| QUALITY | Good | Good |
| COLOR | White | White |
| ODOR | No Odor | No Odor |
| SHAKABILITY | Yes | Yes |

Comments: formulations based on a polyethylene glycol mixture, polymeric agent surfactant, and a silicone produced good (G) white (W) No odor (N.O.) and shakable foams. The propellant can be added at a concentration of about 3% to about 25% or more.

Example 32

Hydrophilic Propylene Glycol Containing Compositions with Another Polymeric (Gelling) Agent and Various Active Agents

| | | | | |
|---|---|---|---|---|
| PROPYLENE GLYCOL | 97.38 | 95.50 | 92.50 | 82.50 |
| Steareth-2 | 2.00 | 2.00 | 2.00 | 2.00 |
| CARBOMER 934 | 0.50 | 0.50 | 0.50 | 0.50 |
| Betamethasone 17 valerate micronized | 0.12 | | | |
| Mupirocin | | 2.00 | | |
| Minoxidil | | | 5.00 | |
| Azelaic acid | | | | 15.00 |
| total | 100.00 | 100.00 | 100.00 | 100.00 |
| RESULTS/APPEARANCE | | | | |
| QUALITY | Good | Good | Good | Good |
| COLOR | White | White | White | White |
| ODOR | No Odor | No Odor | No Odor | No Odor |
| SHAKABILITY | Good | Good | Good | Good |

Comments: formulations based on propylene glycol, polymeric agent and a surfactant, produced good (G), white (W) No odor (N.O.) and shakable foams. The propellant can be added at a concentration of about 3% to about 25% or more.

Example 33

Hydrophilic PEG Containing Compositions with Various Surfactants and Polymeric (Gelling) Agents

A) ASOS

| | SURFACTANT HLB | | |
|---|---|---|---|
| PEG-400 | | 94.00 | 94.00 |
| ALUMINUM STARCH OCTENYLSUCCINATE (ASOS) | | 3.00 | 3.00 |
| Steareth 2 | 4.9 | | 3.00 |
| CETEARYL ALCOHOL (and) CETEARYL GLUCOSIDE | 12.5 (estimated between 11&15.5) | 3.00 | |
| Total | | 100.00 | 100.00 |
| RESULTS | | | |
| APPEARANCE | QUALITY | Good | Good |
| | COLOR | White | White |
| | ODOR | No Odor | No Odor |
| DENSITY | | 0.176 | 0.099 |
| COLLAPSE TIME (sec.) | | >300 | >300 |
| HARDNESS | | 55.72 | 66.82 |

Comments: formulations based on PEG-400, polymeric agent and a surfactant, produced stable, good, white, No odor and shakable foams. The propellant can be added at a concentration of about 3% to about 25% or more.

B) Carbomer

|  | SURFACTANT HLB | PCS001 | PCS002 | PCS003 |
|---|---|---|---|---|
| PEG-400 |  | 97.50 | 97.50 | 97.50 |
| Carbomer 934 |  | 0.50 | 0.50 | 0.50 |
| Steareth 2 | 4.9 |  | 2.00 |  |
| CETEARYL ALCOHOL (and) CETEARYL GLUCOSIDE | 12.5 (estimated between 11&15.5) | 2.00 |  |  |
| PEG-40 Stearate | 17.3 |  |  | 2.00 |
|  | RESULTS |  |  |  |
| APPEARANCE | QUALITY | Good | Good | Good |
|  | COLOR | White | White | White |
|  | ODOR | No Odor | No Odor | No Odor |
| DENSITY |  | 0.139 | 0.100 | 0.088 |
| COLLAPSE TIME (sec.) |  | >300 | 250 | >300 |
| HARDNESS |  | 60.30 | 50.83 |  |

Comments: formulations based on PEG-400, polymeric agent and a surfactant, produced stable, good, white, No odor and shakable foams. The propellant can be added at a concentration of about 3% to about 25% or more.

Example 34

Hydrophilic PEG Containing Compositions with Polymeric (Gelling) Agent and with and without Various Surfactants Ex 34 Part A

|  | SURFACTANT HLB |  |  |  |  |  |
|---|---|---|---|---|---|---|
| PEG-400 |  | 99.50 | 98.00 | 98.00 | 98.00 | 98.00 |
| Hydroxypropyl cellulose |  | 0.50 |  |  |  |  |
| Laureth 4 | 9.7 |  | 2.00 |  |  |  |
| Steareth 2 | 4.9 |  |  | 2.00 |  |  |
| Sorbitan monostearate | 4.7 |  |  |  | 2.00 |  |
| CETEARYL ALCOHOL (and) CETEARYL GLUCOSIDE | 12.5 (estimated between 11&15.5) |  |  |  |  | 2.00 |
| Total |  | 100 | 100 | 100 | 100 | 100 |
|  | RESULTS |  |  |  |  |  |
| APPEARANCE | QUALITY | G | G | E | E | E |
|  | COLOR | W | W | W | W | W |
|  | ODOR | N.O. | N.O. | N.O. | N.O. | N.O. |
| DENSITY |  | 0.137 | 0.123 | 0.073 | 0.103 | 0.077 |
| COLLAPSE TIME (sec.) |  | 75.00 | N/R | >300 | 120.00 | 150.00 |
| HARDNESS |  | 19.29 | N/R | 42.24 | 18.70 | 44.17 |

Ex 34 Part B

|  | SURFACTANT HLB | | | | |
|---|---|---|---|---|---|
| PEG-400 |  | 98.00 | 98.00 | 98.00 | 97.50 |
| Hydroxypropyl cellulose |  |  |  |  | 0.50 |
| sucrose stearic acid esters D-1811 | 11.0 | 2.00 |  |  |  |
| SORBITAN STEARATE AND SUCROSE COCOATE | 6.0 |  | 2.00 |  |  |
| PEG-40 Stearate | 17.3 |  |  | 2.00 |  |
| Isostearath 20 | 15.7 |  |  |  | 2.00 |
| Total |  | 100 | 100 | 100 | 100 |
| RESULTS | | | | | |
| APPEARANCE QUALITY |  | G | E | G | E |
| COLOR |  | W | W | W | W |
| ODOR |  | N.O. | N.O. | N.O. | N.O. |
| DENSITY |  | 0.109 | 0.103 | 0.094 |  |
| COLLAPSE TIME (sec.) |  | >300 | 120.00 | 60.00 |  |
| HARDNESS |  | 27.42 | 12.99 | 19.28 |  |

Comments: Formulations based on PEG-400, polymeric agent and a surfactant, produced stable, good or excellent, white, no odor and shakable foams. This carrier produces an excellent foam. Thus, it is predicted that addition of an active agent such as active steroids in low concentrations of the order of 0.01 to 0.5% for example BMV at 0.12% w/w. together with a modulating agent should have minimal effect on the physical characteristics of the resultant foam. Likewise, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated.
Note: The propellant can be added at a concentration of about 3% to about 25% or more.

Example 35

Hydrophilic PEG 1500/400 Mixture Containing a Surfactant and Polymeric (Gelling) Agent

| PEG 1500 (Solid) | 12.50 |
|---|---|
| PEG 400 (Liquid) | 86.00 |
| Hydroxypropyl cellulose | 0.50 |
| Steareth 2 | 1.00 |
| Total | 100 |
| Propellant | 8.00 |
| RESULTS/APPEARANCE | |
| QUALITY | G |
| COLOR | W |
| ODOR | N.O. |
| SHAKABILITY | Good |

Formulation based on PEG-1500/PEG 400, and relatively low levels of surfactant and polymeric agent produced a good quality white shakable foam. This carrier produces an excellent foam. Thus, it is predicted that addition of an active agent such as active steroids in low concentrations of the order of 0.01 to 0.5% for example BMV at 0.12% w/w. together with a modulating agent should have minimal effect on the physical characteristics of the resultant foam. Likewise, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated. The propellant can be added at a concentration of about 3% to about 25% or more.

Example 36

Hydrophilic High Molecular Weight Peg 4000/400 Mixtures Containing Surfactant with and without a Polymeric (Gelling) Agent that are Suitable for Gels and Ointments

| PEG 4000 | 80.00 | 80.00 | 80.00 | 10.00 | 5.00 | 5.00 |
|---|---|---|---|---|---|---|
| PEG 400 | 3.00 | 2.00 | 8.00 | 87.50 | 93.50 | 93.50 |
| Ethanol 95% | 15.00 | 17.00 |  |  |  |  |
| PPG 15 Stearyl Ether |  |  | 10.00 |  |  |  |
| Hydroxypropyl Cellulose |  |  |  | 0.50 | 0.50 | 0.50 |
| CETEARYL ALCOHOL (and) CETEARYL GLUCOSIDE | 2.00 | 1.00 | 2.00 | 2.00 | 1.00 |  |
| Steareth 2 |  |  |  |  |  | 1.00 |
| Total | 100 | 100 | 100 | 100 | 100 | 100 |

All the above formulations produced an ointment.

Example 37

Hydrophilic PEG 400 Containing a Polymeric Agent with and without a Surfactant

Stock Gel

|  | W/W % | STOCK GEL |
|---|---|---|
| HYDROXYPROPYL CELLULOSE | 2.00 | 98.00 |
| PEG 400 | 98.00 | 98.00 |

|  | W/W % | STOCK GEL | HLB | FOAM QUALITY |
|---|---|---|---|---|
| STEARETH 20 | 2.00 | 98.00 | 15.3 | G |
| CETEARETH 20 | 2.00 | 98.00 | 15.7 | G |
| PEG 40-STEARATE | 2.00 | 98.00 | 16.9 | G |
| ISOSTEARETH 20 | 2.00 | 98.00 | 15.7 | G |
| SUCROSE STEARATE | 2.00 | 98.00 | 11.0 | G |
| METHYL GLUCOSE SESQUISTEARATE | 2.00 | 98.00 | 12.0 | G |
| WITHOUT SURFACTANT | 0.00 | 100.00 |  | G |

Formulations based on PEG-400, polymeric agent and a surfactant, produced stable, good, white, No odor and shakable foams. This carrier produces an excellent foam. Thus, it is predicted that addition of an active agent such as active steroids in low concentrations of the order of 0.01 to 0.5% for example BMV at 0.12% w/w. together with a modulating agent should have minimal effect on the physical characteristics of the resultant foam. Likewise, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated. The propellant can be added at a concentration of about 3% to about 25% or more.

Section B

Example 38

A Tri-Ingredient Waterless Prophetic Formulation with Progesterone and Estrogen

| chemical name | % W/W | % W/W | % W/W |
|---|---|---|---|
| Propylene glycol | 92.00 | 95.9049 | 91.9049 |
| Hydroxypropyl cellulose | 2.00 | 2.00 | 2.00 |
| Steareth 2 | 2.00 | 2.00 | 2.00 |
| Progesterone | 4.00 | — | 4.00 |
| Estradiol hemihydrate | — | 0.0051 | 0.0051 |
| Total | 100.00 | 100 | 100 |
| Propellant* | 8 | 8 | 8 |

*Propellant is for example a mix of propane, butane and isobutane

Thus it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated. Note propylene glycol can act as a penetration enhancer of estrogens and perhaps progesterone. The propellant can be added at a concentration of about 3% to about 25% or more.

Example 39

A Hydrophilic PEG Containing Prophetic Formulation with Progesterone and Estrogen with Polymeric (Gelling) Agent and with and without Various Surfactants Ex 39 Part A

| | SURFACTANT HLB | | | | | |
|---|---|---|---|---|---|---|
| PEG-400 | | 95.50 | 94.00 | 94.00 | 94.00 | 93.9049 |
| Hydroxypropyl cellulose | | 0.50 | | | | |
| Laureth 4 | 9.7 | | 2.00 | | | |
| Steareth 2 | 4.9 | | | 2.00 | | |
| Sorbitan monostearate | 4.7 | | | | 2.00 | |
| CETEARYL ALCOHOL (and) CETEARYL GLUCOSIDE | 12.5 (estimated between 11&15.5) | | | | | 2.00 |
| Progesterone | | 4.00 | 4.00 | 4.00 | 4.00 | 4.00 |
| Estradiol hemihydrate | | | | | | 0.0051 |
| Total | | 100 | 100 | 100 | 100 | 100 |
| Propellant* | | 8 | 8 | 8 | 8 | 8 |

*Propellant is for example a mix of propane, butane and isobutane

Ex 39 Part B

|  | SURFACTANT HLB |  |  |  |  |
|---|---|---|---|---|---|
| PEG-400 |  | 94.00 | 94.00 | 93.9049 | 93.50 |
| Hydroxypropyl cellulose |  |  |  |  | 0.50 |
| sucrose stearic acid esters D-1811 | 11.0 | 2.00 |  |  |  |
| SORBITAN STEARATE AND SUCROSE COCOATE | 6.0 |  | 2.00 |  |  |
| PEG-40 Stearate | 17.3 |  |  | 2.00 |  |
| Isostearath 20 | 15.7 |  |  |  | 2.00 |
| Progesterone |  | 4 | 4 | 4 | 4 |
| Estradiol hemihydrate |  |  |  | 0.0051 |  |
| Total |  | 100 | 100 | 100 | 100 |
| Propellant* |  | 8 | 8 | 8 | 8 |

*Propellant is for example a mix of propane, butane and isobutane

Thus, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated. The propellant can be added at a concentration of about 3% to about 25% or more.

Example 40

Hydrophilic PEG 1500/400 Mixture Prophetic Formulation with Progesterone and Estrogen Containing a Surfactant and Polymeric (Gelling) Agent

| | | | |
|---|---|---|---|
| PEG 1500 (Solid) | 8.50 | 8.4049 | 12.4049 |
| PEG 400 (Liquid) | 86.00 | 86.00 | 86.00 |
| Hydroxypropyl cellulose | 0.50 | 0.50 | 0.50 |
| Steareth 2 | 1.00 | 1.00 | 1.00 |
| Progesterone | 4.00 | 4.00 | — |
| Estradiol hemihydrate | — | 0.0051 | 0.051 |
| Total | 100 | 100 | 100 |
| Propellant* | 8.00 | 8.00 | 8.00 |

*Propellant is for example a mix of propane, butane and isobutane

Thus, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated.

Note: The propellant can be added at a concentration of about 3% to about 25% or more.

Example 41

Hydrophilic High Molecular Weight PEG 4000/400 Mixtures Prophetic Formulation with Progesterone and Estrogen Containing Surfactant with and without a Polymeric (Gelling) Agent that are Suitable for Gels and Ointments

| | | | | | | |
|---|---|---|---|---|---|---|
| PEG 4000 | 76.00 | 76.00 | 76.00 | 5.9049 | 1.00 | 1.00 |
| PEG 400 | 3.00 | 2.00 | 8.00 | 87.50 | 93.50 | 93.50 |
| Ethanol 95% | 15.00 | 17.00 | | | | |
| PPG 15 earyl Ether | | | 10.00 | | | |
| Hydroxypropyl Cellulose | | | | 0.50 | 0.50 | 0.50 |
| CETEARYL ALCOHOL (and) CETEARYL GLUCOSIDE | 2.00 | 1.00 | 2.00 | 2.00 | 1.00 | |
| Steareth 2 | | | | | | 1.00 |
| Progesterone | 4.00 | 4.00 | 4.00 | 4.00 | 4.00 | 4.00 |
| Estradiol hemihydrate | | | | 0.0051 | | |
| Total | 100 | 100 | 100 | 100 | 100 | 100 |

Thus, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant formulation. For body cavity application about for example 0.005% w/w can be used. For topical use approximately a tenfold higher concentration of estradiol hemihydrate at about say 0.05% w/w may be incorporated.

Example 42

Hydrophilic PEG 400 Prophetic Formulation with Progesterone and Estrogen Containing a Polymeric Agent with and without a Surfactant Stock Gel

|  | W/W % |
|---|---|
| HYDROXYPROPYL CELLULOSE | 2.00 |
| PEG 400 | 98.00 |

| | W/W % | STOCK GEL | PROGESTERONE | HLB | PROPELLANT* |
|---|---|---|---|---|---|
| STEARETH 20 | 2.00 | 92.00 | 6.00 | 15.3 | 8 |
| CETEARETH 20 | 2.00 | 94.00 | 4.00 | 15.7 | 8 |
| PEG 40-STEARATE | 2.00 | 94.00 | 4.00 | 16.9 | 8 |
| ISOSTEARETH 20 | 2.00 | 94.00 | 4.00 | 15.7 | 8 |
| SUCROSE STEARATE | 2.00 | 94.00 | 4.00 | 11.0 | 8 |
| METHYL GLUCOSE SESQUISTEARATE | 2.00 | 94.00 | 4.00 | 12.0 | 8 |
| WITHOUT SURFACTANT | 0.00 | 98.00 | 2.00 | | 8 |

*Propellant is for example a mix of propane, butane and isobutane

Thus, it is predicted addition of an active agent such as active steroids in low concentrations of about the order of 0.001 to 0.5% w/w, for example Estradiol hemihydrate at about 0.0051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of esrtadiol hemihydrate at about say 0.05% w/w may be incorporated.

Note: The propellant can be added at a concentration of about 3% to about 25% or more.

Example 43

PEG/PG Estrogen Prophetic Formulation with Polymer

| Ingredients | % w/w |
|---|---|
| PEG 400 | 73.935 |
| Propylene glycol | 20.00 |
| Peg 100 stearate | 2.00 |

-continued

| Ingredients | % w/w |
|---|---|
| Stearyl alcohol | 3.00 |
| Methylcellulose | 0.10 |
| Carbomer 934P | 0.40 |
| TEA (for "neutralization") | 0.56 |
| Estradiol hemihydrate | 0.005 |
| Total | 100.00 |
| Propellant* | 8 |

*Propellant is for example a mix of propane, butane and isobutane

Note: propylene glycol may act as a penetration enhancer.

Example 44

PEG with Surfactant and Silicone and Estradiol

| Ingredient | Estrodiol W/W % |
|---|---|
| PEG-400 | 87.474 |
| Cetyl dimethicone | 5.00 |

-continued

| Ingredient | Estrodiol W/W % |
|---|---|
| Estrodiol | 0.026 |
| Steareth 2 | 7.5 |
| Total | 100 |
| Propellant* | 8.00 |
| | RESULT |
| Foam Quality | Good |

*Propellant is for example a mix of propane, butane and isobutane

Formulation based on PEG-400, and a surfactant, produced good foam with an estrogen. Thus, it is predicted that addition of an active agent such as active steroids in low concentrations of the order of 0.01 to 0.5% for example BMV at 0.12% w/w. together with a modulating agent should have minimal effect on the physical characteristics of the resultant foam. Likewise, it is predicted addition of an active agent such as active steroids in low concentrations of about the order of 0.001 to 0.5% w/w, for example Estradiol hemihydrate at about 0.051% w/w. optionally together with a modulating agent for example sodium citrate and citric acid say at about 0.2% and 0.4% respectively should have minimal effect on the physical characteristics of the resultant foam. For body cavity application about for example 0.005% w/w can be used. For topical use approximately a tenfold higher concentration of estradiol hemihydrate at about say 0.05% w/w may be incorporated. The propellant can be added at a concentration of about 3% to about 25% or more. N/R=Not recorded.

Section C Centrifugation Stable Formulations

Example 45

Waterless Propylene and or Butylene Glycol Formulations

Part A: Propylene Glycol Based Formulation with and without Butylene Glycol.

| Ingredients | HNAC020-080109 | HNAC021-080109 |
|---|---|---|
| Hydroxypropyl cellulose (EF) | 1.00 | 1.00 |
| Steareth-2 | 2.00 | 2.00 |
| Propylene glycol | 96.99 | 48.49 |
| butylene glycol | 0.01 | 48.50 |
| Estradiol hemihydrate | | 0.01 |
| Total | 100.00 | 100.00 |
| Propellant (AP-70) | 8.00 | 8.00 |
| Results | | |
| PFF | | |
| Viscosity | 10669.72 | 13357.15 |
| Centrifgation 1K | stable | stable |
| Centrifgation 3K | stable | stable |
| FOAM | | |
| Quality | G | G |
| Color | White | White |
| Odor | no odor | no odor |
| Collapse time (sec.) | >300/G | >300/G |
| Density (gr/ml) | 0.055 | 0.057 |
| Shakability | 2 | 2 |
| Bubble size (µm) | 49 | 53 |
| Bubble size (%-above 500 µm) | 0 | 0 |

In general terms propylene glycol formulations are sensitive to centrifugation. For example the hydrophobic propellant separates from the hydrophilic propylene glycol. In contrast it has been unexpectedly discovered that propylene glycol formulations are stable even at 3000 rpm for 10 minutes. It was also found to be possible to combine propylene glycol and butylenes glycol in a centrifugation stable formulation.

Part B—Butylene Glycol Based Formulation

| | HNAC010-071226 |
|---|---|
| Hydroxypropyl cellulose (EF) | 1.00 |
| Steareth-2 | 2.00 |
| butylene glycol | 96.99 |
| Estradiol hemihydrate | 0.01 |
| Total | 100.00 |
| Propellant (AP-70) | 8.00 |
| Results | |
| PFF | |
| Viscosity | 7422.41 |
| Centrifugation 1K | stable |
| Centrifugation 3K | stable |
| FOAM | |
| Quality | G |
| Color | White |
| Odor | v.f.odor |
| Collapse time (sec.) | >300/G |
| Density (gr/ml) | 0.058 |
| Shakability | 2 |
| Bubble size (µm) | 58 |
| Bubble size (%-above 500 µm) | 0 |

It has also been unexpectedly discovered that butylene glycol formulations are stable even at 3000 rpm for 10 minutes.

Example 46

Waterless Hexylene Glycol and Butylene Glycol Based Formulations

| | HNAC012-071226 | HNAC013-071226 | HNAC016-071226 | HNAC014-071226 | HNAC017-071226 |
|---|---|---|---|---|---|
| Hydroxypropyl cellulose (EF) | 1.00 | 3.00 | 3.00 | 3.00 | 3.00 |
| Steareth-2 | 2.00 | 6.00 | 4.00 | 6.00 | 6.00 |
| Polysorbate 80 | | | 2.00 | | |
| Peg 100 stearate | | | 3.00 | | 2.00 |
| CETEARETH 20 | | | 2.00 | | |
| Hexylene glycol | 70.00 | 65.00 | 50.00 | 46.00 | 30.00 |
| butylene glycol | 26.99 | 25.99 | 35.99 | 44.99 | 58.99 |
| Progesterone | | | | | |
| Estradiol hemihydrate | 0.01 | 0.01 | 0.01 | 0.01 | 0.01 |
| Total | 100.00 | 100.00 | 100.00 | 100.00 | 100.00 |
| Propellant (AP-70) | 8.00 | 8.00 | 8.00 | 8.00 | 8.00 |
| Results | | | | | |
| PFF | | | | | |
| Viscosity | | | | 857.82 | 19211.9 |
| Centrifugation 1K | | | | stable | stable |
| Centrifugation 3K | | | | stable | stable |

-continued

|  | HNAC012-071226 | HNAC013-071226 | HNAC016-071226 | HNAC014-071226 | HNAC017-071226 |
|---|---|---|---|---|---|
| FOAM |  |  |  |  |  |
| Quality | P | FG (F after ~10 sec.) | FG (F after ~10 sec.) | G- | G |
| Color |  |  |  | White | White |
| Odor |  |  |  | v.f.odor | v.f.odor |
| Collapse time (sec.) |  |  |  | 20/P | 160/F |
| Density (gr/ml) |  |  |  | 0.102 | 0.115 |
| Shakability |  |  |  | 2 | 1 |
| Bubble size (μm) |  |  |  | 125 | 87 |
| Bubble size (%-above 500 μm) |  |  |  | 0 | 0 |

As can be noted from the above hexylene glycol appears to act as a defoamer and that we were able to formulate a composition that generated good quality foam only after the amount of butylenes glycol approached that of hexylene glycol. Not only were such compositions suitable for producing good quality foam but unexpectedly they were also stable to centrifugation.

Example 47

Waterless Estradiol with PEG-400 and Propylene Glycol Based Formulation

|  | HNAC007-071217 Ex. 42 |
|---|---|
| PEG-400 | 74.59 |
| Carbomer 934P | 0.40 |
| Peg 100 stearate | 2.00 |
| Stearyl alcohol | 3.00 |
| Propylene glycol | 20.00 |
| Estradiol hemihydrate | 0.01 |
| Total | 100.00 |
| Propellent (AP-70) | 8.00 |
| Results |  |

-continued

|  | HNAC007-071217 Ex. 42 |
|---|---|
| PFF |  |
| Centrifugation 1K | 50% Cream. + 5% Preci. |
| Centrifugation 3K | 50% Cream. + 5% Preci. |
| FOAM |  |
| Quality | G |
| Color | White |
| Collapse time (sec.) | >300/FG |
| Density (gr/ml) | 0.14 |
| Shakability | 2 |
| Bubble size (μm) | 146 |
| Bubble size (%-above 500 μm) | 0 |

By combining PEG and PG it was possible to formulate a vehicle that generates a good quality foam that has a collapse time in excess of 5 minutes and shows some resistance to creaming. The formulation is suitable to deliver an estrogen or progesterone.

Example 48

Waterless PEG-400 Based Formulations with and without PEG1500

|  | HNAC001-071212 Ex. 40 | HNAC002-071212 Ex. 40 | HNAC004-071212 Ex. 41 | HNAC003-071212 Ex. 41 |
|---|---|---|---|---|
| PEG-400 | 95.50 | 93.50 | 89.99 | 86.04 |
| PEG-1500 |  |  |  | 12.45 |
| Hydroxypropyl cellulose (EF) | 0.50 | 0.50 | 2.00 | 0.50 |
| Steareth-2 |  | 2.00 |  | 1.00 |
| CETEARETH 20 |  |  | 2.00 |  |
| Progesterone | 4.00 | 4.00 | 6.00 |  |
| Estradiol hemihydrate |  |  | 0.01 | 0.01 |
| Total | 100.00 | 100.00 | 100.00 | 100.00 |
| Propellent (AP-70) | 8.00 | 8.00 | 8.00 | 8.00 |
| Results |  |  |  |  |
| PFF |  |  |  |  |
| Viscosity | 168.96 | 6638.58 | 308.93 | 28345.95 |
| Centrifugation 1K | stable | 10% Cream. | 50% Cream. | Stable |
| Centrifugation 3K | stable | 10% Cream. | 50% Cream. | Stable |
| FOAM |  |  |  |  |
| Quality | G | G | G | G |
| Color | White | White | White | White |
| Odor |  |  |  |  |

-continued

|  | HNAC001-071212 Ex. 40 | HNAC002-071212 Ex. 40 | HNAC004-071212 Ex. 41 | HNAC003-071212 Ex. 41 |
|---|---|---|---|---|
| Collapse time (sec.) | 170/F | >300/G | 130/F | >300/G |
| Density (gr/ml) | 0.097 | 0.062 | 0.083 | 0.12 |
| Shakability | 2 | 2 | 2 | 0 |
| Bubble size (μm) | 60 | 59 | 92 | 66 |
| Bubble size (%-above 500 μm) | 0 | 0 | 0 | 0 |

As can be seen from the above whilst foam quality is an important criteria there are other factors as well which help determine the suitability of the formulation. By making changes to the composition for example by adding surfactant or by adding a small amount of PEG 1500 it was possible to extend the collapse time to about almost double. All the formulations showed resistance to creaming. And two showed no creaming. No correlation was noted between viscosity, bubble size or density and resistance to creaming.

Example 49

Waterless PEG-400 PEG 1500 and PEG-4000 Containing Formulations

Part A

| cf | HNAC001-071212 Ex. 40 | HNAC002-071212 Ex. 40 | HNAC019-080106 Ex. 42 |
|---|---|---|---|
| PEG-400 | 95.50 | 93.50 | 92.40 |
| PEG-4000 |  |  | 2.00 |
| Hydroxypropyl cellulose (EF) | 0.50 | 0.50 | 0.50 |
| Steareth-2 |  | 2.00 |  |
| CETEARYL ALCOHOL (and) CETEARYL GLUCOSIDE |  |  | 1.00 |
| Progesterone | 4.00 | 4.00 | 4.00 |
| Estradiol hemihydrate |  |  | 0.10 |
| Total | 100.00 | 100.00 | 100.00 |
| Propellent (AP-70) | 8.00 | 8.00 | 8.00 |
| Results |  |  |  |
| PFF |  |  |  |
| Viscosity | 168.96 | 6638.58 | 51166.90 |
| Centrifgation 1K | stable | 10% Cream. | 3% flotation |
| Centrifgation 3K | stable | 10% Cream. | 3% flotation |
| FOAM |  |  |  |
| Quality | G | G | G |
| Color | White | White | White |
| Odor |  |  | no odor |
| Collapse time (sec.) | 170/F | >300/G | 150/FG |
| Density (gr/ml) | 0.097 | 0.062 | 0.083 |
| Shakability | 2 | 2 | 1 |
| Bubble size (μm) | 60 | 59 | Bubbles observed but not measured* |
| Bubble size (%-above 500 μm) | 0 | 0 |  |

*Too small for accurate measurement

The two PEG-400 formulations were resistant to creaming. The addition of steareth 2, a surfactant, produced a more stable foam and approximately doubled the collapse time. Both formulations showed resistance to creaming but the presence of the surfactant surprisingly lowered slightly the resistance. The addition of a small (2%) but significant amount of PEG-4000 greatly increased the viscosity of the formulation. Surprisingly it was noted that although the density of the expelled formulation was in keeping with that of a foam the bubbles appeared smaller and about at the limits of detection.

Part B

| cf | HNAC004-071212 Ex. 41 | HNAC018-080106 Ex. 42 | HNAC003-071212 Ex. 41 |
|---|---|---|---|
| PEG-400 | 89.99 | 87.40 | 86.04 |
| PEG-1500 |  |  | 12.45 |
| PEG-4000 |  | 6.00 |  |
| Hydroxypropyl cellulose (EF) | 2.00 | 0.50 | 0.50 |
| Steareth-2 |  |  | 1.00 |
| CETEARETH 20 | 2.00 |  |  |
| CETEARYL ALCOHOL (and) CETEARYL GLUCOSIDE |  | 2.00 |  |
| Progesterone | 6.00 | 4.00 |  |
| Estradiol hemihydrate | 0.01 | 0.10 | 0.01 |
| Total | 100.00 | 100.00 | 100.00 |
| Propellent (AP-70) | 8.00 | 8.00 | 8.00 |
| Results |  |  |  |
| PFF |  | semi-solid like ointment |  |
| Viscosity | 308.93 |  | 28345.95 |
| Centrifgation 1K | 50% Cream. |  | Stable |
| Centrifgation 3K | 50% Cream. |  | Stable |
| FOAM |  |  |  |
| Quality | G |  | G |
| Color | White |  | White |
| Odor |  |  |  |
| Collapse time (sec.) | 130/F |  | >300/G |
| Density (gr/ml) | 0.083 |  | 0.12 |
| Shakability | 2 |  | 0 |
| Bubble size (μm) | 92 |  | 66 |
| Bubble size (%-above 500 μm) | 0 |  | 0 |

The formulations with PEG on its own and in combination with PEG-1500 showed resistance to creaming. However, the presence of PEG 1500, which raised substantially the viscosity, appeared to account for the improved the resistance and also the approximately doubled collapse time. As can be seen from Part A with 2% PEG-4000 it is possible still to generate foam. However, once the level was increased to 6%, the formulation resulted in a semi solid like ointment. Increasing the level of PEG-4000 to 50% and to 76% resulted in solid like ointment formulations. These semi solid and solid ointment formulations were not sufficiently miscible with the propellant and were not suitable to make foams.

Section D

Example 50

Bioadhesive Waterless Formulations of Estradiol Hemihydrate

Bioadhesion (adhesive force) is an important property which needs to be examined for the selection of the foam formulation prototype. Adhesiveness is defined as the force (g) needed to overcome attraction between two vaginal tissue-surfaces after being in contact. An animal model system for measuring adhesiveness using pig vaginal tissues was developed for this purpose. Measurements make use of the LFRA Brookfield Texture Analyzer. Two sections of pig vaginal tissue (2×2 cm) are used; one is positioned in the center of a Petri dish and the other is attached to the base of texture analyzer probe. A PFF sample is spread uniformly on the tissue section on the Petri dish. The probe is moved down and up, first bringing the two sections into contact, followed by separation. The Texture Analyzer enables the measurement of the force for separating the tissue sections.

Figure 3:
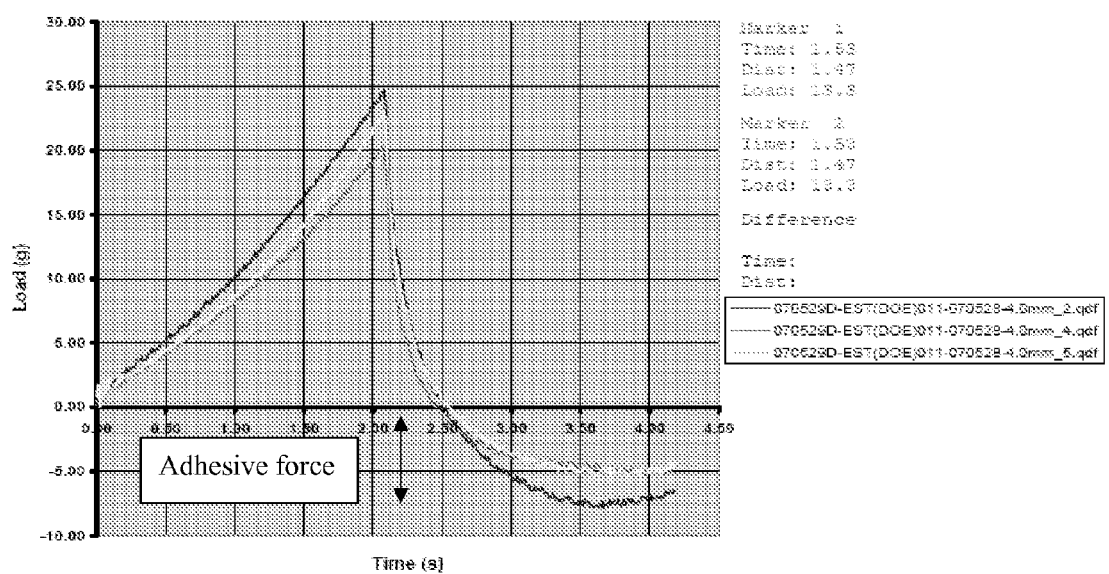
FIG. 3 is a plot of load vs time for the foamable composition as prepared in Example 50, sample EST-011.

Measurement of bioadhesion was performed on formulations EST-010 and 011, which showed suitable physical and chemical properties at T-0 and after storage for 3 weeks at 25° C., 40° C., and 50° C. (See Table 5 below) Adhesive properties of three marketed products (a cream and a gel) were tested in parallel to serve as a reference. Comparative results of the tests performed are shown in Table 1 and in FIGS. 2 and 3 (graphic presentation of results). The first part of each graph is the load applied to the foam and the second part shows measurement of the adhesive force used to separate the probe.

TABLE 1

Adhesiveness Test Results for Selected Estradiol PFF Formulations and Reference Product., Replens Gel ..

| Formulation | Adhesive force (g)* |
|---|---|
| EST-010 | −5.87 |
| EST-011 | −6.12 |
| Replens Gel For vaginal lubrication) | −12.13 |

*results, average of three determinations

TABLE 2

Composition of the Hydrophilic Solvent-Based Formulation EST-010 with carbomer as main mucoadhesive agent and methylcellulose as a second polymer.

| Ingredients | % w/w |
|---|---|
| PEG 400 | 62.36 |
| Propylene glycol | 20.00 |
| PEG-100 stearate | 2.00 |
| Stearyl alcohol | 4.0 |
| Methylcellulose (Methocel A4) | 0.1 |
| Carbomer 934P | 0.20 |
| Purified water | 10.00 |
| Estradiol hemihydrate in PG stock solution* | 0.005 |
| TEA (for neutralization of carbomer solution) | q.s. |

TABLE 2-continued

Composition of the Hydrophilic Solvent-Based Formulation EST-010 with carbomer as main mucoadhesive agent and methylcellulose as a second polymer.

| Ingredients | % w/w |
|---|---|
| Lactic acid (for adjustment of pH to 4.0-4.5) | q.s. |
| Total for PFF | 100.00 |
| Propellant AP-70** | 12.00 |

TABLE 3

Composition of the Hydrophilic Solvent-Based Formulation EST-011 with Polycarbophil as main mucoadhesive agent

| | EST-011 % w/w |
|---|---|
| PEG 400 | 62.36 |
| Stearyl alcohol | 4.00 |
| Polyoxyl 100 stearate | 2.00 |
| Polycarbophil | 0.20 |
| Lactic acid/Triethanolamine | (to pH 4.0-4.5) |
| Propylene glycol | 20.00 |
| Estradiol hemihydrate stock solution* | 0.005 |
| Purified water to 100.00 | 10.10 |
| Propellant AP-70** | 12.00 |

The adhesive force seen with Polycarbophil was slightly greater than with carbomer. Both polymers are crosslinked and the difference in result was not considered to be significant. In order to increase the mucoadesiveness the amounts of crosslinked polymer should be increased. It may also be effective to use a combination of the two crosslinked polymers with or without a second non crosslinked polymer for example like methocellulose.

TABLE 4

Results at T-0, PFFs of Group 3, Hydrophilic Solvent-Based Preparations

| Test Material in Closure System | Test Parameter | Results, T-0 | |
|---|---|---|---|
| | | EST-010 | EST-011 |
| Unpressurized formulations (PFFs) in glass vials | Identification of estradiol | RT of estradiol peak in sample solution corresponds to that from stand. solution | RT of estradiol peak in sample solution corresponds to that from stand. Solution |
| | HPLC assay (% w/w): estradiol: estrone (degrad. prod.) | 0.0040 ND | 0.0044 ND |
| | pH (undiluted) | 3.97 | 4.36 |
| | pH (diluted 1:5 with purified water) | 2.75 | 2.90 |
| | Centrifugation at: | | |
| | 1) 3,000 rpm: | 3000 rpm:. - 15% creaming | 3000 rpm. - 35% creaming |

TABLE 4-continued

Results at T-0, PFFs of Group 3, Hydrophilic Solvent-Based Preparations

| Test Material in Closure System | Test Parameter | Results, T-0 EST-010 | EST-011 |
|---|---|---|---|
| | 2) 10,000 rpm: (% creaming*) | 10,000 rpm: .10% creaming | 10,000 rpm:. - 15% creaming |
| | Viscosity (cPs) | 1678 | 2179 |
| | Microscopic examination (x200) | no crystals observed | no crystals observed |
| | Homogeneity of contents | not homogeneous, *but redispersible after shaking | not homogeneous, *but redispersible after shaking |

*when the formulations including propellant were observed in closed glass bottles under pressure it was noted that after a relatively short period of time the formulations started to reveal creaming.

Abbreviations & Explanations:

RT: retention time; ND: not detected; detection limit for estrone is 0.074 μg/mL; NR: not recorded NE: not established (for information only), specified limits not yet established;

* Creaming is the formation of an opaque, white upper layer and less opaque/transparent lower layer; % creaming indicates the relative volume of the upper layer.

TABLE 5

Physical and Chemical Properties After Three Weeks at Different Storage Conditions

| Test Material in Clos. Sys. | Test Parameter | Storage Conditions | Results, 3 weeks EST-010 | EST-011 |
|---|---|---|---|---|
| Pressurized formulation in aluminum canister | API identification RT of estradiol peak in sample solution corresponds to that from standard solution | T-0 25° C. 40° C. 50° C. (PFF) | conforms conforms conforms conforms | Conforms Conforms Conforms Conforms |
| | HPLC assay (% w/w): estradiol: estrone: | T-0 25° C. 40° C. 50° C. (PFF) 50° C. (PFF in glass bottles) | 0.0035 ND 0.0043 ND 0.0042 ND 0.0043 ND 0.0034 ND | 0.0043 ND 0.0046 ND 0.0048 ND 0.0048 ND 0.0044 ND |
| | Appearance: Quality: G = Good Color: Odor: N0 = No Odor | T-0 FTC 25° C. 40° C. | G/white/NO G/white/NO G/white/NO G/white/NO | G/white/NO G/white/NO G/white/NO G/white/NO |
| | Density (g/mL) | T-0 FTC | 0.063 0.045 | 0.082 0.077 |
| | | 25° C. 40° C. | 0.045 0.038 | 0.075 0.068 |
| | pH diluted 1:5 in purified water | T-0 FTC 25° C. 40° C. | 2.78 2.81 2.88 2.85 | 2.92 2.99 3.00 2.93 |
| | Texture, hardness (g) | T-0 | 81.48 | 100.88 |
| | Expansion time (sec) | T-0 | 32 | 18 |
| | Collapse time (sec) | T-0 | >300 | >300 |
| Pressurized formulation in aluminum canister | Shakabilty | T-0 FTC 25° C. 40° C. | good shakability good shakability good shakability good shakability | Moderate shakability good shakability good shakability good shakability |
| | Microscopic examination (x200) | T-0 FTC 25° C. 40° C. | no crystals no crystals no crystals no crystals | no crystals no crystals no crystals no crystals |
| PFF in aluminum canister | Corrosion and Deterioration | T-0 50° C. | conforms conforms | Conforms Conforms |
| Pressurized formulation in gl. Vessel | Homogeneity of contents* | T-0 25° C. | non homogeneous, redispersible after shaking non homogeneous, redispersible after shaking | Non homogeneous, redispersible after shaking Non homogeneous, redispersible after shaking |

*when the formulations including propellant were observed in closed glass bottles under pressure it was noted that after a relatively short period of time the formulations started to reveal creaming.

Abbreviations & Explanations:
RT: retention time; ND: not detected; detection limit for estrone is 0.074 μg/mL;
NE: not established (for information only), specified limits not yet established;
E, G, FG (grades of foam quality): excellent, good, fairly good;
VFO, NO: very faint odor, no odor
* Creaming is the formation of an opaque, white upper layer and less opaque/transparent lower layer; % creaming indicates the relative volume of the upper layer.

Section E

Example 51

Propylene Glycol (PG) or PEG and Surfactant Ratios and Propellant

Part A—PG

| | |
|---|---|
| Propylene Glycol | 89% |
| Brij 21 | 8% |
| Polysorbate 80 | 3% |

-continued

| | |
|---|---|
| Propellant AP46 (propane, butane and isobutane mixture) | 8% |
| Hardness | 19.78 g |
| Adhessive Force* | −14.58 |

*Measured by applying the foam to a metal surface and testing with a texture analyzer as described in Example 51

Foam quality with AP46 is Good to Excellent. The foam maintains its shape well and can be extruded to form different shapes and maintain them prior to application. The high surfactant level and the ratio of about 8 to 3 of the two surfactants appears to contribute to the dissolution of the hydrophobic propellant in the hydrophilic solvent. Replacing Bij 21 with Brij 2 did not help. Brij 21 or Brij 2 on their own are less satisfactory, although Brij 21 is preferred. When the ratio was the reverse foam quality was only fairly good. The adhesive force and hardness of the PG is more than satisfactory.

Part B—PEG

| | |
|---|---|
| PEG 200 | 89% |
| Brij 21 | 8% |
| Polysorbate 80 | 3% |
| Propellant AP46 (propane, butane and isobutane mixture) | 8% |
| Hardness | 84.65 g |
| Adhessive Force* | −66.59 |

*Measured by applying the foam to a metal surface and testing with a texture analyzer as described in Example 51

Foam quality with AP46 is Good, but extrudes with a less defined shape. The high surfactant level and the ratio of about 8 to 3 of the two surfactants appears to contribute to the dissolution of the hydrophobic propellant in the hydrophilic solvent. Replacing Bij 21 with Brij 2 did not help. Brij 21 or Brij 2 on their own are less satisfactory, although Brij 21 is preferred. When the ratio was the reverse foam quality was only fairly good. Interestingly, PEG contributes to adhesive force and increases hardness when compared to PG.

All references to patents, patent publications, and published articles are hereby incorporated in their entirety by reference.

What is claimed is:

1. A waterless composition suitable for delivery of an active agent to a body surface or cavity comprising:
   a vehicle comprising:
   a) about 70% to about 96.5% by weight of a mixture of PEG 200 and PEG 400;
   b) about 0.01% to about 10% of at least one surface active agent and/or about 0.01% to about 5% of a polymeric agent;
   c) about 0% to about 30% of a secondary hydrophilic solvent; and
   d) about 0% to about 5% of a silicone oil; and
   e) about 3% to about 25% hydrophobic propellant;
   wherein the composition is otherwise substantially free of a hydrophobic solvent; and
   wherein the vehicle and the propellant are sufficiently miscible that the components may be homogeneously distributed with mild shaking.

2. The composition of claim 1, wherein the mixture of PEG 200 and PEG 400 is selected to provide viscosity of the vehicle of less than 52,000 CPs, as measured at room temperature at 10 rpm spindle speed.

3. The composition of claim 1, wherein the components of the composition are sufficiently miscible that the vehicle and the propellant do not phase separate upon centrifugation at 1000 rpm.

4. The composition of claim 3, wherein the composition includes a steareth surface active agent and a hydroxypropylcellulose polymeric agent, is otherwise substantially free of a secondary hydrophilic solvent.

5. The composition of claim 1, wherein one or both of the surface active agent and the polymeric agent are selected to increase the solubility of the propellant in the vehicle.

6. The composition of claim 1 wherein the composition comprises a polymeric agent and the polymeric agent is selected from the group consisting of locust bean gum, sodium alginate, sodium caseinate, egg albumin, gelatin agar, carrageenin gum, xanthan gum, quince seed extract, tragacanth gum, guar gum, cationic guars, hydroxypropyl guar gum, starch, an amine-bearing polymer, chitosan, alginic acid, hyaluronic acid, a chemically modified starch, a carboxyvinyl polymer, polyvinylpyrrolidone, polyvinyl alcohol, a polyacrylic acid polymer, a polymethacrylic acid polymer, polyvinyl acetate, a polyvinyl chloride polymer, a polyvinylidene chloride polymer, methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, a cationic cellulose, PEG 1000, PEG 4000, PEG 6000 and PEG 8000, polycarbophil, carbomer, and acrylates/C10-30 alkyl acrylate crosspolymer.

7. The composition of claim 1, wherein silicone oil is present in the composition and is selected from the group consisting of dimethicone, cyclomethicone and mixtures thereof.

8. The composition of claim 1 wherein the secondary hydrophilic solvent is present in the composition and is a polyol selected from the group consisting of a diol, a triol and a saccharide, wherein the triol is selected from the group consisting of glycerin, butane-1,2,3-triol, butane-1,2,4-triol and hexane-1,2,6-triol, and wherein the diol is selected from the group consisting of propylene glycol, butanediol, butenediol, butynediol, pentanediol, hexanediol, octanediol, neopentyl glycol, 2-methyl-1,3-propanediol, diethylene glycol, triethylene glycol, tetra ethylene glycol, dipropylene glycol and dibutylene glycol.

9. The composition of claim 1, wherein the ratio between the polyethylene glycol and the secondary hydrophilic solvent is between about 9:1 and about 1:1.

10. The composition of claim 1 wherein the composition further comprises one or more modulating agents.

11. The composition of claim 10, wherein the modulating agent is selected from the group of triethanol amine, sodium citrate and citric acid.

12. The composition of claim 1, further comprising an active agent.

13. The composition of claim 12, wherein the active agent is selected from the group consisting of antiinfectives, antifungals, antivirals, anesthesic analgesic, corticosteroids, non steroid anti inflammatory, retinoids, lubricating agents anti warts, antiproliferative, vasoactive, keratolytic, insectiside and repellants, dicarboxylic acids and esters; calcium channel blockers, cholinergic, Noxide doners, photodynamic, anti acne, anti wrinkle, antioxidants, self tanning active herbal extracts, acaricides, age spot and keratose removing agents, allergen, analgesics, local anesthetics, anti acne agents, antiallergic agents, anti aging agents, antibacterials, antibiotics, antibum agents, anticancer agents, antidandruff agents, antidepressants, anti dermatitis agents, antiedemics, antihistamines, antihelminths, antihyperkeratolyte agents, antiinflammatory agents, antiirritants, antilipemics, antimicrobials, antimycotics, antiproliferative agents, antioxidants, antiwrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, nonsteroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamins A, B, C, D, E, K and derivatives, wound healing agents and wart removers.

14. The composition of claim 12, wherein the active agent is selected from the group consisting of: Acyclovir, Azelaic acid, Benzoyl peroxide, Betamethasone 17 valerate micronized, Caffeine, Calcipotriol hydrate, Ciclopiroxolamine, Diclofenac sodium, Ketoconazole, Miconazole nitrate, Minoxidil, Mupirocin, Nifedipine regular, Permethrin BPC cis:trans 25:75, Piroxicam, Salicylic acid, Terbinafine HCl, estradiol hemihydrate and progesterone or combinations thereof.

15. The composition of claim 12, wherein the active agent includes progesterone, estrogen, a derivative thereof or mixtures thereof.

16. The composition of claim 12 wherein the active agent includes a steroid.

17. The composition of claim 12, wherein the active agent includes a vitamin.

18. The composition of claim 17, wherein the vitamin selected from the group consisting of a Vitamin D, retinol, retinoic acid, tocopherol, Vitamin K, Vitamin C, and Vitamin B, or derivatives thereof.

19. The composition of claim 17, wherein the active agent includes a steroid.

20. The composition of claim 1, wherein the composition comprises a polymeric agent and the polymeric agent is selected from the group of bioadhesive polymers.

21. The composition of claim 20, wherein the composition has a bioadhesive force in the range of about −3 g to about −25 g.

22. The composition of claim 20 wherein the polymeric agent is selected from the group consisting of hydroxypropylcellulose and carbomer.

* * * * *

UNITED STATES PATENT AND TRADEMARK OFFICE
CERTIFICATE OF CORRECTION

PATENT NO. : 8,486,374 B2  
APPLICATION NO. : 12/014088  
DATED : July 16, 2013  
INVENTOR(S) : Tamarkin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1236 days.

Signed and Sealed this  
Twenty-fourth Day of February, 2015

Michelle K. Lee  
*Deputy Director of the United States Patent and Trademark Office*